(12) United States Patent
Gegg, Jr. et al.

(10) Patent No.: US 8,288,339 B2
(45) Date of Patent: Oct. 16, 2012

(54) GLP-1 COMPOUNDS

(75) Inventors: Colin Victor Gegg, Jr., Newbury Park, CA (US); Leslie Phillip Miranda, Thousand Oaks, CA (US); Katherine Ann Winters, Thousand Oaks, CA (US); Murielle Veniant-Ellison, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 627 days.

(21) Appl. No.: 12/297,705

(22) PCT Filed: Apr. 20, 2007

(86) PCT No.: PCT/US2007/067150
§ 371 (c)(1),
(2), (4) Date: Jun. 2, 2009

(87) PCT Pub. No.: WO2007/124461
PCT Pub. Date: Nov. 1, 2007

(65) Prior Publication Data
US 2010/0048468 A1    Feb. 25, 2010

Related U.S. Application Data

(60) Provisional application No. 60/793,707, filed on Apr. 20, 2006.

(51) Int. Cl.
*A61K 38/26* (2006.01)
(52) U.S. Cl. .......................... 514/7.2; 530/308
(58) Field of Classification Search .................. None
See application file for complete search history.

(56) References Cited

U.S. PATENT DOCUMENTS

| | | | |
|---|---|---|---|
| 5,118,666 A | 6/1992 | Habener | |
| 5,120,712 A | 6/1992 | Habener | |
| 5,545,618 A | 8/1996 | Buckley et al. | |
| 5,614,492 A | 3/1997 | Habener | |
| 5,705,483 A | 1/1998 | Galloway et al. | |
| 5,958,909 A | 9/1999 | Habener | |
| 5,977,071 A | 11/1999 | Galloway et al. | |
| 6,133,235 A | 10/2000 | Galloway et al. | |
| 6,162,907 A | 12/2000 | Habener | |
| 6,284,727 B1 | 9/2001 | Kim et al. | |
| 6,388,052 B1 | 5/2002 | Crabtree et al. | |
| 6,410,513 B1 | 6/2002 | Galloway et al. | |
| 6,569,832 B1 | 5/2003 | Knudsen et al. | |
| 6,703,365 B2 | 3/2004 | Galloway et al. | |
| 6,828,303 B2 | 12/2004 | Kim et al. | |
| 6,849,708 B1 | 2/2005 | Habener | |
| 7,232,879 B2 | 6/2007 | Galloway et al. | |
| 7,268,213 B2 | 9/2007 | Dong | |
| 2004/0018981 A1 | 1/2004 | Dong | |
| 2004/0242853 A1* | 12/2004 | Greig et al. ............... | 530/399 |

FOREIGN PATENT DOCUMENTS

| | | |
|---|---|---|
| EP | 1083924 | 7/2004 |
| WO | 87/06941 | 11/1987 |
| WO | 90/11296 | 10/1990 |
| WO | 91/11457 | 8/1991 |
| WO | 98/43658 | 10/1998 |
| WO | 99/64061 | 12/1999 |
| WO | 00/34331 | 6/2000 |
| WO | 00/34332 | 6/2000 |
| WO | 01/98331 | 12/2001 |
| WO | 02/46227 | 6/2002 |
| WO | 02/48192 | 6/2002 |
| WO | 03/011892 | 2/2003 |
| WO | 03/018516 | 3/2003 |
| WO | 03/028626 | 4/2003 |
| WO | 03/058203 | 7/2003 |
| WO | 03/103572 | 12/2003 |
| WO | 2004/022004 | 3/2004 |
| WO | 2004/074315 | 9/2004 |
| WO | 2004/093823 | 11/2004 |
| WO | 2004/110472 | 12/2004 |
| WO | 2005/000892 | 1/2005 |
| WO | WO 2005/279978 | * 3/2005 |
| WO | WO 2005/058954 | * 6/2005 |

OTHER PUBLICATIONS

Burcelin et al. ("Long-Lasting Antidiabetic Effect of a Dipeptidyl Peptidase IV-Resistant Analog of Glucagon-Like Peptide-1," Metabolism, 48 (1999) 252-258).*
Andersen et al. ("Medium-Dependence of the Secondary Structure of Exendin-4 and Glucagon-like-peptide-1," Bioorganic & Medicinal Chemistry 10 (2002) 79-85).*
Banerjee et al. ("Aib-based peptide backbone as scaffolds for helical peptide mimics," Chemical Biology & Drug Design 60 (2002) 88-94).*
Bryne and Goke, "Human studies with glucagon-like-peptide-1: potential of the gut hormone for clinical use," Diabet Med 13:854-860, 1996.
Byrne et al., Glucagon-like peptide-1 improves the ability of the β-cell to sense and respond to glucose in subjects with impaired glucose tolerance, Diabetes 46 (Suppl. 1); Abstract 0127, p. 33A, 1997.
Byrne et al., "GLP-1 improves first phase insulin secretion without altering insulin sensitivity in subjects with impaired glucose tolerance" Diabetes 47 (Suppl. 1); Abstract 0744, p. A192, 1998.
Lee et al., "PEGylated glucagon-like peptide-1 displays preserved effects on insulin release in isolated pancreatic islets and improved biological activity in *db/db* mice," Diabetologia 49:1608-1611, 2006.
Wang et al., "Glucagon-like peptide-1 can reverse the age-related decline in glucose tolerance in rats," J Clin Invest 99:2883-2889, 1997.

\* cited by examiner

*Primary Examiner* — Christina Bradley
(74) *Attorney, Agent, or Firm* — Scott L. Ausenhus

(57) ABSTRACT

GLP-1 compounds comprising GLP-1 analogs and methods of using the GLP-1 compounds for treating metabolic disorders, enhancing insulin expression, and promoting insulin secretion in a patient are provided.

7 Claims, 27 Drawing Sheets

Lactam positions:
18-22, 19-23, 20-24, 21-25, 22-26, 23-27, 24-28, 25-29, 26-30

HGEGTFTSDVSSYLEGQAAKEFIAWLVKGRG
7                                                              37

*[Gly8]cyclo[20-24]GLP1(7-37)-Lys/Orn38*

*[Gly8]cyclo[21-25]GLP1(7-37)-Lys/Orn38*

*[Gly8]cyclo[24-28]GLP1(7-37)-Lys/Orn38*

*[Gly8]cyclo[25-29]GLP1(7-37)-Lys/Orn38*

SEQUENCE LISTING

<160> NUMBER OF SEQ ID NOS: 304

<210> SEQ ID NO 1
<211> LENGTH: 31
<212> TYPE: PRT
<213> ORGANISM: Artificial
<220> FEATURE:
<223> OTHER INFORMATION: synthetic

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 31
<212> TYPE: PRT
<213> ORGANISM: Artificial
<220> FEATURE:
<223> OTHER INFORMATION: Synthetic

<400> SEQUENCE: 2

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 31
<212> TYPE: PRT
<213> ORGANISM: Artificial
<220> FEATURE:
<223> OTHER INFORMATION: Synthetic

<400> SEQUENCE: 3

Met His Gly Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg
            20                  25                  30

<210> SEQ ID NO 4
<211> LENGTH: 36
<212> TYPE: PRT
<213> ORGANISM: Artificial
<220> FEATURE:
<223> OTHER INFORMATION: Synthetic

<400> SEQUENCE: 4

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

Gly Gly Gly Cys
        35

<210> SEQ ID NO 5
<211> LENGTH: 39
<212> TYPE: PRT
<213> ORGANISM: Artificial
<220> FEATURE:
<223> OTHER INFORMATION: Synthetic
<220> FEATURE:
<221> NAME/KEY: MISC_FEATURE

```
<222> LOCATION: (1)..(1)
<223> OTHER INFORMATION: X is: L-histidine, D-histidine, desamino-
      histidine, 2-amino-histidine, 3-hydroxy- histidine, homohistidine,
      a-fluoromethyl-histidine or a-methyl-histidine
<220> FEATURE:
<221> NAME/KEY: MISC_FEATURE
<222> LOCATION: (3)..(3)
<223> OTHER INFORMATION: Xaa at position 3 is Glu, Asp, or Lys
<220> FEATURE:
<221> NAME/KEY: MISC_FEATURE
<222> LOCATION: (4)..(4)
<223> OTHER INFORMATION: Xaa at position 4 is Gly or His
<220> FEATURE:
<221> NAME/KEY: MISC_FEATURE
<222> LOCATION: (5)..(5)
<223> OTHER INFORMATION: Xaa at position 5 is Thr, Ala, Gly, Ser, Leu,
      Ile, Val, Glu, Asp, or Lys
<220> FEATURE:
<221> NAME/KEY: MISC_FEATURE
<222> LOCATION: (6)..(6)
<223> OTHER INFORMATION: Xaa at position 6 is: His, Trp, Phe, or Tyr
<220> FEATURE:
<221> NAME/KEY: MISC_FEATURE
<222> LOCATION: (7)..(7)
<223> OTHER INFORMATION: Xaa at position 7 is Thr or Gly
<220> FEATURE:
<221> NAME/KEY: MISC_FEATURE
<222> LOCATION: (8)..(8)
<223> OTHER INFORMATION: Xaa at position 8 is Ser, Ala, Gly, Thr, Leu,
      Ile, Val, Glu, Asp, or Lys
<220> FEATURE:
<221> NAME/KEY: MISC_FEATURE
<222> LOCATION: (9)..(9)
<223> OTHER INFORMATION: Xaa at position 9 is Asp or Glu
<220> FEATURE:
<221> NAME/KEY: MISC_FEATURE
<222> LOCATION: (10)..(10)
<223> OTHER INFORMATION: Xaa at position 10 is Val, Ala, Gly, Ser, Thr,
      Leu, Ile, Tyr, Glu, Asp, Trp, or Lys
<220> FEATURE:
<221> NAME/KEY: MISC_FEATURE
<222> LOCATION: (11)..(11)
<223> OTHER INFORMATION: Xaa at position 11 is Ser, Ala, Gly, Thr, Leu,
      Ile, Val, Glu, Asp, or Lys
<220> FEATURE:
<221> NAME/KEY: MISC_FEATURE
<222> LOCATION: (12)..(12)
<223> OTHER INFORMATION: Xaa at position 12 is Ser, Ala, Gly, Thr, Leu,
      Ile, Val, Glu, Asp, Trp, Tyr, Lys, Homolysine, Ornithine,
      4-carboxy-phenylalanine, beta-glutamic acid, beta-Homoglutamic
      acid, or homoglutamic acid
<220> FEATURE:
<221> NAME/KEY: MISC_FEATURE
<222> LOCATION: (13)..(13)
<223> OTHER INFORMATION: Xaa at position 13 is Tyr, Phe, Trp, Glu, Asp,
      Gln, Lys, Homolysine, Ornithine, 4-carboxy-phenylalanine, beta-
      glutamic acid, beta-Homoglutamic acid, or homoglutamic acid
<220> FEATURE:
<221> NAME/KEY: MISC_FEATURE
<222> LOCATION: (14)..(14)
<223> OTHER INFORMATION: Xaa at position 14 is Leu, Ala, Gly, Ser, Thr,
      Ile, Val, Glu, Asp, Met, Trp, Tyr, Lys, Homolysine, Ornithine,
      4-carboxy-phenylalanine, beta-glutamic acid, or homoglutamic acid
<220> FEATURE:
<221> NAME/KEY: MISC_FEATURE
<222> LOCATION: (15)..(15)
<223> OTHER INFORMATION: Xaa at position 15 is Glu, Asp, Lys,
      Homolysine, Ornithine, 4-carboxy-phenylalanine, beta-glutamic
      acid, beta-Homoglutamic acid, or homoglutamic acid
<220> FEATURE:
<221> NAME/KEY: MISC_FEATURE
<222> LOCATION: (16)..(16)
<223> OTHER INFORMATION: Xaa at position 16 is Gly, Ala, Ser, Thr, Leu,
      Ile, Val, Glu, Asp, Lys, Homolysine, Ornithine, 4-carboxy-
      phenylalanine, beta-glutamic acid, beta-Homoglutamic acid, or
      homoglutamic acid
<220> FEATURE:
<221> NAME/KEY: MISC_FEATURE
<222> LOCATION: (18)..(18)
<223> OTHER INFORMATION: Xaa at position 18 is Ala, Gly, Ser, Thr, Leu,
```

-continued

Ile, Val, Glu, Asp, Lys, Homolysine, Ornithine, 4-carboxy-
phenylalanine, beta-glutamic acid, beta-Homoglutamic acid, or
homoglutamic acid
<220> FEATURE:
<221> NAME/KEY: MISC_FEATURE
<222> LOCATION: (19)..(19)
<223> OTHER INFORMATION: Xaa at position 19 is Lys, Homolysine, Arg,
Gln, Glu, Asp, His, Ornithine, 4-carboxy-phenylalanine, beta-
glutamic acid, or homoglutamic acid
<220> FEATURE:
<221> NAME/KEY: MISC_FEATURE
<222> LOCATION: (20)..(20)
<223> OTHER INFORMATION: Xaa at position 20 is Leu, Glu, Asp, Lys,
Homolysine, Ornithine, 4-carboxy-phenylalanine, beta-glutamic
acid, beta-Homoglutamic acid, or homoglutamic acid
<220> FEATURE:
<221> NAME/KEY: MISC_FEATURE
<222> LOCATION: (21)..(21)
<223> OTHER INFORMATION: Xaa at position 21 is Phe, Trp, Asp, Glu, Lys,
Homolysine, Ornithine, 4-carboxy-phenylalanine, beta-glutamic
acid, beta-Homoglutamic acid, or homoglutamic acid
<220> FEATURE:
<221> NAME/KEY: MISC_FEATURE
<222> LOCATION: (22)..(22)
<223> OTHER INFORMATION: Xaa at position 22 is Ile, Leu, Val, Ala, Phe,
Asp, Glu, Lys, Homolysine, Ornithine, 4-carboxy-phenylalanine,
beta-glutamic acid, beta-Homoglutamic acid, or homoglutamic acid
<220> FEATURE:
<221> NAME/KEY: MISC_FEATURE
<222> LOCATION: (23)..(23)
<223> OTHER INFORMATION: Xaa at position 23 is Ala, Gly, Ser, Thr, Leu,
Ile, Val, Glu, Asp, Lys, Homolysine, Ornithine, 4-carboxy-
phenylalanine, beta-glutamic acid, beta-Homoglutamic acid, or
homoglutamic acid
<220> FEATURE:
<221> NAME/KEY: MISC_FEATURE
<222> LOCATION: (24)..(24)
<223> OTHER INFORMATION: Xaa at position 24 is Trp, Phe, Tyr, Glu, Asp,
or Lys
<220> FEATURE:
<221> NAME/KEY: MISC_FEATURE
<222> LOCATION: (25)..(25)
<223> OTHER INFORMATION: Xaa at position 25 is Leu, Gly, Ala, Ser, Thr,
Ile, Val, Glu, Asp, or Lys
<220> FEATURE:
<221> NAME/KEY: MISC_FEATURE
<222> LOCATION: (26)..(26)
<223> OTHER INFORMATION: Xaa is: Val or Lys
<220> FEATURE:
<221> NAME/KEY: MISC_FEATURE
<222> LOCATION: (27)..(27)
<223> OTHER INFORMATION: Xaa is: Lys or Asn
<220> FEATURE:
<221> NAME/KEY: MISC_FEATURE
<222> LOCATION: (28)..(28)
<223> OTHER INFORMATION: Xaa is: Phe, Trp, Asp, Glu, Lys, Homolysine,
Ornithine, 4-carboxy-phenylalanine, beta-glutamic acid, beta-
Homoglutamic acid, or homoglutamic acid;
<220> FEATURE:
<221> NAME/KEY: MISC_FEATURE
<222> LOCATION: (30)..(30)
<223> OTHER INFORMATION: Xaa is: Gly or Pro
<220> FEATURE:
<221> NAME/KEY: MISC_FEATURE
<222> LOCATION: (31)..(31)
<223> OTHER INFORMATION: Xaa at position 31 is Trp, Phe, Tyr, Glu, Asp,
or Lys
<220> FEATURE:
<221> NAME/KEY: MISC_FEATURE
<222> LOCATION: (39)..(39)
<223> OTHER INFORMATION: Residue 39 is attached to an carboxy group
which is attached to an R1 group, wherein, R1 is OR2 or NR2R3;
R2 and R3 are independently hydrogen or (C1-C8)alkyl

<400> SEQUENCE: 5

Xaa Gly Xaa Xaa Xaa Xaa Xaa Xaa Xaa Xaa Xaa Xaa Xaa Xaa Xaa Xaa
1               5                   10                  15

Cys Xaa Xaa Xaa Xaa Xaa Xaa Xaa Xaa Xaa Xaa Xaa Gly Xaa Xaa Ser

Ser Gly Ala Pro Pro Pro Ser
        35

<210> SEQ ID NO 6
<211> LENGTH: 31
<212> TYPE: PRT
<213> ORGANISM: Artificial
<220> FEATURE:
<223> OTHER INFORMATION: Synthetic

<400> SEQUENCE: 6

His Gly Glu Gly Thr Phe Thr Ser Asp Val Ser Ser Tyr Leu Glu Gly
1               5                   10                  15

Cys Ala Ala Lys Glu Phe Ile Ala Trp Leu Val Lys Gly Arg Gly
            20                  25                  30

<210> SEQ ID NO 7
<211> LENGTH: 39
<212> TYPE: PRT
<213> ORGANISM: Artificial
<220> FEATURE:
<223> OTHER INFORMATION: Synthetic

<400> SEQUENCE: 7

His Gly Glu Gly Thr Phe Thr Ser Asp Val Ser Ser Tyr Leu Glu Gly
1               5                   10                  15

Cys Ala Ala Lys Glu Phe Ile Ala Trp Leu Val Lys Gly Arg Gly Ser
            20                  25                  30

Ser Gly Ala Pro Pro Pro Ser
        35

<210> SEQ ID NO 8
<211> LENGTH: 39
<212> TYPE: PRT
<213> ORGANISM: Artificial
<220> FEATURE:
<223> OTHER INFORMATION: Synthetic

<400> SEQUENCE: 8

His Gly Glu Gly Thr Phe Thr Ser Asp Val Ser Ser Tyr Leu Glu Gly
1               5                   10                  15

Cys Ala Ala Lys Glu Phe Ile Ala Trp Leu Lys Asn Gly Gly Pro Ser
            20                  25                  30

Ser Gly Ala Pro Pro Pro Ser
        35

<210> SEQ ID NO 9
<211> LENGTH: 35
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa at position 1 is: L-histidine, D-histidine,
    desamino-histidine, 2-amino-histidine, 3-hydroxy-histidine,
    homohistidine, a-fluoromethyl-histidine or a-methyl-histidine
<220> FEATURE:
<221> NAME/KEY: MISC_FEATURE
<222> LOCATION: (2)..(2)
<223> OTHER INFORMATION: Xaa at position 2 is Gly, bAla
    (2-aminopropionic acid), 1-amino-cylcopentanecarboxylic acid, Aib
    (2-aminoisobutryic acid) or an alpha-alpha-disubstituted amino
    acid
<220> FEATURE:

```
<221> NAME/KEY: MISC_FEATURE
<222> LOCATION: (3)..(3)
<223> OTHER INFORMATION: Xaa at position 3 is Glu, Asp, or Lys
<220> FEATURE:
<221> NAME/KEY: MISC_FEATURE
<222> LOCATION: (4)..(4)
<223> OTHER INFORMATION: Xaa at position 4 is Gly or His
<220> FEATURE:
<221> NAME/KEY: MISC_FEATURE
<222> LOCATION: (5)..(5)
<223> OTHER INFORMATION: Xaa at position 5 is Thr, Ala, Gly, Ser, Leu,
      Ile, Val, Glu, Asp, or Lys
<220> FEATURE:
<221> NAME/KEY: MISC_FEATURE
<222> LOCATION: (6)..(6)
<223> OTHER INFORMATION: Xaa at position 6 is: His, Trp, Phe, or Tyr
<220> FEATURE:
<221> NAME/KEY: MISC_FEATURE
<222> LOCATION: (7)..(7)
<223> OTHER INFORMATION: Xaa at position 7 is Thr or Gly
<220> FEATURE:
<221> NAME/KEY: MISC_FEATURE
<222> LOCATION: (8)..(8)
<223> OTHER INFORMATION: Xaa at position 8 is Ser, Ala, Gly, Thr, Leu,
      Ile, Val, Glu, Asp, or Lys
<220> FEATURE:
<221> NAME/KEY: MISC_FEATURE
<222> LOCATION: (9)..(9)
<223> OTHER INFORMATION: Xaa at position 9 is Asp or Glu
<220> FEATURE:
<221> NAME/KEY: MISC_FEATURE
<222> LOCATION: (10)..(10)
<223> OTHER INFORMATION: Xaa at position 10 is Val, Ala, Gly, Ser, Thr,
      Leu, Ile, Tyr, Glu, Asp, Trp, or Lys
<220> FEATURE:
<221> NAME/KEY: MISC_FEATURE
<222> LOCATION: (11)..(11)
<223> OTHER INFORMATION: Xaa at position 11 is Ser, Ala, Gly, Thr, Leu,
      Ile, Val, Glu, Asp, or Lys
<220> FEATURE:
<221> NAME/KEY: MISC_FEATURE
<222> LOCATION: (12)..(12)
<223> OTHER INFORMATION: Xaa at position 12 is Ser, Ala, Gly, Thr, Leu,
      Ile, Val, Glu, Asp, Trp, Tyr, Lys,  Homolysine, Ornithine,
      4-carboxy-phenylalanine, beta-glutamic acid, beta-Homoglutamic
      acid, or homoglutamic acid
<220> FEATURE:
<221> NAME/KEY: MISC_FEATURE
<222> LOCATION: (13)..(13)
<223> OTHER INFORMATION: Xaa at position 13 is Tyr, Phe, Trp, Glu, Asp,
      Gln, Lys, Homolysine, Ornithine, 4-carboxy-phenylalanine, beta-
      glutamic acid, beta-Homoglutamic acid, or homoglutamic acid
<220> FEATURE:
<221> NAME/KEY: MISC_FEATURE
<222> LOCATION: (14)..(14)
<223> OTHER INFORMATION: Xaa at position 14 is Leu, Ala, Gly, Ser, Thr,
      Ile, Val, Glu, Asp, Met, Trp, Tyr, Lys, Homolysine, Ornithine,
      4-carboxy-phenylalanine, beta-glutamic acid, or homoglutamic acid
<220> FEATURE:
<221> NAME/KEY: MISC_FEATURE
<222> LOCATION: (15)..(15)
<223> OTHER INFORMATION: Xaa at position 15 is Glu, Asp, Lys,
      Homolysine, Ornithine, 4-carboxy-phenylalanine, beta-glutamic
      acid, beta-Homoglutamic acid, or homoglutamic acid
<220> FEATURE:
<221> NAME/KEY: MISC_FEATURE
<222> LOCATION: (16)..(16)
<223> OTHER INFORMATION: Xaa at position 16 is Gly, Ala, Ser, Thr, Leu,
      Ile, Val, Glu, Asp, Lys, Homolysine, Ornithine, 4-carboxy-
      phenylalanine, beta-glutamic acid, beta-Homoglutamic acid, or
      homoglutamic acid
<220> FEATURE:
<221> NAME/KEY: MISC_FEATURE
<222> LOCATION: (17)..(17)
<223> OTHER INFORMATION: Xaa at position 17 is Gln, Asn, Arg, Glu, Asp,
      Lys, Ornithine, 4-carboxy-phenylalanine, beta-glutamic acid,
      beta-Homoglutamic acid, or homoglutamic acid
<220> FEATURE:
<221> NAME/KEY: MISC_FEATURE
<222> LOCATION: (18)..(18)
```

```
<223> OTHER INFORMATION: Xaa at position 18 is Ala, Gly, Ser, Thr, Leu,
      Ile, Val, Arg, Glu, Asp, Lys, Homolysine, Ornithine, 4-carboxy-
      phenylalanine, beta-glutamic acid, beta-Homoglutamic acid, or
      homoglutamic acid
<220> FEATURE:
<221> NAME/KEY: MISC_FEATURE
<222> LOCATION: (19)..(19)
<223> OTHER INFORMATION: Xaa at position 19 is Ala, Gly, Ser, Thr, Leu,
      Ile, Val, Glu, Asp, Lys, Homolysine, Ornithine, 4-carboxy-
      phenylalanine, beta-glutamic acid, beta-Homoglutamic acid, or
      homoglutamic acid
<220> FEATURE:
<221> NAME/KEY: MISC_FEATURE
<222> LOCATION: (20)..(20)
<223> OTHER INFORMATION: Xaa at position 20 is Lys, Homolysine, Arg,
      Gln, Glu, Asp, His, Ornithine, 4-carboxy-phenylalanine, beta-
      glutamic acid, or homoglutamic acid
<220> FEATURE:
<221> NAME/KEY: MISC_FEATURE
<222> LOCATION: (21)..(21)
<223> OTHER INFORMATION: Xaa at position 21 is Leu, Glu, Asp, Lys,
      Homolysine, Ornithine, 4-carboxy-phenylalanine, beta-glutamic
      acid, beta-Homoglutamic acid, or homoglutamic acid
<220> FEATURE:
<221> NAME/KEY: MISC_FEATURE
<222> LOCATION: (22)..(22)
<223> OTHER INFORMATION: Xaa at position 22 is Phe, Trp, Asp, Glu, Lys,
      Homolysine, Ornithine, 4-carboxy-phenylalanine, beta-glutamic
      acid, beta-Homoglutamic acid, or homoglutamic acid
<220> FEATURE:
<221> NAME/KEY: MISC_FEATURE
<222> LOCATION: (23)..(23)
<223> OTHER INFORMATION: Xaa at position 23 is Ile, Leu, Val, Ala, Phe,
      Asp, Glu, Lys, Homolysine, Ornithine, 4-carboxy-phenylalanine,
      beta-glutamic acid, beta-Homoglutamic acid, or homoglutamic acid
<220> FEATURE:
<221> NAME/KEY: MISC_FEATURE
<222> LOCATION: (24)..(24)
<223> OTHER INFORMATION: Xaa at position 24 is Ala, Gly, Ser, Thr, Leu,
      Ile, Val, Glu, Asp, Lys, Homolysine, Ornithine, 4-carboxy-
      phenylalanine, beta-glutamic acid, beta-Homoglutamic acid, or
      homoglutamic acid
<220> FEATURE:
<221> NAME/KEY: MISC_FEATURE
<222> LOCATION: (25)..(25)
<223> OTHER INFORMATION: Xaa at position 25 is Trp, Phe, Tyr, Glu, Asp,
      or Lys
<220> FEATURE:
<221> NAME/KEY: MISC_FEATURE
<222> LOCATION: (26)..(26)
<223> OTHER INFORMATION: Xaa at position 26 is Leu, Gly, Ala, Ser, Thr,
      Ile, Val, Glu, Asp, or Lys
<220> FEATURE:
<221> NAME/KEY: MISC_FEATURE
<222> LOCATION: (27)..(27)
<223> OTHER INFORMATION: Xaa at position 27 is Val, Gly, Ala, Ser, Thr,
      Leu, Ile, Glu, Asp, or Lys
<220> FEATURE:
<221> NAME/KEY: MISC_FEATURE
<222> LOCATION: (28)..(28)
<223> OTHER INFORMATION: Xaa at position 28 is Asn, Lys, Arg, Glu, Asp,
      or His
<220> FEATURE:
<221> NAME/KEY: MISC_FEATURE
<222> LOCATION: (29)..(29)
<223> OTHER INFORMATION: Xaa at position 29 is Gly, Ala, Ser, Thr, Leu,
      Ile, Val, Glu, Asp, or Lys
<220> FEATURE:
<221> NAME/KEY: MISC_FEATURE
<222> LOCATION: (30)..(30)
<223> OTHER INFORMATION: Xaa at position 30 is Gly, Arg, Lys, Glu, Asp,
      or His
<220> FEATURE:
<221> NAME/KEY: MISC_FEATURE
<222> LOCATION: (31)..(31)
<223> OTHER INFORMATION: Xaa at position 31 is Pro, Gly, Ala, Ser, Thr,
      Leu, Ile, Val, Glu, Asp, or Lys
<220> FEATURE:
<221> NAME/KEY: MISC_FEATURE
<222> LOCATION: (35)..(35)
```

<223> OTHER INFORMATION: Residue 35 is attached to an carboxy group
      which is attached to an R1 group, wherein, R1 is OR2 or NR2R3; R2
      and R3 are independently hydrogen or (C1-C8)alkyl

<400> SEQUENCE: 9

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Cys
                20                  25                  30

Ser Gly Gly
        35

<210> SEQ ID NO 10
<211> LENGTH: 34
<212> TYPE: PRT
<213> ORGANISM: Artificial
<220> FEATURE:
<223> OTHER INFORMATION: Synthetic

<400> SEQUENCE: 10

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Cys
                20                  25                  30

Ser Gly

<210> SEQ ID NO 11
<211> LENGTH: 35
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib

<400> SEQUENCE: 11

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Cys
                20                  25                  30

Ser Gly Gly
        35

<210> SEQ ID NO 12
<211> LENGTH: 35
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is bAla

<400> SEQUENCE: 12

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Cys
                20                  25                  30

Ser Gly Gly
        35

```
<210> SEQ ID NO 13
<211> LENGTH: 35
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa at position 1 is: L-histidine, D-histidine,
      desamino-histidine, 2-amino-histidine, 3-hydroxy-histidine,
      homohistidine, a-fluoromethyl-histidine or a-methyl-histidine
<220> FEATURE:
<221> NAME/KEY: MISC_FEATURE
<222> LOCATION: (2)..(2)
<223> OTHER INFORMATION: Xaa at position 2 is Gly, bAla
      (2-aminopropionic acid), 1-amino-cylcopentanecarboxylic acid, Aib
      (2-aminoisobutryic acid) or an alpha-alpha-disubstituted amino
      acid
<220> FEATURE:
<221> NAME/KEY: MISC_FEATURE
<222> LOCATION: (3)..(3)
<223> OTHER INFORMATION: Xaa at position 3 is Glu, Asp, or Lys
<220> FEATURE:
<221> NAME/KEY: MISC_FEATURE
<222> LOCATION: (4)..(4)
<223> OTHER INFORMATION: Xaa at position 4 is Gly or His
<220> FEATURE:
<221> NAME/KEY: MISC_FEATURE
<222> LOCATION: (5)..(5)
<223> OTHER INFORMATION: Xaa at position 5 is Thr, Ala, Gly, Ser, Leu,
      Ile, Val, Glu, Asp, or Lys
<220> FEATURE:
<221> NAME/KEY: MISC_FEATURE
<222> LOCATION: (6)..(6)
<223> OTHER INFORMATION: Xaa at position 6 is His, Trp, Phe, or Tyr
<220> FEATURE:
<221> NAME/KEY: MISC_FEATURE
<222> LOCATION: (7)..(7)
<223> OTHER INFORMATION: Xaa at position 7 is Thr or Gly
<220> FEATURE:
<221> NAME/KEY: MISC_FEATURE
<222> LOCATION: (8)..(8)
<223> OTHER INFORMATION: Xaa at position 8 is Ser, Ala, Gly, Thr, Leu,
      Ile, Val, Glu, Asp, or Lys
<220> FEATURE:
<221> NAME/KEY: MISC_FEATURE
<222> LOCATION: (9)..(9)
<223> OTHER INFORMATION: Xaa at position 9 is Asp or Glu
<220> FEATURE:
<221> NAME/KEY: MISC_FEATURE
<222> LOCATION: (10)..(10)
<223> OTHER INFORMATION: Xaa at position 10 is Val, Ala, Gly, Ser, Thr,
      Leu, Ile, Tyr, Glu, Asp, Trp, or Lys
<220> FEATURE:
<221> NAME/KEY: MISC_FEATURE
<222> LOCATION: (11)..(11)
<223> OTHER INFORMATION: Xaa at position 11 is Ser, Ala, Gly, Thr, Leu,
      Ile, Val, Glu, Asp, or Lys
<220> FEATURE:
<221> NAME/KEY: MISC_FEATURE
<222> LOCATION: (12)..(12)
<223> OTHER INFORMATION: Xaa at position 12 is Ser, Ala, Gly, Thr, Leu,
      Ile, Val, Glu, Asp, Trp, Tyr, Lys, Homolysine, Ornithine,
      4-carboxy-phenylalanine, beta-glutamic acid, beta-Homoglutamic
      acid, or homoglutamic acid
<220> FEATURE:
<221> NAME/KEY: MISC_FEATURE
<222> LOCATION: (13)..(13)
<223> OTHER INFORMATION: Xaa at position 13 is Tyr, Phe, Trp, Glu, Asp,
      Gln, Lys, Homolysine, Ornithine, 4-carboxy-phenylalanine,
      beta-glutamic acid, beta-Homoglutamic acid, or homoglutamic acid
<220> FEATURE:
<221> NAME/KEY: MISC_FEATURE
<222> LOCATION: (14)..(14)
<223> OTHER INFORMATION: Xaa at position 14 is Leu, Ala, Gly, Ser, Thr,
      Ile, Val, Glu, Asp, Met, Trp, Tyr, Lys, Homolysine, Ornithine,
      4-carboxy-phenylalanine, beta-glutamic acid, or homoglutamic acid
<220> FEATURE:
<221> NAME/KEY: MISC_FEATURE
```

```
<222> LOCATION: (15)..(15)
<223> OTHER INFORMATION: Xaa at position 15 is Glu, Asp, Lys,
      Homolysine, Ornithine, 4-carboxy-phenylalanine, beta-glutamic
      acid, beta-Homoglutamic acid, or homoglutamic acid
<220> FEATURE:
<221> NAME/KEY: MISC_FEATURE
<222> LOCATION: (16)..(16)
<223> OTHER INFORMATION: Xaa at position 16 is Aib (2-aminoisobutyric
      acid), 1-amino-cylcopentanecarboxylic acid, an alpha-alpha-
      disubstituted amino acid, or Aad (2-aminoadipic acid)
<220> FEATURE:
<221> NAME/KEY: MISC_FEATURE
<222> LOCATION: (17)..(17)
<223> OTHER INFORMATION: Xaa at position 17 is Gln, Asn, Arg, Glu, Asp,
      Lys, Ornithine, 4-carboxy-phenylalanine, beta-glutamic acid,
      beta-Homoglutamic acid, or homoglutamic acid
<220> FEATURE:
<221> NAME/KEY: MISC_FEATURE
<222> LOCATION: (18)..(18)
<223> OTHER INFORMATION: Xaa at position 18 is Ala, Gly, Ser, Thr, Leu,
      Ile, Val, Arg, Glu, Asp, Lys, Homolysine, Ornithine, 4-carboxy-
      phenylalanine, beta-glutamic acid, beta-Homoglutamic acid, or
      homoglutamic acid
<220> FEATURE:
<221> NAME/KEY: MISC_FEATURE
<222> LOCATION: (19)..(19)
<223> OTHER INFORMATION: Xaa at position 19 is Ala, Gly, Ser, Thr, Leu,
      Ile, Val, Glu, Asp, Lys, Homolysine, Ornithine, 4-carboxy-
      phenylalanine, beta-glutamic acid, beta-Homoglutamic acid, or
      homoglutamic acid
<220> FEATURE:
<221> NAME/KEY: MISC_FEATURE
<222> LOCATION: (20)..(20)
<223> OTHER INFORMATION: Xaa at position 20 is Lys, Homolysine, Arg,
      Gln, Glu, Asp, His, Ornithine, 4-carboxy-phenylalanine, beta-
      glutamic acid, or homoglutamic acid
<220> FEATURE:
<221> NAME/KEY: MISC_FEATURE
<222> LOCATION: (21)..(21)
<223> OTHER INFORMATION: Xaa at position 21 is Leu, Glu, Asp, Lys,
      Homolysine, Ornithine, 4-carboxy-phenylalanine, beta-glutamic
      acid, beta-Homoglutamic acid, or homoglutamic acid
<220> FEATURE:
<221> NAME/KEY: MISC_FEATURE
<222> LOCATION: (22)..(22)
<223> OTHER INFORMATION: Xaa at position 22 is Phe, Trp, Asp, Glu, Lys,
      Homolysine, Ornithine, 4-carboxy-phenylalanine, beta-glutamic
      acid, beta-Homoglutamic acid, or homoglutamic acid
<220> FEATURE:
<221> NAME/KEY: MISC_FEATURE
<222> LOCATION: (23)..(23)
<223> OTHER INFORMATION: Xaa at position 23 is Ile, Leu, Val, Ala, Phe,
      Asp, Glu, Lys, Homolysine, Ornithine, 4-carboxy-phenylalanine,
      beta-glutamic acid, beta-Homoglutamic acid, or homoglutamic acid
<220> FEATURE:
<221> NAME/KEY: MISC_FEATURE
<222> LOCATION: (24)..(24)
<223> OTHER INFORMATION: Xaa at position 24 is Ala, Gly, Ser, Thr, Leu,
      Ile, Val, Glu, Asp, Lys, Homolysine, Ornithine, 4-carboxy-
      phenylalanine, beta-glutamic acid, beta-Homoglutamic acid, or
      homoglutamic acid
<220> FEATURE:
<221> NAME/KEY: MISC_FEATURE
<222> LOCATION: (25)..(25)
<223> OTHER INFORMATION: Xaa at position 25 is Trp, Phe, Tyr, Glu, Asp,
      or Lys
<220> FEATURE:
<221> NAME/KEY: MISC_FEATURE
<222> LOCATION: (26)..(26)
<223> OTHER INFORMATION: Xaa at position 26 is Leu, Gly, Ala, Ser, Thr,
      Ile, Val, Glu, Asp, or Lys
<220> FEATURE:
<221> NAME/KEY: MISC_FEATURE
<222> LOCATION: (27)..(27)
<223> OTHER INFORMATION: Xaa at position 27 is Val, Gly, Ala, Ser, Thr,
      Leu, Ile, Glu, Asp, or Lys
<220> FEATURE:
<221> NAME/KEY: MISC_FEATURE
<222> LOCATION: (28)..(28)
<223> OTHER INFORMATION: Xaa at position 28 is Asn, Lys, Arg, Glu, Asp,
```

```
        or His
<220> FEATURE:
<221> NAME/KEY: MISC_FEATURE
<222> LOCATION: (29)..(29)
<223> OTHER INFORMATION: Xaa at position 29 is Gly, Ala, Ser, Thr, Leu,
      Ile, Val, Glu, Asp, or Lys
<220> FEATURE:
<221> NAME/KEY: MISC_FEATURE
<222> LOCATION: (30)..(30)
<223> OTHER INFORMATION: Xaa at position 30 is Gly, Arg, Lys, Glu, Asp,
      or His
<220> FEATURE:
<221> NAME/KEY: MISC_FEATURE
<222> LOCATION: (32)..(32)
<223> OTHER INFORMATION: Xaa at position 32 is Cys, Gly, or is omitted
<220> FEATURE:
<221> NAME/KEY: MISC_FEATURE
<222> LOCATION: (33)..(33)
<223> OTHER INFORMATION: Xaa at position 33 is Ala, Gly, Ser, Cys, or
      is omitted
<220> FEATURE:
<221> NAME/KEY: MISC_FEATURE
<222> LOCATION: (34)..(34)
<223> OTHER INFORMATION: Xaa at position 34 is Gly or is omitted
<220> FEATURE:
<221> NAME/KEY: MISC_FEATURE
<222> LOCATION: (35)..(35)
<223> OTHER INFORMATION: Xaa at position 35 is Gly or is omitted
<220> FEATURE:
<221> NAME/KEY: MISC_FEATURE
<222> LOCATION: (35)..(35)
<223> OTHER INFORMATION: Residue 35 is attached to an carboxy group
      which is attached to an R1 group, wherein, R1 is OR2 or NR2R3;
      R2 and R3 are independently hydrogen or (C1-C8)alkyl

<400> SEQUENCE: 13

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Gly Xaa
            20                  25                  30

Xaa Xaa Xaa
        35

<210> SEQ ID NO 14
<211> LENGTH: 30
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aib
<220> FEATURE:
<221> NAME/KEY: MISC_FEATURE
<222> LOCATION: (30)..(30)
<223> OTHER INFORMATION: residue 30 is amidated

<400> SEQUENCE: 14

His Ala Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg
            20                  25                  30

<210> SEQ ID NO 15
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
```

```
<223> OTHER INFORMATION: X is Aib
<220> FEATURE:
<221> NAME/KEY: MISC_FEATURE
<222> LOCATION: (31)..(31)
<223> OTHER INFORMATION: residue 31 amidated

<400> SEQUENCE: 15

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly
            20                  25                  30

<210> SEQ ID NO 16
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aib

<400> SEQUENCE: 16

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

<210> SEQ ID NO 17
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aib
<220> FEATURE:
<221> NAME/KEY: MISC_FEATURE
<222> LOCATION: (32)..(32)
<223> OTHER INFORMATION: residue 32 is amidated

<400> SEQUENCE: 17

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

<210> SEQ ID NO 18
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aib
<220> FEATURE:
<221> NAME/KEY: MISC_FEATURE
<222> LOCATION: (33)..(33)
<223> OTHER INFORMATION: residue 33 is amidated

<400> SEQUENCE: 18

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
```

```
                    20                  25                  30
Ala

<210> SEQ ID NO 19
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aib

<400> SEQUENCE: 19

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

Gly

<210> SEQ ID NO 20
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aib
<220> FEATURE:
<221> NAME/KEY: MISC_FEATURE
<222> LOCATION: (33)..(33)
<223> OTHER INFORMATION: residue 33 is amidated

<400> SEQUENCE: 20

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

Gly

<210> SEQ ID NO 21
<211> LENGTH: 34
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aib

<400> SEQUENCE: 21

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

Ser Gly

<210> SEQ ID NO 22
<211> LENGTH: 34
<212> TYPE: PRT
<213> ORGANISM: Artificial
<220> FEATURE:
```

```
<223> OTHER INFORMATION: Synthetic
<220> FEATURE:
<221> NAME/KEY: MISC_FEATURE
<222> LOCATION: (16)..(16)
<223> OTHER INFORMATION: X is Aib
<220> FEATURE:
<221> NAME/KEY: MISC_FEATURE
<222> LOCATION: (34)..(34)
<223> OTHER INFORMATION: Residue 34 is amidated

<400> SEQUENCE: 22

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

Ser Gly

<210> SEQ ID NO 23
<211> LENGTH: 35
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aib

<400> SEQUENCE: 23

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

Ser Gly Gly
        35

<210> SEQ ID NO 24
<211> LENGTH: 35
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aib
<220> FEATURE:
<221> NAME/KEY: MISC_FEATURE
<222> LOCATION: (35)..(35)
<223> OTHER INFORMATION: residue 35 is amidated

<400> SEQUENCE: 24

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

Ser Gly Gly
        35

<210> SEQ ID NO 25
<211> LENGTH: 34
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
```

```
<223> OTHER INFORMATION: X is Aib
<220> FEATURE:
<221> NAME/KEY: MISC_FEATURE
<222> LOCATION: (16)..(16)
<223> OTHER INFORMATION: X is Aib

<400> SEQUENCE: 25

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

Ser Gly

<210> SEQ ID NO 26
<211> LENGTH: 35
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib
<220> FEATURE:
<221> NAME/KEY: MISC_FEATURE
<222> LOCATION: (16)..(16)
<223> OTHER INFORMATION: X is Aib

<400> SEQUENCE: 26

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

Ser Gly Gly
        35

<210> SEQ ID NO 27
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Aib
<220> FEATURE:
<221> NAME/KEY: MISC_FEATURE
<222> LOCATION: (16)..(16)
<223> OTHER INFORMATION: X is Aib

<400> SEQUENCE: 27

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Gly
            20                  25                  30

Cys

<210> SEQ ID NO 28
<211> LENGTH: 34
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aad
```

<400> SEQUENCE: 28

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

Ser Gly

<210> SEQ ID NO 29
<211> LENGTH: 35
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa at position 1 is: L-histidine, D-histidine,
      desamino-histidine, 2-amino-histidine, 3-hydroxy-histidine,
      homohistidine, a-fluoromethyl-histidine or a-methyl-histidine
<220> FEATURE:
<221> NAME/KEY: MISC_FEATURE
<222> LOCATION: (2)..(2)
<223> OTHER INFORMATION: Xaa at position 2 is Gly, bAla
      (2-aminopropionic acid), 1-amino-cylcopentanecarboxylic acid,
      2-aminoisobutryic acid or an alpha-alpha-disubstituted amino acid
<220> FEATURE:
<221> NAME/KEY: MISC_FEATURE
<222> LOCATION: (3)..(3)
<223> OTHER INFORMATION: Xaa at position 3 is Glu, Asp, or Lys
<220> FEATURE:
<221> NAME/KEY: MISC_FEATURE
<222> LOCATION: (4)..(4)
<223> OTHER INFORMATION: Xaa at position 4 is Gly or His
<220> FEATURE:
<221> NAME/KEY: MISC_FEATURE
<222> LOCATION: (5)..(5)
<223> OTHER INFORMATION: Xaa at position 5 is Thr, Ala, Gly, Ser, Leu,
      Ile, Val, Glu, Asp, or Lys
<220> FEATURE:
<221> NAME/KEY: MISC_FEATURE
<222> LOCATION: (6)..(6)
<223> OTHER INFORMATION: Xaa at position 6 is: His, Trp, Phe, or Tyr
<220> FEATURE:
<221> NAME/KEY: MISC_FEATURE
<222> LOCATION: (7)..(7)
<223> OTHER INFORMATION: Xaa at position 7 is Thr or Gly
<220> FEATURE:
<221> NAME/KEY: MISC_FEATURE
<222> LOCATION: (8)..(8)
<223> OTHER INFORMATION: Xaa at position 8 is Ser, Ala, Gly, Thr, Leu,
      Ile, Val, Glu, Asp, or Lys
<220> FEATURE:
<221> NAME/KEY: MISC_FEATURE
<222> LOCATION: (9)..(9)
<223> OTHER INFORMATION: Xaa at position 9 is Asp or Glu
<220> FEATURE:
<221> NAME/KEY: MISC_FEATURE
<222> LOCATION: (10)..(10)
<223> OTHER INFORMATION: Xaa at position 10 is Val, Ala, Gly, Ser, Thr,
      Leu, Ile, Tyr, Glu, Asp, Trp, or Lys
<220> FEATURE:
<221> NAME/KEY: MISC_FEATURE
<222> LOCATION: (11)..(11)
<223> OTHER INFORMATION: Xaa at position 11 is Ser, Ala, Gly, Thr, Leu,
      Ile, Val, Glu, Asp, or Lys
<220> FEATURE:
<221> NAME/KEY: MISC_FEATURE
<222> LOCATION: (12)..(12)
<223> OTHER INFORMATION: Xaa at position 12 is Ser, Ala, Gly, Thr, Leu,
      Ile, Val, Glu, Asp, Trp, Tyr, Lys, Homolysine, Ornithine,
      4-carboxy-phenylalanine, beta-glutamic acid, beta-Homoglutamic
      acid, or homoglutamic acid
<220> FEATURE:
<221> NAME/KEY: MISC_FEATURE
<222> LOCATION: (13)..(13)

```
<223> OTHER INFORMATION: Xaa at position 13 is Tyr, Phe, Trp, Glu, Asp,
      Gln, Lys, Homolysine, Ornithine, 4-carboxy-phenylalanine, beta-
      glutamic acid, beta-Homoglutamic acid, or homoglutamic acid
<220> FEATURE:
<221> NAME/KEY: MISC_FEATURE
<222> LOCATION: (14)..(14)
<223> OTHER INFORMATION: Xaa at position 14 is Leu, Ala, Gly, Ser, Thr,
      Ile, Val, Glu, Asp, Met, Trp, Tyr, Lys, Homolysine, Ornithine,
      4-carboxy-phenylalanine, beta-glutamic acid, or homoglutamic acid
<220> FEATURE:
<221> NAME/KEY: MISC_FEATURE
<222> LOCATION: (15)..(15)
<223> OTHER INFORMATION: Xaa at position 15 is Glu, Asp, Lys,
      Homolysine, Ornithine, 4-carboxy-phenylalanine, beta-glutamic
      acid, beta-Homoglutamic acid, or homoglutamic acid
<220> FEATURE:
<221> NAME/KEY: MISC_FEATURE
<222> LOCATION: (16)..(16)
<223> OTHER INFORMATION: Xaa at position 16 is Gly, Ala, Ser, Thr, Leu,
      Ile, Val, Glu, Asp, Lys, Homolysine, Ornithine, 4-carboxy-
      phenylalanine, beta-glutamic acid, beta-Homoglutamic acid, or
      homoglutamic acid
<220> FEATURE:
<221> NAME/KEY: MISC_FEATURE
<222> LOCATION: (17)..(17)
<223> OTHER INFORMATION: Xaa at position 17 is Gln, Asn, Arg, Glu, Asp,
      Lys, Ornithine, 4-carboxy-phenylalanine, beta-glutamic acid,
      beta-Homoglutamic acid, or homoglutamic acid
<220> FEATURE:
<221> NAME/KEY: MISC_FEATURE
<222> LOCATION: (18)..(18)
<223> OTHER INFORMATION: Xaa at position 18 is Ala, Gly, Ser, Thr, Leu,
      Ile, Val, Arg, Glu, Asp, Lys, Homolysine, Ornithine, 4-carboxy-
      phenylalanine, beta-glutamic acid, beta-Homoglutamic acid, or
      homoglutamic acid
<220> FEATURE:
<221> NAME/KEY: MISC_FEATURE
<222> LOCATION: (19)..(19)
<223> OTHER INFORMATION: Xaa at position 19 is Ala, Gly, Ser, Thr, Leu,
      Ile, Val, Glu, Asp, Lys, Homolysine, Ornithine, 4-carboxy-
      phenylalanine, beta-glutamic acid, beta-Homoglutamic acid, or
      homoglutamic acid
<220> FEATURE:
<221> NAME/KEY: MISC_FEATURE
<222> LOCATION: (20)..(20)
<223> OTHER INFORMATION: Xaa at position 20 is Lys, Homolysine, Arg,
      Gln, Glu, Asp, His, Ornithine, 4-carboxy-phenylalanine, beta-
      glutamic acid, or homoglutamic acid
<220> FEATURE:
<221> NAME/KEY: MISC_FEATURE
<222> LOCATION: (21)..(21)
<223> OTHER INFORMATION: Xaa at position 21 is Leu, Glu, Asp, Lys,
      Homolysine, Ornithine, 4-carboxy-phenylalanine, beta-glutamic
      acid, beta-Homoglutamic acid, or homoglutamic acid
<220> FEATURE:
<221> NAME/KEY: MISC_FEATURE
<222> LOCATION: (22)..(22)
<223> OTHER INFORMATION: Xaa at position 22 is Phe, Trp, Asp, Glu,
      Lys, Homolysine, Ornithine, 4-carboxy-phenylalanine, beta-glutamic
      acid, beta-Homoglutamic acid, or homoglutamic acid
<220> FEATURE:
<221> NAME/KEY: MISC_FEATURE
<222> LOCATION: (23)..(23)
<223> OTHER INFORMATION: Xaa at position 23 is Ile, Leu, Val, Ala, Phe,
      Asp, Glu, Lys, Homolysine, Ornithine, 4-carboxy-phenylalanine,
      beta-glutamic acid, beta-Homoglutamic acid, or homoglutamic acid
<220> FEATURE:
<221> NAME/KEY: MISC_FEATURE
<222> LOCATION: (24)..(24)
<223> OTHER INFORMATION: Xaa at position 24 is Ala, Gly, Ser, Thr, Leu,
      Ile, Val, Glu, Asp, Lys, Homolysine, Ornithine, 4-carboxy-
      phenylalanine, beta-glutamic acid, beta-Homoglutamic acid, or
      homoglutamic acid
<220> FEATURE:
<221> NAME/KEY: MISC_FEATURE
<222> LOCATION: (25)..(25)
<223> OTHER INFORMATION: Xaa at position 25 is Trp, Phe, Tyr, Glu, Asp,
      or Lys
<220> FEATURE:
<221> NAME/KEY: MISC_FEATURE
```

```
<222> LOCATION: (26)..(26)
<223> OTHER INFORMATION: Xaa at position 26 is Leu, Gly, Ala, Ser, Thr,
      Ile, Val, Glu, Asp, or Lys
<220> FEATURE:
<221> NAME/KEY: MISC_FEATURE
<222> LOCATION: (27)..(27)
<223> OTHER INFORMATION: Xaa at position 27 is Val, Gly, Ala, Ser, Thr,
      Leu, Ile, Glu, Asp, or Lys
<220> FEATURE:
<221> NAME/KEY: MISC_FEATURE
<222> LOCATION: (28)..(28)
<223> OTHER INFORMATION: Xaa at position 28 is Asn, Lys, Arg, Glu, Asp,
      or His
<220> FEATURE:
<221> NAME/KEY: MISC_FEATURE
<222> LOCATION: (29)..(29)
<223> OTHER INFORMATION: Xaa at position 29 is Gly, Ala, Ser, Thr, Leu,
      Ile, Val, Glu, Asp, or Lys
<220> FEATURE:
<221> NAME/KEY: MISC_FEATURE
<222> LOCATION: (30)..(30)
<223> OTHER INFORMATION: Xaa at position 30 is Gly, Arg, Lys, Glu, Asp,
      or His
<220> FEATURE:
<221> NAME/KEY: MISC_FEATURE
<222> LOCATION: (31)..(31)
<223> OTHER INFORMATION: Xaa at position 31 is Pro, Gly, Ala, Ser, Thr,
      Leu, Ile, Val, Glu, Asp, or Lys
<220> FEATURE:
<221> NAME/KEY: MISC_FEATURE
<222> LOCATION: (32)..(32)
<223> OTHER INFORMATION: Xaa at position 32 is Gly, Ser, Lys, Cys, or
      is omitted
<220> FEATURE:
<221> NAME/KEY: MISC_FEATURE
<222> LOCATION: (33)..(33)
<223> OTHER INFORMATION: Xaa at position 33 is Gly, Ala, Ser, Thr, Ile,
      Val, Leu, Phe, Pro, Cys or is omitted
<220> FEATURE:
<221> NAME/KEY: MISC_FEATURE
<222> LOCATION: (34)..(34)
<223> OTHER INFORMATION: Xaa at position 34 is Gly, Cys, or is omitted
<220> FEATURE:
<221> NAME/KEY: MISC_FEATURE
<222> LOCATION: (35)..(35)
<223> OTHER INFORMATION: Xaa at position 35 is Gly or is omitted
<220> FEATURE:
<221> NAME/KEY: MISC_FEATURE
<222> LOCATION: (35)..(35)
<223> OTHER INFORMATION: Residue 35 is attached to an carboxy group
      which is attached to an R1 group, wherein, R1 is OR2 or NR2R3;
      R2 and R3 are independently hydrogen or (C1-C8)alkyl

<400> SEQUENCE: 29

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 30
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: Residue 31 is amidated

<400> SEQUENCE: 30

His Gly Glu Gly Thr Phe Thr Ser Asp Val Ser Ser Tyr Leu Glu Glu
1               5                   10                  15
```

```
Gln Ala Ala Lys Glu Phe Ile Ala Trp Leu Val Lys Gly Arg Gly
            20                  25                  30
```

<210> SEQ ID NO 31
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (33)..(33)
<223> OTHER INFORMATION: Residue 33 is amidated

<400> SEQUENCE: 31

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Cys
            20                  25                  30

Ala
```

<210> SEQ ID NO 32
<211> LENGTH: 34
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (34)..(34)
<223> OTHER INFORMATION: Residue 34 is amidated

<400> SEQUENCE: 32

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Cys
            20                  25                  30

Ser Gly
```

<210> SEQ ID NO 33
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys and is amidated

<400> SEQUENCE: 33

```
His Gly Glu Gly Thr Phe Thr Ser Asp Val Ser Glu Tyr Leu Glu Lys
1               5                   10                  15

Gln Ala Ala Lys Glu Phe Ile Ala Trp Leu Val Lys Gly Arg Gly Xaa
            20                  25                  30
```

<210> SEQ ID NO 34
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys and is amidated

```
<400> SEQUENCE: 34

His Gly Glu Gly Thr Phe Thr Ser Asp Val Ser Ser Glu Leu Glu Gly
1               5                   10                  15

Lys Ala Ala Lys Glu Phe Ile Ala Trp Leu Val Lys Gly Arg Gly Xaa
            20                  25                  30

<210> SEQ ID NO 35
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys and is amidated

<400> SEQUENCE: 35

His Gly Glu Gly Thr Phe Thr Ser Asp Val Ser Ser Tyr Glu Glu Gly
1               5                   10                  15

Gln Lys Ala Lys Glu Phe Ile Ala Trp Leu Val Lys Gly Arg Gly Xaa
            20                  25                  30

<210> SEQ ID NO 36
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys and is amidated

<400> SEQUENCE: 36

His Gly Glu Gly Thr Phe Thr Ser Asp Val Ser Ser Tyr Leu Glu Gly
1               5                   10                  15

Gln Ala Lys Lys Glu Phe Ile Ala Trp Leu Val Lys Gly Arg Gly Xaa
            20                  25                  30

<210> SEQ ID NO 37
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys and is amidated

<400> SEQUENCE: 37

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Xaa
            20                  25                  30

<210> SEQ ID NO 38
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys and is amidated
```

-continued

```
<400> SEQUENCE: 38

His Gly Glu Gly Thr Phe Thr Ser Asp Val Ser Ser Tyr Leu Glu Gly
1               5                   10                  15

Glu Ala Ala Lys Lys Phe Ile Ala Trp Leu Val Lys Gly Arg Gly Xaa
            20                  25                  30

<210> SEQ ID NO 39
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys and is amidated

<400> SEQUENCE: 39

His Gly Glu Gly Thr Phe Thr Ser Asp Val Ser Ser Tyr Leu Glu Gly
1               5                   10                  15

Gln Glu Ala Lys Glu Lys Ile Ala Trp Leu Val Lys Gly Arg Gly Xaa
            20                  25                  30

<210> SEQ ID NO 40
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys and is amidated

<400> SEQUENCE: 40

His Gly Glu Gly Thr Phe Thr Ser Asp Val Ser Ser Tyr Leu Glu Gly
1               5                   10                  15

Gln Ala Glu Lys Glu Phe Lys Ala Trp Leu Val Lys Gly Arg Gly Xaa
            20                  25                  30

<210> SEQ ID NO 41
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys and is amidated

<400> SEQUENCE: 41

His Gly Glu Gly Thr Phe Thr Ser Asp Val Ser Ser Tyr Leu Glu Gly
1               5                   10                  15

Gln Ala Ala Glu Glu Phe Ile Lys Trp Leu Val Lys Gly Arg Gly Xaa
            20                  25                  30

<210> SEQ ID NO 42
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys and is amidated
```

```
<400> SEQUENCE: 42

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Xaa
            20                  25                  30

<210> SEQ ID NO 43
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aad
<220> FEATURE:
<221> NAME/KEY: MISC_FEATURE
<222> LOCATION: (31)..(31)
<223> OTHER INFORMATION: residue 31 is amidated

<400> SEQUENCE: 43

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly
            20                  25                  30

<210> SEQ ID NO 44
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aad
<220> FEATURE:
<221> NAME/KEY: MISC_FEATURE
<222> LOCATION: (33)..(33)
<223> OTHER INFORMATION: X is amidated

<400> SEQUENCE: 44

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

Ala

<210> SEQ ID NO 45
<211> LENGTH: 34
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aad
<220> FEATURE:
<221> NAME/KEY: MISC_FEATURE
<222> LOCATION: (34)..(34)
<223> OTHER INFORMATION: X is amidated

<400> SEQUENCE: 45

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
```

-continued

```
            20                  25                  30
Ser Gly

<210> SEQ ID NO 46
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys and is amidated

<400> SEQUENCE: 46

His Gly Glu Gly Thr Phe Thr Ser Asp Val Ser Xaa Tyr Leu Glu Lys
1               5                   10                  15

Gln Ala Ala Lys Glu Phe Ile Ala Trp Leu Val Lys Gly Arg Gly Xaa
            20                  25                  30

<210> SEQ ID NO 47
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys and is amidated

<400> SEQUENCE: 47

His Gly Glu Gly Thr Phe Thr Ser Asp Val Ser Ser Xaa Leu Glu Gly
1               5                   10                  15

Lys Ala Ala Lys Glu Phe Ile Ala Trp Leu Val Lys Gly Arg Gly Xaa
            20                  25                  30

<210> SEQ ID NO 48
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys and is amidated

<400> SEQUENCE: 48

His Gly Glu Gly Thr Phe Thr Ser Asp Val Ser Ser Tyr Xaa Glu Gly
1               5                   10                  15

Gln Lys Ala Lys Glu Phe Ile Ala Trp Leu Val Lys Gly Arg Gly Xaa
            20                  25                  30

<210> SEQ ID NO 49
<211> LENGTH: 32
<212> TYPE: PRT
```

```
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 49

His Gly Glu Gly Thr Phe Thr Ser Asp Val Ser Ser Tyr Leu Xaa Gly
1               5                   10                  15

Gln Ala Lys Lys Glu Phe Ile Ala Trp Leu Val Lys Gly Arg Gly Xaa
            20                  25                  30

<210> SEQ ID NO 50
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: X is Aad
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 50

His Gly Glu Gly Thr Phe Thr Ser Asp Val Ser Ser Tyr Leu Xaa Gln
1               5                   10                  15

Ala Ala Lys Glu Phe Ile Ala Trp Leu Val Lys Gly Arg Gly Xaa
            20                  25                  30

<210> SEQ ID NO 51
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (17)..(17)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 51

His Gly Glu Gly Thr Phe Thr Ser Asp Val Ser Ser Tyr Leu Glu Gly
1               5                   10                  15

Xaa Ala Ala Lys Lys Phe Ile Ala Trp Leu Val Lys Gly Arg Gly Xaa
            20                  25                  30

<210> SEQ ID NO 52
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: X is Aad
<220> FEATURE:
```

```
<221> NAME/KEY: MISC_FEATURE
<222> LOCATION: (32)..(32)
<223> OTHER INFORMATION: X is Lys, Orn, or Cys, and is amidated

<400> SEQUENCE: 52

His Gly Glu Gly Thr Phe Thr Ser Asp Val Ser Ser Tyr Leu Glu Gly
1               5                   10                  15

Gln Xaa Ala Lys Glu Lys Ile Ala Trp Leu Val Lys Gly Arg Gly Xaa
            20                  25                  30

<210> SEQ ID NO 53
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 53

His Gly Glu Gly Thr Phe Thr Ser Asp Val Ser Ser Tyr Leu Glu Gly
1               5                   10                  15

Gln Ala Xaa Lys Glu Phe Lys Ala Trp Leu Val Lys Gly Arg Gly Xaa
            20                  25                  30

<210> SEQ ID NO 54
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 54

His Gly Glu Gly Thr Phe Thr Ser Asp Val Ser Ser Tyr Leu Glu Gly
1               5                   10                  15

Gln Ala Ala Xaa Glu Phe Ile Lys Trp Leu Val Lys Gly Arg Gly Xaa
            20                  25                  30

<210> SEQ ID NO 55
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 55

His Gly Glu Gly Thr Phe Thr Ser Asp Val Ser Ser Tyr Leu Xaa Gly
1               5                   10                  15
```

Gln Ala Ala Lys Glu Phe Ile Ala Trp Leu Val Lys Gly Arg Gly Xaa
            20                  25                  30

<210> SEQ ID NO 56
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is Aad
<220> FEATURE:
<221> NAME/KEY: MISC_FEATURE
<222> LOCATION: (31)..(31)
<223> OTHER INFORMATION: residue 31 is amidated

<400> SEQUENCE: 56

His Gly Glu Gly Thr Phe Thr Ser Asp Val Ser Ser Tyr Leu Glu Lys
1               5                   10                  15

Gln Ala Ala Xaa Glu Phe Ile Ala Trp Leu Val Lys Gly Arg Gly
            20                  25                  30

<210> SEQ ID NO 57
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is Aad
<220> FEATURE:
<221> NAME/KEY: MISC_FEATURE
<222> LOCATION: (33)..(33)
<223> OTHER INFORMATION: Residue 33 is amidated

<400> SEQUENCE: 57

His Gly Glu Gly Thr Phe Thr Ser Asp Val Ser Ser Tyr Leu Glu Lys
1               5                   10                  15

Gln Ala Ala Xaa Glu Phe Ile Ala Trp Leu Val Lys Gly Arg Gly Cys
            20                  25                  30

Ala

<210> SEQ ID NO 58
<211> LENGTH: 34
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is Aad
<220> FEATURE:
<221> NAME/KEY: MISC_FEATURE
<222> LOCATION: (34)..(34)
<223> OTHER INFORMATION: Residue 34 is amidated

<400> SEQUENCE: 58

His Gly Glu Gly Thr Phe Thr Ser Asp Val Ser Ser Tyr Leu Glu Lys
1               5                   10                  15

Gln Ala Ala Xaa Glu Phe Ile Ala Trp Leu Val Lys Gly Arg Gly Cys
            20                  25                  30

Ser Gly

```
<210> SEQ ID NO 59
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 59

His Gly Glu Gly Thr Phe Thr Ser Asp Val Ser Lys Tyr Leu Glu Xaa
1               5                   10                  15

Gln Ala Ala Lys Glu Phe Ile Ala Trp Leu Val Lys Gly Arg Gly Xaa
            20                  25                  30

<210> SEQ ID NO 60
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (17)..(17)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 60

His Gly Glu Gly Thr Phe Thr Ser Asp Val Ser Ser Lys Leu Glu Gly
1               5                   10                  15

Xaa Ala Ala Lys Glu Phe Ile Ala Trp Leu Val Lys Gly Arg Gly Xaa
            20                  25                  30

<210> SEQ ID NO 61
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 61

His Gly Glu Gly Thr Phe Thr Ser Asp Val Ser Ser Tyr Lys Glu Gly
1               5                   10                  15

Gln Xaa Ala Lys Glu Phe Ile Ala Trp Leu Val Lys Gly Arg Gly Xaa
            20                  25                  30

<210> SEQ ID NO 62
<211> LENGTH: 32
<212> TYPE: PRT
<213> ORGANISM: Artificial
<220> FEATURE:
<223> OTHER INFORMATION: Synthetic
<220> FEATURE:
```

```
<221> NAME/KEY: MISC_FEATURE
<222> LOCATION: (19)..(19)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 62

His Gly Glu Gly Thr Phe Thr Ser Asp Val Ser Ser Tyr Leu Lys Gly
1               5                   10                  15

Gln Ala Xaa Lys Glu Phe Ile Ala Trp Leu Val Lys Gly Arg Gly Xaa
            20                  25                  30

<210> SEQ ID NO 63
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 63

His Gly Glu Gly Thr Phe Thr Ser Asp Val Ser Ser Tyr Leu Glu Lys
1               5                   10                  15

Gln Ala Ala Xaa Glu Phe Ile Ala Trp Leu Val Lys Gly Arg Gly Xaa
            20                  25                  30

<210> SEQ ID NO 64
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (21)..(21)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 64

His Gly Glu Gly Thr Phe Thr Ser Asp Val Ser Ser Tyr Leu Glu Gly
1               5                   10                  15

Lys Ala Ala Lys Xaa Phe Ile Ala Trp Leu Val Lys Gly Arg Gly Xaa
            20                  25                  30

<210> SEQ ID NO 65
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (22)..(22)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated
```

<400> SEQUENCE: 65

His Gly Glu Gly Thr Phe Thr Ser Asp Val Ser Ser Tyr Leu Glu Gly
1               5                   10                  15

Gln Lys Ala Lys Glu Xaa Ile Ala Trp Leu Val Lys Gly Arg Gly Xaa
            20                  25                  30

<210> SEQ ID NO 66
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (23)..(23)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 66

His Gly Glu Gly Thr Phe Thr Ser Asp Val Ser Ser Tyr Leu Glu Gly
1               5                   10                  15

Gln Ala Lys Lys Glu Phe Xaa Ala Trp Leu Val Lys Gly Arg Gly Xaa
            20                  25                  30

<210> SEQ ID NO 67
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (24)..(24)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 67

His Gly Glu Gly Thr Phe Thr Ser Asp Val Ser Ser Tyr Leu Glu Gly
1               5                   10                  15

Gln Ala Ala Lys Glu Phe Ile Xaa Trp Leu Val Lys Gly Arg Gly Xaa
            20                  25                  30

<210> SEQ ID NO 68
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 68

His Gly Glu Gly Thr Phe Thr Ser Asp Val Ser Ser Tyr Leu Lys Gly
1               5                   10                  15

Gln Ala Ala Xaa Glu Phe Ile Ala Trp Leu Val Lys Gly Arg Gly Xaa
            20                  25                  30

```
<210> SEQ ID NO 69
<211> LENGTH: 30
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (30)..(30)
<223> OTHER INFORMATION: Residue 30 is amidated

<400> SEQUENCE: 69

His Gly Glu Gly Thr Phe Thr Ser Asp Val Ser Ser Tyr Leu Glu Glu
1               5                   10                  15

Gln Ala Ala Glu Phe Ile Ala Trp Leu Val Lys Gly Arg Gly
            20                  25                  30

<210> SEQ ID NO 70
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: Residue 32 is amidated

<400> SEQUENCE: 70

His Gly Glu Gly Thr Phe Thr Ser Asp Val Ser Ser Tyr Leu Glu Glu
1               5                   10                  15

Gln Ala Ala Glu Phe Ile Ala Trp Leu Val Lys Gly Arg Gly Cys Ala
            20                  25                  30

<210> SEQ ID NO 71
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (33)..(33)
<223> OTHER INFORMATION: Residue 33 is amidated

<400> SEQUENCE: 71

His Gly Glu Gly Thr Phe Thr Ser Asp Val Ser Ser Tyr Leu Glu Glu
1               5                   10                  15

Gln Ala Ala Glu Phe Ile Ala Trp Leu Val Lys Gly Arg Gly Cys Ser
            20                  25                  30

Gly

<210> SEQ ID NO 72
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 72

His Gly Glu Gly Thr Phe Thr Ser Asp Val Ser Glu Tyr Leu Glu Gln
1               5                   10                  15

Ala Ala Lys Glu Phe Ile Ala Trp Leu Val Lys Gly Arg Gly Xaa
```

<210> SEQ ID NO 73
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 73

His Gly Glu Gly Thr Phe Thr Ser Asp Val Ser Ser Glu Leu Glu Gly
1               5                   10                  15

Ala Ala Lys Glu Phe Ile Ala Trp Leu Val Lys Gly Arg Gly Xaa
            20                  25                  30

<210> SEQ ID NO 74
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 74

His Gly Glu Gly Thr Phe Thr Ser Asp Val Ser Ser Tyr Glu Glu Gly
1               5                   10                  15

Gln Ala Lys Glu Phe Ile Ala Trp Leu Val Lys Gly Arg Gly Xaa
            20                  25                  30

<210> SEQ ID NO 75
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 75

His Gly Glu Gly Thr Phe Thr Ser Asp Val Ser Ser Tyr Leu Glu Gly
1               5                   10                  15

Gln Ala Lys Glu Phe Ile Ala Trp Leu Val Lys Gly Arg Gly Xaa
            20                  25                  30

<210> SEQ ID NO 76
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 76

His Gly Glu Gly Thr Phe Thr Ser Asp Val Ser Ser Tyr Leu Glu Glu
1               5                   10                  15

Gln Ala Ala Glu Phe Ile Ala Trp Leu Val Lys Gly Arg Gly Xaa 20                  25                  30

<210> SEQ ID NO 77
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 77

His Gly Glu Gly Thr Phe Thr Ser Asp Val Ser Ser Tyr Leu Glu Gly
1               5                   10                  15

Glu Ala Ala Lys Phe Ile Ala Trp Leu Val Lys Gly Arg Gly Xaa
            20                  25                  30

<210> SEQ ID NO 78
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 78

His Gly Glu Gly Thr Phe Thr Ser Asp Val Ser Ser Tyr Leu Glu Gly
1               5                   10                  15

Gln Glu Ala Lys Glu Ile Ala Trp Leu Val Lys Gly Arg Gly Xaa
            20                  25                  30

<210> SEQ ID NO 79
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 79

His Gly Glu Gly Thr Phe Thr Ser Asp Val Ser Ser Tyr Leu Glu Gly
1               5                   10                  15

Gln Ala Glu Lys Glu Phe Ala Trp Leu Val Lys Gly Arg Gly Xaa
            20                  25                  30

<210> SEQ ID NO 80
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 80

His Gly Glu Gly Thr Phe Thr Ser Asp Val Ser Ser Tyr Leu Glu Gly
1               5                   10                  15

Gln Ala Ala Glu Glu Phe Ile Trp Leu Val Lys Gly Arg Gly Xaa

<210> SEQ ID NO 81
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 81

His Gly Glu Gly Thr Phe Thr Ser Asp Val Ser Ser Tyr Leu Glu Gly
1               5                   10                  15
Gln Ala Ala Glu Phe Ile Ala Trp Leu Val Lys Gly Arg Gly Xaa
            20                  25                  30

<210> SEQ ID NO 82
<211> LENGTH: 30
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (30)..(30)
<223> OTHER INFORMATION: Residue 30 is amidated

<400> SEQUENCE: 82

His Gly Glu Gly Thr Phe Thr Ser Asp Val Ser Ser Tyr Leu Glu Gln
1               5                   10                  15
Ala Ala Glu Glu Phe Ile Ala Trp Leu Val Lys Gly Arg Gly
            20                  25                  30

<210> SEQ ID NO 83
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: Residue 32 is amidated

<400> SEQUENCE: 83

His Gly Glu Gly Thr Phe Thr Ser Asp Val Ser Ser Tyr Leu Glu Gln
1               5                   10                  15
Ala Ala Glu Glu Phe Ile Ala Trp Leu Val Lys Gly Arg Gly Cys Ala
            20                  25                  30

<210> SEQ ID NO 84
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (33)..(33)
<223> OTHER INFORMATION: Residue 33 is amidated

<400> SEQUENCE: 84

His Gly Glu Gly Thr Phe Thr Ser Asp Val Ser Ser Tyr Leu Glu Gln
1               5                   10                  15
Ala Ala Glu Glu Phe Ile Ala Trp Leu Val Lys Gly Arg Gly Cys Ser

```
            20                  25                  30

Gly

<210> SEQ ID NO 85
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 85

His Gly Glu Gly Thr Phe Thr Ser Asp Val Ser Tyr Leu Glu Glu Gln
1               5                   10                  15

Ala Ala Lys Glu Phe Ile Ala Trp Leu Val Lys Gly Arg Gly Xaa
            20                  25                  30

<210> SEQ ID NO 86
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 86

His Gly Glu Gly Thr Phe Thr Ser Asp Val Ser Ser Leu Glu Gly Glu
1               5                   10                  15

Ala Ala Lys Glu Phe Ile Ala Trp Leu Val Lys Gly Arg Gly Xaa
            20                  25                  30

<210> SEQ ID NO 87
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 87

His Gly Glu Gly Thr Phe Thr Ser Asp Val Ser Ser Tyr Glu Gly Gln
1               5                   10                  15

Glu Ala Lys Glu Phe Ile Ala Trp Leu Val Lys Gly Arg Gly Xaa
            20                  25                  30

<210> SEQ ID NO 88
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 88

His Gly Glu Gly Thr Phe Thr Ser Asp Val Ser Ser Tyr Leu Gly Gln
1               5                   10                  15
```

Ala Glu Lys Glu Phe Ile Ala Trp Leu Val Lys Gly Arg Gly Xaa
            20                  25                  30

<210> SEQ ID NO 89
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 89

His Gly Glu Gly Thr Phe Thr Ser Asp Val Ser Ser Tyr Leu Glu Gln
1               5                   10                  15

Ala Ala Glu Glu Phe Ile Ala Trp Leu Val Lys Gly Arg Gly Xaa
            20                  25                  30

<210> SEQ ID NO 90
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 90

His Gly Glu Gly Thr Phe Thr Ser Asp Val Ser Ser Tyr Leu Glu Gly
1               5                   10                  15

Ala Ala Lys Glu Phe Ile Ala Trp Leu Val Lys Gly Arg Gly Xaa
            20                  25                  30

<210> SEQ ID NO 91
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 91

His Gly Glu Gly Thr Phe Thr Ser Asp Val Ser Ser Tyr Leu Glu Gly
1               5                   10                  15

Gln Ala Lys Glu Glu Ile Ala Trp Leu Val Lys Gly Arg Gly Xaa
            20                  25                  30

<210> SEQ ID NO 92
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 92

His Gly Glu Gly Thr Phe Thr Ser Asp Val Ser Ser Tyr Leu Glu Gly
1               5                   10                  15

Gln Ala Lys Glu Phe Glu Ala Trp Leu Val Lys Gly Arg Gly Xaa
            20                  25                  30

<210> SEQ ID NO 93
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 93

His Gly Glu Gly Thr Phe Thr Ser Asp Val Ser Ser Tyr Leu Glu Gly
1               5                   10                  15

Gln Ala Ala Glu Phe Ile Glu Trp Leu Val Lys Gly Arg Gly Xaa
            20                  25                  30

<210> SEQ ID NO 94
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 94

His Gly Glu Gly Thr Phe Thr Ser Asp Val Ser Ser Tyr Leu Gly Gln
1               5                   10                  15

Ala Ala Glu Glu Phe Ile Ala Trp Leu Val Lys Gly Arg Gly Xaa
            20                  25                  30

<210> SEQ ID NO 95
<211> LENGTH: 30
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (30)..(30)
<223> OTHER INFORMATION: Residue 30 is amidated

<400> SEQUENCE: 95

His Gly Glu Gly Thr Phe Thr Ser Asp Val Ser Ser Tyr Leu Glu Asp
1               5                   10                  15

Gln Ala Ala Glu Phe Ile Ala Trp Leu Val Lys Gly Arg Gly
            20                  25                  30

<210> SEQ ID NO 96
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: Residue 32 is amidated

<400> SEQUENCE: 96

His Gly Glu Gly Thr Phe Thr Ser Asp Val Ser Ser Tyr Leu Glu Asp
1               5                   10                  15

Gln Ala Ala Glu Phe Ile Ala Trp Leu Val Lys Gly Arg Gly Cys Ala
            20                  25                  30

<210> SEQ ID NO 97
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (33)..(33)
<223> OTHER INFORMATION: Residue 33 is amidated

<400> SEQUENCE: 97

His Gly Glu Gly Thr Phe Thr Ser Asp Val Ser Ser Tyr Leu Glu Asp
1               5                   10                  15

Gln Ala Ala Glu Phe Ile Ala Trp Leu Val Lys Gly Arg Gly Cys Ser
            20                  25                  30

Gly

<210> SEQ ID NO 98
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 98

His Gly Glu Gly Thr Phe Thr Ser Asp Val Ser Asp Tyr Leu Glu Gln
1               5                   10                  15

Ala Ala Lys Glu Phe Ile Ala Trp Leu Val Lys Gly Arg Gly Xaa
            20                  25                  30

<210> SEQ ID NO 99
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 99

His Gly Glu Gly Thr Phe Thr Ser Asp Val Ser Ser Asp Leu Glu Gly
1               5                   10                  15

Ala Ala Lys Glu Phe Ile Ala Trp Leu Val Lys Gly Arg Gly Xaa
            20                  25                  30

<210> SEQ ID NO 100
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 100

His Gly Glu Gly Thr Phe Thr Ser Asp Val Ser Ser Tyr Asp Glu Gly
1               5                   10                  15

Gln Ala Lys Glu Phe Ile Ala Trp Leu Val Lys Gly Arg Gly Xaa
            20                  25                  30

<210> SEQ ID NO 101
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 101

His Gly Glu Gly Thr Phe Thr Ser Asp Val Ser Ser Tyr Leu Asp Gly
1               5                   10                  15

Gln Ala Lys Glu Phe Ile Ala Trp Leu Val Lys Gly Arg Gly Xaa
            20                  25                  30

<210> SEQ ID NO 102
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 102

His Gly Glu Gly Thr Phe Thr Ser Asp Val Ser Ser Tyr Leu Glu Asp
1               5                   10                  15

Gln Ala Ala Glu Phe Ile Ala Trp Leu Val Lys Gly Arg Gly Xaa
            20                  25                  30

<210> SEQ ID NO 103
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 103

His Gly Glu Gly Thr Phe Thr Ser Asp Val Ser Ser Tyr Leu Glu Gly
1               5                   10                  15

Asp Ala Ala Lys Phe Ile Ala Trp Leu Val Lys Gly Arg Gly Xaa
            20                  25                  30

<210> SEQ ID NO 104
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 104

```
His Gly Glu Gly Thr Phe Thr Ser Asp Val Ser Ser Tyr Leu Glu Gly
1               5                   10                  15

Gln Asp Ala Lys Glu Ile Ala Trp Leu Val Lys Gly Arg Gly Xaa
            20                  25                  30

<210> SEQ ID NO 105
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 105

His Gly Glu Gly Thr Phe Thr Ser Asp Val Ser Ser Tyr Leu Glu Gly
1               5                   10                  15

Gln Ala Asp Lys Glu Phe Ala Trp Leu Val Lys Gly Arg Gly Xaa
            20                  25                  30

<210> SEQ ID NO 106
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 106

His Gly Glu Gly Thr Phe Thr Ser Asp Val Ser Ser Tyr Leu Glu Gly
1               5                   10                  15

Gln Ala Ala Asp Glu Phe Ile Trp Leu Val Lys Gly Arg Gly Xaa
            20                  25                  30

<210> SEQ ID NO 107
<211> LENGTH: 30
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (30)..(30)
<223> OTHER INFORMATION: Residue 30 is amidated

<400> SEQUENCE: 107

His Gly Glu Gly Thr Phe Thr Ser Asp Val Ser Ser Tyr Leu Glu Gln
1               5                   10                  15

Ala Ala Asp Glu Phe Ile Ala Trp Leu Val Lys Gly Arg Gly
            20                  25                  30

<210> SEQ ID NO 108
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: Residue 32 is amidated

<400> SEQUENCE: 108
```

His Gly Glu Gly Thr Phe Thr Ser Asp Val Ser Ser Tyr Leu Glu Gln
1               5                   10                  15

Ala Ala Asp Glu Phe Ile Ala Trp Leu Val Lys Gly Arg Gly Cys Ala
            20                  25                  30

<210> SEQ ID NO 109
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (33)..(33)
<223> OTHER INFORMATION: Residue 33 is amidated

<400> SEQUENCE: 109

His Gly Glu Gly Thr Phe Thr Ser Asp Val Ser Ser Tyr Leu Glu Gln
1               5                   10                  15

Ala Ala Asp Glu Phe Ile Ala Trp Leu Val Lys Gly Arg Gly Cys Ser
            20                  25                  30

Gly

<210> SEQ ID NO 110
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 110

His Gly Glu Gly Thr Phe Thr Ser Asp Val Ser Tyr Leu Glu Asp Gln
1               5                   10                  15

Ala Ala Lys Glu Phe Ile Ala Trp Leu Val Lys Gly Arg Gly Xaa
            20                  25                  30

<210> SEQ ID NO 111
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 111

His Gly Glu Gly Thr Phe Thr Ser Asp Val Ser Ser Leu Glu Gly Asp
1               5                   10                  15

Ala Ala Lys Glu Phe Ile Ala Trp Leu Val Lys Gly Arg Gly Xaa
            20                  25                  30

<210> SEQ ID NO 112
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated -continued

```
<400> SEQUENCE: 112

His Gly Glu Gly Thr Phe Thr Ser Asp Val Ser Ser Tyr Gly Gly Gln
1               5                   10                  15

Asp Ala Lys Glu Phe Ile Ala Trp Leu Val Lys Gly Arg Gly Xaa
            20                  25                  30

<210> SEQ ID NO 113
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 113

His Gly Glu Gly Thr Phe Thr Ser Asp Val Ser Ser Tyr Leu Gly Gln
1               5                   10                  15

Ala Asp Lys Glu Phe Ile Ala Trp Leu Val Lys Gly Arg Gly Xaa
            20                  25                  30

<210> SEQ ID NO 114
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 114

His Gly Glu Gly Thr Phe Thr Ser Asp Val Ser Ser Tyr Leu Glu Gln
1               5                   10                  15

Ala Ala Asp Glu Phe Ile Ala Trp Leu Val Lys Gly Arg Gly Xaa
            20                  25                  30

<210> SEQ ID NO 115
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 115

His Gly Glu Gly Thr Phe Thr Ser Asp Val Ser Ser Tyr Leu Glu Gly
1               5                   10                  15

Ala Ala Lys Asp Phe Ile Ala Trp Leu Val Lys Gly Arg Gly Xaa
            20                  25                  30

<210> SEQ ID NO 116
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated
```

-continued

```
<400> SEQUENCE: 116

His Gly Glu Gly Thr Phe Thr Ser Asp Val Ser Ser Tyr Leu Glu Gly
1               5                   10                  15

Gln Ala Lys Glu Asp Ile Ala Trp Leu Val Lys Gly Arg Gly Xaa
            20                  25                  30

<210> SEQ ID NO 117
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 117

His Gly Glu Gly Thr Phe Thr Ser Asp Val Ser Ser Tyr Leu Glu Gly
1               5                   10                  15

Gln Ala Lys Glu Phe Asp Ala Trp Leu Val Lys Gly Arg Gly Xaa
            20                  25                  30

<210> SEQ ID NO 118
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 118

His Gly Glu Gly Thr Phe Thr Ser Asp Val Ser Ser Tyr Leu Glu Gly
1               5                   10                  15

Gln Ala Ala Glu Phe Ile Asp Trp Leu Val Lys Gly Arg Gly Xaa
            20                  25                  30

<210> SEQ ID NO 119
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 119

His Gly Glu Gly Thr Phe Thr Ser Asp Val Ser Ser Tyr Leu Glu Gly
1               5                   10                  15

Gln Ala Ala Glu Phe Ile Ala Trp Leu Val Lys Gly Arg Gly Xaa
            20                  25                  30

<210> SEQ ID NO 120
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated
```

-continued

```
<400> SEQUENCE: 120

His Gly Glu Gly Thr Phe Thr Ser Asp Val Ser Ser Tyr Leu Gly Gln
1               5                   10                  15

Ala Ala Glu Glu Phe Ile Ala Trp Leu Val Lys Gly Arg Gly Xaa
            20                  25                  30

<210> SEQ ID NO 121
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 121

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Xaa
            20                  25                  30

<210> SEQ ID NO 122
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 122

His Gly Glu Gly Thr Phe Thr Ser Asp Val Ser Ser Tyr Leu Lys Gly
1               5                   10                  15

Gln Ala Ala Glu Glu Phe Ile Ala Trp Leu Val Lys Gly Arg Gly Xaa
            20                  25                  30

<210> SEQ ID NO 123
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 123

His Gly Glu Gly Thr Phe Thr Ser Asp Val Ser Ser Tyr Leu Xaa Gly
1               5                   10                  15

Gln Ala Ala Lys Glu Phe Ile Ala Trp Leu Val Lys Gly Arg Gly Xaa
            20                  25                  30

<210> SEQ ID NO 124
<211> LENGTH: 32
<212> TYPE: PRT
<213> ORGANISM: Artificial
<220> FEATURE:
<223> OTHER INFORMATION: Synthetic
<220> FEATURE:
```

```
<221> NAME/KEY: MISC_FEATURE
<222> LOCATION: (20)..(20)
<223> OTHER INFORMATION: X is Aad
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 124

His Gly Glu Gly Thr Phe Thr Ser Asp Val Ser Ser Tyr Leu Lys Gly
 1               5                  10                  15

Gln Ala Ala Xaa Glu Phe Ile Ala Trp Leu Val Lys Gly Arg Gly Xaa
            20                  25                  30

<210> SEQ ID NO 125
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 125

His Gly Glu Gly Thr Phe Thr Ser Asp Val Ser Ser Tyr Leu Asp Gly
 1               5                  10                  15

Gln Ala Ala Glu Phe Ile Ala Trp Leu Val Lys Gly Arg Gly Xaa
            20                  25                  30

<210> SEQ ID NO 126
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 126

His Gly Glu Gly Thr Phe Thr Ser Asp Val Ser Ser Tyr Leu Gly Gln
 1               5                  10                  15

Ala Ala Asp Glu Phe Ile Ala Trp Leu Val Lys Gly Arg Gly Xaa
            20                  25                  30

<210> SEQ ID NO 127
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 127

His Gly Glu Gly Thr Phe Thr Ser Asp Val Ser Ser Tyr Leu Asp Gly
 1               5                  10                  15

Gln Ala Ala Lys Glu Phe Ile Ala Trp Leu Val Lys Gly Arg Gly Xaa
            20                  25                  30

<210> SEQ ID NO 128
<211> LENGTH: 32
<212> TYPE: PRT
```

```
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 128

His Gly Glu Gly Thr Phe Thr Ser Asp Val Ser Ser Tyr Leu Lys Gly
1               5                   10                  15

Gln Ala Ala Asp Glu Phe Ile Ala Trp Leu Val Lys Gly Arg Gly Xaa
            20                  25                  30

<210> SEQ ID NO 129
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 129

His Gly Glu Gly Thr Phe Thr Ser Asp Val Ser Ser Tyr Leu Xaa Gly
1               5                   10                  15

Gln Ala Ala Glu Phe Ile Ala Trp Leu Val Lys Gly Arg Gly Xaa
            20                  25                  30

<210> SEQ ID NO 130
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 130

His Gly Glu Gly Thr Phe Thr Ser Asp Val Ser Ser Tyr Leu Gly Gln
1               5                   10                  15

Ala Ala Xaa Glu Phe Ile Ala Trp Leu Val Lys Gly Arg Gly Xaa
            20                  25                  30

<210> SEQ ID NO 131
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated
```

```
<400> SEQUENCE: 131

His Gly Glu Gly Thr Phe Thr Ser Asp Val Ser Ser Tyr Leu Xaa Gly
1               5                   10                  15

Gln Ala Ala Lys Glu Phe Ile Ala Trp Leu Val Lys Gly Arg Gly Xaa
            20                  25                  30

<210> SEQ ID NO 132
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 132

His Gly Glu Gly Thr Phe Thr Ser Asp Val Ser Ser Tyr Leu Lys Gly
1               5                   10                  15

Gln Ala Ala Xaa Glu Phe Ile Ala Trp Leu Val Lys Gly Arg Gly Xaa
            20                  25                  30

<210> SEQ ID NO 133
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 133

His Gly Glu Gly Thr Phe Thr Ser Asp Val Ser Ser Tyr Leu Xaa Gly
1               5                   10                  15

Gln Ala Ala Lys Glu Phe Ile Ala Trp Leu Val Lys Gly Arg Gly Xaa
            20                  25                  30

<210> SEQ ID NO 134
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 134

His Gly Glu Gly Thr Phe Thr Ser Asp Val Ser Ser Tyr Leu Lys Gly
1               5                   10                  15

Gln Ala Ala Xaa Glu Phe Ile Ala Trp Leu Val Lys Gly Arg Gly Xaa
            20                  25                  30
```

<210> SEQ ID NO 135
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)

<400> SEQUENCE: 135

His Gly Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg Gly
            20                  25                  30

<210> SEQ ID NO 136
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (33)..(33)
<223> OTHER INFORMATION: Residue 33 is amidated

<400> SEQUENCE: 136

His Gly Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg Gly Cys
            20                  25                  30

Ala

<210> SEQ ID NO 137
<211> LENGTH: 34
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (34)..(34)
<223> OTHER INFORMATION: Residue 34 is amidated

<400> SEQUENCE: 137

His Gly Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg Gly Cys
            20                  25                  30

Ser Gly

<210> SEQ ID NO 138
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 138

His Gly Glu Gly Thr Phe Thr Ser Asp Val Ser Asp Tyr Leu Glu Lys
1               5                   10                  15

Gln Ala Ala Lys Glu Phe Ile Ala Trp Leu Val Lys Gly Arg Gly Xaa
            20                  25                  30

<210> SEQ ID NO 139
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 139

His Gly Glu Gly Thr Phe Thr Ser Asp Val Ser Ser Asp Leu Glu Gly
1               5                   10                  15

Lys Ala Ala Lys Glu Phe Ile Ala Trp Leu Val Lys Gly Arg Gly Xaa
            20                  25                  30

<210> SEQ ID NO 140
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 140

His Gly Glu Gly Thr Phe Thr Ser Asp Val Ser Ser Tyr Asp Glu Gly
1               5                   10                  15

Gln Lys Ala Lys Glu Phe Ile Ala Trp Leu Val Lys Gly Arg Gly Xaa
            20                  25                  30

<210> SEQ ID NO 141
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 141

His Gly Glu Gly Thr Phe Thr Ser Asp Val Ser Ser Tyr Leu Asp Gly
1               5                   10                  15

Gln Ala Lys Lys Glu Phe Ile Ala Trp Leu Val Lys Gly Arg Gly Xaa
            20                  25                  30

<210> SEQ ID NO 142
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 142

His Gly Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg Gly Xaa
            20                  25                  30

<210> SEQ ID NO 143
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 143

His Gly Glu Gly Thr Phe Thr Ser Asp Val Ser Ser Tyr Leu Glu Gly
1               5                   10                  15

Asp Ala Ala Lys Lys Phe Ile Ala Trp Leu Val Lys Gly Arg Gly Xaa
            20                  25                  30

<210> SEQ ID NO 144
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 144

His Gly Glu Gly Thr Phe Thr Ser Asp Val Ser Ser Tyr Leu Glu Gly
1               5                   10                  15

Gln Asp Ala Lys Glu Lys Ile Ala Trp Leu Val Lys Gly Arg Gly Xaa
            20                  25                  30

<210> SEQ ID NO 145
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 145

His Gly Glu Gly Thr Phe Thr Ser Asp Val Ser Ser Tyr Leu Glu Gly
1               5                   10                  15

Gln Ala Asp Lys Glu Phe Lys Ala Trp Leu Val Lys Gly Arg Gly Xaa
            20                  25                  30

<210> SEQ ID NO 146
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 146

His Gly Glu Gly Thr Phe Thr Ser Asp Val Ser Ser Tyr Leu Glu Gly
1               5                   10                  15

```
Gln Ala Ala Asp Glu Phe Ile Lys Trp Leu Val Lys Gly Arg Gly Xaa
            20                  25                  30
```

<210> SEQ ID NO 147
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: Residue 31 is amidated

<400> SEQUENCE: 147

```
His Gly Glu Gly Thr Phe Thr Ser Asp Val Ser Ser Tyr Leu Glu Lys
1               5                   10                  15

Gln Ala Ala Asp Glu Phe Ile Ala Trp Leu Val Lys Gly Arg Gly
            20                  25                  30
```

<210> SEQ ID NO 148
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (33)..(33)
<223> OTHER INFORMATION: Residue 33 is amidated

<400> SEQUENCE: 148

```
His Gly Glu Gly Thr Phe Thr Ser Asp Val Ser Ser Tyr Leu Glu Lys
1               5                   10                  15

Gln Ala Ala Asp Glu Phe Ile Ala Trp Leu Val Lys Gly Arg Gly Cys
            20                  25                  30

Ala
```

<210> SEQ ID NO 149
<211> LENGTH: 34
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (34)..(34)
<223> OTHER INFORMATION: X is Lys, Orn, or Cys, and is amidated

<400> SEQUENCE: 149

```
His Gly Glu Gly Thr Phe Thr Ser Asp Val Ser Ser Tyr Leu Glu Lys
1               5                   10                  15

Gln Ala Ala Asp Glu Phe Ile Ala Trp Leu Val Lys Gly Arg Gly Cys
            20                  25                  30

Ser Gly
```

<210> SEQ ID NO 150
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 150

His Gly Glu Gly Thr Phe Thr Ser Asp Val Ser Lys Tyr Leu Glu Asp
1               5                   10                  15

Gln Ala Ala Lys Glu Phe Ile Ala Trp Leu Val Lys Gly Arg Gly Xaa
            20                  25                  30

<210> SEQ ID NO 151
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 151

His Gly Glu Gly Thr Phe Thr Ser Asp Val Ser Ser Lys Leu Glu Gly
1               5                   10                  15

Asp Ala Ala Lys Glu Phe Ile Ala Trp Leu Val Lys Gly Arg Gly Xaa
            20                  25                  30

<210> SEQ ID NO 152
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 152

His Gly Glu Gly Thr Phe Thr Ser Asp Val Ser Ser Tyr Lys Glu Gly
1               5                   10                  15

Gln Asp Ala Lys Glu Phe Ile Ala Trp Leu Val Lys Gly Arg Gly Xaa
            20                  25                  30

<210> SEQ ID NO 153
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 153

His Gly Glu Gly Thr Phe Thr Ser Asp Val Ser Ser Tyr Leu Lys Gly
1               5                   10                  15

Gln Ala Asp Lys Glu Phe Ile Ala Trp Leu Val Lys Gly Arg Gly Xaa
            20                  25                  30

<210> SEQ ID NO 154
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 154

His Gly Glu Gly Thr Phe Thr Ser Asp Val Ser Ser Tyr Leu Glu Lys
1               5                   10                  15

Gln Ala Ala Asp Glu Phe Ile Ala Trp Leu Val Lys Gly Arg Gly Xaa
            20                  25                  30

<210> SEQ ID NO 155
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 155

His Gly Glu Gly Thr Phe Thr Ser Asp Val Ser Ser Tyr Leu Glu Gly
1               5                   10                  15

Lys Ala Ala Lys Asp Phe Ile Ala Trp Leu Val Lys Gly Arg Gly Xaa
            20                  25                  30

<210> SEQ ID NO 156
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 156

His Gly Glu Gly Thr Phe Thr Ser Asp Val Ser Ser Tyr Leu Glu Gly
1               5                   10                  15

Gln Lys Ala Lys Glu Asp Ile Ala Trp Leu Val Lys Gly Arg Gly Xaa
            20                  25                  30

<210> SEQ ID NO 157
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 157

His Gly Glu Gly Thr Phe Thr Ser Asp Val Ser Ser Tyr Leu Glu Gly
1               5                   10                  15

Gln Ala Lys Lys Glu Phe Asp Ala Trp Leu Val Lys Gly Arg Gly Xaa
            20                  25                  30

<210> SEQ ID NO 158
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 158

```
His Gly Glu Gly Thr Phe Thr Ser Asp Val Ser Ser Tyr Leu Glu Gly
1               5                   10                  15

Gln Ala Ala Lys Glu Phe Ile Asp Trp Leu Val Lys Gly Arg Gly Xaa
            20                  25                  30
```

<210> SEQ ID NO 159
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: Residue 31 is amidated

<400> SEQUENCE: 159

```
His Gly Glu Gly Thr Phe Thr Ser Asp Val Ser Ser Tyr Leu Glu Lys
1               5                   10                  15

Gln Ala Ala Glu Glu Phe Ile Ala Trp Leu Val Lys Gly Arg Gly
            20                  25                  30
```

<210> SEQ ID NO 160
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (33)..(33)
<223> OTHER INFORMATION: Residue 33 is amidated

<400> SEQUENCE: 160

```
His Gly Glu Gly Thr Phe Thr Ser Asp Val Ser Ser Tyr Leu Glu Lys
1               5                   10                  15

Gln Ala Ala Glu Glu Phe Ile Ala Trp Leu Val Lys Gly Arg Gly Cys
            20                  25                  30

Ala
```

<210> SEQ ID NO 161
<211> LENGTH: 34
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (34)..(34)
<223> OTHER INFORMATION: Residue 34 is amidated

<400> SEQUENCE: 161

```
His Gly Glu Gly Thr Phe Thr Ser Asp Val Ser Ser Tyr Leu Glu Lys
1               5                   10                  15

Gln Ala Ala Glu Glu Phe Ile Ala Trp Leu Val Lys Gly Arg Gly Cys
            20                  25                  30

Ser Gly
```

<210> SEQ ID NO 162
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 162

His Gly Glu Gly Thr Phe Thr Ser Asp Val Ser Lys Tyr Leu Glu Glu
1               5                   10                  15

Gln Ala Ala Lys Glu Phe Ile Ala Trp Leu Val Lys Gly Arg Gly Xaa
            20                  25                  30

<210> SEQ ID NO 163
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 163

His Gly Glu Gly Thr Phe Thr Ser Asp Val Ser Ser Lys Leu Glu Gly
1               5                   10                  15

Glu Ala Ala Lys Glu Phe Ile Ala Trp Leu Val Lys Gly Arg Gly Xaa
            20                  25                  30

<210> SEQ ID NO 164
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 164

His Gly Glu Gly Thr Phe Thr Ser Asp Val Ser Ser Tyr Lys Glu Gly
1               5                   10                  15

Gln Glu Ala Lys Glu Phe Ile Ala Trp Leu Val Lys Gly Arg Gly Xaa
            20                  25                  30

<210> SEQ ID NO 165
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 165

His Gly Glu Gly Thr Phe Thr Ser Asp Val Ser Ser Tyr Leu Lys Gly
1               5                   10                  15

Gln Ala Glu Lys Glu Phe Ile Ala Trp Leu Val Lys Gly Arg Gly Xaa
            20                  25                  30

<210> SEQ ID NO 166
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE

```
<222> LOCATION: (32)..(32)
<223> OTHER INFORMATION: X is Lys, Orn, or Cys, and is amidated

<400> SEQUENCE: 166

His Gly Glu Gly Thr Phe Thr Ser Asp Val Ser Ser Tyr Leu Glu Lys
1               5                   10                  15

Gln Ala Ala Glu Glu Phe Ile Ala Trp Leu Val Lys Gly Arg Gly Xaa
            20                  25                  30

<210> SEQ ID NO 167
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 167

His Gly Glu Gly Thr Phe Thr Ser Asp Val Ser Ser Tyr Leu Glu Gly
1               5                   10                  15

Lys Ala Ala Lys Glu Phe Ile Ala Trp Leu Val Lys Gly Arg Gly Xaa
            20                  25                  30

<210> SEQ ID NO 168
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 168

His Gly Glu Gly Thr Phe Thr Ser Asp Val Ser Ser Tyr Leu Glu Gly
1               5                   10                  15

Gln Lys Ala Lys Glu Glu Ile Ala Trp Leu Val Lys Gly Arg Gly Xaa
            20                  25                  30

<210> SEQ ID NO 169
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 169

His Gly Glu Gly Thr Phe Thr Ser Asp Val Ser Ser Tyr Leu Glu Gly
1               5                   10                  15

Gln Ala Lys Lys Glu Phe Glu Ala Trp Leu Val Lys Gly Arg Gly Xaa
            20                  25                  30

<210> SEQ ID NO 170
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
```

<222> LOCATION: (32)..(32)
<223> OTHER INFORMATION: X is Lys, Orn, or Cys, and is amidated

<400> SEQUENCE: 170

His Gly Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly Xaa
            20                  25                  30

<210> SEQ ID NO 171
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 171

His Gly Glu Gly Thr Phe Thr Ser Asp Val Ser Ser Xaa Leu Glu Gly
1               5                   10                  15

Gln Ala Ala Lys Glu Phe Ile Ala Trp Leu Val Lys Gly Arg Gly Xaa
            20                  25                  30

<210> SEQ ID NO 172
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 172

His Gly Glu Gly Thr Phe Thr Ser Asp Val Ser Ser Lys Leu Glu Gly
1               5                   10                  15

Gln Ala Ala Xaa Glu Phe Ile Ala Trp Leu Val Lys Gly Arg Gly Xaa
            20                  25                  30

<210> SEQ ID NO 173
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 173

His Gly Glu Gly Thr Phe Thr Ser Asp Val Ser Ser Xaa Leu Glu Gly
1               5                   10                  15

Gln Ala Ala Glu Phe Ile Ala Trp Leu Val Lys Gly Arg Gly Xaa
            20                  25                  30

<210> SEQ ID NO 174
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 174

His Gly Glu Gly Thr Phe Thr Ser Asp Val Ser Ser Leu Glu Gly Gln
1               5                   10                  15
Ala Ala Xaa Glu Phe Ile Ala Trp Leu Val Lys Gly Arg Gly Xaa
            20                  25                  30

<210> SEQ ID NO 175
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is beta-glutamic acid
<220> FEATURE:
<221> NAME/KEY: MISC_FEATURE
<222> LOCATION: (31)..(31)
<223> OTHER INFORMATION: Residue 31 is amidated

<400> SEQUENCE: 175

His Gly Glu Gly Thr Phe Thr Ser Asp Val Ser Ser Tyr Leu Glu Xaa
1               5                   10                  15
Gln Ala Ala Lys Glu Phe Ile Ala Trp Leu Val Lys Gly Arg Gly
            20                  25                  30

<210> SEQ ID NO 176
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is beta-glutamic acid
<220> FEATURE:
<221> NAME/KEY: MISC_FEATURE
<222> LOCATION: (33)..(33)
<223> OTHER INFORMATION: Redisue 33 is amidated

<400> SEQUENCE: 176

His Gly Glu Gly Thr Phe Thr Ser Asp Val Ser Ser Tyr Leu Glu Xaa
1               5                   10                  15
Gln Ala Ala Lys Glu Phe Ile Ala Trp Leu Val Lys Gly Arg Gly Cys
            20                  25                  30
Ala

<210> SEQ ID NO 177
<211> LENGTH: 34

```
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is beta-glutamic acid
<220> FEATURE:
<221> NAME/KEY: MISC_FEATURE
<222> LOCATION: (34)..(34)
<223> OTHER INFORMATION: Residue 177 is amidated

<400> SEQUENCE: 177

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

Ser Gly

<210> SEQ ID NO 178
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 178

His Gly Glu Gly Thr Phe Thr Ser Asp Val Ser Xaa Tyr Leu Glu Lys
1               5                   10                  15

Gln Ala Ala Lys Glu Phe Ile Ala Trp Leu Val Lys Gly Arg Gly Xaa
            20                  25                  30

<210> SEQ ID NO 179
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 179

His Gly Glu Gly Thr Phe Thr Ser Asp Val Ser Ser Xaa Leu Glu Gly
1               5                   10                  15

Lys Ala Ala Lys Glu Phe Ile Ala Trp Leu Val Lys Gly Arg Gly Xaa
            20                  25                  30

<210> SEQ ID NO 180
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
```

```
<222> LOCATION: (14)..(14)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 180

His Gly Glu Gly Thr Phe Thr Ser Asp Val Ser Ser Tyr Xaa Glu Gly
1               5                   10                  15

Gln Lys Ala Lys Glu Phe Ile Ala Trp Leu Val Lys Gly Arg Gly Xaa
            20                  25                  30

<210> SEQ ID NO 181
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 181

His Gly Glu Gly Thr Phe Thr Ser Asp Val Ser Ser Tyr Leu Xaa Gly
1               5                   10                  15

Gln Ala Lys Lys Glu Phe Ile Ala Trp Leu Val Lys Gly Arg Gly Xaa
            20                  25                  30

<210> SEQ ID NO 182
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 182

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Xaa
            20                  25                  30

<210> SEQ ID NO 183
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (17)..(17)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 183
```

His Gly Glu Gly Thr Phe Thr Ser Asp Val Ser Ser Tyr Leu Glu Gly
1               5                   10                  15

Xaa Ala Ala Lys Lys Phe Ile Ala Trp Leu Val Lys Gly Arg Gly Xaa
            20                  25                  30

<210> SEQ ID NO 184
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 184

His Gly Glu Gly Thr Phe Thr Ser Asp Val Ser Ser Tyr Leu Glu Gly
1               5                   10                  15

Gln Xaa Ala Lys Glu Lys Ile Ala Trp Leu Val Lys Gly Arg Gly Xaa
            20                  25                  30

<210> SEQ ID NO 185
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 185

His Gly Glu Gly Thr Phe Thr Ser Asp Val Ser Ser Tyr Leu Glu Gly
1               5                   10                  15

Gln Ala Xaa Lys Glu Phe Lys Ala Trp Leu Val Lys Gly Arg Gly Xaa
            20                  25                  30

<210> SEQ ID NO 186
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 186

His Gly Glu Gly Thr Phe Thr Ser Asp Val Ser Ser Tyr Leu Glu Gly
1               5                   10                  15

Gln Ala Ala Xaa Glu Phe Ile Lys Trp Leu Val Lys Gly Arg Gly Xaa
            20                  25                  30

<210> SEQ ID NO 187
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 187

His Gly Glu Gly Thr Phe Thr Ser Asp Val Ser Lys Tyr Leu Glu Xaa
1               5                   10                  15

Gln Ala Ala Lys Glu Phe Ile Ala Trp Leu Val Lys Gly Arg Gly Xaa
            20                  25                  30

<210> SEQ ID NO 188
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is beta-glutamic acid
<220> FEATURE:
<221> NAME/KEY: MISC_FEATURE
<222> LOCATION: (31)..(31)
<223> OTHER INFORMATION: Residue 32 is amidated

<400> SEQUENCE: 188

His Gly Glu Gly Thr Phe Thr Ser Asp Val Ser Ser Tyr Leu Glu Lys
1               5                   10                  15

Gln Ala Ala Xaa Glu Phe Ile Ala Trp Leu Val Lys Gly Arg Gly
            20                  25                  30

<210> SEQ ID NO 189
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is beta-glutamic acid
<220> FEATURE:
<221> NAME/KEY: MISC_FEATURE
<222> LOCATION: (33)..(33)
<223> OTHER INFORMATION: Residue 33 is amidated

<400> SEQUENCE: 189

His Gly Glu Gly Thr Phe Thr Ser Asp Val Ser Ser Tyr Leu Glu Lys
1               5                   10                  15

Gln Ala Ala Xaa Glu Phe Ile Ala Trp Leu Val Lys Gly Arg Gly Cys
            20                  25                  30

Ala

<210> SEQ ID NO 190
<211> LENGTH: 34
<212> TYPE: PRT
<213> ORGANISM: Artificial
<220> FEATURE:
<223> OTHER INFORMATION: Synthetic

```
<220> FEATURE:
<221> NAME/KEY: MISC_FEATURE
<222> LOCATION: (20)..(20)
<223> OTHER INFORMATION: X is beta-glutamic acid
<220> FEATURE:
<221> NAME/KEY: MISC_FEATURE
<222> LOCATION: (34)..(34)
<223> OTHER INFORMATION: Residue 34 is amidated

<400> SEQUENCE: 190

His Gly Glu Gly Thr Phe Thr Ser Asp Val Ser Ser Tyr Leu Glu Lys
1               5                   10                  15

Gln Ala Ala Xaa Glu Phe Ile Ala Trp Leu Val Lys Gly Arg Gly Cys
            20                  25                  30

Ser Gly

<210> SEQ ID NO 191
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (17)..(17)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 191

His Gly Glu Gly Thr Phe Thr Ser Asp Val Ser Ser Lys Leu Glu Gly
1               5                   10                  15

Xaa Ala Ala Lys Glu Phe Ile Ala Trp Leu Val Lys Gly Arg Gly Xaa
            20                  25                  30

<210> SEQ ID NO 192
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 192

His Gly Glu Gly Thr Phe Thr Ser Asp Val Ser Ser Tyr Lys Glu Gly
1               5                   10                  15

Gln Xaa Ala Lys Glu Phe Ile Ala Trp Leu Val Lys Gly Arg Gly Xaa
            20                  25                  30

<210> SEQ ID NO 193
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: X is beta-glutamic acid
<220> FEATURE:
<221> NAME/KEY: MISC_FEATURE
```

```
<222> LOCATION: (32)..(32)
<223> OTHER INFORMATION: X is Lys, Orn, or Cys, and is amidated

<400> SEQUENCE: 193

His Gly Glu Gly Thr Phe Thr Ser Asp Val Ser Ser Tyr Leu Lys Gly
1               5                   10                  15

Gln Ala Xaa Lys Glu Phe Ile Ala Trp Leu Val Lys Gly Arg Gly Xaa
            20                  25                  30

<210> SEQ ID NO 194
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 194

His Gly Glu Gly Thr Phe Thr Ser Asp Val Ser Ser Tyr Leu Glu Lys
1               5                   10                  15

Gln Ala Ala Xaa Glu Phe Ile Ala Trp Leu Val Lys Gly Arg Gly Xaa
            20                  25                  30

<210> SEQ ID NO 195
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (21)..(21)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 195

His Gly Glu Gly Thr Phe Thr Ser Asp Val Ser Ser Tyr Leu Glu Gly
1               5                   10                  15

Lys Ala Ala Lys Xaa Phe Ile Ala Trp Leu Val Lys Gly Arg Gly Xaa
            20                  25                  30

<210> SEQ ID NO 196
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (22)..(22)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 196

His Gly Glu Gly Thr Phe Thr Ser Asp Val Ser Ser Tyr Leu Glu Gly
1               5                   10                  15
```

```
Gln Lys Ala Lys Glu Xaa Ile Ala Trp Leu Val Lys Gly Arg Gly Xaa
            20                  25                  30

<210> SEQ ID NO 197
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (23)..(23)
<223> OTHER INFORMATION: X is beta-glutamic acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 197

His Gly Glu Gly Thr Phe Thr Ser Asp Val Ser Ser Tyr Leu Glu Gly
1               5                   10                  15

Gln Ala Lys Lys Glu Phe Xaa Ala Trp Leu Val Lys Gly Arg Gly Xaa
            20                  25                  30

<210> SEQ ID NO 198
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (24)..(24)
<223> OTHER INFORMATION: X is beta-glutaimc acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 198

His Gly Glu Gly Thr Phe Thr Ser Asp Val Ser Ser Tyr Leu Glu Gly
1               5                   10                  15

Gln Ala Ala Lys Glu Phe Ile Xaa Trp Leu Val Lys Gly Arg Gly Xaa
            20                  25                  30

<210> SEQ ID NO 199
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: Residue 31 is amidated

<400> SEQUENCE: 199

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly
            20                  25                  30

<210> SEQ ID NO 200
<211> LENGTH: 33
<212> TYPE: PRT
<213> ORGANISM: Artificial
```

```
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is 4-carboxy-phenyl-alanine
<220> FEATURE:
<221> NAME/KEY: MISC_FEATURE
<222> LOCATION: (33)..(33)
<223> OTHER INFORMATION: residue 33 is amidated

<400> SEQUENCE: 200

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

Ala

<210> SEQ ID NO 201
<211> LENGTH: 34
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is 4-carboxy-phenyl-alanine
<220> FEATURE:
<221> NAME/KEY: MISC_FEATURE
<222> LOCATION: (34)..(34)
<223> OTHER INFORMATION: Residue 34 is amidated

<400> SEQUENCE: 201

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Cys
            20                  25                  30

Ser Gly

<210> SEQ ID NO 202
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 202

His Gly Glu Gly Thr Phe Thr Ser Asp Val Ser Xaa Tyr Leu Glu Lys
1               5                   10                  15

Gln Ala Ala Lys Glu Phe Ile Ala Trp Leu Val Lys Gly Arg Gly Xaa
            20                  25                  30

<210> SEQ ID NO 203
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
```

```
<222> LOCATION: (13)..(13)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 203

His Gly Glu Gly Thr Phe Thr Ser Asp Val Ser Ser Xaa Leu Glu Gly
1               5                   10                  15

Lys Ala Ala Lys Glu Phe Ile Ala Trp Leu Val Lys Gly Arg Gly Xaa
            20                  25                  30

<210> SEQ ID NO 204
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 204

His Gly Glu Gly Thr Phe Thr Ser Asp Val Ser Ser Tyr Xaa Glu Gly
1               5                   10                  15

Gln Lys Ala Lys Glu Phe Ile Ala Trp Leu Val Lys Gly Arg Gly Xaa
            20                  25                  30

<210> SEQ ID NO 205
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 205

His Gly Glu Gly Thr Phe Thr Ser Asp Val Ser Ser Tyr Leu Xaa Gly
1               5                   10                  15

Gln Ala Lys Lys Glu Phe Ile Ala Trp Leu Val Lys Gly Arg Gly Xaa
            20                  25                  30

<210> SEQ ID NO 206
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 206
```

His Gly Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Gly Xaa
            20                  25                  30

<210> SEQ ID NO 207
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (17)..(17)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 207

His Gly Glu Gly Thr Phe Thr Ser Asp Val Ser Ser Tyr Leu Glu Gly
1               5                   10                  15

Xaa Ala Ala Lys Lys Phe Ile Ala Trp Leu Val Lys Gly Arg Gly Xaa
            20                  25                  30

<210> SEQ ID NO 208
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 208

His Gly Glu Gly Thr Phe Thr Ser Asp Val Ser Ser Tyr Leu Glu Gly
1               5                   10                  15

Gln Xaa Ala Lys Glu Lys Ile Ala Trp Leu Val Lys Gly Arg Gly Xaa
            20                  25                  30

<210> SEQ ID NO 209
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 209

His Gly Glu Gly Thr Phe Thr Ser Asp Val Ser Ser Tyr Leu Glu Gly
1               5                   10                  15

Gln Ala Xaa Lys Glu Phe Lys Ala Trp Leu Val Lys Gly Arg Gly Xaa
            20                  25                  30

```
<210> SEQ ID NO 210
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 210

His Gly Glu Gly Thr Phe Thr Ser Asp Val Ser Ser Tyr Leu Glu Gly
1               5                   10                  15

Gln Ala Ala Xaa Glu Phe Ile Lys Trp Leu Val Lys Gly Arg Gly Xaa
            20                  25                  30

<210> SEQ ID NO 211
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 211

His Gly Glu Gly Thr Phe Thr Ser Asp Val Ser Lys Tyr Leu Glu Xaa
1               5                   10                  15

Gln Ala Ala Lys Glu Phe Ile Ala Trp Leu Val Lys Gly Arg Gly Xaa
            20                  25                  30

<210> SEQ ID NO 212
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: Residue 31 is amidated

<400> SEQUENCE: 212

His Gly Glu Gly Thr Phe Thr Ser Asp Val Ser Ser Tyr Leu Glu Lys
1               5                   10                  15

Gln Ala Ala Xaa Glu Phe Ile Ala Trp Leu Val Lys Gly Arg Gly
            20                  25                  30

<210> SEQ ID NO 213
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
```

```
<222> LOCATION: (20)..(20)
<223> OTHER INFORMATION: X is 4-carboxy-phenyl-alanine
<220> FEATURE:
<221> NAME/KEY: MISC_FEATURE
<222> LOCATION: (33)..(33)
<223> OTHER INFORMATION: Residue 33 is amidated

<400> SEQUENCE: 213

His Gly Glu Gly Thr Phe Thr Ser Asp Val Ser Ser Tyr Leu Glu Lys
1               5                   10                  15

Gln Ala Ala Xaa Glu Phe Ile Ala Trp Leu Val Lys Gly Arg Gly Cys
            20                  25                  30

Ala

<210> SEQ ID NO 214
<211> LENGTH: 34
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is 4-carboxy-phenyl-alanine
<220> FEATURE:
<221> NAME/KEY: MISC_FEATURE
<222> LOCATION: (34)..(34)
<223> OTHER INFORMATION: Residue 34 is amidated

<400> SEQUENCE: 214

His Gly Glu Gly Thr Phe Thr Ser Asp Val Ser Ser Tyr Leu Glu Lys
1               5                   10                  15

Gln Ala Ala Xaa Glu Phe Ile Ala Trp Leu Val Lys Gly Arg Gly Cys
            20                  25                  30

Ser Gly

<210> SEQ ID NO 215
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (17)..(17)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 215

His Gly Glu Gly Thr Phe Thr Ser Asp Val Ser Ser Lys Leu Glu Gly
1               5                   10                  15

Xaa Ala Ala Lys Glu Phe Ile Ala Trp Leu Val Lys Gly Arg Gly Xaa
            20                  25                  30

<210> SEQ ID NO 216
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: X is 4-carboxy-phenyl-alanine
<220> FEATURE:
<221> NAME/KEY: MISC_FEATURE
```

-continued

```
<222> LOCATION: (32)..(32)
<223> OTHER INFORMATION: X is Lys, Orn, or Cys, and is amidated

<400> SEQUENCE: 216

His Gly Glu Gly Thr Phe Thr Ser Asp Val Ser Ser Tyr Lys Glu Gly
1               5                   10                  15

Gln Xaa Ala Lys Glu Phe Ile Ala Trp Leu Val Lys Gly Arg Gly Xaa
            20                  25                  30

<210> SEQ ID NO 217
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 217

His Gly Glu Gly Thr Phe Thr Ser Asp Val Ser Ser Tyr Leu Lys Gly
1               5                   10                  15

Gln Ala Xaa Lys Glu Phe Ile Ala Trp Leu Val Lys Gly Arg Gly Xaa
            20                  25                  30

<210> SEQ ID NO 218
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 218

His Gly Glu Gly Thr Phe Thr Ser Asp Val Ser Ser Tyr Leu Glu Lys
1               5                   10                  15

Gln Ala Ala Xaa Glu Phe Ile Ala Trp Leu Val Lys Gly Arg Gly Xaa
            20                  25                  30

<210> SEQ ID NO 219
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (21)..(21)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 219

His Gly Glu Gly Thr Phe Thr Ser Asp Val Ser Ser Tyr Leu Glu Gly
1               5                   10                  15
```

```
Lys Ala Ala Lys Xaa Phe Ile Ala Trp Leu Val Lys Gly Arg Gly Xaa
            20                  25                  30

<210> SEQ ID NO 220
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (22)..(22)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 220

His Gly Glu Gly Thr Phe Thr Ser Asp Val Ser Ser Tyr Leu Glu Gly
1               5                   10                  15

Gln Lys Ala Lys Glu Xaa Ile Ala Trp Leu Val Lys Gly Arg Gly Xaa
            20                  25                  30

<210> SEQ ID NO 221
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (23)..(23)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 221

His Gly Glu Gly Thr Phe Thr Ser Asp Val Ser Ser Tyr Leu Glu Gly
1               5                   10                  15

Gln Ala Lys Lys Glu Phe Xaa Ala Trp Leu Val Lys Gly Arg Gly Xaa
            20                  25                  30

<210> SEQ ID NO 222
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (24)..(24)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 222

His Gly Glu Gly Thr Phe Thr Ser Asp Val Ser Ser Tyr Leu Glu Gly
1               5                   10                  15

Gln Ala Ala Lys Glu Phe Ile Xaa Trp Leu Val Lys Gly Arg Gly Xaa
            20                  25                  30

<210> SEQ ID NO 223
<211> LENGTH: 30
<212> TYPE: PRT
<213> ORGANISM: Artificial
```

```
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is 4-carboxy-phenyl-alanine
<220> FEATURE:
<221> NAME/KEY: MISC_FEATURE
<222> LOCATION: (30)..(30)
<223> OTHER INFORMATION: Residue 30 is amidated

<400> SEQUENCE: 223

His Gly Glu Gly Thr Phe Thr Ser Asp Val Ser Ser Tyr Leu Glu Xaa
1               5                   10                  15

Gln Ala Ala Glu Phe Ile Ala Trp Leu Val Lys Gly Arg Gly
            20                  25                  30

<210> SEQ ID NO 224
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: Residue 32 is amidated

<400> SEQUENCE: 224

His Gly Glu Gly Thr Phe Thr Ser Asp Val Ser Ser Tyr Leu Glu Xaa
1               5                   10                  15

Gln Ala Ala Glu Phe Ile Ala Trp Leu Val Lys Gly Arg Gly Cys Ala
            20                  25                  30

<210> SEQ ID NO 225
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is 4-carboxy-phenyl-alanine
<220> FEATURE:
<221> NAME/KEY: MISC_FEATURE
<222> LOCATION: (16)..(16)
<223> OTHER INFORMATION: Residue 33 is amidated

<400> SEQUENCE: 225

His Gly Glu Gly Thr Phe Thr Ser Asp Val Ser Ser Tyr Leu Glu Xaa
1               5                   10                  15

Gln Ala Ala Glu Phe Ile Ala Trp Leu Val Lys Gly Arg Gly Cys Ser
            20                  25                  30

Gly

<210> SEQ ID NO 226
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: X is 4-carboxy-phenyl-alanine
```

```
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 226

His Gly Glu Gly Thr Phe Thr Ser Asp Val Ser Xaa Tyr Leu Glu Gln
1               5                   10                  15

Ala Ala Lys Glu Phe Ile Ala Trp Leu Val Lys Gly Arg Gly Xaa
            20                  25                  30

<210> SEQ ID NO 227
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 227

His Gly Glu Gly Thr Phe Thr Ser Asp Val Ser Ser Xaa Leu Glu Gly
1               5                   10                  15

Ala Ala Lys Glu Phe Ile Ala Trp Leu Val Lys Gly Arg Gly Xaa
            20                  25                  30

<210> SEQ ID NO 228
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 228

His Gly Glu Gly Thr Phe Thr Ser Asp Val Ser Ser Tyr Xaa Glu Gly
1               5                   10                  15

Gln Ala Lys Glu Phe Ile Ala Trp Leu Val Lys Gly Arg Gly Xaa
            20                  25                  30

<210> SEQ ID NO 229
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 229

His Gly Glu Gly Thr Phe Thr Ser Asp Val Ser Ser Tyr Leu Xaa Gly
```

```
1               5                   10                  15
Gln Ala Lys Glu Phe Ile Ala Trp Leu Val Lys Gly Arg Gly Xaa
            20                  25                  30

<210> SEQ ID NO 230
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 230

His Gly Glu Gly Thr Phe Thr Ser Asp Val Ser Ser Tyr Leu Glu Xaa
1               5                   10                  15

Gln Ala Ala Glu Phe Ile Ala Trp Leu Val Lys Gly Arg Gly Xaa
            20                  25                  30

<210> SEQ ID NO 231
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (17)..(17)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 231

His Gly Glu Gly Thr Phe Thr Ser Asp Val Ser Ser Tyr Leu Glu Gly
1               5                   10                  15

Xaa Ala Ala Lys Phe Ile Ala Trp Leu Val Lys Gly Arg Gly Xaa
            20                  25                  30

<210> SEQ ID NO 232
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 232

His Gly Glu Gly Thr Phe Thr Ser Asp Val Ser Ser Tyr Leu Glu Gly
1               5                   10                  15

Gln Xaa Ala Lys Glu Ile Ala Trp Leu Val Lys Gly Arg Gly Xaa
            20                  25                  30

<210> SEQ ID NO 233
<211> LENGTH: 31
```

```
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 233

His Gly Glu Gly Thr Phe Thr Ser Asp Val Ser Ser Tyr Leu Glu Gly
1               5                   10                  15

Gln Ala Xaa Lys Glu Phe Ala Trp Leu Val Lys Gly Arg Gly Xaa
            20                  25                  30

<210> SEQ ID NO 234
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 234

His Gly Glu Gly Thr Phe Thr Ser Asp Val Ser Ser Tyr Leu Glu Gly
1               5                   10                  15

Gln Ala Ala Xaa Glu Phe Ile Trp Leu Val Lys Gly Arg Gly Xaa
            20                  25                  30

<210> SEQ ID NO 235
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 235

His Gly Glu Gly Thr Phe Thr Ser Asp Val Ser Tyr Leu Glu Xaa Gln
1               5                   10                  15

Ala Ala Lys Glu Phe Ile Ala Trp Leu Val Lys Gly Arg Gly Xaa
            20                  25                  30

<210> SEQ ID NO 236
<211> LENGTH: 30
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: X is 4-carboxy-phenyl-alanine
```

```
<220> FEATURE:
<221> NAME/KEY: MISC_FEATURE
<222> LOCATION: (30)..(30)
<223> OTHER INFORMATION: Residue 30 is amidated

<400> SEQUENCE: 236

His Gly Glu Gly Thr Phe Thr Ser Asp Val Ser Ser Tyr Leu Glu Gln
 1               5                  10                  15

Ala Ala Xaa Glu Phe Ile Ala Trp Leu Val Lys Gly Arg Gly
            20                  25                  30

<210> SEQ ID NO 237
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: X is 4-carboxy-phenyl-alanine
<220> FEATURE:
<221> NAME/KEY: MISC_FEATURE
<222> LOCATION: (32)..(32)
<223> OTHER INFORMATION: Residue 32 is amidated

<400> SEQUENCE: 237

His Gly Glu Gly Thr Phe Thr Ser Asp Val Ser Ser Tyr Leu Glu Gln
 1               5                  10                  15

Ala Ala Xaa Glu Phe Ile Ala Trp Leu Val Lys Gly Arg Gly Cys Ala
            20                  25                  30

<210> SEQ ID NO 238
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: X is 4-carboxy-phenyl-alanine

<400> SEQUENCE: 238

His Gly Glu Gly Thr Phe Thr Ser Asp Val Ser Ser Tyr Leu Glu Gln
 1               5                  10                  15

Ala Ala Xaa Glu Phe Ile Ala Trp Leu Val Lys Gly Arg Gly Cys Ser
            20                  25                  30

Gly

<210> SEQ ID NO 239
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 239

His Gly Glu Gly Thr Phe Thr Ser Asp Val Ser Ser Leu Glu Gly Xaa
 1               5                  10                  15
```

Ala Ala Lys Glu Phe Ile Ala Trp Leu Val Lys Gly Arg Gly Xaa
            20                  25                  30

<210> SEQ ID NO 240
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (17)..(17)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 240

His Gly Glu Gly Thr Phe Thr Ser Asp Val Ser Ser Tyr Glu Gly Gln
1               5                   10                  15
Xaa Ala Lys Glu Phe Ile Ala Trp Leu Val Lys Gly Arg Gly Xaa
            20                  25                  30

<210> SEQ ID NO 241
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 241

His Gly Glu Gly Thr Phe Thr Ser Asp Val Ser Ser Tyr Leu Gly Gln
1               5                   10                  15
Ala Xaa Lys Glu Phe Ile Ala Trp Leu Val Lys Gly Arg Gly Xaa
            20                  25                  30

<210> SEQ ID NO 242
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 242

His Gly Glu Gly Thr Phe Thr Ser Asp Val Ser Ser Tyr Leu Glu Gln
1               5                   10                  15
Ala Ala Xaa Glu Phe Ile Ala Trp Leu Val Lys Gly Arg Gly Xaa
            20                  25                  30

<210> SEQ ID NO 243
<211> LENGTH: 31
<212> TYPE: PRT
<213> ORGANISM: Artificial

```
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 243

His Gly Glu Gly Thr Phe Thr Ser Asp Val Ser Ser Tyr Leu Glu Gly
1               5                   10                  15

Ala Ala Lys Xaa Phe Ile Ala Trp Leu Val Lys Gly Arg Gly Xaa
            20                  25                  30

<210> SEQ ID NO 244
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (21)..(21)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 244

His Gly Glu Gly Thr Phe Thr Ser Asp Val Ser Ser Tyr Leu Glu Gly
1               5                   10                  15

Gln Ala Lys Glu Xaa Ile Ala Trp Leu Val Lys Gly Arg Gly Xaa
            20                  25                  30

<210> SEQ ID NO 245
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (22)..(22)
<223> OTHER INFORMATION: X is 4-carboxy-phenyl-alanine
<220> FEATURE:
<221> NAME/KEY: MISC_FEATURE
<222> LOCATION: (31)..(31)
<223> OTHER INFORMATION: X is Lys, Orn, or Cys, and is amidated

<400> SEQUENCE: 245

His Gly Glu Gly Thr Phe Thr Ser Asp Val Ser Ser Tyr Leu Glu Gly
1               5                   10                  15

Gln Ala Lys Glu Phe Xaa Ala Trp Leu Val Lys Gly Arg Gly Xaa
            20                  25                  30

<210> SEQ ID NO 246
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (23)..(23)
<223> OTHER INFORMATION: X is 4-carboxy-phenyl-alanine
<220> FEATURE:
<221> NAME/KEY: MISC_FEATURE
```

```
<222> LOCATION: (31)..(31)
<223> OTHER INFORMATION: X is Lys, Orn, or Cys, and is amidated

<400> SEQUENCE: 246

His Gly Glu Gly Thr Phe Thr Ser Asp Val Ser Ser Tyr Leu Glu Gly
1               5                   10                  15

Gln Ala Ala Glu Phe Ile Xaa Trp Leu Val Lys Gly Arg Gly Xaa
            20                  25                  30

<210> SEQ ID NO 247
<211> LENGTH: 31
<212> TYPE: PRT
<213> ORGANISM: Artificial
<220> FEATURE:
<223> OTHER INFORMATION: Synthetic

<400> SEQUENCE: 247

Ala His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg
            20                  25                  30

<210> SEQ ID NO 248
<211> LENGTH: 31
<212> TYPE: PRT
<213> ORGANISM: Artificial
<220> FEATURE:
<223> OTHER INFORMATION: Synthetic

<400> SEQUENCE: 248

Gly His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg
            20                  25                  30

<210> SEQ ID NO 249
<211> LENGTH: 31
<212> TYPE: PRT
<213> ORGANISM: Artificial
<220> FEATURE:
<223> OTHER INFORMATION: Synthetic

<400> SEQUENCE: 249

Pro His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg
            20                  25                  30

<210> SEQ ID NO 250
<211> LENGTH: 31
<212> TYPE: PRT
<213> ORGANISM: Artificial
<220> FEATURE:
<223> OTHER INFORMATION: Synthetic

<400> SEQUENCE: 250

Ser His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg
            20                  25                  30

<210> SEQ ID NO 251
<211> LENGTH: 31
<212> TYPE: PRT
<213> ORGANISM: Artificial
```

```
<220> FEATURE:
<223> OTHER INFORMATION: Synthetic

<400> SEQUENCE: 251

Thr His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg
            20                  25                  30

<210> SEQ ID NO 252
<211> LENGTH: 31
<212> TYPE: PRT
<213> ORGANISM: Artificial
<220> FEATURE:
<223> OTHER INFORMATION: Synthetic

<400> SEQUENCE: 252

Val His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg
            20                  25                  30

<210> SEQ ID NO 253
<211> LENGTH: 32
<212> TYPE: PRT
<213> ORGANISM: Artificial
<220> FEATURE:
<223> OTHER INFORMATION: Synthetic

<400> SEQUENCE: 253

Met Gln His Ala Glu Gly Thr Phe Thr Ser Asp Val Ser Ser Tyr Leu
1               5                   10                  15

Glu Gly Gln Ala Ala Lys Glu Phe Ile Ala Trp Leu Val Lys Gly Arg
            20                  25                  30

<210> SEQ ID NO 254
<211> LENGTH: 32
<212> TYPE: PRT
<213> ORGANISM: Artificial
<220> FEATURE:
<223> OTHER INFORMATION: Synthetic

<400> SEQUENCE: 254

Met Arg His Ala Glu Gly Thr Phe Thr Ser Asp Val Ser Ser Tyr Leu
1               5                   10                  15

Glu Gly Gln Ala Ala Lys Glu Phe Ile Ala Trp Leu Val Lys Gly Arg
            20                  25                  30

<210> SEQ ID NO 255
<211> LENGTH: 32
<212> TYPE: PRT
<213> ORGANISM: Artificial
<220> FEATURE:
<223> OTHER INFORMATION: Synthetic

<400> SEQUENCE: 255

Met Lys His Ala Glu Gly Thr Phe Thr Ser Asp Val Ser Ser Tyr Leu
1               5                   10                  15

Glu Gly Gln Ala Ala Lys Glu Phe Ile Ala Trp Leu Val Lys Gly Arg
            20                  25                  30

<210> SEQ ID NO 256
<211> LENGTH: 31
<212> TYPE: PRT
<213> ORGANISM: Artificial
```

```
<220> FEATURE:
<223> OTHER INFORMATION: Synthetic

<400> SEQUENCE: 256

Met His Ala Glu Gly Thr Phe Thr Ser Asp Val Ser Ser Tyr Leu Glu
1               5                   10                  15
Gly Gln Ala Ala Lys Glu Phe Ile Ala Trp Leu Val Lys Gly Arg
            20                  25                  30

<210> SEQ ID NO 257
<211> LENGTH: 32
<212> TYPE: PRT
<213> ORGANISM: Artificial
<220> FEATURE:
<223> OTHER INFORMATION: Synthetic

<400> SEQUENCE: 257

Met His His Ala Glu Gly Thr Phe Thr Ser Asp Val Ser Ser Tyr Leu
1               5                   10                  15
Glu Gly Gln Ala Ala Lys Glu Phe Ile Ala Trp Leu Val Lys Gly Arg
            20                  25                  30

<210> SEQ ID NO 258
<211> LENGTH: 33
<212> TYPE: PRT
<213> ORGANISM: Artificial
<220> FEATURE:
<223> OTHER INFORMATION: Synthetic

<400> SEQUENCE: 258

Met His His His Ala Glu Gly Thr Phe Thr Ser Asp Val Ser Ser Tyr
1               5                   10                  15
Leu Glu Gly Gln Ala Ala Lys Glu Phe Ile Ala Trp Leu Val Lys Gly
            20                  25                  30
Arg

<210> SEQ ID NO 259
<211> LENGTH: 32
<212> TYPE: PRT
<213> ORGANISM: Artificial
<220> FEATURE:
<223> OTHER INFORMATION: Synthetic

<400> SEQUENCE: 259

Met Tyr His Ala Glu Gly Thr Phe Thr Ser Asp Val Ser Ser Tyr Leu
1               5                   10                  15
Glu Gly Gln Ala Ala Lys Glu Phe Ile Ala Trp Leu Val Lys Gly Arg
            20                  25                  30

<210> SEQ ID NO 260
<211> LENGTH: 32
<212> TYPE: PRT
<213> ORGANISM: Artificial
<220> FEATURE:
<223> OTHER INFORMATION: Synthetic

<400> SEQUENCE: 260

Met Ile His Ala Glu Gly Thr Phe Thr Ser Asp Val Ser Ser Tyr Leu
1               5                   10                  15
Glu Gly Gln Ala Ala Lys Glu Phe Ile Ala Trp Leu Val Lys Gly Arg
            20                  25                  30

<210> SEQ ID NO 261
<211> LENGTH: 32
```

```
<212> TYPE: PRT
<213> ORGANISM: Artificial
<220> FEATURE:
<223> OTHER INFORMATION: Synthetic

<400> SEQUENCE: 261

Met Asp His Ala Glu Gly Thr Phe Thr Ser Asp Val Ser Ser Tyr Leu
1               5                   10                  15
Glu Gly Gln Ala Ala Lys Glu Phe Ile Ala Trp Leu Val Lys Gly Arg
            20                  25                  30

<210> SEQ ID NO 262
<211> LENGTH: 32
<212> TYPE: PRT
<213> ORGANISM: Artificial
<220> FEATURE:
<223> OTHER INFORMATION: Synthetic

<400> SEQUENCE: 262

Met Leu His Ala Glu Gly Thr Phe Thr Ser Asp Val Ser Ser Tyr Leu
1               5                   10                  15
Glu Gly Gln Ala Ala Lys Glu Phe Ile Ala Trp Leu Val Lys Gly Arg
            20                  25                  30

<210> SEQ ID NO 263
<211> LENGTH: 32
<212> TYPE: PRT
<213> ORGANISM: Artificial
<220> FEATURE:
<223> OTHER INFORMATION: Synthetic

<400> SEQUENCE: 263

Met Asn His Ala Glu Gly Thr Phe Thr Ser Asp Val Ser Ser Tyr Leu
1               5                   10                  15
Glu Gly Gln Ala Ala Lys Glu Phe Ile Ala Trp Leu Val Lys Gly Arg
            20                  25                  30

<210> SEQ ID NO 264
<211> LENGTH: 32
<212> TYPE: PRT
<213> ORGANISM: Artificial
<220> FEATURE:
<223> OTHER INFORMATION: Synthetic

<400> SEQUENCE: 264

Met Glu His Ala Glu Gly Thr Phe Thr Ser Asp Val Ser Ser Tyr Leu
1               5                   10                  15
Glu Gly Gln Ala Ala Lys Glu Phe Ile Ala Trp Leu Val Lys Gly Arg
            20                  25                  30

<210> SEQ ID NO 265
<211> LENGTH: 32
<212> TYPE: PRT
<213> ORGANISM: Artificial
<220> FEATURE:
<223> OTHER INFORMATION: Synthetic

<400> SEQUENCE: 265

Met Trp His Ala Glu Gly Thr Phe Thr Ser Asp Val Ser Ser Tyr Leu
1               5                   10                  15
Glu Gly Gln Ala Ala Lys Glu Phe Ile Ala Trp Leu Val Lys Gly Arg
            20                  25                  30

<210> SEQ ID NO 266
<211> LENGTH: 32
```

<212> TYPE: PRT
<213> ORGANISM: Artificial
<220> FEATURE:
<223> OTHER INFORMATION: Synthetic

<400> SEQUENCE: 266

Met Phe His Ala Glu Gly Thr Phe Thr Ser Asp Val Ser Ser Tyr Leu
1               5                   10                  15

Glu Gly Gln Ala Ala Lys Glu Phe Ile Ala Trp Leu Val Lys Gly Arg
            20                  25                  30

<210> SEQ ID NO 267
<211> LENGTH: 32
<212> TYPE: PRT
<213> ORGANISM: Artificial
<220> FEATURE:
<223> OTHER INFORMATION: Synthetic

<400> SEQUENCE: 267

Met Met His Ala Glu Gly Thr Phe Thr Ser Asp Val Ser Ser Tyr Leu
1               5                   10                  15

Glu Gly Gln Ala Ala Lys Glu Phe Ile Ala Trp Leu Val Lys Gly Arg
            20                  25                  30

<210> SEQ ID NO 268
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (33)..(33)
<223> OTHER INFORMATION: Residue 33 is amidated

<400> SEQUENCE: 268

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Cys
            20                  25                  30

Ala

<210> SEQ ID NO 269
<211> LENGTH: 31
<212> TYPE: PRT
<213> ORGANISM: Artificial
<220> FEATURE:
<223> OTHER INFORMATION: Synthetic

<400> SEQUENCE: 269

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly
            20                  25                  30

<210> SEQ ID NO 270
<211> LENGTH: 31
<212> TYPE: PRT
<213> ORGANISM: Artificial
<220> FEATURE:
<223> OTHER INFORMATION: Synthetic

<400> SEQUENCE: 270

His Gly Glu Gly Thr Phe Thr Ser Asp Val Ser Ser Tyr Leu Glu Gly
1               5                   10                  15

-continued

Gln Ala Ala Lys Glu Phe Ile Ala Trp Leu Lys Asn Gly Gly Gly
            20                  25                  30

<210> SEQ ID NO 271
<211> LENGTH: 30
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (30)..(30)
<223> OTHER INFORMATION: Residue 30 is amidated

<400> SEQUENCE: 271

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 272
<211> LENGTH: 30
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: X is Aib
<220> FEATURE:
<221> NAME/KEY: MISC_FEATURE
<222> LOCATION: (30)..(30)
<223> OTHER INFORMATION: Residue 30 is amidated

<400> SEQUENCE: 272

His Gly Glu Gly Thr Phe Thr Ser Asp Leu Ser Lys Gln Met Glu Xaa
1               5                   10                  15

Glu Ala Val Arg Leu Phe Ile Glu Trp Leu Lys Asn Gly Gly
            20                  25                  30

<210> SEQ ID NO 273
<211> LENGTH: 26
<212> TYPE: PRT
<213> ORGANISM: Artificial
<220> FEATURE:
<223> OTHER INFORMATION: Synthetic

<400> SEQUENCE: 273

His Gly Glu Gly Thr Phe Thr Ser Asp Val Ser Ser Tyr Leu Glu Gly
1               5                   10                  15

Gln Ala Ala Lys Glu Phe Ile Ala Trp Leu
            20                  25

<210> SEQ ID NO 274
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: Residue 31 is amidated

<400> SEQUENCE: 274

His Gly Glu Gly Thr Phe Thr Ser Asp Val Ser Ser Tyr Leu Glu Glu
1               5                   10                  15

```
Gln Ala Lys Lys Glu Phe Ile Ala Trp Leu Val Lys Gly Arg Gly
            20                  25                  30
```

<210> SEQ ID NO 275
<211> LENGTH: 34
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (34)..(34)
<223> OTHER INFORMATION: Residue 34 is amidated

<400> SEQUENCE: 275

```
His Gly Glu Gly Thr Phe Thr Ser Asp Val Ser Ser Tyr Leu Glu Glu
1               5                   10                  15

Gln Ala Lys Lys Glu Phe Ile Ala Trp Leu Val Lys Gly Arg Gly Cys
            20                  25                  30

Gly Ser
```

<210> SEQ ID NO 276
<211> LENGTH: 33
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa at position 1 is  Met or omitted
<220> FEATURE:
<221> NAME/KEY: MISC_FEATURE
<222> LOCATION: (2)..(2)
<223> OTHER INFORMATION: Xaa at position 2 is  Met, His, or omitted
<220> FEATURE:
<221> NAME/KEY: MISC_FEATURE
<222> LOCATION: (3)..(3)
<223> OTHER INFORMATION: Xaa at position 3 is Met, Ala, Gly, Pro, Ser,
      Thr, Val, Gln, Arg, Lys, His, Tyr, Ile, Asp, Leu, Asn, Glu, Trp,
      or Phe
<220> FEATURE:
<221> NAME/KEY: MISC_FEATURE
<222> LOCATION: (33)..(33)
<223> OTHER INFORMATION: Residue 33 is attached to an carboxy group
      which is attached to an R1 group, wherein, R1 is OR2 or NR2R3;
      R2 and R3 are independently hydrogen or (C1-C8)alkyl

<400> SEQUENCE: 276

```
Xaa Xaa Xaa His Ala Glu Gly Thr Phe Thr Ser Asp Val Ser Ser Trp
1               5                   10                  15

Leu Glu Gly Gln Ala Ala Lys Glu Phe Ile Ala Trp Leu Val Lys Gly
            20                  25                  30

Arg
```

<210> SEQ ID NO 277
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: Residue 31 is amidated

<400> SEQUENCE: 277

```
His Gly Glu Gly Thr Phe Thr Ser Asp Val Ser Ser Tyr Leu Glu Gly
1               5                   10                  15
```

```
Gln Ala Lys Lys Glu Phe Ile Ala Trp Leu Glu Lys Gly Arg Lys
            20                  25                  30
```

<210> SEQ ID NO 278
<211> LENGTH: 4
<212> TYPE: PRT
<213> ORGANISM: Artificial
<220> FEATURE:
<223> OTHER INFORMATION: Synthetic

<400> SEQUENCE: 278

```
Cys Ser Gly Gly
1
```

<210> SEQ ID NO 279
<211> LENGTH: 31
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (20)..(20)
<223> OTHER INFORMATION: X is alpha, gamma-diaminobutyric acid

<400> SEQUENCE: 279

```
His Gly Glu Gly Thr Phe Thr Ser Asp Val Ser Ser Tyr Leu Glu Glu
1               5                   10                  15
Gln Ala Ala Xaa Glu Phe Ile Ala Trp Leu Val Lys Gly Arg Gly
            20                  25                  30
```

<210> SEQ ID NO 280
<211> LENGTH: 33
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (20)..(20)
<223> OTHER INFORMATION: X is alpha, gamma-diaminobutyric acid

<400> SEQUENCE: 280

```
His Gly Glu Gly Thr Phe Thr Ser Asp Val Ser Ser Tyr Leu Glu Glu
1               5                   10                  15
Gln Ala Ala Xaa Glu Phe Ile Ala Trp Leu Val Lys Gly Arg Gly Cys
            20                  25                  30
Ala
```

<210> SEQ ID NO 281
<211> LENGTH: 34
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (20)..(20)
<223> OTHER INFORMATION: X is alpha, gamma-diaminobutyric acid

<400> SEQUENCE: 281

```
His Gly Glu Gly Thr Phe Thr Ser Asp Val Ser Ser Tyr Leu Glu Glu
1               5                   10                  15
Gln Ala Ala Xaa Glu Phe Ile Ala Trp Leu Val Lys Gly Arg Gly Cys
            20                  25                  30
Ser Gly
```

```
<210> SEQ ID NO 282
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (16)..(16)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 282

His Gly Glu Gly Thr Phe Thr Ser Asp Val Ser Glu Tyr Leu Glu Xaa
 1               5                  10                  15

Gln Ala Ala Lys Glu Phe Ile Ala Trp Leu Val Lys Gly Arg Gly Xaa
             20                  25                  30

<210> SEQ ID NO 283
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (17)..(17)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 283

His Gly Glu Gly Thr Phe Thr Ser Asp Val Ser Ser Glu Leu Glu Gly
 1               5                  10                  15

Xaa Ala Ala Lys Glu Phe Ile Ala Trp Leu Val Lys Gly Arg Gly Xaa
             20                  25                  30

<210> SEQ ID NO 284
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (18)..(18)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 284

His Gly Glu Gly Thr Phe Thr Ser Asp Val Ser Ser Tyr Glu Glu Gly
 1               5                  10                  15

Gln Xaa Ala Lys Glu Phe Ile Ala Trp Leu Val Lys Gly Arg Gly Xaa
             20                  25                  30

<210> SEQ ID NO 285
<211> LENGTH: 32
<212> TYPE: PRT
<213> ORGANISM: Artificial
<220> FEATURE:
<223> OTHER INFORMATION: synthetic
<220> FEATURE:
```

```
<221> NAME/KEY: MISC_FEATURE
<222> LOCATION: (19)..(19)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 285

His Gly Glu Gly Thr Phe Thr Ser Asp Val Ser Ser Tyr Leu Glu Gly
1               5                   10                  15

Gln Ala Xaa Lys Glu Phe Ile Ala Trp Leu Val Lys Gly Arg Gly Xaa
            20                  25                  30

<210> SEQ ID NO 286
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (20)..(20)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 286

His Gly Glu Gly Thr Phe Thr Ser Asp Val Ser Ser Tyr Leu Glu Glu
1               5                   10                  15

Gln Ala Ala Xaa Glu Phe Ile Ala Trp Leu Val Lys Gly Arg Gly Xaa
            20                  25                  30

<210> SEQ ID NO 287
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (21)..(21)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 287

His Gly Glu Gly Thr Phe Thr Ser Asp Val Ser Ser Tyr Leu Glu Gly
1               5                   10                  15

Glu Ala Ala Lys Xaa Phe Ile Ala Trp Leu Val Lys Gly Arg Gly Xaa
            20                  25                  30

<210> SEQ ID NO 288
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (22)..(22)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated
```

-continued

```
<400> SEQUENCE: 288

His Gly Glu Gly Thr Phe Thr Ser Asp Val Ser Ser Tyr Leu Glu Gly
1               5                   10                  15

Gln Glu Ala Lys Glu Xaa Ile Ala Trp Leu Val Lys Gly Arg Gly Xaa
            20                  25                  30

<210> SEQ ID NO 289
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (23)..(23)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 289

His Gly Glu Gly Thr Phe Thr Ser Asp Val Ser Ser Tyr Leu Glu Gly
1               5                   10                  15

Gln Ala Glu Lys Glu Phe Xaa Ala Trp Leu Val Lys Gly Arg Gly Xaa
            20                  25                  30

<210> SEQ ID NO 290
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (24)..(24)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 290

His Gly Glu Gly Thr Phe Thr Ser Asp Val Ser Ser Tyr Leu Glu Gly
1               5                   10                  15

Gln Ala Ala Glu Glu Phe Ile Xaa Trp Leu Val Lys Gly Arg Gly Xaa
            20                  25                  30

<210> SEQ ID NO 291
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (20)..(20)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 291

His Gly Glu Gly Thr Phe Thr Ser Asp Val Ser Ser Tyr Leu Glu Gly
1               5                   10                  15

Gln Ala Ala Xaa Glu Phe Ile Ala Trp Leu Val Lys Gly Arg Gly Xaa
            20                  25                  30
```

<210> SEQ ID NO 292
<211> LENGTH: 31
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (16)..(16)
<223> OTHER INFORMATION: X is alpha, gamma-diaminobutyric acid
<220> FEATURE:
<221> NAME/KEY: MISC_FEATURE
<222> LOCATION: (31)..(31)
<223> OTHER INFORMATION: residue 31 is amidated

<400> SEQUENCE: 292

His Gly Glu Gly Thr Phe Thr Ser Asp Val Ser Ser Tyr Leu Glu Xaa
1               5                   10                  15

Gln Ala Ala Glu Glu Phe Ile Ala Trp Leu Val Lys Gly Arg Gly
            20                  25                  30

<210> SEQ ID NO 293
<211> LENGTH: 33
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (16)..(16)
<223> OTHER INFORMATION: X is alpha, gamma-diaminobutyric acid
<220> FEATURE:
<221> NAME/KEY: MISC_FEATURE
<222> LOCATION: (33)..(33)
<223> OTHER INFORMATION: residue 33 is amidated

<400> SEQUENCE: 293

His Gly Glu Gly Thr Phe Thr Ser Asp Val Ser Ser Tyr Leu Glu Xaa
1               5                   10                  15

Gln Ala Ala Glu Glu Phe Ile Ala Trp Leu Val Lys Gly Arg Gly Cys
            20                  25                  30

Ala

<210> SEQ ID NO 294
<211> LENGTH: 34
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (16)..(16)
<223> OTHER INFORMATION: X is alpha, gamma-diaminobutyric acid
<220> FEATURE:
<221> NAME/KEY: MISC_FEATURE
<222> LOCATION: (34)..(34)
<223> OTHER INFORMATION: residue 34 is amidated

<400> SEQUENCE: 294

His Gly Glu Gly Thr Phe Thr Ser Asp Val Ser Ser Tyr Leu Glu Xaa
1               5                   10                  15

Gln Ala Ala Glu Glu Phe Ile Ala Trp Leu Val Lys Gly Arg Gly Cys
            20                  25                  30

Ser Gly

<210> SEQ ID NO 295
<211> LENGTH: 32
<212> TYPE: PRT

```
<213> ORGANISM: Artificial
<220> FEATURE:
<223> OTHER INFORMATION: synthetic
<220> FEATURE:
<221> NAME/KEY: MISC_FEATURE
<222> LOCATION: (12)..(12)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 295

His Gly Glu Gly Thr Phe Thr Ser Asp Val Ser Xaa Tyr Leu Glu Glu
1               5                   10                  15

Gln Ala Ala Lys Glu Phe Ile Ala Trp Leu Val Lys Gly Arg Gly Xaa
            20                  25                  30

<210> SEQ ID NO 296
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (13)..(13)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 296

His Gly Glu Gly Thr Phe Thr Ser Asp Val Ser Ser Xaa Leu Glu Gly
1               5                   10                  15

Glu Ala Ala Lys Glu Phe Ile Ala Trp Leu Val Lys Gly Arg Gly Xaa
            20                  25                  30

<210> SEQ ID NO 297
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (14)..(14)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 297

His Gly Glu Gly Thr Phe Thr Ser Asp Val Ser Ser Tyr Xaa Glu Gly
1               5                   10                  15

Gln Glu Ala Lys Glu Phe Ile Ala Trp Leu Val Lys Gly Arg Gly Xaa
            20                  25                  30

<210> SEQ ID NO 298
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (15)..(15)
<223> OTHER INFORMATION: X is alpha, gamma-diaminobutyric acid
<220> FEATURE:
```

```
<221> NAME/KEY: MISC_FEATURE
<222> LOCATION: (32)..(32)
<223> OTHER INFORMATION: X is Lys, Orn, or Cys, and is amidated

<400> SEQUENCE: 298

His Gly Glu Gly Thr Phe Thr Ser Asp Val Ser Ser Tyr Leu Xaa Gly
1               5                   10                  15

Gln Ala Glu Lys Glu Phe Ile Ala Trp Leu Val Lys Gly Arg Gly Xaa
            20                  25                  30

<210> SEQ ID NO 299
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (16)..(16)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 299

His Gly Glu Gly Thr Phe Thr Ser Asp Val Ser Ser Tyr Leu Glu Xaa
1               5                   10                  15

Gln Ala Ala Glu Glu Phe Ile Ala Trp Leu Val Lys Gly Arg Gly Xaa
            20                  25                  30

<210> SEQ ID NO 300
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (17)..(17)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 300

His Gly Glu Gly Thr Phe Thr Ser Asp Val Ser Ser Tyr Leu Glu Gly
1               5                   10                  15

Xaa Ala Ala Lys Glu Phe Ile Ala Trp Leu Val Lys Gly Arg Gly Xaa
            20                  25                  30

<210> SEQ ID NO 301
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (18)..(18)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 301

His Gly Glu Gly Thr Phe Thr Ser Asp Val Ser Ser Tyr Leu Glu Gly
1               5                   10                  15
```

```
Gln Xaa Ala Lys Glu Glu Ile Ala Trp Leu Val Lys Gly Arg Gly Xaa
        20                  25                  30
```

<210> SEQ ID NO 302
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (19)..(19)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 302

```
His Gly Glu Gly Thr Phe Thr Ser Asp Val Ser Ser Tyr Leu Glu Gly
1               5                   10                  15

Gln Ala Xaa Lys Glu Phe Glu Ala Trp Leu Val Lys Gly Arg Gly Xaa
        20                  25                  30
```

<210> SEQ ID NO 303
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (20)..(20)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 303

```
His Gly Glu Gly Thr Phe Thr Ser Asp Val Ser Ser Tyr Leu Glu Gly
1               5                   10                  15

Gln Ala Ala Xaa Glu Phe Ile Glu Trp Leu Val Lys Gly Arg Gly Xaa
        20                  25                  30
```

<210> SEQ ID NO 304
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (15)..(15)
<223> OTHER INFORMATION: X is alpha, gamma-diaminobutyric acid
<220> FEATURE:
<221> NAME/KEY: MISC_FEATURE
<222> LOCATION: (32)..(32)
<223> OTHER INFORMATION: X is Lys, Orn, or Cys, and is amidated

<400> SEQUENCE: 304

```
His Gly Glu Gly Thr Phe Thr Ser Asp Val Ser Ser Tyr Leu Xaa Gly
1               5                   10                  15

Gln Ala Ala Glu Glu Phe Ile Ala Trp Leu Val Lys Gly Arg Gly Xaa
        20                  25                  30
```

GLP-1 COMPOUNDS

CROSS-REFERENCE TO RELATED APPLICATIONS

This application is a National Stage application under 35 U.S.C. §371 of International Application No. PCT/US2007/067150 (which designated the United States), having an international filing date of Apr. 20, 2007, which claims the benefit of U.S. Provisional Patent Application Ser. No. 60/793,707, filed Apr. 20, 2006, each of which is explicitly incorporated herein by reference in its entirety for all purposes.

REFERENCE TO THE SEQUENCE LISTING

The present application is being filed along with a Sequence Listing in electronic format. The Sequence Listing is provided as a file entitled A1113USPCT_SEQUENCE_LISTING RV2, created Oct. 26, 2009, which is 168 KB in size. The information in the electronic format of the Sequence Listing is incorporated herein by reference in its entirety.

BACKGROUND

Glucagon-like peptide 1 (GLP-1) and the related peptide glucagon are produced via differential processing of proglucagon and have opposing biological activities.

Proglucagon itself is produced in α-cells of the pancreas and in the enteroendocrine L-cells, which are located primarily in the distal small intestine and colon. In the pancreas, glucagon is selectively cleaved from proglucagon. In the intestine, in contrast, proglucagon is processed to form GLP-1 and glucagon-like peptide 2 (GLP-2), which correspond to amino acid residues 78-107 and 126-158 of proglucagon, respectively (see, e.g., Irwin and Wong, 1995, *Mol. Endocrinol.* 9:267-277 and Bell et al., 1983, *Nature* 304:368-371). By convention, the numbering of the amino acids of GLP-1 is based on the GLP-1 (1-37) formed from cleavage of proglucagon. The biologically active forms are generated from further processing of this peptide, which yields GLP-1 (7-37)-OH and GLP-1 (7-36)-NH$_2$. The first amino acid of these processed peptides is His7. Both GLP-1 (7-37)-OH (or simply GLP-1 (7-37)) and GLP-1 (7-36)-NH$_2$ have the same activities. For convenience, the term "GLP-1", is used to refer to both of these forms.

Glucagon is secreted from the α-cells of the pancreas in response to low blood glucose, with the main target organ for glucagon being the liver. Glucagon stimulates glycogen breakdown and inhibits glycogen biosynthesis. It also inhibits fatty acid synthesis, but enhances gluconeogenesis. The net result of these actions is to significantly increase the release of glucose from the liver. GLP-1, in contrast, lowers glucagon secretion, while stimulating insulin secretion, glucose uptake and cyclic-AMP (cAMP) formation in response to absorption of nutrients by the gut. Various clinical data provide evidence of these activities. The administration of GLP-1, for example, in poorly controlled type 2 diabetics normalized their fasting blood glucose levels (see, e.g., Gutniak, et al., 1992, *New Eng. J. Med.* 326:1316-1322).

GLP-1 has a number of other important activities. For instance, GLP-1 also inhibits gastric motility and gastric secretion (see, e.g., Tolessa, 1998, *J. Clin. Invest.* 102:764-774). This effect, sometimes referred to as the ileal brake effect, results in a lag phase in the availability of nutrients, thus significantly reducing the need for rapid insulin response.

Studies also indicate that GLP-1 can promote cell differentiation and replication, which in turn aids in the preservation of pancreatic islet cells and an increase in β-cell mass (See, e.g., Andreasen et al., 1994, *Digestion* 55:221-228; Wang, et al., 1997, *J. Clin. Invest.* 99:2883-2889; Mojsov, 1992, *Int. J. Pep. Prot. Res.* 40:333-343; and Xu et al., 1999, *Diabetes* 48:2270-2276). Evidence also indicates that GLP-1 can increase satiety and decrease food intake (see, e.g., Toft-Nielsen et al., 1999, *Diabetes Care* 22:1137-1143; Flint et al., 1998, *J. Clin. Invest.* 101:515-520; Gutswiller et al., 1999 *Gut* 44:81-86).

Other research indicates that GLP-1 induces β-cell-specific gene expression, including GLUT-1 transporter, insulin receptor and hexokinase-1 (see, e.g., Perfetti and Merkel, 2000, *Eur. J. Endocrinol.* 143:717-725). Such induction could reverse glucose intolerance often associated with aging.

Because GLP-1 plays a key role in regulating metabolic homeostasis, it is an attractive target for treating a variety of metabolic disorders, including diabetes, obesity and metabolic syndrome. Current treatments for diabetes include insulin injection and administration of sulfonylureas, metformin and TZDs. These approaches, however, have significant shortcomings. Insulin injections, for instance, require complicated dosing considerations, and treatment with sulfonylureas often becomes ineffective over time, metformin can induce hypoglycemia and TZDs have side effects such as body weight gain and edema. Potential advantages of GLP-1 therapy include: 1) increased safety because insulin secretion is dependent on hyperglycemia, 2) suppression of glucagon secretion which in turn suppresses excessive glucose output, and 3) slowing of gastric emptying, which in turn slows nutrient absorption and prevents sudden glucose increases.

A key hurdle for effective treatment with GLP-1, however, has been the very short half-life of the peptide, which typically is only a few minutes (see, e.g., Holst, 1994, *Gastroenterology* 107:1848-1855). Various analogs have been developed with the goal of extending the half-life of the molecule. Some of these, however, have significant gastrointestinal side effects, including vomiting and nausea (see, e.g., Agerso et al., 2002, *Diabetologia* 45:195-202).

Accordingly, there thus remains a need for improved molecules that have GLP-1 type activity, for use in the treatment of various metabolic diseases such as diabetes, obesity, irritable bowel syndrome and metabolic syndrome.

SUMMARY

GLP-1 compounds that comprise GLP-1 analogs and have an activity of GLP-1 (e.g., insulinotropic activity) are disclosed herein. Methods for treating a variety of diseases by administering an effective amount of the compositions are also provided.

Such methods can be used to treat, for example, diabetes, impaired glucose tolerance, insulin resistance, various lipid disorders, obesity, cardiovascular diseases and bone disorders.

Some of the GLP-1 compounds that are provided herein, for example, comprise a GLP-1 analog that comprises the amino acid sequence of formula I (SEQ ID NO: 5):

(Formula I, SEQ ID NO: 5)
Xaa$_7$-Gly-Xaa$_9$-Xaa$_{10}$-Xaa$_{11}$-Xaa$_{12}$-Xaa$_{13}$-Xaa$_{14}$-Xaa$_{15}$-
Xaa$_{16}$-Xaa$_{17}$-Xaa$_{18}$-Xaa$_{19}$-Xaa$_{20}$-Xaa$_{21}$-Xaa$_{22}$-Cys-

-continued

Xaa₂₄-Xaa₂₅-Xaa₂₆-Xaa₂₇-Xaa₂₈-Xaa₂₉-Xaa₃₀-Xaa₃₁-

Xaa₃₂-Xaa₃₃-Xaa₃₄-Gly-Xaa₃₆-Xaa₃₇-Ser-Ser-Gly-Ala-

Pro-Pro-Pro-Ser-C(O)-R₁ wherein,
- R₁ is OR₂ or NR₂R₃;
- R₂ and R₃ are independently hydrogen or (C₁-C₈)alkyl;
- Xaa at position 7 is: L-histidine, D-histidine, desamino-histidine, 2-amino-histidine, 3-hydroxy-histidine, homohistidine, α-fluoromethyl-histidine or α-methyl-histidine;
- Xaa at position 9 is Glu, Asp, or Lys;
- Xaa at position 10 is Gly or His;
- Xaa at position 11 is Thr, Ala, Gly, Ser, Leu, Ile, Val, Glu, Asp, or Lys;
- Xaa at position 12 is: His, Trp, Phe, or Tyr;
- Xaa at position 13 is Thr or Gly;
- Xaa at position 14 is Ser, Ala, Gly, Thr, Leu, Ile, Val, Glu, Asp, or Lys;
- Xaa at position 15 is Asp or Glu;
- Xaa at position 16 is Val, Ala, Gly, Ser, Thr, Leu, Ile, Tyr, Glu, Asp, Trp, or Lys;
- Xaa at position 17 is Ser, Ala, Gly, Thr, Leu, Ile, Val, Glu, Asp, or Lys;
- Xaa at position 18 is Ser, Ala, Gly, Thr, Leu, Ile, Val, Glu, Asp, Trp, Tyr, Lys, Homolysine, Ornithine, 4-carboxy-phenylalanine, beta-glutamic acid, beta-Homoglutamic acid, or homoglutamic acid;
- Xaa at position 19 is Tyr, Phe, Trp, Glu, Asp, Gln, Lys, Homolysine, Ornithine, 4-carboxy-phenylalanine, beta-glutamic acid, beta-Homoglutamic acid, or homoglutamic acid;
- Xaa at position 20 is Leu, Ala, Gly, Ser, Thr, Ile, Val, Glu, Asp, Met, Trp, Tyr, Lys, Homolysine, Ornithine, 4-carboxy-phenylalanine, beta-glutamic acid, or homoglutamic acid;
- Xaa at position 21 is Glu, Asp, Lys, Homolysine, Ornithine, 4-carboxy-phenylalanine, beta-glutamic acid, beta-Homoglutamic acid, or homoglutamic acid;
- Xaa at position 22 is Gly, Ala, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;
- Xaa at position 24 is Ala, Gly, Ser, Thr, Leu, Ile, Val, Arg, Glu, Asp, Lys, Homolysine, Ornithine, 4-carboxy-phenylalanine, beta-glutamic acid, beta-Homoglutamic acid, or homoglutamic acid;
- Xaa at position 25 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;
- Xaa at position 26 is Lys, Homolysine, Arg, Gln, Glu, Asp, His, Ornithine, 4-carboxy-phenylalanine, beta-glutamic acid, or homoglutamic acid;
- Xaa at position 27 is Leu, Glu, Asp, Lys, Homolysine, Ornithine, 4-carboxy-phenylalanine, beta-glutamic acid, beta-Homoglutamic acid, or homoglutamic acid;
- Xaa at position 28 is Phe, Trp, Asp, Glu, Lys, Homolysine, Ornithine, 4-carboxy-phenylalanine, beta-glutamic acid, beta-Homoglutamic acid, or homoglutamic acid;
- Xaa at position 29 is Ile, Leu, Val, Ala, Phe, Asp, Glu, Lys, Homolysine, Ornithine, 4-carboxy-phenylalanine, beta-glutamic acid, beta-Homoglutamic acid, or homoglutamic acid;
- Xaa at position 30 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;
- Xaa at position 31 is Trp, Phe, Tyr, Glu, Asp, or Lys;
- Xaa at position 32 is Leu, Gly, Ala, Ser, Thr, Ile, Val, Glu, Asp, or Lys;
- Xaa₃₃ is: Val or Lys;
- Xaa₃₄ is: Lys or Asn;
- Xaa₃₆ is: Arg or Gly;
- Xaa₃₇ is: Gly or Pro;

wherein the compound has a GLP-1 activity. In a particular aspect, the GLP-1 analog has the amino acid sequence of SEQ ID NO: 7 or 8 with no more than 5 conservative amino acid substitutions, provided that the conservative amino acid substitutions are not at amino acid Xaa₈, Xaa₂₃, or any of Xaa₃₈ to Xaa₄₅. In another particular aspect, the GLP-1 analog has the amino acid sequence of any of SEQ ID NO: 7 or 8.

Other GLP-1 compounds as provided herein comprise a GLP-1 analog that comprises the amino acid sequence of formula II (SEQ ID NO: 9)

(Formula II, SEQ ID NO: 9)
Xaa₇-Xaa₈-Xaa₉-Xaa₁₀-Xaa₁₁-Xaa₁₂-Xaa₁₃-Xaa₁₄-

Xaa₁₅-Xaa₁₆-Xaa₁₇-Xaa₁₈-Xaa₁₉-Xaa₂₀-Xaa₂₁-Xaa₂₂

Xaa₂₃-Xaa₂₄-Xaa₂₅-Xaa₂₆-Xaa₂₇-Xaa₂₈-Xaa₂₉-Xaa₃₀

Xaa₃₁-Xaa₃₂-Xaa₃₃-Xaa₃₄-Xaa₃₅-Xaa₃₆-Xaa₃₇-Cys-Ser-

Gly-Gly-C(O)-R₁ wherein,
- R₁ is OR₂ or NR₂R₃;
- R₂ and R₃ are independently hydrogen or (C₁-C₈)alkyl;
- Xaa at position 7 is: L-histidine, D-histidine, desamino-histidine, 2-amino-histidine, 3-hydroxy-histidine, homohistidine, α-fluoromethyl-histidine or α-methyl-histidine;
- Xaa at position 8 is Gly, bAla (2-aminopropionic acid), 1-amino-cylcopentanecarboxylic acid, Aib (2-aminoisobutryic acid) or an alpha-alpha-disubstituted amino acid;
- Xaa at position 9 is Glu, Asp, or Lys;
- Xaa at position 10 is Gly or His;
- Xaa at position 11 is Thr, Ala, Gly, Ser, Leu, Ile, Val, Glu, Asp, or Lys;
- Xaa at position 12 is: His, Trp, Phe, or Tyr;
- Xaa at position 13 is Thr or Gly;
- Xaa at position 14 is Ser, Ala, Gly, Thr, Leu, Ile, Val, Glu, Asp, or Lys;
- Xaa at position 15 is Asp or Glu;
- Xaa at position 16 is Val, Ala, Gly, Ser, Thr, Leu, Ile, Tyr, Glu, Asp, Trp, or Lys;
- Xaa at position 17 is Ser, Ala, Gly, Thr, Leu, Ile, Val, Glu, Asp, or Lys;
- Xaa at position 18 is Ser, Ala, Gly, Thr, Leu, Ile, Val, Glu, Asp, Trp, Tyr, Lys, Homolysine, Ornithine, 4-carboxy-phenylalanine, beta-glutamic acid, beta-Homoglutamic acid, or homoglutamic acid;
- Xaa at position 19 is Tyr, Phe, Trp, Glu, Asp, Gln, Lys, Homolysine, Ornithine, 4-carboxy-phenylalanine, beta-glutamic acid, beta-Homoglutamic acid, or homoglutamic acid;
- Xaa at position 20 is Leu, Ala, Gly, Ser, Thr, Ile, Val, Glu, Asp, Met, Trp, Tyr, Lys, Homolysine, Ornithine, 4-carboxy-phenylalanine, beta-glutamic acid, or homoglutamic acid;

Xaa at position 21 is Glu, Asp, Lys, Homolysine, Ornithine, 4-carboxy-phenylalanine, beta-glutamic acid, beta-Homoglutamic acid, or homoglutamic acid;

Xaa at position 22 is Gly, Ala, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;

Xaa at position 23 is Gln, Asn, Arg, Glu, Asp, Lys, Ornithine, 4-carboxy-phenylalanine, beta-glutamic acid, beta-Homoglutamic acid, or homoglutamic acid;

Xaa at position 24 is Ala, Gly, Ser, Thr, Leu, Ile, Val, Arg, Glu, Asp, Lys, Homolysine, Ornithine, 4-carboxy-phenylalanine, beta-glutamic acid, beta-Homoglutamic acid, or homoglutamic acid;

Xaa at position 25 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;

Xaa at position 26 is Lys, Homolysine, Arg, Gln, Glu, Asp, His, Ornithine, 4-carboxy-phenylalanine, beta-glutamic acid, or homoglutamic acid;

Xaa at position 27 is Leu, Glu, Asp, Lys, Homolysine, Ornithine, 4-carboxy-phenylalanine, beta-glutamic acid, beta-Homoglutamic acid, or homoglutamic acid;

Xaa at position 28 is Phe, Trp, Asp, Glu, Lys, Homolysine, Ornithine, 4-carboxy-phenylalanine, beta-glutamic acid, beta-Homoglutamic acid, or homoglutamic acid;

Xaa at position 29 is Ile, Leu, Val, Ala, Phe, Asp, Glu, Lys, Homolysine, Ornithine, 4-carboxy-phenylalanine, beta-glutamic acid, beta-Homoglutamic acid, or homoglutamic acid;

Xaa at position 30 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;

Xaa at position 31 is Trp, Phe, Tyr, Glu, Asp, or Lys;

Xaa at position 32 is Leu, Gly, Ala, Ser, Thr, Ile, Val, Glu, Asp, or Lys;

Xaa at position 33 is Val, Gly, Ala, Ser, Thr, Leu, Ile, Glu, Asp, or Lys;

Xaa at position 34 is Asn, Lys, Arg, Glu, Asp, or His;

Xaa at position 35 is Gly, Ala, Ser, Thr, Leu, Ile, Val, Glu, Asp, or Lys;

Xaa at position 36 is Gly, Arg, Lys, Glu, Asp, or His;

Xaa at position 37 is Pro, Gly, Ala, Ser, Thr, Leu, Ile, Val, Glu, Asp, or Lys;

wherein the compound has a GLP-1 activity. In a particular aspect, the GLP-1 analog has the amino acid sequence of SEQ ID NO: 11 or 12 with no more than 5 conservative amino acid substitutions, provided that the conservative amino acid substitutions are not at amino acid $Xaa_8$ or any of $Xaa_{38}$ to $Xaa_{41}$. In another particular aspect, the GLP-1 analog has the amino acid sequence of SEQ ID NO: 11 or 12.

Still other GLP-1 compounds as provided herein comprise a GLP-1 analog that comprises the amino acid sequence of formula III (SEQ ID NO: 13)

(Formula III, SEQ ID NO: 13)
$Xaa_7$-$Xaa_8$-$Xaa_9$-$Xaa_{10}$-$Xaa_{11}$-$Xaa_{12}$-$Xaa_{13}$-$Xaa_{14}$-

$Xaa_{15}$-$Xaa_{16}$-$Xaa_{17}$-$Xaa_{18}$-$Xaa_{19}$-$Xaa_{20}$-$Xaa_{21}$-$Xaa_{22}$-

$Xaa_{23}$-$Xaa_{24}$-$Xaa_{25}$-$Xaa_{26}$-$Xaa_{27}$-$Xaa_{28}$-$Xaa_{29}$-$Xaa_{30}$-

$Xaa_{31}$-$Xaa_{32}$-$Xaa_{33}$-$Xaa_{34}$-$Xaa_{35}$-$Xaa_{36}$-Gly-$Xaa_{38}$-

$Xaa_{39}$-$Xaa_{40}$-$Xaa_{41}$-C(O)-$R_1$ wherein, $R_1$ is $OR_2$ or $NR_2R_3$;

$R_2$ and $R_3$ are independently hydrogen or $(C_1$-$C_8)$alkyl;

Xaa at position 7 is: L-histidine, D-histidine, desamino-histidine, 2-amino-histidine, 3-hydroxy-histidine, homohistidine, α-fluoromethyl-histidine or α-methyl-histidine;

Xaa at position 8 is Gly, bAla (2-aminopropionic acid), 1-amino-cylcopentanecarboxylic acid, Aib (2-aminoisobutyric acid) or an alpha-alpha-disubstituted amino acid;

Xaa at position 9 is Glu, Asp, or Lys;

Xaa at position 10 is Gly or His;

Xaa at position 11 is Thr, Ala, Gly, Ser, Leu, Ile, Val, Glu, Asp, or Lys;

Xaa at position 12 is His, Trp, Phe, or Tyr;

Xaa at position 13 is Thr or Gly;

Xaa at position 14 is Ser, Ala, Gly, Thr, Leu, Ile, Val, Glu, Asp, or Lys;

Xaa at position 15 is Asp or Glu;

Xaa at position 16 is Val, Ala, Gly, Ser, Thr, Leu, Ile, Tyr, Glu, Asp, Trp, or Lys;

Xaa at position 17 is Ser, Ala, Gly, Thr, Leu, Ile, Val, Glu, Asp, or Lys;

Xaa at position 18 is Ser, Ala, Gly, Thr, Leu, Ile, Val, Glu, Asp, Trp, Tyr, Lys, Homolysine, Ornithine, 4-carboxy-phenylalanine, beta-glutamic acid, beta-Homoglutamic acid, or homoglutamic acid;

Xaa at position 19 is Tyr, Phe, Trp, Glu, Asp, Gln, Lys, Homolysine, Ornithine, 4-carboxy-phenylalanine, beta-glutamic acid, beta-Homoglutamic acid, or homoglutamic acid;

Xaa at position 20 is Leu, Ala, Gly, Ser, Thr, Ile, Val, Glu, Asp, Met, Trp, Tyr, Lys, Homolysine, Ornithine, 4-carboxy-phenylalanine, beta-glutamic acid, or homoglutamic acid;

Xaa at position 21 is Glu, Asp, Lys, Homolysine, Ornithine, 4-carboxy-phenylalanine, beta-glutamic acid, beta-Homoglutamic acid, or homoglutamic acid;

Xaa at position 22 is Aib (2-aminoisobutyric acid), 1-amino-cylcopentanecarboxylic acid, an alpha-alpha-disubstituted amino acid, or Aad (2-aminoadipic acid);

Xaa at position 23 is Gln, Asn, Arg, Glu, Asp, Lys, Ornithine, 4-carboxy-phenylalanine, beta-glutamic acid, beta-Homoglutamic acid, or homoglutamic acid;

Xaa at position 24 is Ala, Gly, Ser, Thr, Leu, Ile, Val, Arg, Glu, Asp, Lys, Homolysine, Ornithine, 4-carboxy-phenylalanine, beta-glutamic acid, beta-Homoglutamic acid, or homoglutamic acid;

Xaa at position 25 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;

Xaa at position 26 is Lys, Homolysine, Arg, Gln, Glu, Asp, His, Ornithine, 4-carboxy-phenylalanine, beta-glutamic acid, or homoglutamic acid;

Xaa at position 27 is Leu, Glu, Asp, Lys, Homolysine, Ornithine, 4-carboxy-phenylalanine, beta-glutamic acid, beta-Homoglutamic acid, or homoglutamic acid;

Xaa at position 28 is Phe, Trp, Asp, Glu, Lys, Homolysine, Ornithine, 4-carboxy-phenylalanine, beta-glutamic acid, beta-Homoglutamic acid, or homoglutamic acid;

Xaa at position 29 is Ile, Leu, Val, Ala, Phe, Asp, Glu, Lys, Homolysine, Ornithine, 4-carboxy-phenylalanine, beta-glutamic acid, beta-Homoglutamic acid, or homoglutamic acid;

Xaa at position 30 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;

Xaa at position 31 is Trp, Phe, Tyr, Glu, Asp, or Lys;

Xaa at position 32 is Leu, Gly, Ala, Ser, Thr, Ile, Val, Glu, Asp, or Lys;

Xaa at position 33 is Val, Gly, Ala, Ser, Thr, Leu, Ile, Glu, Asp, or Lys;

Xaa at position 34 is Asn, Lys, Arg, Glu, Asp, or His;

Xaa at position 35 is Gly, Ala, Ser, Thr, Leu, Ile, Val, Glu, Asp, or Lys;

Xaa at position 36 is Gly, Arg, Lys, Glu, Asp, or His;

Xaa at position 38 is Cys, Gly, or is omitted;

Xaa at position 39 is Ala, Gly, Ser, Cys, or is omitted;

Xaa at position 40 is Gly or is omitted;

Xaa at position 41 is Gly or is omitted;

provided that when the amino acid at position 38, 39, 40, or 41 is omitted, then each amino acid downstream of that amino acid is also omitted, and wherein the compound has a GLP-1 activity. In a particular aspect, the GLP-1 analog has the amino acid sequence of any of SEQ ID NO: 16 to 28 with no more than 5 conservative amino acid substitutions, provided that the conservative amino acid substitutions are not at amino acid $Xaa_8$, $Xaa_{22}$, or any of $Xaa_{38}$ to $Xaa_{41}$. In another particular aspect, the GLP-1 analog has the amino acid sequence of any of SEQ ID NO: 16 to 28.

Certain GLP-1 compounds as provided herein comprise a GLP-1 analog that comprises the amino acid sequence of Formula IV (SEQ ID NO: 29)

(Formula IV, SEQ ID NO: 29)
$Xaa_7$-$Xaa_8$-$Xaa_9$-$Xaa_{10}$-$Xaa_{11}$-$Xaa_{12}$-$Xaa_{13}$-$Xaa_{14}$-

$Xaa_{15}$-$Xaa_{16}$-$Xaa_{17}$-$Xaa_{18}$-$Xaa_{19}$-$Xaa_{20}$-$Xaa_{21}$-$Xaa_{22}$-

$Xaa_{23}$-$Xaa_{24}$-$Xaa_{25}$-$Xaa_{26}$-$Xaa_{27}$-$Xaa_{28}$-$Xaa_{29}$-$Xaa_{30}$-

$Xaa_{31}$-$Xaa_{32}$-$Xaa_{33}$-$Xaa_{34}$-$Xaa_{35}$-$Xaa_{36}$-$Xaa_{37}$-$Xaa_{38}$-

$Xaa_{39}$-$Xaa_{40}$-$Xaa_{41}$C(O)–$R_1$ wherein, $R_1$ is $OR_2$ or $NR_2R_3$;

$R_2$ and $R_3$ are independently hydrogen or $(C_1-C_8)$alkyl;

Xaa at position 7 is: L-histidine, D-histidine, desamino-histidine, 2-amino-histidine, 3-hydroxy-histidine, homohistidine, α-fluoromethyl-histidine or α-methyl-histidine;

Xaa at position 8 is Gly, bAla (2-aminopropionic acid), 1-amino-cylcopentanecarboxylic acid, 2-aminoisobutryic acid or an alpha-alpha-disubstituted amino acid;

Xaa at position 9 is Glu, Asp, or Lys;

Xaa at position 10 is Gly or His;

Xaa at position 11 is Thr, Ala, Gly, Ser, Leu, Ile, Val, Glu, Asp, or Lys;

Xaa at position 12 is: His, Trp, Phe, or Tyr;

Xaa at position 13 is Thr or Gly;

Xaa at position 14 is Ser, Ala, Gly, Thr, Leu, Ile, Val, Glu, Asp, or Lys;

Xaa at position 15 is Asp or Glu;

Xaa at position 16 is Val, Ala, Gly, Ser, Thr, Leu, Ile, Tyr, Glu, Asp, Trp, or Lys;

Xaa at position 17 is Ser, Ala, Gly, Thr, Leu, Ile, Val, Glu, Asp, or Lys;

Xaa at position 18 is Ser, Ala, Gly, Thr, Leu, Ile, Val, Glu, Asp, Trp, Tyr, Lys, Homolysine, Ornithine, 4-carboxy-phenylalanine, beta-glutamic acid, beta-Homoglutamic acid, or homoglutamic acid;

Xaa at position 19 is Tyr, Phe, Trp, Glu, Asp, Gln, Lys, Homolysine, Ornithine, 4-carboxy-phenylalanine, beta-glutamic acid, beta-Homoglutamic acid, alpha, gamma-diaminobutryic acid, or homoglutamic acid;

Xaa at position 20 is Leu, Ala, Gly, Ser, Thr, Ile, Val, Glu, Asp, Met, Trp, Tyr, Lys, Homolysine, Ornithine, 4-carboxy-phenylalanine, beta-glutamic acid, alpha, gamma-diaminobutryic acid, or homoglutamic acid;

Xaa at position 21 is Glu, Asp, Lys, Homolysine, Ornithine, 4-carboxy-phenylalanine, beta-glutamic acid, beta-Homoglutamic acid, or alpha, gamma-diaminobutryic acid, homoglutamic acid;

Xaa at position 22 is Gly, Ala, Ser, Thr, Leu, Ile, Val, Glu, Asp, Lys, Homolysine, Ornithine, 4-carboxy-phenylalanine, beta-glutamic acid, beta-Homoglutamic acid, alpha, gamma-diaminobutryic acid, or homoglutamic acid;

Xaa at position 23 is Gln, Asn, Arg, Glu, Asp, Lys, Ornithine, 4-carboxy-phenylalanine, beta-glutamic acid, beta-Homoglutamic acid, alpha, gamma-diaminobutryic acid, or homoglutamic acid;

Xaa at position 24 is Ala, Gly, Ser, Thr, Leu, Ile, Val, Arg, Glu, Asp, Lys, Homolysine, Ornithine, 4-carboxy-phenylalanine, beta-glutamic acid, beta-Homoglutamic acid, alpha, gamma-diaminobutryic acid, or homoglutamic acid;

Xaa at position 25 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, alpha, gamma-diaminobutryic acid, or homoglutamic acid;

Xaa at position 26 is Lys, Homolysine, Arg, Gln, Glu, Asp, His, Ornithine, 4-carboxy-phenylalanine, beta-glutamic acid, alpha, gamma-diaminobutryic acid, or homoglutamic acid;

Xaa at position 27 is Leu, Glu, Asp, Lys, Homolysine, Ornithine, 4-carboxy-phenylalanine, beta-glutamic acid, beta-Homoglutamic acid, alpha, gamma-diaminobutryic acid, or homoglutamic acid;

Xaa at position 28 is Phe, Trp, Asp, Glu, Lys, Homolysine, Ornithine, 4-carboxy-phenylalanine, beta-glutamic acid, beta-Homoglutamic acid, alpha, gamma-diaminobutryic acid, or homoglutamic acid;

Xaa at position 29 is Ile, Leu, Val, Ala, Phe, Asp, Glu, Lys, Homolysine, Ornithine, 4-carboxy-phenylalanine, beta-glutamic acid, beta-Homoglutamic acid, alpha, gamma-diaminobutryic acid, or homoglutamic acid;

Xaa at position 30 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, alpha, gamma-diaminobutryic acid, or homoglutamic acid;

Xaa at position 31 is Trp, Phe, Tyr, Glu, Asp, or Lys;

Xaa at position 32 is Leu, Gly, Ala, Ser, Thr, Ile, Val, Glu, Asp, or Lys;

Xaa at position 33 is Val, Gly, Ala, Ser, Thr, Leu, Ile, Glu, Asp, or Lys;

Xaa at position 34 is Asn, Lys, Arg, Glu, Asp, or His;

Xaa at position 35 is Gly, Ala, Ser, Thr, Leu, Ile, Val, Glu, Asp, or Lys;

Xaa at position 36 is Gly, Arg, Lys, Glu, Asp, or His;

Xaa at position 37 is Pro, Gly, Ala, Ser, Thr, Leu, Ile, Val, Glu, Asp, or Lys;

Xaa at position 38 is Gly, Ser, Lys, Cys, or is omitted;

Xaa at position 39 is Gly, Ala, Ser, Thr, Ile, Val, Leu, Phe, Pro, Cys or is omitted;

Xaa at position 40 is Gly, Cys, or is omitted;

Xaa at position 41 is Gly or is omitted;

wherein two amino acids selected from $Xaa_{18}$, $Xaa_{19}$, $Xaa_{20}$, $Xaa_{21}$, $Xaa_{22}$, $Xaa_{23}$, $Xaa_{24}$, $Xaa_{25}$, $Xaa_{26}$, $Xaa_{27}$, $Xaa_{28}$, $Xaa_{29}$, and $Xaa_{30}$ are joined to form a ring and the two amino acids forming the ring are separated by 0, 1, 2, 3, 4 or 5 amino acids, and wherein the compound has a GLP-1 activity. In a particular aspect, the GLP-1 analog has the amino acid sequence of any of SEQ ID NO: 30 to 246 with no more than 5 conservative amino acid substitutions. In another particular aspect, the GLP-1 analog has the amino acid sequence of any of SEQ ID NO: 30 to 246.

In still another aspect, a GLP-1 compound as provided herein comprises a GLP-1 analog comprising the amino acid sequence shown in formula VI:

(Formula VI, SEQ ID NO: 276)
$Xaa_4$-$Xaa_5$-$Xaa_6$-$His_7$-$Ala_8$-$Glu_9$-$Gly_{10}$-$Thr_{11}$-$Phe_{12}$-

$Thr_{13}$-$Ser_{14}$-$Asp_{15}$-$Val_{16}$-$Ser_{17}$-$Ser_{18}$-$Tyr_{19}$-$Leu_{20}$-

$Glu_{21}$-$Gly_{22}$-$Gln_{23}$-$Ala_{24}$-$Ala_{25}$-$Lys_{26}$-$Glu_{27}$-$Phe_{28}$-

$Ile_{29}$-$Ala_{30}$-$Trp_{31}$-$Leu_{32}$-$Val_{33}$-$Lys_{34}$-$Gly_{35}$-$Arg_{36}$-

C(O)-$R_1$ wherein, $R_1$ is $OR_2$ or $NR_2R_3$;

$R_2$ and $R_3$ are independently hydrogen or ($C_1$-$C_8$)alkyl;

Xaa at position 4 is: Met or omitted;

Xaa at position 5 is: Met, His, or omitted;

Xaa at position 6 is: Met, Ala, Gly, Pro, Ser, Thr, Val, Gln, Arg, Lys, His, Tyr, Ile, Asp, Leu, Asn, Glu, Trp, or Phe; provided that when the amino acid at position 5 is omitted, then the amino acid at position 4 is also omitted, wherein the compound has a GLP-1 activity.

Also provided are pharmaceutical compositions comprising a pharmaceutically acceptable carrier and an effective amount of a GLP-1 compound as described herein.

In addition, methods are provided for treating a subject with a metabolic disorder, comprising administering to the subject an effective amount of a GLP-1 compound as provided herein or a pharmaceutical composition comprising a GLP-1 compound as provided herein, wherein the metabolic disorder is selected from the group of diabetes, obesity and metabolic syndrome.

In addition, methods are provided for enhancing insulin expression in a subject and methods for promoting insulin secretion in a subject, comprising administering to the subject an effective amount of a GLP-1 compound as provided herein or a pharmaceutical composition comprising a GLP-1 compound as provided herein.

In certain aspects, a GLP-1 compound as provided herein can be covalently modified with a water-soluble polymer, such as polyethylene glycol, monomethoxy-polyethylene glycol, dextran, cellulose, poly-(N-vinyl pyrrolidone) polyethylene glycol, propylene glycol homopolymers, polypropylene oxide/ethylene oxide co-polymers, polyoxyethylated polyols, or polyvinyl alcohol.

Specific embodiments will become evident from the following more detailed description of certain embodiments and the claims.

DETAILED DESCRIPTION

I. Definitions

Figure 1:
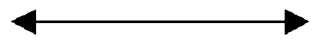
FIG. 1 is a schematic representation of examples of the positions within GLP-1 separated by 3 amino acids that can be joined to form a cyclic lactam.
Figure 2A:
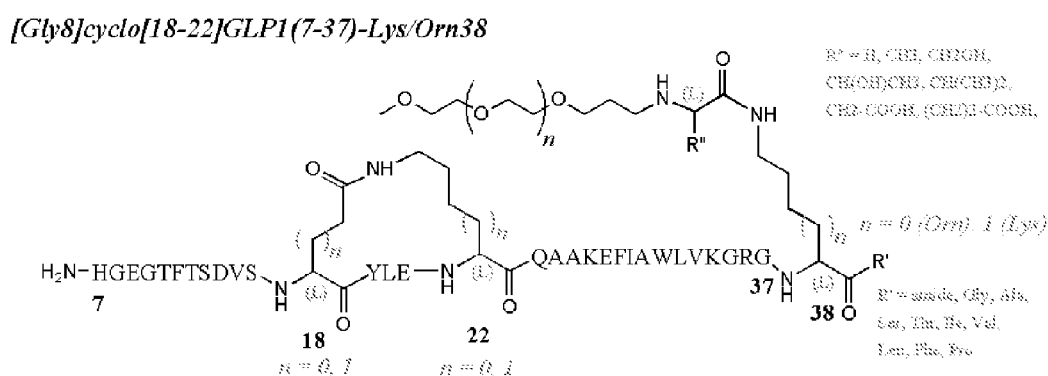
FIGS. 2A through 2I depict chemical structures of exemplary GLP-1 analogs in which the side chains of a glutamic acid/lysine amino acid pair are joined to form a ring. GLP-1 residues are shown in single letter code, whereas atoms for expanded amino acids are shown using normal chemical abbreviations for the elements. The number of ethylene glycol repeating units —[CH2CH2-O]n- can vary depending on the size of polyeyhleneglycol desired (e.g, 5 kDa to 60 kDa).
Figure 2B:
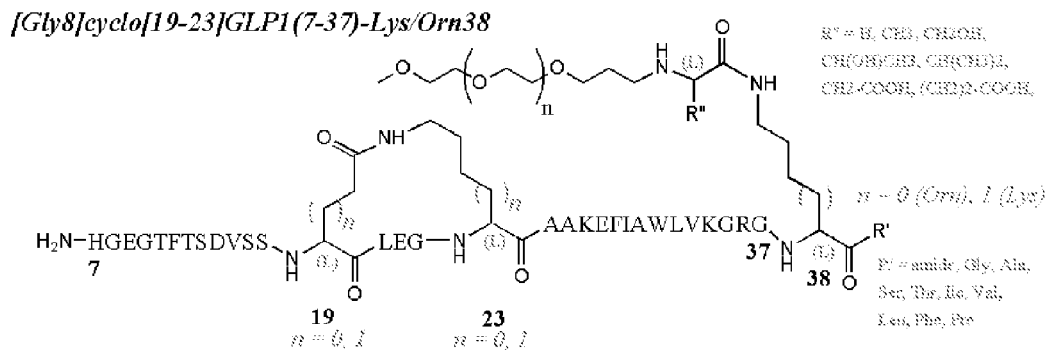
Figure 2C:
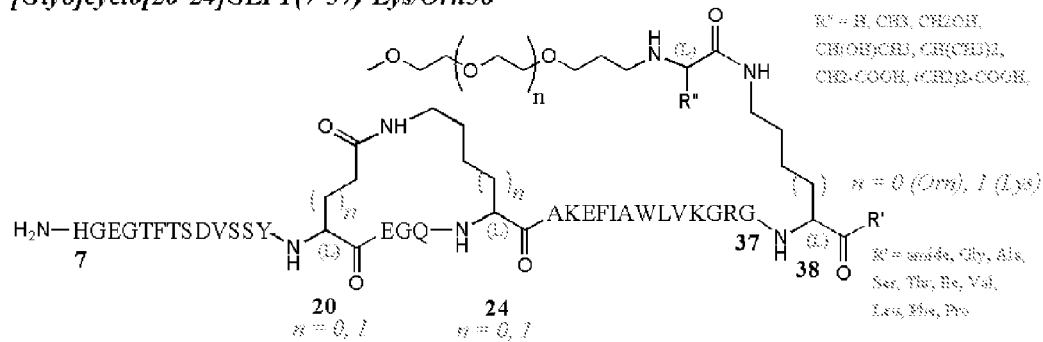
Figure 2D:
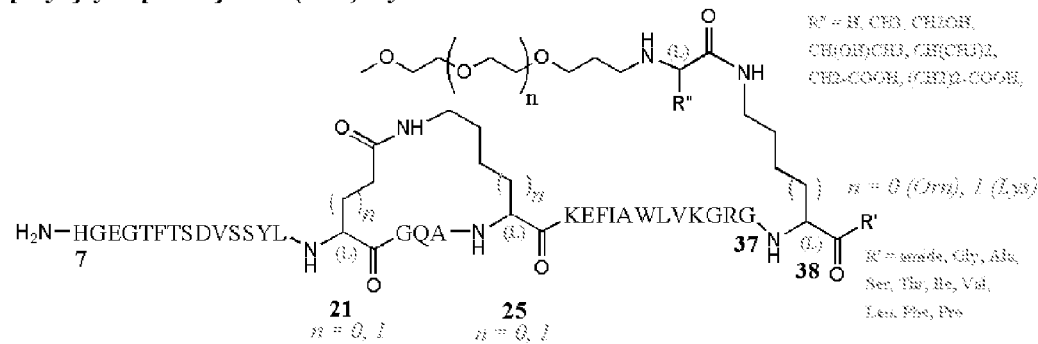
Figure 2E:
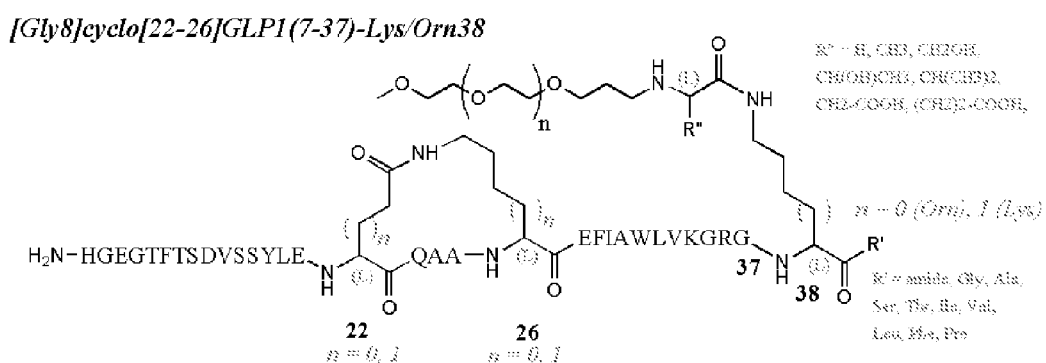
Figure 2F:
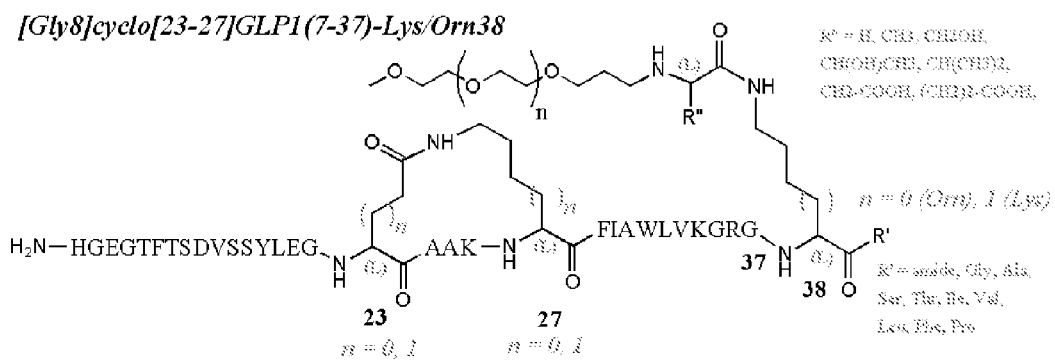
Figure 2G:
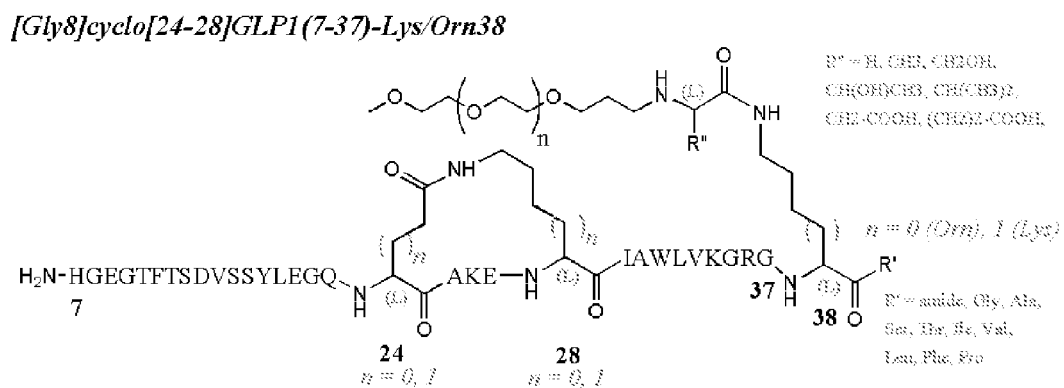
Figure 2H:
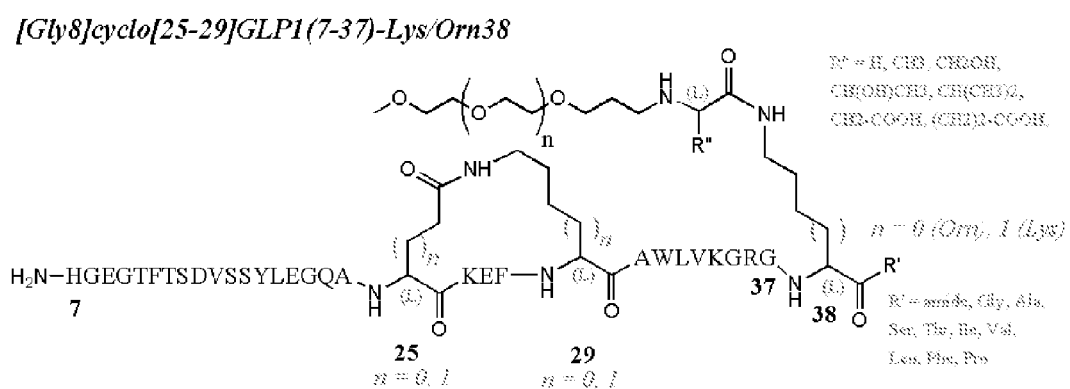
Figure 2I:
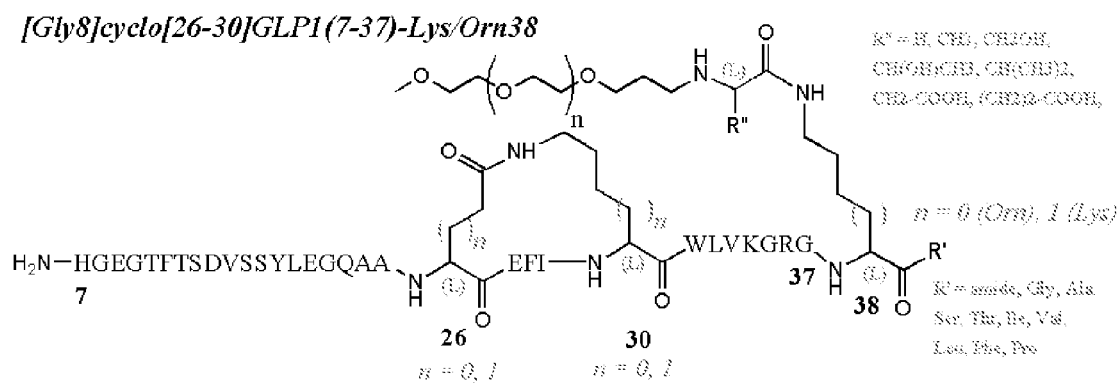

As used in this specification and the appended claims, the singular forms "a," "an" and "the" include plural references unless the content clearly dictates otherwise.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991).

As used herein, the following terms have the meanings ascribed to them unless specified otherwise.

"Insulinotropic activity" refers to the ability to increase insulin synthesis, release or secretion in a glucose-dependent manner. The insulinotropic effect can result from any of a number of different mechanisms, including, but not limited to, an increase in the number of insulin positive cells and/or due to an increase in the amount of insulin synthesized or released from existing insulin positive cells in a given time period.

Insulinotropic activity can be assayed using methods known in the art, such as in vivo and in vitro experiments that measure GLP-1 receptor binding activity or receptor activation (for example, assays using pancreatic islet cells or insulinoma cells as described in EP 619,322 and U.S. Pat. No. 5,120,712). In humans, insulinotropic activity can be measured by examining insulin levels or C-peptide levels.

The terms "nucleic acid," "polynucleotide," and "oligonucleotide" are used herein to include a polymeric form of nucleotides of any length, including, but not limited to, ribonucleotides or deoxyribonucleotides.

"Polypeptide" and "protein" are used interchangeably herein and include a molecular chain of amino acids linked through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or unnatural amino acids are included.

The terms "identical" or percent "identity," in the context of two or more nucleic acids or polypeptides, refer to two or more sequences or subsequences that are the same or have a specified percentage of nucleotides or amino acid residues that are the same, when compared and aligned for maximum correspondence, as measured using a sequence comparison algorithm such as those described below for example, or by visual inspection.

The phrase "substantially identical" as used herein refers to two or more sequences or subsequences that have at least 75%, preferably at least 85%, more preferably at least 90%, 95%, 96%, 97%, 98%, 99% or higher nucleotide or amino acid residue identity, when compared and aligned for maximum correspondence, as measured using a sequence comparison algorithm such as those described below for example, or by visual inspection. Most preferably the sequences are substantially identical over the full length of the sequences being compared, such as the coding region of a nucleotide for example.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, 1981, *Adv. Appl. Math.* 2:482, by the homology alignment algorithm of Needleman & Wunsch, 1970, *J. Mol. Biol.* 48:443, by the search for similarity method of Pearson & Lipman, 1988, *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection [see generally, Current Protocols in Molecular Biology, (Ausubel, F. M. et al., eds.) John Wiley & Sons, Inc., New York (1987-1999, including supplements such as supplement 46 (April 1999)]. Use of these programs to conduct sequence comparisons are typically conducted using the default parameters specific for each program.

Another example of algorithm that is suitable for determining percent sequence identity and sequence similarity is the BLAST algorithm, which is described in Altschul et al., 1990, *J. Mol. Biol.* 215:403-410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, 1989, *Proc. Natl. Acad. Sci. USA* 89:10915).

In addition to calculating percent sequence identity, the BLAST algorithm also performs a statistical analysis of the similarity between two sequences (see, e.g., Karlin & Altschul, 1993, *Proc. Nat'l. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A polypeptide is typically substantially identical to a second polypeptide, for example, where the two polypeptides differ only by conservative substitutions. A "conservative substitution" when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are described herein and are well-known in the art (see, e.g., Creighton, 1984, Proteins, W.H. Freeman and Company). In addition, individual substitutions, deletions or additions that alter, add or delete a single amino acid or a small percentage of amino acids in an encoded sequence without substantially altering the protein's activity are also "conservatively modified variations."

As used herein, the twenty conventional amino acids and their single letter and three letter abbreviations follow conventional usage. See IMMUNOLOGY—A SYNTHESIS, 2nd Edition, (E. S. Golub and D. R. Gren, Eds.), Sinauer Associates: Sunderland, Mass., 1991, incorporated herein by reference for any purpose. Stereoisomers (e.g., D-amino acids) of the twenty conventional amino acids; unnatural amino acids such as α-, α-disubstituted amino acids, N-alkyl amino acids, lactic acid, and other unconventional amino acids may also be suitable components for polypeptides provided herein. Examples of unconventional amino acids include: 4-hydroxyproline, γ-carboxyglutamate, εN,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). Certain amino acid analogs that are referrenced herein are abbreviated as follows:

bAla is beta-aminopropionic acid;
J is Aad (2-aminoadipic acid; also called homoglutamic acid);
Z is Aib (2-aminoisobutyric acid);
O is ornithine;
Cpa is 4-carboxy-phenylalanine; and
B is beta glutamic acid.

When amino acids abbreviations are separated by a forward slash (i.e., a "/"), this means that any one of the amino acids separated by the forward slash can occur at the indicated position. For instance, K/O/C means that any one of lysine, ornithine or cysteine can occur at the indicated position.

The term alpha-alpha disubstituted amino acids as used herein has its normal meaning in the art and includes, for example, alpha-methyl-leucine, alpha-methyl-phenylalanine, alpha-methyl-tryptophan, 4-amino-1-piperidine, 2-amino-2,2-diphenylacetic acid.

In the polypeptide notation used herein, the left-hand direction is the amino terminal direction and the right-hand direction is the carboxyl-terminal direction, in accordance with standard usage and convention. The term "downstream" when used in reference to a GLP-1 compound means positions that are located toward the carboxyl end of the polypeptide relative to the position being referenced, i.e., to the right of the position being referenced. The term "upstream" when used in reference to a GLP-1 compound means positions that are located toward the amino terminal end of the polypeptide relative to the position being referenced, i.e., to the left of the position being referenced. The recommended IUPAC-IUB Nomenclature and Symbolism for Amino Acids and Peptides have been published in J. Biochem., 1984, 219, 345-373; Eur. J. Biochem., 1984, 138, 9-37; 1985, 152, 1; 1993, 213, 2; Internat. J. Pept. Prot. Res., 1984, 24, following p 84; J. Biol. Chem., 1985, 260, 14-42; Pure Appl. Chem., 1984, 56, 595-624; Amino Acids and Peptides, 1985, 16, 387-410; Biochemical Nomenclature and Related Documents, 2nd edition, Portland Press, 1992, pages 39-69.

Naturally occurring residues may be divided into classes based on common side chain properties:
1) hydrophobic: norleucine (Nor), Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. Such substituted residues may be introduced into regions of the human antibody that are homologous with non-human antibodies, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

Herein, the use of the protecting groups, linkers, and solid phase supports, as well as specific protection and deprotection reaction conditions, linker cleavage conditions, use of scavengers, and other aspects of solid phase peptide synthesis are well known and are also described in "Protecting Groups in Organic Synthesis," 3rd Edition, T. W. Greene and P. G. M. Wuts, Eds., John Wiley & Sons, Inc., 1999; NovaBiochem Catalog, 2000; "Synthetic Peptides, A User's Guide," G. A. Grant, Ed., W.H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L. Peterson, M. R. Rhodes, and H. H. Saneii, Eds., Advanced Chemtech, 1998; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; "Protecting Groups," P. J. Kocienski, Ed., Georg Thieme Verlag, Stuttgart, Germany, 1994; "Fmoc Solid Phase Peptide Synthesis, A Practical Approach," W. C. Chan and P. D. White, Eds., Oxford Press, 2000, G. B. Fields et al., Synthetic Peptides: A User's Guide, 1990, 77-183, and elsewhere.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose to not make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See, for example, Moult, 1996, *Curr. Op. in Biotech.* 7:422-427; Chou et al, 1974, *Biochemistry* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276; and Chou et al., 1979, *Biophys. J.* 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-87; Sippl et al., 1996, Structure 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (See Holm, 1999, supra; and Brenner, 1997, supra).

According to certain embodiments, amino acid substitutions are those that: (1) reduce susceptibility to proteolysis, (2) reduce susceptibility to oxidation, (3) alter binding affinity for forming protein complexes, (4) alter binding affinities, and/or (5) confer or modify other physicochemical or functional properties on such polypeptides.

According to certain embodiments, single or multiple amino acid substitutions (in certain embodiments, conservative amino acid substitutions) may be made in the naturally occurring sequence (in certain embodiments, in the portion of the polypeptide outside the domain(s) forming intermolecular contacts). In certain embodiments, a conservative amino acid substitution typically does not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in PROTEINS, STRUCTURES AND MOLECULAR PRINCIPLES, (Creighton, Ed.), 1984, W. H. Freeman and Company, New York; INTRODUCTION TO PROTEIN STRUCTURE (C. Branden and J. Tooze, eds.), 1991, Garland Publishing, New York, N.Y.; and Thornton et al., 1991, *Nature* 354:105, each of which are incorporated herein by reference.

Peptide analogs are commonly used in the pharmaceutical industry as non-peptide drugs with properties analogous to those of the template peptide. These types of non-peptide compound are termed "peptide mimetics" or "peptidomimetics". See Fauchere, 1986, *Adv. Drug Res.* 15:29; Veber & Freidinger, 1985, *TINS* p. 392; and Evans et al., 1987, *J. Med. Chem.* 30:1229, which are incorporated herein by reference for any purpose. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —$CH_2$—NH—, —$CH_2$—S—, —$CH_2$—$CH_2$—, —CH=CH-(cis and trans), —$COCH_2$—, —CH(OH)$CH_2$—, and —$CH_2$SO—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo & Gierasch, 1992, *Ann. Rev. Biochem.* 61:387, incorporated herein by reference for any purpose); for example, by adding internal cysteine residues capable of forming intramolecular disulfide bridges which cyclize the peptide.

II. Overview

A variety of GLP-1 compounds are provided herein that comprise a GLP-1 analog, and which retain at least one activity of GLP-1. The GLP-1 analogs that are disclosed include one or more of the following characteristics: 1) amino acid substitutions at particular locations of GLP-1, 2) added amino acids at the N-terminus and/or the C-terminus of GLP-1, 3) absence of amino acids at the N-terminus and/or the C-terminus of GLP-1, and/or 4) presence of a ring formed by joining the side chains of specific amino acids with the polypeptide.

As described in greater detail below, the GLP-1 compounds that are provided can be administered therapeutically or prophylactically to treat a variety of diseases.

Examples of diseases that can be treated with the compounds include, but are not limited to, diabetes, impaired glucose tolerance, insulin resistance, hyperglycemia, metabolic syndrome, various lipid disorders, obesity, coronary diseases, bone disorders, and irritable bowel syndrome.

III. GLP-1 Compounds

A. Structure

As noted above, the term "GLP-1" refers to GLP-1 (7-37)-OH and GLP-1 (7-36)-$NH_2$. The numbering of the amino acids of GLP-1 as used herein is based on GLP-1 (1-37) formed from cleavage of proglucagon.

Native GLP-1 (7-37)-OH has the following amino acid sequence:

(SEQ ID NO: 1)
$^7$His-$^8$Ala-$^9$Glu-$^{10}$Gly-$^{11}$Thr-$^{12}$Phe-$^{13}$Thr-$^{14}$Ser- $^{15}$Asp-$^{16}$Val-$^{17}$Ser-$^{18}$Ser-$^{19}$Tyr-$^{20}$Leu-$^{21}$Glu-$^{22}$Gly- $^{23}$Gln-$^{24}$Ala-$^{25}$Ala-$^{26}$Lys-$^{27}$Glu-$^{28}$Phe-$^{29}$Ile-$^{30}$Ala- $^{31}$Trp-$^{32}$Leu-$^{33}$Val-$^{34}$Lys-$^{35}$Gly-$^{36}$Arg-$^{37}$Gly.

As indicated in this formula, the amino terminal His residue is customarily referred to as amino acid residue 7 to reflect processing from GLP-1 (1-37); the carboxyl terminal Gly in turn is conventionally referred to as amino acid residue 37. As described in the Background section, the carboxyl terminus of GLP-1 (7-37)-OH can be cleaved to produce GLP-1 (7-36)-$NH_2$. The other amino acids located between these two termini are numbered consecutively as shown. Thus, for example, the amino acid at position 8 is Ala and the amino acid at position 26 is Lys. Likewise, when reference is made herein to making a substitution at a specified position, the same numbering system applies. Hence, for example, a substitution of Ala at position 22 means that the Gly at position 22 has been substituted with Ala. If amino acids are added at the amino terminus of GLP-1 (7-36), the positions are consecutively numbered in decreasing order, such that the amino acid immediately upstream of position 7 is amino acid 6, and the next upstream amino acid is at position 5 and so on. If amino acids are added at the carboxyl terminus of GLP-1 (7-36), the positions are consecutively numbered in increasing order, such that the amino acid immediately downstream of position 36 is amino acid 37, and the next downstream amino acid is at position 38 and so on. As discussed above, both GLP-1 (7-37)-OH, also referred to as GLP-1 (7-37), and GLP-1 (7-36)-NH₂ have the same activities. For convenience, the terms "GLP-1" and "native GLP-1" are used to refer to both of these biologically active forms.

A "GLP-1 compound" as used herein refers to a molecule that comprises a GLP-1 analog and may include one or more additional components (e.g., a component that extends the half-life of the compound in vivo).

The phase "GLP-1 activity" or grammatical equivalents thereof refers broadly to any activity associated with GLP-1. Examples of such activities include, but are not limited to, insulinotropic activity, inhibition of gastric motility, inhibition of gastric secretion, promotion of β-cell proliferation and replication, increase in β-cell mass, increase in satiety and decrease in food intake when GLP-1 is administered to a subject.

As used herein, the term "GLP-1 analog" refers to a polypeptide with one or more alterations in the amino acid sequence of native GLP-1 (7-37)-OH or GLP-1 (7-36)-NH2 but that retains at least one activity of native GLP-1. The GLP-1 analogs as provided herein as described herein include, for example, specific amino acid substitutions at particular residues of GLP-1. Some of the analogs also include added amino acid residues at the C-terminus, whereas others are shortened at the C-terminus. The GLP-1 analogs as provided herein markedly decrease blood glucose levels in various in vivo models and have extended half-lives relative to native GLP-1. As described herein, the GLP-1 analogs can be pegylated with one or more molecules of polyethylene glycol (PEG) to increase the in vivo half-life of the analog. Alternatively, GLP-1 analogs can be joined to another polypeptide to form a fusion protein, as described herein. In the formulas listed herein, R₁ can be a carboxyl group, an amine, an ester, or a substituted amine. Thus, the GLP-1 analogs as provided herein can have a carboxyl or an amide group at its C-terminal end.

In certain embodiments, a GLP-1 analog as provided herein has one or more of the following characteristics:
  1) One or more amino acid substitutions (e.g., 1, 2, 3, 4, 5, 6, 7, 8, 9, or 10) relative to GLP-1;
  2) The addition of one or more additional amino acid residues at the C-terminus or N-terminus of GLP-1 (e.g., 1, 2, 3, 4, 5, 6, 7, 8, 9 or 10 amino acids);
  3) Truncation of one or more amino acids at the N- or C-terminus (typically by 1, 2, 3, 4 or 5 amino acids); and/or
  4) A cyclic ring structure formed between side-chains on certain amino acids within the analog.

Certain GLP-1 analogs that are provided, for instance, include a specific amino acid substitution at one or more of positions 8, 22, 23, 26, 33, 34, 35, 36, and/or 37, including, but not limited to, the following substitutions:
  ⁸Ala: substitution with Gly, 2-aminoisobutryic acid (Aib) or beta-aminopropionic acid (bAla);
  ²²Gly: substitution with 2-aminoisobutyric acid (Aib), 1-amino-cylcopentanecarboxylic acid, an alpha-alpha-disubstituted amino acid, or 2-aminoadipic acid;
  ²³Gln: substitution with Cys;
  ²⁶Lys: substitution with ornithine or homolysine;
  ³³Val: substitution with Lys;
  ³⁴Lys: substitution with Asn;
  ³⁶Arg: substitution with Gly;
  ³⁷Gly: substitution with Pro.

Some of the GLP-1 analogs include specific C-terminal extensions, including, for instance, the addition of Cys, Cys-Ala, Cys-Gly, Cys-Ser-Gly, Cys-Ser-Gly-Gly (SEQ ID NO: 278), or Gly-Cys (each of the foregoing being listed in the amino to carboxyl direction) to the amino acid at position 37.

Other GLP-1 analogs include specific N-terminal additions such as the addition of Met, Ala, Gly, Pro, Ser, Thr, Val, Gln, Arg, Lys, His, Tyr, Ile, Asp, Leu, Asn, Glu, Trp or Phe at the N-terminus of GLP-1. Some analogs are extended at the N-terminus by the addition of a MQ, MR, MK, MH, MY, MI, MD, ML, MN, ME, MW, MF or MM dipeptide to the amino terminus. Still other analogs have a MHH tripeptide added to the amino terminus.

The GLP-1 analogs can for ease of discussion be classified into certain families of molecules that share certain structural features. These can be most readily described by the general Formulas provided as follows.

One family, for instance, comprises or consists of the amino acid sequence shown in formula I:

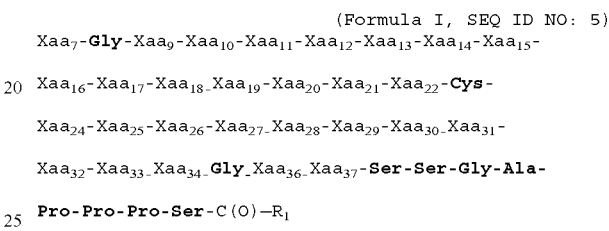

wherein,
  $R_1$ is $OR_2$ or $NR_2R_3$;
  $R_2$ and $R_3$ are independently hydrogen or $(C_1-C_8)$alkyl;
  Xaa at position 7 is: L-histidine, D-histidine, desamino-histidine, 2-amino-histidine, 3-hydroxy-histidine, homohistidine, α-fluoromethyl-histidine or α-methyl-histidine;
  Xaa at position 9 is Glu, Asp, or Lys;
  Xaa at position 10 is Gly or His;
  Xaa at position 11 is Thr, Ala, Gly, Ser, Leu, Ile, Val, Glu, Asp, or Lys;
  Xaa at position 12 is: His, Trp, Phe, or Tyr;
  Xaa at position 13 is Thr or Gly;
  Xaa at position 14 is Ser, Ala, Gly, Thr, Leu, Ile, Val, Glu, Asp, or Lys;
  Xaa at position 15 is Asp or Glu;
  Xaa at position 16 is Val, Ala, Gly, Ser, Thr, Leu, Ile, Tyr, Glu, Asp, Trp, or Lys;
  Xaa at position 17 is Ser, Ala, Gly, Thr, Leu, Ile, Val, Glu, Asp, or Lys;
  Xaa at position 18 is Ser, Ala, Gly, Thr, Leu, Ile, Val, Glu, Asp, Trp, Tyr, Lys, Homolysine, Ornithine, 4-carboxy-phenylalanine, beta-glutamic acid, beta-Homoglutamic acid, or homoglutamic acid;
  Xaa at position 19 is Tyr, Phe, Trp, Glu, Asp, Gln, Lys, Homolysine, Ornithine, 4-carboxy-phenylalanine, beta-glutamic acid, beta-Homoglutamic acid, or homoglutamic acid;
  Xaa at position 20 is Leu, Ala, Gly, Ser, Thr, Ile, Val, Glu, Asp, Met, Trp, Tyr, Lys, Homolysine, Ornithine, 4-carboxy-phenylalanine, beta-glutamic acid, or homoglutamic acid;
  Xaa at position 21 is Glu, Asp, Lys, Homolysine, Ornithine, 4-carboxy-phenylalanine, beta-glutamic acid, beta-Homoglutamic acid, or homoglutamic acid;
  Xaa at position 22 is Gly, Ala, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;
  Xaa at position 24 is Ala, Gly, Ser, Thr, Leu, Ile, Val, Arg, Glu, Asp, Lys, Homolysine, Ornithine, 4-carboxy-phenylalanine, beta-glutamic acid, beta-Homoglutamic acid, or homoglutamic acid;

Xaa at position 25 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;

Xaa at position 26 is Lys, Homolysine, Arg, Gln, Glu, Asp, His, Ornithine, 4-carboxy-phenylalanine, beta-glutamic acid, or homoglutamic acid;

Xaa at position 27 is Leu, Glu, Asp, Lys, Homolysine, Ornithine, 4-carboxy-phenylalanine, beta-glutamic acid, beta-Homoglutamic acid, or homoglutamic acid;

Xaa at position 28 is Phe, Trp, Asp, Glu, Lys, Homolysine, Ornithine, 4-carboxy-phenylalanine, beta-glutamic acid, beta-Homoglutamic acid, or homoglutamic acid;

Xaa at position 29 is Ile, Leu, Val, Ala, Phe, Asp, Glu, Lys, Homolysine, Ornithine, 4-carboxy-phenylalanine, beta-glutamic acid, beta-Homoglutamic acid, or homoglutamic acid;

Xaa at position 30 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;

Xaa at position 31 is Trp, Phe, Tyr, Glu, Asp, or Lys;

Xaa at position 32 is Leu, Gly, Ala, Ser, Thr, Ile, Val, Glu, Asp, or Lys;

$Xaa_{33}$ is: Val or Lys;

$Xaa_{34}$ is: Lys or Asn;

$Xaa_{36}$ is: Arg or Gly;

$Xaa_{37}$ is: Gly or Pro;

wherein the compound has a GLP-1 activity.

In the formulas listed herein, $R_1$ can be a carboxyl group, an amine, an ester, or a substituted amine. Thus, the GLP-1 analogs as provided herein can have a carboxyl or an amide group at its C-terminal end.

A second family of GLP-1 analogs comprises or consists of the amino acid sequence shown in formula II:

(Formula II, SEQ ID NO: 9)
$Xaa_7$-$Xaa_8$-$Xaa_9$-$Xaa_{10}$-$Xaa_{11}$-$Xaa_{12}$-$Xaa_{13}$-$Xaa_{14}$-

$Xaa_{15}$-$Xaa_{16}$-$Xaa_{17}$-$Xaa_{18}$-$Xaa_{19}$-$Xaa_{20}$-$Xaa_{21}$-$Xaa_{22}$-

$Xaa_{23}$-$Xaa_{24}$-$Xaa_{25}$-$Xaa_{26}$-$Xaa_{27}$-$Xaa_{28}$-$Xaa_{29}$-$Xaa_{30}$-

$Xaa_{31}$-$Xaa_{32}$-$Xaa_{33}$-$Xaa_{34}$-$Xaa_{35}$-$Xaa_{36}$-$Xaa_{37}$-Cys-Ser-Gly-Gly-C(O)-$R_1$ wherein, $R_1$ is $OR_2$ or $NR_2R_3$;

$R_2$ and $R_3$ are independently hydrogen or $(C_1-C_8)$alkyl;

Xaa at position 7 is: L-histidine, D-histidine, desamino-histidine, 2-amino-histidine, 3-hydroxy-histidine, homohistidine, α-fluoromethyl-histidine or α-methyl-histidine;

Xaa at position 8 is Gly, bAla (2-aminopropionic acid), 1-amino-cylcopentanecarboxylic acid, 2-aminoisobutryic acid or an alpha-alpha-disubstituted amino acid;

Xaa at position 9 is Glu, Asp, or Lys;

Xaa at position 10 is Gly or His;

Xaa at position 11 is Thr, Ala, Gly, Ser, Leu, Ile, Val, Glu, Asp, or Lys;

Xaa at position 12 is: His, Trp, Phe, or Tyr;

Xaa at position 13 is Thr or Gly;

Xaa at position 14 is Ser, Ala, Gly, Thr, Leu, Ile, Val, Glu, Asp, or Lys;

Xaa at position 15 is Asp or Glu;

Xaa at position 16 is Val, Ala, Gly, Ser, Thr, Leu, Ile, Tyr, Glu, Asp, Trp, or Lys;

Xaa at position 17 is Ser, Ala, Gly, Thr, Leu, Ile, Val, Glu, Asp, or Lys;

Xaa at position 18 is Ser, Ala, Gly, Thr, Leu, Ile, Val, Glu, Asp, Trp, Tyr, Lys, Homolysine, Ornithine, 4-carboxy-phenylalanine, beta-glutamic acid, beta-Homoglutamic acid, or homoglutamic acid;

Xaa at position 19 is Tyr, Phe, Trp, Glu, Asp, Gln, Lys, Homolysine, Ornithine, 4-carboxy-phenylalanine, beta-glutamic acid, beta-Homoglutamic acid, or homoglutamic acid;

Xaa at position 20 is Leu, Ala, Gly, Ser, Thr, Ile, Val, Glu, Asp, Met, Trp, Tyr, Lys, Homolysine, Ornithine, 4-carboxy-phenylalanine, beta-glutamic acid, or homoglutamic acid;

Xaa at position 21 is Glu, Asp, Lys, Homolysine, Ornithine, 4-carboxy-phenylalanine, beta-glutamic acid, beta-Homoglutamic acid, or homoglutamic acid;

Xaa at position 22 is Gly, Ala, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;

Xaa at position 23 is Gln, Asn, Arg, Glu, Asp, Lys, Ornithine, 4-carboxy-phenylalanine, beta-glutamic acid, beta-Homoglutamic acid, or homoglutamic acid;

Xaa at position 24 is Ala, Gly, Ser, Thr, Leu, Ile, Val, Arg, Glu, Asp, Lys, Homolysine, Ornithine, 4-carboxy-phenylalanine, beta-glutamic acid, beta-Homoglutamic acid, or homoglutamic acid;

Xaa at position 25 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;

Xaa at position 26 is Lys, Homolysine, Arg, Gln, Glu, Asp, His, Ornithine, 4-carboxy-phenylalanine, beta-glutamic acid, or homoglutamic acid;

Xaa at position 27 is Leu, Glu, Asp, Lys, Homolysine, Ornithine, 4-carboxy-phenylalanine, beta-glutamic acid, beta-Homoglutamic acid, or homoglutamic acid;

Xaa at position 28 is Phe, Trp, Asp, Glu, Lys, Homolysine, Ornithine, 4-carboxy-phenylalanine, beta-glutamic acid, beta-Homoglutamic acid, or homoglutamic acid;

Xaa at position 29 is Ile, Leu, Val, Ala, Phe, Asp, Glu, Lys, Homolysine, Ornithine, 4-carboxy-phenylalanine, beta-glutamic acid, beta-Homoglutamic acid, or homoglutamic acid;

Xaa at position 30 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid; Xaa at position 31 is Trp, Phe, Tyr, Glu, Asp, or Lys;

Xaa at position 32 is Leu, Gly, Ala, Ser, Thr, Ile, Val, Glu, Asp, or Lys;

Xaa at position 33 is Val, Gly, Ala, Ser, Thr, Leu, Ile, Glu, Asp, or Lys;

Xaa at position 34 is Asn, Lys, Arg, Glu, Asp, or His;

Xaa at position 35 is Gly, Ala, Ser, Thr, Leu, Ile, Val, Glu, Asp, or Lys;

Xaa at position 36 is Gly, Arg, Lys, Glu, Asp, or His;

Xaa at position 37 is Pro, Gly, Ala, Ser, Thr, Leu, Ile, Val, Glu, Asp, or Lys;

wherein the compound has a GLP-1 activity.

A third family of GLP-1 analogs comprises or consists of the amino acid sequence shown in formula III (SEQ ID NO: 13):

(Formula III, SEQ ID NO: 13)
Xaa$_7$-Xaa$_8$-Xaa$_9$-Xaa$_{10}$-Xaa$_{11}$-Xaa$_{12}$-Xaa$_{13}$-Xaa$_{14}$-

Xaa$_{15}$-Xaa$_{16}$-Xaa$_{17}$-Xaa$_{18}$-Xaa$_{19}$-Xaa$_{20}$-Xaa$_{21}$-Xaa$_{22}$-

Xaa$_{23}$-Xaa$_{24}$-Xaa$_{25}$-Xaa$_{26}$-Xaa$_{27}$-Xaa$_{28}$-Xaa$_{29}$-Xaa$_{30}$-

Xaa$_{31}$-Xaa$_{32}$-Xaa$_{33}$-Xaa$_{34}$-Xaa$_{35}$-Xaa$_{36}$-Gly-Xaa$_{38}$-

Xaa$_{39}$-Xaa$_{40}$-Xaa$_{41}$-C(O)—R$_1$ wherein,
R$_1$ is OR$_2$ or NR$_2$R$_3$;
R$_2$ and R$_3$ are independently hydrogen or (C$_1$-C$_8$)alkyl;
Xaa at position 7 is: L-histidine, D-histidine, desamino-histidine, 2-amino-histidine, 3-hydroxy-histidine, homohistidine, α-fluoromethyl-histidine or α-methyl-histidine;
Xaa at position 8 is Gly, bAla (2-aminopropionic acid), 1-amino-cylcopentanecarboxylic acid, 2-aminoisobutryic acid or an alpha-alpha-disubstituted amino acid;
Xaa at position 9 is Glu, Asp, or Lys;
Xaa at position 10 is Gly or His;
Xaa at position 11 is Thr, Ala, Gly, Ser, Leu, Ile, Val, Glu, Asp, or Lys;
Xaa at position 12 is His, Trp, Phe, or Tyr;
Xaa at position 13 is Thr or Gly;
Xaa at position 14 is Ser, Ala, Gly, Thr, Leu, Ile, Val, Glu, Asp, or Lys;
Xaa at position 15 is Asp or Glu;
Xaa at position 16 is Val, Ala, Gly, Ser, Thr, Leu, Ile, Tyr, Glu, Asp, Trp, or Lys;
Xaa at position 17 is Ser, Ala, Gly, Thr, Leu, Ile, Val, Glu, Asp, or Lys;
Xaa at position 18 is Ser, Ala, Gly, Thr, Leu, Ile, Val, Glu, Asp, Trp, Tyr, Lys, Homolysine, Ornithine, 4-carboxy-phenylalanine, beta-glutamic acid, beta-Homoglutamic acid, or homoglutamic acid;
Xaa at position 19 is Tyr, Phe, Trp, Glu, Asp, Gln, Lys, Homolysine, Ornithine, 4-carboxy-phenylalanine, beta-glutamic acid, beta-Homoglutamic acid, or homoglutamic acid;
Xaa at position 20 is Leu, Ala, Gly, Ser, Thr, Ile, Val, Glu, Asp, Met, Trp, Tyr, Lys, Homolysine, Ornithine, 4-carboxy-phenylalanine, beta-glutamic acid, or homoglutamic acid;
Xaa at position 21 is Glu, Asp, Lys, Homolysine, Ornithine, 4-carboxy-phenylalanine, beta-glutamic acid, beta-Homoglutamic acid, or homoglutamic acid;
Xaa at position 22 is 2-aminoisobutyric acid, 1-amino-cylcopentanecarboxylic acid, an alpha-alpha-disubstituted amino acid, or 2-aminoadipic acid;
Xaa at position 23 is Gln, Asn, Arg, Glu, Asp, Lys, Ornithine, 4-carboxy-phenylalanine, beta-glutamic acid, beta-Homoglutamic acid, or homoglutamic acid;
Xaa at position 24 is Ala, Gly, Ser, Thr, Leu, Ile, Val, Arg, Glu, Asp, Lys, Homolysine, Ornithine, 4-carboxy-phenylalanine, beta-glutamic acid, beta-Homoglutamic acid, or homoglutamic acid;
Xaa at position 25 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;
Xaa at position 26 is Lys, Homolysine, Arg, Gln, Glu, Asp, His, Ornithine, 4-carboxy-phenylalanine, beta-glutamic acid, or homoglutamic acid;
Xaa at position 27 is Leu, Glu, Asp, Lys, Homolysine, Ornithine, 4-carboxy-phenylalanine, beta-glutamic acid, beta-Homoglutamic acid, or homoglutamic acid;
Xaa at position 28 is Phe, Trp, Asp, Glu, Lys, Homolysine, Ornithine, 4-carboxy-phenylalanine, beta-glutamic acid, beta-Homoglutamic acid, or homoglutamic acid;
Xaa at position 29 is Ile, Leu, Val, Ala, Phe, Asp, Glu, Lys, Homolysine, Ornithine, 4-carboxy-phenylalanine, beta-glutamic acid, beta-Homoglutamic acid, or homoglutamic acid;
Xaa at position 30 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, or homoglutamic acid;
Xaa at position 31 is Trp, Phe, Tyr, Glu, Asp, or Lys;
Xaa at position 32 is Leu, Gly, Ala, Ser, Thr, Ile, Val, Glu, Asp, or Lys;
Xaa at position 33 is Val, Gly, Ala, Ser, Thr, Leu, Ile, Glu, Asp, or Lys;
Xaa at position 34 is Asn, Lys, Arg, Glu, Asp, or His;
Xaa at position 35 is Gly, Ala, Ser, Thr, Leu, Ile, Val, Glu, Asp, or Lys;
Xaa at position 36 is Gly, Arg, Lys, Glu, Asp, or His;
Xaa at position 38 is Cys, Gly, or is omitted;
Xaa at position 39 is Ala, Gly, Ser, Cys, or is omitted;
Xaa at position 40 is Gly or is omitted;
Xaa at position 41 is Gly or is omitted;
provided that when the amino acid at position 38, 39, 40, or 41 is omitted, then each amino acid downstream of that amino acid is also omitted, and wherein the compound has a GLP-1 activity. Thus, for example, if the amino acid at position 38 is omitted, then there are also no amino acids at positions 39-41. Similarly, if the amino acid at position 39 is omitted, there are also no amino acids at positions 40 and 41. And if the amino acid at position 40 is omitted, then there is no amino acid at position 41.

Another family of GLP-1 analogs includes a ring or cyclic structure that is formed when two amino acids within the analog are joined together, typically via their side chains. The side chains may be joined directly to one another or via a linker.

Certain GLP-1 analogs in this family have the general structure shown in Formula V:

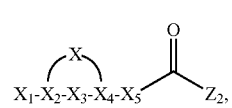

(Formula V)

wherein
X is —N(Z$_1$)—C(O)— or —C(O)—N(Z$_1$)—;
Z$_1$ is hydrogen or (C$_1$-C$_8$)alkyl;
X$_1$ is at least 11 amino acids;
X$_2$ is an amino acid;
X$_3$ is a bond or 1-5 amino acids;
X$_4$ is an amino acid;
X$_5$ is at least 10 amino acids;
Z$_2$ is —OZ$_3$ or —NZ$_4$Z$_5$; and
Z$_3$, Z$_4$, and Z$_5$ are independently hydrogen or (C$_1$-C$_8$)alkyl;
and wherein the amino acids comprising X1 and X5 correspond to amino acids from the amino and carboxyl portions of GLP-1, respectively, or similar sequences in which amino acids in the native GLP-1 sequence have been substituted with an amino acid such as described in Formulas X to Y.

Some cyclic GLP-1 analogs, for instance, comprise or consist of the amino acid sequence shown in formula IV:

(Formula IV, SEQ ID NO: 29)
Xaa$_7$-Xaa$_8$-Xaa$_9$-Xaa$_{10}$-Xaa$_{11}$-Xaa$_{12}$-Xaa$_{13}$-Xaa$_{14}$-

Xaa$_{15}$-Xaa$_{16}$-Xaa$_{17}$-Xaa$_{18}$-Xaa$_{19}$-Xaa$_{20}$-Xaa$_{21}$-Xaa$_{22}$-

Xaa$_{23}$-Xaa$_{24}$-Xaa$_{25}$-Xaa$_{26}$-Xaa$_{27}$-Xaa$_{28}$-Xaa$_{29}$-Xaa$_{30}$-

Xaa$_{31}$-Xaa$_{32}$-Xaa$_{33}$-Xaa$_{34}$-Xaa$_{35}$-Xaa$_{36}$-Xaa$_{37}$-Xaa$_{38}$-

Xaa$_{39}$-Xaa$_{40}$-Xaa$_{41}$C(O)—R$_1$ wherein,
R$_1$ is OR$_2$ or NR$_2$R$_3$;
R$_2$ and R$_3$ are independently hydrogen or (C$_1$-C$_8$)alkyl;
Xaa at position 7 is: L-histidine, D-histidine, desamino-histidine, 2-amino-histidine, 3-hydroxy-histidine, homohistidine, α-fluoromethyl-histidine or α-methyl-histidine;
Xaa at position 8 is Gly, bAla (2-aminopropionic acid), 1-amino-cylcopentanecarboxylic acid, 2-aminoisobutryic acid or an alpha-alpha-disubstituted amino acid;
Xaa at position 9 is Glu, Asp, or Lys;
Xaa at position 10 is Gly or His;
Xaa at position 11 is Thr, Ala, Gly, Ser, Leu, Ile, Val, Glu, Asp, or Lys;
Xaa at position 12 is: His, Trp, Phe, or Tyr;
Xaa at position 13 is Thr or Gly;
Xaa at position 14 is Ser, Ala, Gly, Thr, Leu, Ile, Val, Glu, Asp, or Lys;
Xaa at position 15 is Asp or Glu;
Xaa at position 16 is Val, Ala, Gly, Ser, Thr, Leu, Ile, Tyr, Glu, Asp, Trp, or Lys;
Xaa at position 17 is Ser, Ala, Gly, Thr, Leu, Ile, Val, Glu, Asp, or Lys;
Xaa at position 18 is Ser, Ala, Gly, Thr, Leu, Ile, Val, Glu, Asp, Trp, Tyr, Lys, Homolysine, Ornithine, 4-carboxy-phenylalanine, beta-glutamic acid, beta-Homoglutamic acid, alpha, gamma-diaminobutryic acid, or homoglutamic acid;
Xaa at position 19 is Tyr, Phe, Trp, Glu, Asp, Gln, Lys, Homolysine, Ornithine, 4-carboxy-phenylalanine, beta-glutamic acid, beta-Homoglutamic acid, alpha, gamma-diaminobutryic acid, or homoglutamic acid;
Xaa at position 20 is Leu, Ala, Gly, Ser, Thr, Ile, Val, Glu, Asp, Met, Trp, Tyr, Lys, Homolysine, Ornithine, 4-carboxy-phenylalanine, beta-glutamic acid, alpha, gamma-diaminobutryic acid, or homoglutamic acid;
Xaa at position 21 is Glu, Asp, Lys, Homolysine, Ornithine, 4-carboxy-phenylalanine, beta-glutamic acid, beta-Homoglutamic acid, alpha, gamma-diaminobutryic acid, or homoglutamic acid;
Xaa at position 22 is Gly, Ala, Ser, Thr, Leu, Ile, Val, Glu, Asp, Lys, Homolysine, Ornithine, 4-carboxy-phenylalanine, beta-glutamic acid, beta-Homoglutamic acid, alpha, gamma-diaminobutryic acid, or homoglutamic acid;
Xaa at position 23 is Gln, Asn, Arg, Glu, Asp, Lys, Ornithine, 4-carboxy-phenylalanine, beta-glutamic acid, beta-Homoglutamic acid, alpha, gamma-diaminobutryic acid, or homoglutamic acid;
Xaa at position 24 is Ala, Gly, Ser, Thr, Leu, Ile, Val, Arg, Glu, Asp, Lys, Homolysine, Ornithine, 4-carboxy-phenylalanine, beta-glutamic acid, beta-Homoglutamic acid, alpha, gamma-diaminobutryic acid, or homoglutamic acid;
Xaa at position 25 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, alpha, gamma-diaminobutryic acid, or homoglutamic acid;
Xaa at position 26 is Lys, Homolysine, Arg, Gln, Glu, Asp, His, Ornithine, 4-carboxy-phenylalanine, beta-glutamic acid, alpha, gamma-diaminobutryic acid, or homoglutamic acid;
Xaa at position 27 is Leu, Glu, Asp, Lys, Homolysine, Ornithine, 4-carboxy-phenylalanine, beta-glutamic acid, beta-Homoglutamic acid, alpha, gamma-diaminobutryic acid, or homoglutamic acid;
Xaa at position 28 is Phe, Trp, Asp, Glu, Lys, Homolysine, Ornithine, 4-carboxy-phenylalanine, beta-glutamic acid, beta-Homoglutamic acid, alpha, gamma-diaminobutryic acid, or homoglutamic acid;
Xaa at position 29 is Ile, Leu, Val, Ala, Phe, Asp, Glu, Lys, Homolysine, Ornithine, 4-carboxy-phenylalanine, beta-glutamic acid, beta-Homoglutamic acid, alpha, gamma-diaminobutryic acid, or homoglutamic acid;
Xaa at position 30 is Ala, Gly, Ser, Thr, Leu, Ile, Val, Glu, Asp, Lys, Homolysine, Ornithine, 4-carboxy-phenylalanine, beta-glutamic acid, beta-Homoglutamic acid, alpha, gamma-diaminobutryic acid, or homoglutamic acid;
Xaa at position 31 is Trp, Phe, Tyr, Glu, Asp, or Lys;
Xaa at position 32 is Leu, Gly, Ala, Ser, Thr, Ile, Val, Glu, Asp, or Lys;
Xaa at position 33 is Val, Gly, Ala, Ser, Thr, Leu, Ile, Glu, Asp, or Lys;
Xaa at position 34 is Asn, Lys, Arg, Glu, Asp, or His;
Xaa at position 35 is Gly, Ala, Ser, Thr, Leu, Ile, Val, Glu, Asp, or Lys;
Xaa at position 36 is Gly, Arg, Lys, Glu, Asp, or His;
Xaa at position 37 is Pro, Gly, Ala, Ser, Thr, Leu, Ile, Val, Glu, Asp, or Lys;
Xaa at position 38 is Gly, Ser, Lys, Cys, or is omitted;
Xaa at position 39 is Gly, Ala, Ser, Thr, Ile, Val, Leu, Phe, Pro, Cys or is omitted;
Xaa at position 40 is Gly, Cys, or is omitted;
Xaa at position 41 is Gly or is omitted;
wherein two amino acids selected from Xaa$_{18}$, Xaa$_{19}$, Xaa$_{20}$, Xaa$_{21}$, Xaa$_{22}$, Xaa$_{23}$, Xaa$_{24}$, Xaa$_{25}$, Xaa$_{26}$, Xaa$_{27}$, Xaa$_{28}$, Xaa$_{29}$, and Xaa$_{30}$ are joined to form a ring and the two amino acids forming the ring are separated by 0, 1, 2, 3, 4 or 5 amino acids, and wherein the compound has a GLP-1 activity.

In counting the number of amino acids involved in the separation, the two amino acids whose side chains are joined are excluded. Thus, for instance, the two amino acids whose side chains are joined to form a ring have 0 amino acids separating them when the two amino acids are beside each other (e.g., when the amino acids at positions Xaa$_{18}$ and Xaa$_{19}$ are joined to form a ring).

In a particular embodiment, the two amino acids that are joined to form a ring are separated by 3 or 4 amino acids, including for example when:
Xaa$_{18}$ is joined to either Xaa$_{22}$ or Xaa$_{23}$; or
Xaa$_{19}$ is joined to either Xaa$_{23}$ or Xaa$_{24}$; or
Xaa$_{20}$ is joined to either Xaa$_{24}$ or Xaa$_{25}$ or
Xaa$_{21}$ is joined to either Xaa$_{25}$ or Xaa$_{26}$; or
Xaa$_{22}$ is joined to either Xaa$_{26}$ or Xaa$_{27}$; or
Xaa$_{23}$ is joined to either Xaa$_{27}$ or Xaa$_{28}$; or
Xaa$_{24}$ is joined to either Xaa$_{28}$ or Xaa$_{29}$; or
Xaa$_{25}$ is joined to either Xaa$_{29}$ or Xaa$_{30}$ or
Xaa$_{26}$ is joined to either Xaa$_{30}$ or Xaa$_{31}$.

A variety of different amino acids, amino acid analogs (e.g., unnatural amino acids) can be inserted at these positions. The amino acid or analogs are chosen to have reactive functional groups in the side chain that can be reacted together directly or via a linker to form a ring. The ring in some cyclic analogs, for instance, is formed by reacting a carboxyl group in the side chain of one amino acid or analog with an amino group in the side chain of the second amino acid or analog to form a cyclic lactam. Thus, for example, in certain embodiments, a ring structure is formed between the side chains of any two of Glu (E), Asp (D), Lys (K), Ornithine (O), 4-carboxy-phenylalanine (Cpa), beta-homoglutamic acid (B), alpha, gamma-diaminobutryic acid (Dab), and homoglutamic acid (J) that are located at the positions specified above as exemplified below:

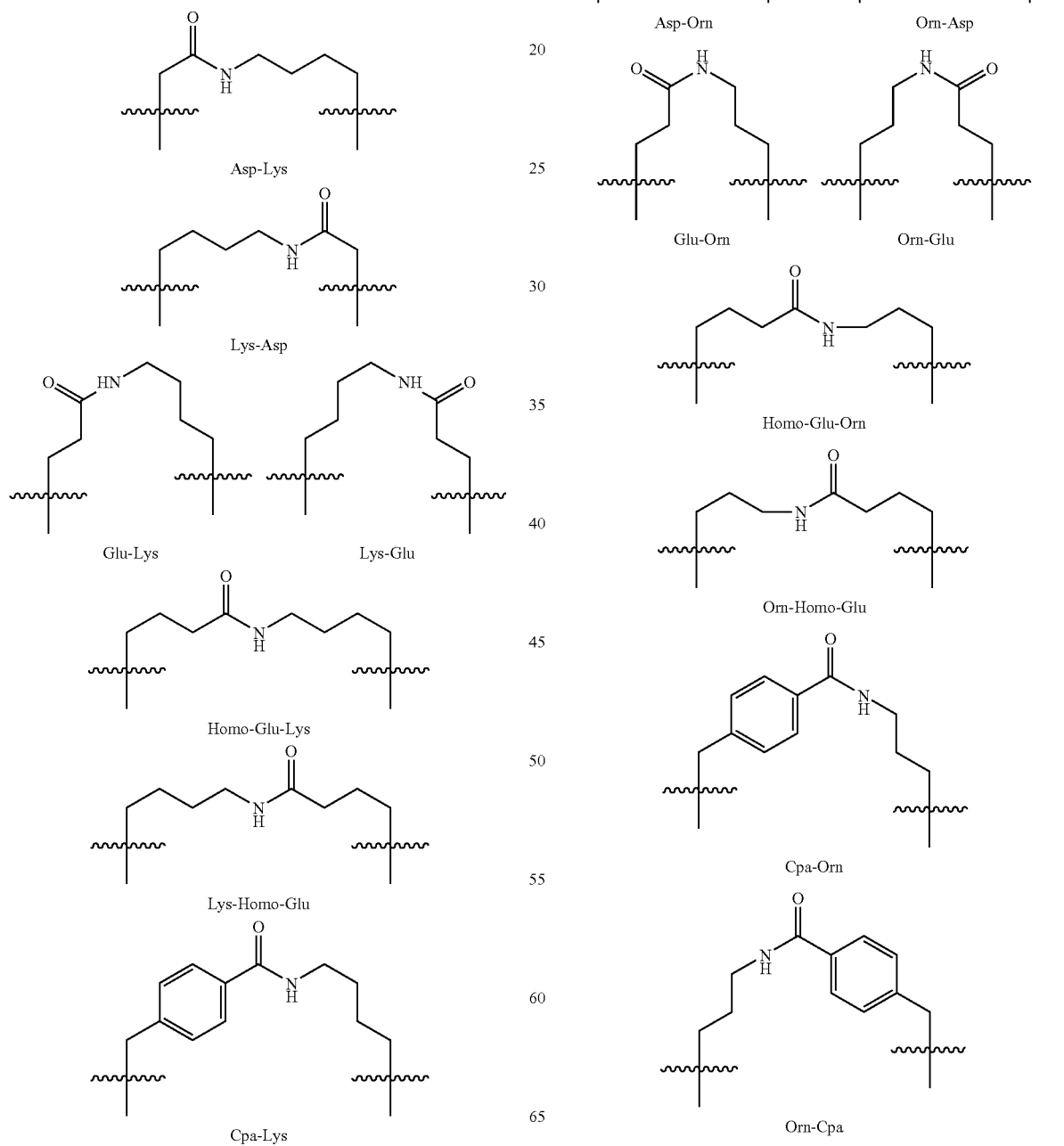

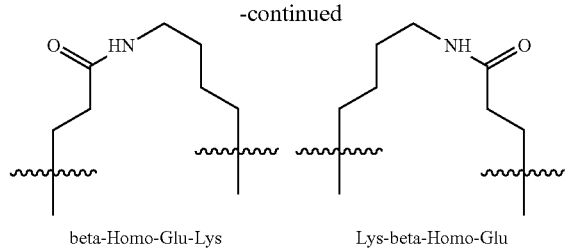

beta-Homo-Glu-Lys      Lys-beta-Homo-Glu

FIG. 1, for example, depicts examples of the positions within GLP-1 that are separated by 3 amino acids that can be joined to form a cyclic lactam.

FIGS. 2A through 2I provide chemical structures in which a glutamic acid/lysine amino acid pair are joined to form a ring. It will be appreciated by those skilled in the art that the particular pairing can be replaced with any of the other pairings shown above, as well as other pairings.

Specific examples of the sequences of GLP-1 analogs that have the requisite amino acids at the appropriate locations that can be joined to form a cyclic lactam are set forth in SEQ ID NOS: 30 to 246 and are shown in Table 2, with the two amino acids that are joined to form the ring being indicated by bold and underlined type.

Some GLP-1 analogs include two cyclic structures. One example is (SEQ ID NO: 277)
HGEGT FTSDV SSYLE GQAKK EFIAW LEKGR K

In this analog, the first E and K pair (at positions 21 and 25, respectively) form one cyclic lactam and the second E and K pair (at positions 33 and 37, respectively) form a second cyclic lactam. One or both pairs of the Glu (E) and Lys (K) residues can be substituted with the other amino acids or amino acid analogs such as those listed and illustrated above to form the cyclic lactam rings.

A final family of GLP-1 analogs comprises or consists of the amino acid sequence shown in formula VI:

(Formula VI, SEQ ID NO: 276)
$Xaa_4$-$Xaa_5$-$Xaa_6$-$His_7$-$Ala_8$-$Glu_9$-$Gly_{10}$-$Thr_{11}$-$Phe_{12}$-$Thr_{13}$-$Ser_{14}$-$Asp_{15}$-$Val_{16}$-$Ser_{17}$-$Ser_{18}$-$Tyr_{19}$-$Leu_{20}$-$Glu_{21}$-$Gly_{22}$-$Gln_{23}$-$Ala_{24}$-$Ala_{25}$-$Lys_{26}$-$Glu_{27}$-$Phe_{28}$-$Ile_{29}$-$Ala_{30}$-$Trp_{31}$-$Leu_{32}$-$Val_{33}$-$Lys_{34}$-$Gly_{35}$-$Arg_{36}$-$C(O)$-$R_1$ wherein,
$R_1$ is $OR_2$ or $NR_2R_3$;
$R_2$ and $R_3$ are independently hydrogen or $(C_1$-$C_8)$alkyl;
Xaa at position 4 is: Met or omitted;
Xaa at position 5 is: Met, His, or omitted;
Xaa at position 6 is: Met, Ala, Gly, Pro, Ser, Thr, Val, Gln, Arg, Lys, His, Tyr, Ile, Asp, Leu, Asn, Glu, Trp, or Phe; provided that when the amino acid at position 5 is omitted, then the amino acid at position 4 is also omitted, wherein the compound has a GLP-1 activity.

Certain GLP-1 analogs are exemplified in Table 2. Several of the sequences listed in Table 2 are shown as having a C-terminal amide. It should be understood, however, that all of the sequences listed in the Table 2 and described elsewhere in the specification can have a C-terminal carboxyl group or a C-terminal amide group. As used in Table 2: bAla is beta-aminopropionic acid; Aad is 2-aminoadipic acid; Z is Aib (2 aminoisobutyric acid); O is ornithine; Cpa is 4-carboxy-phenylalanine; Dab is alpha, gamma-diaminobutryic acid, and B is beta homoglutamic acid; J is homoglutamic acid. [K/O/C] means that the amino acid sequence optionally comprises any one of lysine, ornithine or cysteine at this position, but may include none of these amino acids.

Residues that are highlighted in bold and underlined indicate the amino acids that are joined (typically via their side chains) to form a ring or cyclic structure.

TABLE 2

| GLP-1 Analog | Internal Ref. | SEQ ID NO: |
|---|---|---|
| HGEGT FTSDV SSYLE GQAAK EFIAW LVKGR G | | 2 |
| MHGEGT FTSDV SSYLE GQAAK EFIAW LVKGR | | 3 |
| HGEGT FTSDV SSYLE GQAAK EFIAW LVKGR GGGGG C | cgGLP-11 | 4 |
| XGXXX XXXXX XXXXX XCXXX XXXXX XXXGX XSSGA PPPS | Formula I | 5 |
| HGEGT FTSDV SSYLE GCAAK EFIAW LVKGR G | cgGLP-1-3, 7, 9 | 6 |
| HGEGT FTSDV SSYLE GCAAK EFIAW LVKGR GSSGA PPPS | cgGLP-12, 14 | 7 |
| HGEGT FTSDV SSYLE GCAAK EFIAW LKNGG PSSGA PPPS | cgGLP-13, 15 | 8 |
| XXXXX XXXXX XXXXX XXXXX XXXXX XXXXX XCSGG | Formula II | 9 |
| HGEGT FTSDV SSYLE GQAAK EFIAW LVKGR GCSG | cgGLP-4-6, 8, 10, 16 | 10 |
| HZEGT FTSDV SSYLE GQAAK EFIAW LVKGR GCSGG | cgGLP-17 | 11 |
| H[bAla]EGT FTSDV SSYLE GQAAK EFIAW LVKGR GCSGG | cgGLP-18 | 12 |
| XXXXX XXXXX XXXXX XXXXX XXXXX XXXXX GXXXX | Formula III | 13 |
| HAEGT FTSDV SSYLE ZQAAK EFIAW LVKGR-amide | | 14 |
| HGEGT FTSDV SSYLE ZQAAK EFIAW LYKGR G-amide | | 15 |

TABLE 2-continued

| GLP-1 Analog | Internal Ref. | SEQ ID NO: |
|---|---|---|
| HGEGT FTSDV SSYLE ZQAAK EFIAW LVKGR GC | | 16 |
| HGEGT FTSDV SSYLE ZQAAK EFIAW LYKGR GC-amide | cgGLP-23 | 17 |
| HGEGT FTSDV SSYLE ZQAAK EFIAW LYKGR GCA-amide | cgGLP30 and mgGLP 20 | 18 |
| HGEGT FTSDV SSYLE ZQAAK EFIAW LVKGR GCG | | 19 |
| HGEGT FTSDV SSYLE ZQAAK EFIAW LVKGR GCG-amide | mgGLP-16 | 20 |
| HGEGT FTSDV SSYLE ZQAAK EFIAW LVKGR GCSG | cgGLP-19 | 21 |
| HGEGT FTSDV SSYLE ZQAAK EFIAW LVKGR GCSG-amide | cgGLP-24-29 mgGLP22, mgGLP-33, mgGLP-27 | 22 |
| HGEGT FTSDV SSYLE ZQAAK EFIAW LVKGR GCSGG | | 23 |
| HGEGT FTSDV SSYLE ZQAAK EFIAW LVKGR GCSGG-amide | mgGLP-15 | 24 |
| HZEGT FTSDV SSYLE ZQAAK EFIAW LVKGR GCSG | cgGLP-20 | 25 |
| HZEGT FTSDV SSYLE ZQAAK EFIAW LVKGR GCSGG | | 26 |
| HZEGT FTSDV SSYLE ZQAAK EFIAW LVKGR GGC | cgGLP-22 | 27 |
| HGEGT FTSDV SSYLE [Aad]QAAK EFIAW LVKGR GCSG | cgGLP-21 Formula IV | 28 29 |
| HGEGT FTSDV SSYLE EQAAK EFIAW LVKGR G-amide | cycloE22-K26 (mgGLP-24) | 30 |
| HGEGT FTSDV SSYLE EQAAK EFIAW LVKGR GCA-amide | | 31 |
| HGEGT FTSDV SSYLE EQAAK EFIAW LVKGR GCSG-amide | cycloE22-K26/ CSG | 32 |
| HGEGT FTSDV SEYLE KQAAK EFIAW LVKGR G[K/O/C]-amide | G8 cyclo [18-22]-Lys/Orn 38 | 33 |
| HGEGT FTSDV SSELE GKAAK EFIAW LVKGR G[K/O/C]-amide | G8 cyclo [19-23]-Lys/Orn 38 | 34 |
| HGEGT FTSDV SSYEE GQKAK EFIAW LVKGR G[K/O/C]-amide | [Gly8]GLP1(7-37) cyclo[Glu14-Lys18]38 | 35 |
| HGEGT FTSDV SSYLE GQAKK EFIAW LVKGR G[K/O/C]-amide | [Gly8]GLP1(7-37) cyc[Glu15-Lys19] | 36 |
| HGEGT FTSDV SSYLE EQAAK EFIAW LVKGR G[K/O/C]-amide | G8 cyclo [22-26]-Lys/Orn 38 | 37 |
| HGEGT FTSDV SSYLE GEAAK KFIAW LVKGR G[K/O/C]-amide | [Gly8]GLP1(7-37) cyclo[Glu17-Lys21] | 38 |
| HGEGT FTSDV SSYLE GQEAK EKIAW LVKGR G[K/O/C]-amide | [Gly8]GLP1(7-37) cyclo[Glu18-Lys22] | 39 |
| HGEGT FTSDV SSYLE GQAEK EFKAW LVKGR G[K/O/C]-amide | G8 cyclo [25-29]-Lys/Orn 38 | 40 |
| HGEGT FTSDV SSYLE GQAAE EFIKW LVKGR G[K/O/C]-amide | G8 cyclo [26-30]-Lys/Orn 38 | 41 |
| HGEGT FTSDV SSYLE GQAAK EFIAW LVKGR G[K/O/C]-amide | [Gly8]cyclo[21-26] GLP1(7-37)-amide | 42 |
| HGEGT FTSDV SSYLE JQAAK EFIAW LVKGR G-amide | cycloJ22-K26 | 43 |
| HGEGT FTSDV SSYLE JQAAK EFIAW LVKGR GCA-amide | cycloJ22-K26 | 44 |
| HGEGT FTSDV SSYLE JQAAK EFIAW LVKGR GCSG-amide | cycloJ22-K26/ CSG | 45 |

TABLE 2-continued

| GLP-1 Analog | Internal Ref. | SEQ ID NO: |
|---|---|---|
| HGEGT FTSDV SJYLE KQAAK EFIAW LVKGR G[K/O/C]-amide | G8 cyclo [18-22]-Lys/Orn/Cys 38 | 46 |
| HGEGT FTSDV SSJLE GKAAK EFIAW LVKGR G[K/O/C]-amide | G8 cyclo [19-23]-Lys/Orn/Cys 38 | 47 |
| HGEGT FTSDV SSYJE GQKAK EFIAW LVKGR G[K/O/C]-amide | G8 cyclo [20-24]-Lys/Orn/Cys 38 | 48 |
| HGEGT FTSDV SSYLJ GQAKK EFIAW LVKGR G[K/O/C]-amide | G8 cyclo [21-25]-Lys/Orn/Cys 38 | 49 |
| HGEGT FTSDV SSYLE JQAAK EFIAW LVKGR G[K/O/C]-amide | G8 cyclo [22-26]-Lys/Orn/Cys 38 | 50 |
| HGEGT FTSDV SSYLE GJAAK KFIAW LVKGR G[K/O/C]-amide | G8 cyclo [23-27]-Lys/Orn/Cys 38 | 51 |
| HGEGT FTSDV SSYLE GQJAK EKIAW LVKGR G[K/O/C]-amide | G8 cyclo [24-28]-Lys/Orn/Cys 38 | 52 |
| HGEGT FTSDV SSYLE GQAJK EFKAW LVKGR G[K/O/C]-amide | G8 cyclo [25-29]-Lys/Orn/Cys 38 | 53 |
| HGEGT FTSDV SSYLE GQAAJ EFIKW LVKGR G[K/O/C]-amide | G8 cyclo [26-30]-Lys/Orn/Cys 38 | 54 |
| HGEGT FTSDV SSYLJ GQAAK EFIAW LVKGR G[K/O/C]-amide | G8 cyclo [21-26]-Lys/Orn/Cys 38 | 55 |
| HGEGT FTSDV SSYLE KQAAJ EFIAW LVKGR G-amide | | 56 |
| HGEGT FTSDV SSYLE KQAAJ EFIAW LVKGR GCA-amide | | 57 |
| HGEGT FTSDV SSYLE KQAAJ EFIAW LVKGR GCSG-amide | | 58 |
| HGEGT FTSDV SKYLE JQAAK EFIAW LVKGR G[K/O/C]-amide | | 59 |
| HGEGT FTSDV SSKLE GJAAK EFIAW LVKGR G[K/O/C]-amide | | 60 |
| HGEGT FTSDV SSYKE GQJAK EFIAW LVKGR G[K/O/C]-amide | | 61 |
| HGEGT FTSDV SSYLK GQAJK EFIAW LVKGR G[K/O/C]-amide | | 62 |
| HGEGT FTSDV SSYLE KQAAJ EFIAW LVKGR G[K/O/C]-amide | | 63 |
| HGEGT FTSDV SSYLE GKAAK JFIAW LVKGR G[K/O/C]-amide | | 64 |
| HGEGT FTSDV SSYLE GQKAK EJIAW LVKGR G[K/O/C]-amide | | 65 |
| HGEGT FTSDV SSYLE GQAKK EFJAW LVKGR G[K/O/C]-amide | | 66 |
| HGEGT FTSDV SSYLE GQAAK EFIJW LVKGR G[K/O/C]-amide | | 67 |
| HGEGT FTSDV SSYLK GQAAJ EFIAW LVKGR G[K/O/C]-amide | | 68 |
| HGEGT FTSDV SSYLE EQAAO EFIAW LVKGR G-amide | cycloE22-O26 | 69 |
| HGEGT FTSDV SSYLE EQAAO EFIAW LVKGR GCA-amide | cycloE22-O26 | 70 |
| HGEGT FTSDV SSYLE EQAAO EFIAW LVKGR GCSG-amide | cycloE22-O26/CSG | 71 |
| HGEGT FTSDV SEYLE OQAAK EFIAW LVKGR G[K/O/C]-amide | G8 cycle [18-22]-Lys/Orn/Cys 38 | 72 |
| HGEGT FTSDV SSELE GOAAK EFIAW LVKGR G[K/O/C]-amide | G8 cyclo [19-23]-Lys/Orn/Cys 38 | 73 |
| HGEGT FTSDV SSYEE GQOAK EFIAW LVKGR G[K/O/C]-amide | G8 cycle [20-24]-Lys/Orn/Cys 38 | 74 |
| HGEGT FTSDV SSYLE GQAOK EFIAW LVKGR G[K/O/C]-amide | G8 cycle [21-25]-Lys/Orn/Cys 38 | 75 |
| HGEGT FTSDV SSYLE EQAAO EFIAW LVKGR G[K/O/C]-amide | G8 cyclo [22-26]-Lys/Orn/Cys 38 | 76 |

TABLE 2-continued

| GLP-1 Analog | Internal Ref. | SEQ ID NO: |
|---|---|---|
| HGEGT FTSDV SSYLE GEAAK OFIAW LVKGR G[K/O/C]-amide | G8 cyclo [23-27]-Lys/Orn/Cys 38 | 77 |
| HGEGT FTSDV SSYLE GQEAK EOIAW LVKGR G[K/O/C]-amide | G8 cycle [24-28]-Lys/Orn/Cys 38 | 78 |
| HGEGT FTSDV SSYLE GQAEK EFOAW LVKGR G[K/O/C]-amide | G8 cyclo [25-29]-Lys/Orn/Cys 38 | 79 |
| HGEGT FTSDV SSYLE GQAAE EFIOW LVKGR G[K/O/C]-amide | G8 cyclo [26-30]-Lys/Orn/Cys 38 | 80 |
| HGEGT FTSDV SSYLE GQAAO EFIAW LVKGR G[K/O/C]-amide | G8 cyclo [21-26]-Lys/Orn/Cys 38 | 81 |
| HGEGT FTSDV SSYLE OQAAE EFIAW LVKGR G-amide | | 82 |
| HGEGT FTSDV SSYLE OQAAE EFIAW LVKGR GCA-amide | | 83 |
| HGEGT FTSDV SSYLE OQAAE EFIAW LVKGR GCSG-amide | | 84 |
| HGEGT FTSDV SOYLE EQAAK EFIAW LVKGR G[K/O/C]-amide | | 85 |
| HGEGT FTSDV SSOLE GEAAK EFIAW LVKGR G[K/O/C]-amide | | 86 |
| HGEGT FTSDV SSYOE GQEAK EFIAW LVKGR G[K/O/C]-amide | | 87 |
| HGEGT FTSDV SSYLO GQAEK EFIAW LVKGR G[K/O/C]-amide | | 88 |
| HGEGT FTSDV SSYLE OQAAE EFIAW LVKGR G[K/O/C]-amide | | 89 |
| HGEGT FTSDV SSYLE GOAAK EFIAW LVKGR G[K/O/C]-amide | | 90 |
| HGEGT FTSDV SSYLE GQOAK EEIAW LVKGR G[K/O/C]-amide | | 91 |
| HGEGT FTSDV SSYLE GQAOK EFEAW LVKGR G[K/O/C]-amide | | 92 |
| HGEGT FTSDV SSYLE GQAAO EFIEW LVKGR G[K/O/C]-amide | | 93 |
| HGEGT FTSDV SSYLO GQAAE EFIAW LVKGR G[K/O/C]-amide | | 94 |
| HGEGT FTSDV SSYLE DQAAO EFIAW LVKGR G-amide | cycloD22-K26 | 95 |
| HGEGT FTSDV SSYLE DQAAO EFIAW LVKGR GCA-amide | cycloD22-K26 | 96 |
| HGEGT FTSDV SSYLE DQAAO EFIAW LVKGR GCSG-amide | cycloD22-K26/CSG | 97 |
| HGEGT FTSDV SDYLE OQAAK EFIAW LVKGR G[K/O/C]-amide | G8 cyclo [18-22]-Lys/Orn/Cys 38 | 98 |
| HGEGT FTSDV SSDLE GOAAK EFIAW LVKGR G[K/O/C]-amide | G8 cyclo [19-23]-Lys/Orn/Cys 38 | 99 |
| HGEGT FTSDV SSYDE GQOAK EFIAW LVKGR G[K/O/C]-amide | G8 cyclo [20-24]-Lys/Orn/Cys 38 | 100 |
| HGEGT FTSDV SSYLD GQAOK EFIAW LVKGR G[K/O/C]-amide | G8 cyclo [21-25]-Lys/Orn/Cys 38 | 101 |
| HGEGT FTSDV SSYLE DQAAO EFIAW LVKGR G[K/O/C]-amide | G8 cyclo [22-26]-Lys/Orn/Cys 38 | 102 |
| HGEGT FTSDV SSYLE GDAAK OFIAW LVKGR G[K/O/C]-amide | G8 cyclo [23-27]-Lys/Orn/Cys 38 | 103 |
| HGEGT FTSDV SSYLE GQDAK EOIAW LVKGR G[K/O/C]-amide | G8 cyclo [24-28]-Lys/Orn/Cys 38 | 104 |
| HGEGT FTSDV SSYLE GQADK EFOAW LVKGR G[K/O/C]-amide | G8 cyclo [25-29]-Lys/Orn/Cys 38 | 105 |
| HGEGT FTSDV SSYLE GQAAD EFIOW LVKGR G[K/O/C]-amide | G8 cyclo [26-30]-Lys/Orn/Cys 38 | 106 |
| HGEGT FTSDV SSYLE OQAAD EFIAW LVKGR G-amide | | 107 |

TABLE 2-continued

| GLP-1 Analog | Internal Ref. | SEQ ID NO: |
|---|---|---|
| HGEGT FTSDV SSYLE OQAAD EFIAW LVKGR GCA-amide | | 108 |
| HGEGT FTSDV SSYLE OQAAD EFIAW LVKGR GCSG-amide | | 109 |
| HGEGT FTSDV SOYLE DQAAK EFIAW LVKGR G[K/O/C]-amide | | 110 |
| HGEGT FTSDV SSOLE GDAAK EFIAW LVKGR G[K/O/C]-amide | | 111 |
| HGEGT FTSDV SSYOE GDDAK EFIAW LVKGR G[K/O/C]-amide | | 112 |
| HGEGT FTSDV SSYLO GQADK EFIAW LVKGR G[K/O/C]-amide | | 113 |
| HGEGT FTSDV SSYLE OQAAD EFIAW LVKGR G[K/O/C]-amide | | 114 |
| HGEGT FTSDV SSYLE GOAAK DFIAW LVKGR G[K/O/C]-amide | | 115 |
| HGEGT FTSDV SSYLE GQOAK EDIAW LVKGR G[K/O/C]-amide | | 116 |
| HGEGT FTSDV SSYLE GQAOK EFDAW LVKGR G[K/O/C]-amide | | 117 |
| HGEGT FTSDV SSYLE GQAAO EFIDW LVKGR G[K/O/C]-amide | | 118 |
| HGEGT FTSDV SSYLE GQAAO EFIAW LVKGR G[K/O/C]-amide | G8 cyclo[21-26]-Lys/Orn/Cys 38 | 119 |
| HGEGT FTSDV SSYLO GQAAE EFIAW LVKGR G[K/O/C]-amide | | 120 |
| HGEGT FTSDV SSYLE GQAAK EFIAW LVKGR G[K/O/C]-amide | G8 cyclo[21-26]-Lys/Orn/Cys 38 | 121 |
| HGEGT FTSDV SSYLK GQAAE EFIAW LVKGR G[K/O/C]-amide | | 122 |
| HGEGT FTSDV SSYLJ GQAAK EFIAW LVKGR G[K/O/C]-amide | | 123 |
| HGEGT FTSDV SSYLK GQAAJ EFIAW LVKGR G[K/O/C]-amide | | 124 |
| HGEGT FTSDV SSYLD GQAAO EFIAW LVKGR G[K/O/C]-amide | | 125 |
| HGEGT FTSDV SSYLO GQAAD EFIAW LVKGR G[K/O/C]-amide | | 126 |
| HGEGT FTSDV SSYLD GQAAK EFIAW LVKGR G[K/O/C]-amide | | 127 |
| HGEGT FTSDV SSYLK GQAAD EFIAW LVKGR G[K/O/C]-amide | | 128 |
| HGEGT FTSDV SSYL**[Cpa]** GQAAO EFIAW LVKGR G[K/O/C]-amide | | 129 |
| HGEGT FTSDV SSYLO GQAA**[Cpa]** EFIAW LVKGR G[K/O/C]-amide | | 130 |
| HGEGT FTSDV SSYL**[Cpa]** GQAAK EFIAW LVKGR G[K/O/C]-amide | | 131 |
| HGEGT FTSDV SSYLK GQAA**[Cpa]** EFIAW LVKGR G[K/O/C]-amide | | 132 |
| HGEGT FTSDV SSYLB GQAAK EFIAW LVKGR G[K/O/C]-amide | | 133 |
| HGEGT FTSDV SSYLK GQAAB EFIAW LVKGR G[K/O/C]-amide | | 134 |
| HGEGT FTSDV SSYLE DQAAK EFIAW LVKGR G-amide | cycloD22-K26 | 135 |
| HGEGT FTSDV SSYLE DQAAK EFIAW LVKGR GCA-amide | cycloD22-K26 | 136 |
| HGEGT FTSDV SSYLE DQAAK EFIAW LVKGR GCSG-amide | cycloD22-K26/CSG | 137 |
| HGEGT FTSDV SDYLE KQAAK EFIAW LVKGR G[K/O/C]-amide | G8 cyclo [18-22]-Lys/Orn/Cys 38 | 138 |
| HGEGT FTSDV SSDLE GKAAK EFIAW LVKGR G[K/O/C]-amide | G8 cyclo [19-23] Lys/Orn/Cys 38 | 139 |
| HGEGT FTSDV SSYDE GQKAK EFIAW LVKGR G[K/O/C]-amide | G8 cyclo [20-24]-Lys/Orn/Cys 38 | 140 |
| HGEGT FTSDV SSYLD GQAKK EFIAW LVKGR G[K/O/C]-amide | G8 cyclo [21-25]-Lys/Orn/Cys 38 | 141 |

TABLE 2-continued

| GLP-1 Analog | Internal Ref. | SEQ ID NO: |
|---|---|---|
| HGEGT FTSDV SSYLE D QAA K EFIAW LVKGR G[K/O/C]-amide | G8 cyclo [22-26]-Lys/Orn/Cys 38 | 142 |
| HGEGT FTSDV SSYLE GD AAK K FIAW LVKGR G[K/O/C]-amide | G8 cyclo [23-27]-Lys/Orn/Cys 38 | 143 |
| HGEGT FTSDV SSYLE GQ D AK E KIAW LVKGR G[K/O/C]-amide | G8 cyclo [24-28]-Lys/Orn/Cys 38 | 144 |
| HGEGT FTSDV SSYLE GQA D K EF K AW LVKGR G[K/O/C]-amide | G8 cyclo [25-29]-Lys/Orn/Cys 38 | 145 |
| HGEGT FTSDV SSYLE GQAA D EFI K W LVKGR G[K/O/C]-amide | G8 cyclo [26-30]-Lys/Orn/Cys 38 | 146 |
| HGEGT FTSDV SSYLE K QAA D EFIAW LVKGR G-amide | | 147 |
| HGEGT FTSDV SSYLE K QAA D EFIAW LVKGR GCA-amide | | 148 |
| HGEGT FTSDV SSYLE K QAA D EFIAW LVKGR GCSG-amide | | 149 |
| HGEGT FTSDV S K YLE D QAAK EFIAW LVKGR G[K/O/C]-amide | | 150 |
| HGEGT FTSDV SS K LE G D AAK EFIAW LVKGR G[K/O/C]-amide | | 151 |
| HGEGT FTSDV SSY K E GQ D AK EFIAW LVKGR G[K/O/C]-amide | | 152 |
| HGEGT FTSDV SSYL K GQA D K EFIAW LVKGR G[K/O/C]-amide | | 153 |
| HGEGT FTSDV SSYLE K QAA D EFIAW LVKGR G[K/O/C]-amide | | 154 |
| HGEGT FTSDV SSYLE G K AAK D FIAW LVKGR G[K/O/C]-amide | | 155 |
| HGEGT FTSDV SSYLE GQ K AK E D IAW LVKGR G[K/O/C]-amide | | 156 |
| HGEGT FTSDV SSYLE GQA K K EF D AW LVKGR G[K/O/C]-amide | | 157 |
| HGEGT FTSDV SSYLE GQAA K EFI D W LVKGR G[K/O/C]-amide | | 158 |
| HGEGT FTSDV SSYLE K QAA E EFIAW LVKGR G-amide | GLP1(7-37) cyclo[Lys16-Glu20] | 159 |
| HGEGT FTSDV SSYLE K QAA E EFIAW LVKGR GCA-amide | cycloK22-E26 | 160 |
| HGEGT FTSDV SSYLE K QAA E EFIAW LVKGR GCSG-amide | cycloK22-E26/CSG | 161 |
| HGEGT FTSDV S K YLE E QAAK EFIAW LVKGR G[K/O/C]-amide | G8 cyclo [18-22]-Lys/Orn/Cys 38 | 162 |
| HGEGT FTSDV SS K LE G E AAK EFIAW LVKGR G[K/O/C]-amide | G8 cyclo [19-23]-Lys/Orn/Cys 38 | 163 |
| HGEGT FTSDV SSY K E GQ E AK EFIAW LVKGR G[K/O/C]-amide | G8 cyclo [20-24]-Lys/Orn/Cys 38 | 164 |
| HGEGT FTSDV SSYL K GQA E K EFIAW LVKGR G[K/O/C]-amide | G8 cyclo [21-25]-Lys/Orn/Cys 38 | 165 |
| HGEGT FTSDV SSYLE K QAA E EFIAW LVKGR G[K/O/C]-amide | G8 cyclo [22-26]-Lys/Orn/Cys 38 | 166 |
| HGEGT FTSDV SSYLE G K AAK E FIAW LVKGR G[K/O/C]-amide | G8 cyclo [23-27]-Lys/Orn/Cys 38 | 167 |
| HGEGT FTSDV SSYLE GQ K AK E E IAW LVKGR G[K/O/C]-amide | G8 cyclo [24-28]-Lys/Orn/Cys 38 | 168 |
| HGEGT FTSDV SSYLE GQA K K EF E AW LVKGR G[K/O/C]-amide | G8 cyclo [25-29]-Lys/Orn/Cys 38 | 169 |
| HGEGT FTSDV SSYLE GQAA K EFI E W LVKGR G[K/O/C]-amide | G8 cyclo [26-30]-Lys/Orn/Cys 38 | 170 |
| HGEGT FTSDV SS[Cpa]LE GQAA K EFIAW LVKGR G[K/O/C]-amide | G8 cyclo[19-26]-Lys/Orn/Cys 38 | 171 |

TABLE 2-continued

| GLP-1 Analog | Internal Ref. | SEQ ID NO: |
|---|---|---|
| HGEGT FTSDV SSKLE GQAA[Cpa] EFIAW LVKGR G[K/O/C]-amide | | 172 |
| HGEGT FTSDV SS[Cpa]LE GQAAO EFIAW LVKGR G[K/O/C]-amide | G8 cyclo[19-26]-Lys/Orn/Cys 38 | 173 |
| HGEGT FTSDV SSOLE GQAA[Cpa] EFIAW LVKGR G[K/O/C]-amide | | 174 |
| HGEGT FTSDV SSYLE BQAAK EFIAW LVKGR G-amide | | 175 |
| HGEGT FTSDV SSYLE BQAAK EFIAW LVKGR GCA-amide | | 176 |
| HGEGT FTSDV SSYLE BQAAK EFIAW LVKGR GCSG-amide | | 177 |
| HGEGT FTSDV SBYLE KQAAK EFIAW LVKGR G[K/O/C]-amide | G8 cyclo [18-22]-Lys/Orn/Cys 38 | 178 |
| HGEGT FTSDV SSBLE GKAAK EFIAW LVKGR G[K/O/C]-amide | | 179 |
| HGEGT FTSDV SSYBE GQKAK EFIAW LVKGR G[K/O/C]-amide | | 180 |
| HGEGT FTSDV SSYLB GQAKK EFIAW LVKGR G[K/O/C]-amide | | 181 |
| HGEGT FTSDV SSYLE BQAAK EFIAW LVKGR G[K/O/C]-amide | | 182 |
| HGEGT FTSDV SSYLE GBAAK KFIAW LVKGR G[K/O/C]-amide | | 183 |
| HGEGT FTSDV SSYLE GQBAK EKIAW LVKGR G[K/O/C]-amide | | 184 |
| HGEGT FTSDV SSYLE GQABK EFKAW LVKGR G[K/O/C]-amide | | 185 |
| HGEGT FTSDV SSYLE GQAAB EFIKW LVKGR G[K/O/C]-amide | | 186 |
| HGEGT FTSDV SKYLE BQAAK EFIAW LVKGR G[K/O/C]-amide | | 187 |
| HGEGT FTSDV SSYLE KQAAB EFIAW LVKGR G-amide | | 188 |
| HGEGT FTSDV SSYLE KQAAB EFIAW LVKGR GCA-amide | | 189 |
| HGEGT FTSDV SSYLE KQAAB EFIAW LVKGR GCSG-amide | | 190 |
| HGEGT FTSDV SSKLE GBAAK EFIAW LVKGR G[K/O/C]-amide | | 191 |
| HGEGT FTSDV SSYKE GQBAK EFIAW LVKGR G[K/O/C]-amide | | 192 |
| HGEGT FTSDV SSYLK GQABK EFIAW LVKGR G[K/O/C]-amide | | 193 |
| HGEGT FTSDV SSYLE KQAAB EFIAW LVKGR G[K/O/C]-amide | | 194 |
| HGEGT FTSDV SSYLE GKAAK BFIAW LVKGR G[K/O/C]-amide | | 195 |
| HGEGT FTSDV SSYLE GQKAK EBIAW LVKGR G[K/O/C]-amide | | 196 |
| HGEGT FTSDV SSYLE GQAKK EFBAW LVKGR G[K/O/C]-amide | | 197 |
| HGEGT FTSDV SSYLE GQAAK EFIBW LVKGR G[K/O/C]-amide | | 198 |
| HGEGT FTSDV SSYLE [Cpa]QAAK EFIAW LVKGR G-amide | | 199 |
| HGEGT FTSDV SSYLE [Cpa]QAAK EFIAW LVKGR GCA-amide | | 200 |
| HGEGT FTSDV SSYLE [Cpa]QAAK EFIAW LVKGR GCSG-amide | | 201 |
| HGEGT FTSDV S[Cpa]YLE KQAAK EFIAW LVKGR G[K/O/C]-amide | | 202 |
| HGEGT FTSDV SS[Cpa]LE GKAAK EFIAW LVKGR G[K/O/C]-amide | | 203 |
| HGEGT FTSDV SSY[Cpa]E GQKAK EFIAW LVKGR G[K/O/C]-amide | | 204 |
| HGEGT FTSDV SSYL[Cpa] GQAKK EFIAW LVKGR G[K/O/C]-amide | | 205 |
| HGEGT FTSDV SSYLE [Cpa]QAAK EFIAW LVKGR G[K/O/C]-amide | | 206 |
| HGEGT FTSDV SSYLE G[Cpa]AAK KFIAW LVKGR G[K/O/C]-amide | | 207 |
| HGEGT FTSDV SSYLE GQ[Cpa]AK EKIAW LVKGR G[K/O/C]-amide | | 208 |

TABLE 2-continued

| GLP-1 Analog | Internal Ref. | SEQ ID NO: |
|---|---|---|
| HGEGT FTSDV SSYLE GQA[Cpa]K EFKAW LVKGR G[K/O/C]-amide | | 209 |
| HGEGT FTSDV SSYLE GQAA[Cpa] EFIKW LVKGR G[K/O/C]-amide | | 210 |
| HGEGT FTSDV SKYLE [Cpa]QAAK EFIAW LVKGR G[K/O/C]-amide | | 211 |
| HGEGT FTSDV SSYLE KQAA[Cpa] EFIAW LVKGR G-amide | | 212 |
| HGEGT FTSDV SSYLE KQAA[Cpa] EFIAW LVKGR GCA-amide | | 213 |
| HGEGT FTSDV SSYLE KQAA[Cpa] EFIAW LVKGR GCSG-amide | | 214 |
| HGEGT FTSDV SSKLE G[Cpa]AAK EFIAW LVKGR G[K/O/C]-amide | | 215 |
| HGEGT FTSDV SSYKE GQ[Cpa]AK EFIAW LVKGR G[K/O/C]-amide | | 216 |
| HGEGT FTSDV SSYLK GQA[Cpa]K EFIAW LVKGR G[K/O/C]-amide | | 217 |
| HGEGT FTSDV SSYLE KQAA[Cpa] EFIAW LVKGR G[K/O/C]-amide | | 218 |
| HGEGT FTSDV SSYLE GKAAK [Cpa]FIAW LVKGR G[K/O/C]-amide | | 219 |
| HGEGT FTSDV SSYLE GQKAK E[Cpa]IAW LVKGR G[K/O/C]-amide | | 220 |
| HGEGT FTSDV SSYLE GQAKK EF[Cpa]AW LVKGR G[K/O/C]-amide | | 221 |
| HGEGT FTSDV SSYLE GQAAK EFI[Cpa]W LVKGR G[K/O/C]-amide | | 222 |
| HGEGT FTSDV SSYLE [Cpa]QAAO EFIAW LVKGR G-amide | | 223 |
| HGEGT FTSDV SSYLE [Cpa]QAAO EFIAW LVKGR GCA-amide | | 224 |
| HGEGT FTSDV SSYLE [Cpa]QAAO EFIAW LVKGR GCSG-amide | | 225 |
| HGEGT FTSDV S[Cpa]YLE OQAAK EFIAW LVKGR G[K/O/C]-amide | | 226 |
| HGEGT FTSDV SS[Cpa]LE GOAAK EFIAW LVKGR G[K/O/C]-amide | | 227 |
| HGEGT FTSDV SSY[Cpa]E GQOAK EFIAW LVKGR G[K/O/C]-amide | | 228 |
| HGEGT FTSDV SSYL[Cpa] GQAOK EFIAW LVKGR G[K/O/C]-amide | | 229 |
| HGEGT FTSDV SSYLE [Cpa]QAAO EFIAW LVKGR G[K/O/C]-amide | | 230 |
| HGEGT FTSDV SSYLE G[Cpa]AAK OFIAW LVKGR G[K/O/C]-amide | | 231 |
| HGEGT FTSDV SSYLE GQ[Cpa]AK EOIAW LVKGR G[K/O/C]-amide | | 232 |
| HGEGT FTSDV SSYLE GQA[Cpa]K EFOAW LVKGR G[K/O/C]-amide | | 233 |
| HGEGT FTSDV SSYLE GQAA[Cpa] EFIOW LVKGR G[K/O/C]-amide | | 234 |
| HGEGT FTSDV SOYLE [Cpa]QAAK EFIAW LVKGR G[K/O/C]-amide | | 235 |
| HGEGT FTSDV SSYLE OQAA[Cpa] EFIAW LVKGR G-amide | | 236 |
| HGEGT FTSDV SSYLE OQAA[Cpa] EFIAW LVKGR GCA-amide | | 237 |
| HGEGT FTSDV SSYLE OQAA[Cpa] EFIAW LVKGR GCSG-amide | | 238 |
| HGEGT FTSDV SSOLE G[Cpa]AAK EFIAW LVKGR G[K/O/C]-amide | | 239 |
| HGEGT FTSDV SSYOE GQ[Cpa]AK EFIAW LVKGR G[K/O/C]-amide | | 240 |
| HGEGT FTSDV SSYLO GQA[Cpa]K EFIAW LVKGR G[K/O/C]-amide | | 241 |
| HGEGT FTSDV SSYLE OQAA[Cpa] EFIAW LVKGR G[K/O/C]-amide | | 242 |
| HGEGT FTSDV SSYLE GOAAK [Cpa]FIAW LVKGR G[K/O/C]-amide | | 243 |
| HGEGT FTSDV SSYLE GQOAK E[Cpa]IAW LVKGR G[K/O/C]-amide | | 244 |
| HGEGT FTSDV SSYLE GQAOK EF[Cpa]AW LVKGR G[K/O/C]-amide | | 245 |
| HGEGT FTSDV SSYLE GQAAO10 EFI[Cpa]W LVKGR G[K/O/C]-amide | | 246 |
| A HAEGT FTSDV SSYLE GQAAK EFIAW LVKGR | A-GLP-1 | 247 |

TABLE 2-continued

| GLP-1 Analog | Internal Ref. | SEQ ID NO: |
|---|---|---|
| G HAEGT FTSDV SSYLE GQAAK EFIAW LVKGR | G-GLP-1 | 248 |
| P HAEGT FTSDV SSYLE GQAAK EFIAW LVKGR | P-CLP-1 | 249 |
| S HAEGT FTSDV SSYLE GQAAK EFIAW LVKGR | S-CLP-1 | 250 |
| T HAEGT FTSDV SSYLE GQAAK EFIAW LVKGR | T-GLP-1 | 251 |
| V HAEGT FTSDV SSYLE GQAAK EFIAW LVKGR | V-GLP-1 | 252 |
| MQ HAEGT FTSDV SSYLE GQAAK EFIAW LVKGR | MQ-GLP1 | 253 |
| MR HAEGT FTSDV SSYLE GQAAK EFIAW LVKGR | MR-GLP1 | 254 |
| MK HAEGT FTSDV SSYLE GQAAK EFIAW LVKGR | MK-GLP1 | 255 |
| M HAEGT FTSDV SSYLE GQAAK EFIAW LVKGR | M-GLP1 | 256 |
| MH HAEGT FTSDV SSYLE GQAAK EFIAW LVKGR | MH-GLP1 | 257 |
| MHH HAEGT FTSDV SSYLE GQAAK EFIAW LVKGR | MHH-GLP1 | 258 |
| MY HAEGT FTSDV SSYLE GQAAK EFIAW LVKGR | MY-GLP1 | 259 |
| MI HAECT FTSDV SSYLE GQAAK EFIAW LVKGR | MI-GLP1 | 260 |
| MD HAEGT FTSDV SSYLE GQAAK EFIAW LVKGR | MD-GLP1 | 261 |
| ML HAEGT FTSDV SSYLE GQAAK EFIAW LVKGR | ML-GLP1 | 262 |
| MN HAEGT FTSDV SSYLE GQAAK EFIAW LVKGR | MN-GLP1 | 263 |
| ME HAEGT FTSDV SSYLE GQAAK EFIAW LVKGR | ME-GLP1 | 264 |
| MW HAEGT FTSDV SSYLE GQAAK EFIAW LVKGR | MW-GLP1 | 265 |
| MF HAEGT FTSDV SSYLE GQAAK EFIAW LVKGR | MF-GLP1 | 266 |
| MM HAEGT FTSDV SSYLE GQAAK EFIAW LVKGR | MM-GLP1 | 267 |
| HGEGT FTSDV SSYLE GQAAK EFIAW LVKGR GCA-amide | | 268 |
| HGEGT FTSDV SSYLE GQAAK EFIAW LVKGG G | | 269 |
| HGEGT FTSDV SSYLE GQAAK EFIAW LKNGG G | | 270 |
| HGEGT FTSDL SKQME EEAVR LFIEW LKNGG-amide | | 271 |
| HGEGT FTSDL SKQME ZEAVR LFIEW LKNGG-amide | | 272 |
| HGEGT FTSDV SSYLE GQAAK EFIAW L | | 273 |
| HGEGT FTSDV SSYLE EQAKK EFIAW LVKGR C-amide | | 274 |
| HGEGT FTSDV SSYLE EQAKK EFIAW LVKGR GCGS-amide | | 275 |
| HGEGT FTSDV SSYLE GQAKK EFIAW LEKGR K-amide | | 277 |
| HGEGT FTSDV SSYLE EQAADab EFIAW LVKGR G-amide | | 279 |
| HGEGT FTSDV SSYLE EQAADab EFIAW LVKGR GCA-amide | | 280 |
| HGEGT FTSDV SSYLE EQAADab EFIAW LVKGR GCSG-amide | | 281 |
| HGEGT FTSDV SEYLE DabQAAK EFIAW LVKGR G[K/O/C]-amide | | 282 |
| HGEGT FTSDV SSELE GDabAAK EFIAW LVKGR G[K/O/C]-amide | | 283 |
| HGEGT FTSDV SSYEE GQDabAK EFIAW LVKGR G[K/O/C]-amide | | 284 |
| HGEGT FTSDV SSYLE GQADabK EFIAW LVKGR G[K/O/C]-amide | | 285 |
| HGEGT FTSDV SSYLE EQAADab EFIAW LVKGR G[K/O/C]-amide | | 286 |
| HGEGT FTSDV SSYLE GEAAK DabFIAW LVKGR G[K/O/C]-amide | | 287 |

TABLE 2-continued

| GLP-1 Analog | Internal Ref. | SEQ ID NO: |
|---|---|---|
| HGEGT FTSDV SSYLE GQEAK EDabIAW LVKGR G[K/O/C]-amide | | 288 |
| HGEGT FTSDV SSYLE GQAEK EFDabAW LVKGR G[K/O/C]-amide | | 289 |
| HGEGT FTSDV SSYLE GQAAE EFIDabW LVKGR G[K/O/C]-amide | | 290 |
| HGEGT FTSDV SSYLE GQAADab EFIAW LVKGR G[K/O/C]-amide | | 291 |
| HGEGT FTSDV SSYLE DabQAAE EFIAW LVKGR G-amide | | 292 |
| HGEGT FTSDV SSYLE DabQAAE EFIAW LVKGR GCA-amide | | 293 |
| HGEGT FTSDV SSYLE DabQAAE EFIAW LVKGR GCSG-amide | | 294 |
| HGEGT FTSDV SDabYLE EQAAK EFIAW LVKGR G[K/O/C]-amide | | 295 |
| HGEGT FTSDV SSDabLE GEAAK EFIAW LVKGR G[K/O/C]-amide | | 296 |
| HGEGT FTSDV SSYDabE GQEAK EFIAW LVKGR G[K/O/C]-amide | | 297 |
| HGEGT FTSDV SSYLDab GQAEK EFIAW LVKGR G[K/O/C]-amide | | 298 |
| HGEGT FTSDV SSYLE DabQAAE EFIAW LVKGR G[K/O/C]-amide | | 299 |
| HGEGT FTSDV SSYLE GDabAAK EFIAW LVKGR G[K/O/C]-amide | | 300 |
| HGEGT FTSDV SSYLE GQDabAK EEIAW LVKGR G[K/O/C]-amide | | 301 |
| HGEGT FTSDV SSYLE GQADabK EFEAW LVKGR G[K/O/C]-amide | | 302 |
| HGEGT FTSDV SSYLE GQAADab EFIEW LVKGR G[K/O/C]-amide | | 303 |
| HGEGT FTSDV SSYLDab GQAAE EFIAW LVKGR G[K/O/C]-amide | | 304 |

The term "GLP-1 analog" also includes variants, fragments and derivatives of the foregoing GLP-1 analogs that are functional equivalents to one of the foregoing GLP-1 analogs in that the variant, fragment or derivative has a similar amino acid sequence (e.g. comprising conservative substitutions) and retains, to some extent, at least one activity of the GLP-1 analog.

"GLP-1 variants" include polypeptides that are "substantially identical" (see definition supra) to the GLP-1 analogs in the families listed above and in Table 2. Such variants include proteins having amino acid alterations such as deletions, insertions and/or substitutions. Typically, such alterations are conservative in nature (see, e.g., Creighton, 1984, Proteins, W.H. Freeman and Company and discussion supra) such that the activity of the variant polypeptide is substantially similar to one of the GLP-1 analogs that are disclosed herein (e.g., has a GLP-1 activity such as insulinotropic activity). In the case of substitutions, the amino acid replacing another amino acid usually has similar structural and/or chemical properties. Insertions and deletions relative to the GLP-1 analogs that are listed in the families above are typically involve 1, 2, 3, 4, 5, 6, 7, 8, 9 or 10 amino acids. In other instances, there are 1, 2, 3, 4 or 5 amino acid insertions or deletions.

A GLP-1 variant can have at least 75%, preferably at least 85%, more preferably at least 90%, 95%, 96%, 97%, 98%, or 99% amino acid identity with a GLP-1 analog as described herein (i.e., the analogs in the different families listed above and those listed in Table 2), provided the variant still has a GLP-1 activity. For example, a variant can have at least 75%, 85%, 90%, 95%, 96%, 97%, 98%, or 99% amino acid identity with a GLP-1 analog of SEQ ID NO:7 or 8, provided that amino acid $Xaa_8$, $Xaa_{23}$ or any of $Xaa_{38}$ to $Xaa_{45}$ are unaltered. Other variants have at least 75%, 85%, 90%, 95%, 96%, 97%, 98%, or 99% amino acid identity with a GLP-1 analog of SEQ ID NO:11 or 12, provided that amino acid $Xaa_8$ or any of $Xaa_{38}$ to $Xaa_{41}$ are unaltered. Certain other variants have at least 75%, 85%, 90%, 95%, 96%, 97%, 98%, or 99% amino acid identity with a GLP-1 analog of any one of SEQ ID NO:16-28, provided that amino acid $Xaa_8$, $Xaa_{22}$, or any of $Xaa_{38}$ to $Xaa_{41}$ when present, are unaltered. Still other variants have at least 75%, 85%, 90%, 95%, 96%, 97%, 98%, or 99% amino acid identity with a GLP-1 analog of any one of SEQ ID NO: 30 to 246 provided that two amino acids selected from $Xaa_{18}$, $Xaa_{19}$, $Xaa_{20}$, $Xaa_{21}$, $Xaa_{22}$, $Xaa_{23}$, $Xaa_{24}$, $Xaa_{25}$, $Xaa_{26}$, $Xaa_{27}$, $Xaa_{28}$, $Xaa_{29}$, and $Xaa_{30}$ are joined to form a ring. Still other variants have at least 75%, 85%, 90%, 95%, 96%, 97%, 98%, or 99% amino acid identity with a GLP-1 analog of any one of SEQ ID NO: 247 to 267 with no more than 1, 2, 3, 4, or 5 conservative amino acid substitutions, provided that the amino acids $Xaa_4$, $Xaa_5$, or $Xaa_6$, when present, are unaltered. Still other variants have at least 75%, 85%, 90%, 95%, 96%, 97%, 98%, or 99% amino acid identity with a GLP-1 analog of any one of SEQ ID NO: 268 to 275 with no more than 1, 2, 3, 4, or 5 conservative amino acid substitutions.

In certain embodiments, a GLP-1 variant comprises SEQ ID NO:7 or 8 with no more than 1, 2, 3, 4 or 5 conservative amino acid substitutions, provided that the conservative amino acid substitutions are not at amino acid $Xaa_8$, $Xaa_{23}$, or any of $Xaa_{38}$ to $Xaa_{45}$ and the variant has a GLP-1 activity (e.g., insulinotropic activity).

In certain embodiments, a GLP-1 variant comprises SEQ ID NO:11 or 12 with no more than 1, 2, 3, 4 or 5 conservative amino acid substitutions, provided that the conservative amino acid substitutions are not at amino acid $Xaa_8$ or any of $Xaa_{38}$ to $Xaa_{41}$ and the variant has a GLP-1 activity (e.g., insulinotropic activity).

In certain embodiments, a GLP-1 variant comprises any one of SEQ ID NO: 16-28 with no more than 1, 2, 3, 4, or 5 conservative amino acid substitutions, provided that the conservative amino acid substitutions are not at amino acid $Xaa_8$, $Xaa_{22}$, or any of $Xaa_{38}$ to $Xaa_{41}$.

In certain embodiments, a GLP-1 variant comprises any one of SEQ ID NO: 30 to 246 with no more than 1, 2, 3, 4 or 5 conservative amino acid substitutions, provided that two amino acids selected from $Xaa_{18}$, $Xaa_{19}$, $Xaa_{20}$, $Xaa_{21}$, $Xaa_{22}$, $Xaa_{23}$, $Xaa_{24}$, $Xaa_{25}$, $Xaa_{26}$, $Xaa_{27}$, $Xaa_{28}$, $Xaa_{29}$, and $Xaa_{30}$ are joined to form a ring.

In certain embodiments, a GLP-1 variant comprises any one of SEQ ID NO: 247 to 267 with no more than 1, 2, 3, 4, or 5 conservative amino acid substitutions, provided that the conservative amino acid substitutions are not at amino acid $Xaa_4$, $Xaa_5$, or $Xaa_6$.

A "GLP-1 derivative" as used herein refers to one of the GLP-1 analogs listed in the families above and in Table 2 in which one or more amino acids has been: 1) substituted with the corresponding D-amino acid, 2) altered to a non-naturally occurring amino acid residue, and/or 3) chemically modified. Examples of chemical modification include, but are not limited to alkylation, acylation, deamidation, esterification, phosphorylation, and glycosylation of the peptide backbone and/or amino acid side chains.

A "GLP-1 fragment" refers to truncated forms of the GLP-1 analogs listed in the families above or in Table 2 or variants or derivatives thereof. The fragments typically are truncated by 1, 2, 3, 4 or 5 amino acids relative to the GLP-1 analogs set forth in the families above. Truncation can be at either the amino and/or carboxyl terminus.

GLP-1 compounds as provided herein can be complexed with suitable divalent metal cations. Divalent metal complexes of GLP-1 compounds as provided herein can be administered subcutaneously as suspensions, and have a decreased rate of release in vivo, because such complexes of GLP-1 compounds as provided herein are generally insoluble in aqueous solutions of about physiological pH. Non-limiting examples of divalent metal cations suitable for complexing with a GLP-1 compound as provided herein include $Zn^{++}$, $Mn^{++}$, $Fe^{++}$, $Ca^{++}$, $Co^{++}$, $Cd^{++}$, $Ni^{++}$, and the like. Divalent metal complexes of GLP-1 compounds as provided herein can be obtained, for example, using techniques as described in WO 01/98331, which is incorporated herein by reference.

The GLP-1 compounds that are provided may simply comprise a GLP-1 analog as disclosed herein or include an additional component, typically chosen to extend the half-life of the analog in vivo. Some GLP-1 compounds, for instance, are pegylated to extend the half-life of the molecule and/or reduce clearance. Other GLP-1 analogs are modified with a water-soluble polymer other than PEG. Suitable water-soluble polymers or mixtures thereof include, but are not limited to, N-linked or O-linked carbohydrates, sugars (e.g. various polysaccharides such as chitosan, xanthan gum, cellulose and its derivatives, acacia gum, karaya gum, guar gum, carrageenan, and agarose), phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), polyoxyethylene-polyoxypropylene, polyvinyl alcohol, and copolymers of the foregoing.

The GLP-1 compound, for instance, can include various components chosen to increase the in vivo half-life of the GLP-1 analog.

Yet another option is to fuse the GLP-1 analog to another polypeptide or polypeptide domain. Thus, the GLP-1 compound can be a fusion protein in which the GLP-1 analogs disclosed herein are fused to various proteins such as the Fc region of an immunoglobulin, transferrin, or a blood component such as serum albumin (e.g., human serum albumin), or fragments of these proteins. Exemplary amino acid sequences for human albumin are discussed in Lawn et al., 1981, *Nucleic Acids Research* 9:6102-6114; Meloun et al., 1975, *FEBS Lett.* 58:136; and Minghetti et al., 1986, *J. Biol. Chem.* 261:6747). Such fusion proteins can be prepared using standard recombinant techniques such as those described herein and as known in the art.

Fusions can be made either at the amino-terminus, at the carboxyl-terminus of the GLP-1 analog or at both terminii. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

B. Pegylation

In certain embodiments, a GLP-1 analog as provided herein is pegylated. As used herein, the terms "pegylated" and "pegylation" have their general meaning in the art and refer generally, for example, to the process of chemically modifying a GLP-1 analog as described herein by covalent attachment of one or more molecules of polyethylene glycol or a derivative thereof, such as by reacting a polyalkylene glycol, preferably an activated polyalkylene glycol, with a suitable reactive group or moiety such as an amino acid, e.g. lysine, to form a covalent bond. Although "pegylation" is often carried out using polyethylene glycol or derivatives thereof, such as methoxy polyethylene glycol, the term as used herein also includes any other useful polyalkylene glycol, such as, for example polypropylene glycol. As used herein, the term "PEG" refers to polyethylene glycol and its derivatives as understood in the art (see for example U.S. Pat. Nos. 5,445, 090, 5,900,461, 5,932,462, 6,436,386, 6,448,369, 6,437,025, 6,448,369, 6,495,659, 6,515,100, and 6,514,491).

GLP-1 analogs as provided herein can be pegylated at random positions within the peptide, or at predetermined positions within the molecule and can include one or more attached molecules, typically one, two, three, four, or five molecules.

The polymer used for peglylation can be of any molecular weight, and can be branched or unbranched. For polyethylene glycol, generally the molecular weight is between about 1 kDa and about 100 kDa (the term "about" indicating that in preparations of polyethylene glycol, some molecules will weigh more, some less, than the stated molecular weight) for ease in handling and manufacturing. For example, the polyethylene glycol can have an average molecular weight of about 1, 5, 10, 15, 20, 25, 30, 35, 40, 50, 60, 70, 80, 90 or 100 kDa. Some GLP-1 compounds are pegylated with one or more molecules that are less than 40, 30 or 20 kDa. Other sizes can be used, depending on the desired therapeutic profile (e.g., the duration of circulating half-life desired, the effects, if any on biological activity, the ease in handling, the degree or lack of antigenicity and other known effects of the polyethylene glycol to a therapeutic protein or analog).

The PEG molecules (or other water-soluble polymers described herein) should be attached to the GLP-1 analogs with consideration of effects on functional or antigenic domains of the polypeptides or proteins. For example, PEG can be covalently bound through amino acid residues via a reactive group, such as, a free amino, carboxyl group or sulfhydryl group. Reactive groups are those to which an activated PEG molecule can be bound. Examples of naturally occurring amino acid residues having a free amino group include lysine residues and the N-terminal amino acid residues; those having a free carboxyl group include aspartic acid residues glutamic acid residues and the C-terminal amino acid residue. Sulfhydryl groups (e.g., on cysteine) can also be used as a reactive group for attaching the polyethylene glycol molecules. PEG molecules may also be incorporated by conjugation to reactive functional groups introduced synthetically as unnatural amino acids or alternatively, PEG may be conjugated to the peptide using orthogonal methods during peptide synthesis.

A variety of strategies can be used for pegylation of a GLP-1 analog (see, e.g., WO 2005/042027, WO 2004/060386, Veronese, 2001, *Biomaterials* 22:405-417; Roberts et al., 2002, *Advanced Drug Delivery Reviews* 54:459-476; see also EP 0 401 384 (coupling PEG to G-CSF), and Malik et al., 1992, *Exp. Hematol.* 20:1028-1035 (reporting pegylation of GM-CSF using tresyl chloride). For example, PEG can be linked to GLP-1 analogs via covalent bonds to lysine, histidine, aspartic acid, glutamic acid, or cysteine residues. One or more reaction chemistries can be employed to attach polyethylene glycol to specific amino acid residues (e.g., lysine, histidine, aspartic acid, glutamic acid, or cysteine) of the GLP-1 analog or to more than one type of amino acid residue (e.g., lysine, histidine, aspartic acid, glutamic acid, cysteine and combinations thereof) of the GLP-1 analog.

One such strategy is to link a PEG to a cysteine that is part of the GLP-1 analog. As shown supra, several of the GLP-1 analogs that are provided include a cysteine residue at or near the C-terminus at which PEG can be attached. Attachment to cysteine can be achieved using various approaches. One common method involves reacting a PEG-maleimide to the thiol group of cysteine.

Another approach is to attach PEG to the carboxy-terminus of the GLP-1 analog via enzymatic coupling (see, e.g., U.S. Pat. No. 4,343,898).

PEG can be attached to the GLP-1 analog either directly or by an intervening linker. Linkerless systems for attaching polyethylene glycol to proteins and polypeptides are described in Delgado et al., Crit. Rev. Thera. Drug Carrier Sys. 9:249-304, 1992; Francis et al., 1998, *Intern. J. of Hematol.* 68:1-18; U.S. Pat. No. 4,002,531; U.S. Pat. No. 5,349,052; WO 95/06058; and WO 98/32466.

One method for attaching PEG directly to amino acid residues of GLP-1 analogs without an intervening linker employs tresylated MPEG, which is produced by the modification of monmethoxy polyethylene glycol (MPEG) using tresylchloride ($ClSO_2 CH_2 CF_3$). Upon reaction of the protein or polypeptide with tresylated MPEG, polyethylene glycol is directly attached to amine groups of the protein or polypeptide. Thus, GLP-1 analog-PEG conjugates can be produced by reacting GLP-1 analogs with a PEG molecule having a 2,2,2-trifluoreothane sulphonyl group.

PEG can also be attached to GLP-1 analogs using a number of different intervening linkers. For example, U.S. Pat. No. 5,612,460 discloses urethane linkers for connecting PEG to GLP-1 analogs. GLP-1 analog-PEG conjugates wherein the PEG is attached to the GLP-1 analog by a linker can also be produced by reaction of GLP-1 analogs with compounds such as MPEG-succinimidylsuccinate, MPEG activated with 1,1'-carbonyldiimidazole, MPEG-2,4,5-trichloropenylcarbonate, MPEG-.rho.-nitrophenolcarbonate, and various MPEG-succinate derivatives. A number of additional polyethylene glycol derivatives and reaction chemistries for attaching polyethylene glycol to proteins and polypeptides are described in WO 98/32466.

The number of polyethylene glycol moieties attached to each GLP-1 analog (i.e., the degree of substitution) can also vary. For example, the pegylated GLP-1 analogs can be linked, on average, to 1, 2, 3, 4, or 5, or more polyethylene glycol molecules. Methods for determining the degree of substitution are discussed, for example, in Delgado et al., 1992, *Crit. Rev. Thera. Drug Carrier Sys.* 9:249-304.

To effect covalent attachment of PEG to a GLP-1 analog, the hydroxyl end groups of the PEG must first be converted into reactive functional groups. This process is frequently referred to as "activation" and the product is called "activated PEG." Methoxy polyethylene glycol (mPEG), distally capped with a reactive functional group is often used. One such activated PEG is succinimidyl succinate derivative of PEG (SS-PEG). See also Abuchowski et al., 1984, *Cancer Biochem. Biophys.* 7:175-186; and U.S. Pat. No. 5,122,614 which discloses polyethylene glycol-N-succinimide carbonate and its preparation.

The Example section below provides detailed guidance on strategies for pegylating the GLP-1 compounds that are disclosed herein.

IV. Nucleic Acids and Methods of Preparing the GLP-1 Compounds and Analogs

The GLP-1 analogs that are provided can be produced using various methods that are established in the art, including chemical synthesis and/or recombinant methods.

Different strategies for attaching PEG to the peptide have been set forth above.

If the GLP-1 analog is prepared by chemical synthesis, such methods typically involve solid-state approaches, but can also utilize solution-based chemistries or combinations of solid-state and solution approaches. The Example section below includes detailed guidance on the synthesis of the GLP-1 compounds described herein, including the various cyclic compounds that include a ring.

Examples of solid-state methodologies for synthesizing proteins are described by Merrifield, 1964, *J. Am. Chem. Soc.* 85:2149; and Houghton, 1985, *Proc. Natl. Acad. Sci.* 82:5132. Fragments of the GLP-1 analog can also be synthesized and then joined together. Methods for conducting such reactions are described by Grant, 1992, Synthetic Peptides: A User Guide, W.H. Freeman and Co., N.Y.; and in "Principles of Peptide Synthesis," 1993 (Bodansky and Trost, ed.), Springer-Verlag, Inc. N.Y. Further guidance on methods for preparing peptides sufficient to guide the skilled practitioner in the preparation of the GLP-1 analogs described herein is provided by: Liu et al., 1996, *J. Am. Chem. Soc.* 118:307-312; Kullmann, 1987, Enzymatic Peptide Synthesis, CRC Press, Boca Raton, Fla., pp. 41-59; Dryland et al., 1986, *J. Chem. Soc., Perkin Trans.* 1:125-137; Jones, 1991, The Chemical Synthesis of Peptides, Clarendon Press; and Bodanszky, M. and Bodanszky A., 1994, The Practice of Peptide Synthesis, $2^{nd}$ Ed., Springer-Verlag).

Alternatively, the GLP-1 analogs can be prepared using established recombinant techniques. For example, a GLP-1 analog can be expressed in a host cell by introducing into the cell a recombinant nucleic acid construct encoding a GLP-1 analog. According to such embodiments, the cells are transformed with the recombinant nucleic acid construct using any method for introducing polynucleotides into a host cell, including, for example packaging the polynucleotide in a virus (or into a viral vector) and transducing a host cell with the virus (or vector), or by transfection procedures known in the art, as exemplified by U.S. Pat. Nos. 4,399,216, 4,912,040, 4,740,461, and 4,959,455 (which are hereby incorporated herein by reference for any purpose). The transformation procedure used may depend upon the cell to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into cells and cell nuclei.

A nucleic acid molecule encoding all or a functional portion of the GLP-1 analog amino acid sequence can be inserted into an appropriate expression vector using conventional recombinant genetic techniques. The vector is typically selected to be functional in the particular host cell employed (i.e., the vector is compatible with the host cell machinery, permitting amplification and/or expression of the gene). For a review of expression vectors, see Nolan and Shatzman, 1998, *Curr. Opin. Biotechnol.* 9:447-450.

Expression vectors may be constructed from a convenient starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding GLP-1 analog has been inserted into the proper site of the vector, the completed vector may be inserted into a suitable host cell for amplification and/or polypeptide expression. The transformation of an expression vector encoding GLP-1 analog into a selected host cell may be accomplished by well-known methods including methods such as transfection, infection, calcium chloride, electroporation, microinjection, lipofection, DEAE-dextran method, or other known techniques as described above. The method selected will in part be a function of the type of host cell to be used. These methods and other suitable methods are well known to the skilled artisan, and are set forth, for example, in Sambrook et al., 2001, MOLECULAR CLONING: A LABORATORY MANUAL, 3d ed., Cold Spring Harbor Laboratory Press, Cold Spring Harbor, N.Y.

A host cell, when cultured under appropriate conditions, synthesizes a GLP-1 analog that can subsequently be collected from the culture medium (if the host cell secretes it into the medium) or directly from the host cell producing it (if it is not secreted) if collection of the protein is desired. Selection of an appropriate host cell will depend upon a number of different factors, such as desired expression levels, polypeptide modifications that are desirable or necessary for activity (such as glycosylation or phosphorylation) and ease of folding into a biologically-active molecule.

Mammalian cell lines available as host cells for expression are well known in the art and include, but are not limited to, many immortalized cell lines available from the American Type Culture Collection (ATCC), such as Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels of GLP-1 analog.

V. Exemplary Therapeutic Utilities

In view of the various activities associated with GLP-1 (see Background), the GLP-1 compounds that are described herein can be used generally to achieve one or more of the following biological activities: 1) stimulate insulin release, 2) reduce blood glucose levels, 3) increase plasma insulin levels, 4) stimulate transcription of β-cell-specific genes (e.g., GLUT-1 transporter, insulin receptor and hexokinase-1), 5) increase β-cell mass by inhibiting β-cell apoptosis and increasing β-cell proliferation and replication, 6) induce satiety thereby reducing food intake and promoting weight loss, 7) reduce gastric secretion, 8) delay gastric emptying, and 9) reduce gastric motility.

The GLP-1 compounds can thus be used to treat a number of different forms of diabetes or diseases closely related thereto, including but not limited to, diabetes mellitus of Type I or Type II, impaired glucose tolerance, insulin resistance, latent autoimmune diabetes Adult (LADA), gestational diabetes, metabolic syndrome, and maturity-onset diabetes of the young (MODY). Thus, the GLP-1 compounds can be used to treat individuals having decreased sensitivity to insulin due to infection, stress, stroke, or due to a decreased sensitivity induced during pregnancy. Other types of diabetes that can be treated are those in which diabetes is linked to another endocrine disease such as glucagonoma, primary aldosteronism, Cushing's syndrome and somatostatinoma, or diabetes that arises due to administration of certain drugs or hormones (e.g., estrogen-containing pharmaceuticals, psychoactive drugs, antihypertensive drugs, and thiazide diuretics).

The GLP-1 compounds can also be used to treat various coronary diseases and diseases associated with lipid disorders, including, for instance, hypertension, coronary artery disease, hyperlipidemia, cardiovascular disease, atherosclerosis and hypercholesteremia and myocardial infarction.

Bone disorders, osteoporosis and other related diseases can also be treated with the GLP-1 compositions.

Additional diseases that can be treated with the GLP-1 compounds include: obesity, irritable bowel syndrome, stroke, catabolic changes after surgery, myocardial infarction,), and hyperglycemia. The GLP-1 compounds can also be used as a sedative.

The GLP-1 compounds can also be used prophylactically, including treating individuals at risk for developing a disease such as listed above. As a specific example, the compounds can be administered prophylactically to an individual at risk for non-insulin dependent diabetes or becoming obese. Such individuals include, for instance, those that have impaired glucose tolerance, those that are overweight and those with a genetic predisposition to the foregoing diseases (e.g., individuals from families with a history of diabetes).

A variety of different subjects can be treated with the GLP-1 compounds. The term "subject" or "patient" as used herein, typically refers to a mammal, and often, but not necessarily, is a human that has or is at risk for one of the foregoing diseases. The subject, however, can also be a non-human primate (e.g., ape, monkey, gorilla, chimpanzee). The subject can also be a mammal other than a primate such as a veterinarian animal (e.g., a horse, bovine, sheep or pig), a domestic animal (e.g., cat or dog) or a laboratory animal (e.g., mouse or rat).

VI. Pharmaceutical Compositions

A. Composition

The GLP-1 compounds that are provided herein can be used as the active ingredient in pharmaceutical compositions formulated for the treatment of the diseases listed in the section on therapeutic utilities. Thus, the GLP-1 compounds that are disclosed can be used in the preparation of a medicament for use in various therapeutic applications, including those listed supra.

In addition to the GLP-1 compound, pharmaceutical compositions can also include one or more other therapeutic agents that are useful in treating one or more the various disorders for which the GLP-1 compounds have utility. General classes of other therapeutic agents that can be combined with certain GLP-1 compositions include, but are not limited to, insulin releasing agents, inhibitors of glucagon secretion, protease inhibitors, glucagon antagonists, anti-obesity agents, compounds that reduce caloric intake, selective estrogen receptor modulators, steroid or non-steroid hormones, growth factors, and dietary nutrients.

Such additional therapeutic agents can include, for instance, agents for treating hyperglycemia, diabetes, hypertension, obesity and bone disorders. Examples of other therapeutic agents for treating diabetes that can be included in the compositions include those used in treating lipid disorders. Specific examples of such agents include, but are not limited to, bile acid sequestrants (e.g., cholestyramine, lipostabil, tetrahydrolipstatin), HMG-CoA reductase inhibitors (see, e.g., U.S. Pat. Nos. 4,346,227; 5,354,772; 5,177,080; 5,385,929; and 5,753,675), nicotinic acid, MTP inhibitors (see, e.g., U.S. Pat. Nos. 5,595,872; 5,760,246; 5,885,983; and 5,962,440), lipoxygenase inhibitors, fibric acid derivatives, cholesterol absorption inhibitors, squalene synthetase inhibitors (see, e.g., U.S. Pat. Nos. 4,871,721; 5,712,396; and 4,924,024) and inhibitors of the ileal sodium/bile acid cotransporter. Other anti-diabetic agents that can be incorporated into the compositions include meglitinides, thiazolidinediones, biguanides, insulin secretagogues, insulin sensitizers, glycogen phosphorylase inhibitors, PPAR-alpha agonists, PPAR-gamma agonists.

An inhibitor of dipeptidylpeptidase IV activity can also be included to inhibit cleavage at the N-terminus of the GLP-1 analog.

The pharmaceutical compositions can include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. In cases such as this where the pharmaceutical composition includes a polypeptide (e.g., the GLP-1 analog), the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate.

The GLP-1 analog of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

The pharmaceutical compositions can also be formulated as part of a controlled-release system. Such systems can include an implantable osmotic pump, liposomes or a transdermal patch. Methods for delivery using pumps are described, for example, by Langer, 1990, *Science* 249:1527-33; and Saudek et al., 1989, *N. Engl. J. Med.* 321:574). Delivery options for using liposomes are discussed, for instance, by Treat et al., 1989, in Liposomes in the Terapy of Infetious Disease and Cancer, (Lopez-Berestein and Fidler, eds.), Liss, New York, pp. 353-65; and Langer, 1990, *Science* 249:1527-33).

Further guidance regarding formulations that are suitable for various types of administration can be found in Remington's Pharmaceutical Sciences, 1985, Mace Publishing Company, Philadelphia, Pa., 17th ed. For a brief review of methods for drug delivery, see, Langer, 1990, *Science* 249:1527-1533.

2. Dosage

As noted above, the pharmaceutical compositions can be administered for prophylactic and/or therapeutic treatments. An "effective amount" refers generally to an amount that is a sufficient, but non-toxic, amount of the active ingredient (i.e., GLP-1 compound or GLP-1 analog) to achieve the desired effect, which is a reduction or elimination in the severity and/or frequency of symptoms and/or improvement or remediation of damage. A "therapeutically effective amount" refers to an amount that is sufficient to remedy a disease state or symptoms, or otherwise prevent, hinder, retard or reverse the progression of a disease or any other undesirable symptom. A "prophylactically effective amount" refers to an amount that is effective to prevent, hinder, or retard the onset of a disease state or symptom.

In general, toxicity and therapeutic efficacy of the GLP-1 compound can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are desirable.

The data obtained from cell culture and/or animal studies can be used in formulating a range of dosages for humans. The dosage of the active ingredient typically lines within a range of circulating concentrations that include the $ED_{50}$ with little or no toxicity. The dosage can vary within this range depending upon the dosage form employed and the route of administration utilized.

The amount of active ingredient administered will depend upon various factors that can be assessed by the attending clinician, such as the severity of the disease, the age and size of the subject to be treated and the particular disease itself. In general, however, the total amount of the GLP-1 analog itself that is administered typically ranges from 1 µg/kg body weight/day to 100 mg/kg/day. In some instances, the dosage ranges from 10 µg/kg/day to 10 mg/kg/day. In other treatment regimens, the GLP-1 compound is administered at 50 ug/kg/day to 5 mg/kg/day or from 100 ug/kg/day to 1 mg/kg/day.

C. Administration

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Suitable formulations for rectal administration include, for example, suppositories, which consist of the packaged active ingredient with a suppository base. Suitable suppository bases include natural or synthetic triglycerides or paraffin hydrocarbons. In addition, it is also possible to use gelatin rectal capsules which consist of a combination of the packaged active ingredient with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

EXAMPLES

The following examples, including the experiments conducted and results achieved are provided for illustrative purposes only and are not to be construed as limiting the invention.

Example 1

Synthesis of GLP-1 Compounds

Peptide Synthesis

The following protocol was used to generate GLP-1 analogs as described herein. $N^\alpha$-Fmoc, side-chain protected amino acids, Wang resin, and Rink amide resin were used. The following side-chain protection strategies were employed: Asp(OtBu), Arg(Pbf), Cys(Acm), Glu(OtBu), Glu(O2-PhiPr), His(Trt), Lys($N^\epsilon$-Boc), Lys($N^\epsilon$-Mtt), Ser(OtBu), Thr(OtBu) and Tyr(OtBu). GLP-1 peptide derivatives were synthesized in a stepwise manner on an ABI433 peptide synthesizer by SPPS using O-Benzotriazole-N,N,N',N'-tetramethyl-uronium-hexafluoro-phosphate (HBTU)/N,N-diisopropylethylamine (DIEA)/N,N-dimethylformamide (DMF) coupling chemistry at 0.2 mmol equivalent resin scale (Fmoc-deprotected Rink amide resin). For each coupling cycle, 1 mmol $N^\alpha$-Fmoc-amino acid, 4 mmol DIEA and 1 mmol equivalents of HBTU were used. The concentration of the HBTU-activated Fmoc amino acids was 0.5 M in DMF, and the coupling time was 45 min. Fmoc deprotections were carried out with two treatments using a 30% piperidine in DMF solution first for 2 min and then for an additional 20 min.

Lactam Formation

Side-chain to side-chain lactam formation was carried out on the assembled N-terminally Fmoc-protected peptide resin. The peptide-resin was solvated in DCM for 30 mins, and drained. The Mtt and 2-PhiPr groups (protecting at the specified lactam bond forming site) were removed with 1% TFA in DCM solution containing 5% TIS.

Treatment of the peptide-resin with the 1% TFA in DCM solution was repeated 8 times in 30 min increments, and each treatment was followed by extensive DCM washes. The liberate carboxyl and amino groups were then condensed by the addition of 5 equiv of 0.5M benzotriazole-1-yl-oxy-tris-pyrrolidino-phosphonium hexafluorophosphate (PyBOP) and 10 equiv of DIEA in DMF were added to the peptide resin, and left for 24 h. The resin was then wash thoroughly with DMF, DCM, and DCM/MeOH, and dried.

Side Chain Deprotection and Cleavage from Resin

Following synthesis and modification, the resin was then drained, and washed with DCM, DMF, DCM, and then dried in vacuo. The peptide-resin was deprotected and released from the resin by treatment with a trifluoroacetic acid (TFA)/1,2-ethanedithiol (EDT)/triisopropyl-silane (TIS)/$H_2O$ (92.5:2.5:2.5:2.5 v/v) solution at room temperature for 90 min. The volatiles were then removed with a stream of nitrogen gas, the crude peptide precipitated twice with diethyl ether and collected by centrifugation.

Acm Deprotection

Crude GLP-1 Cys(Acm)-protected peptide was dissolved in 10% aq AcOH containing freshly added mercury(II) acetate (15 mg/mL). The solution was agitated at ambient temperature for 4 hours. 80% aq. 2-mercaptoethanol was then added to a give 20% v/v composition, mixed thoroughly, and left overnight. It was then diluted with 0.1% aq. TFA, and the grey precipitate containing mercury salts was removed by centrifugation and filtration. The deprotected peptide was then subjected to reversed-phase HPLC purification.

Specific Examples

Figure 3:
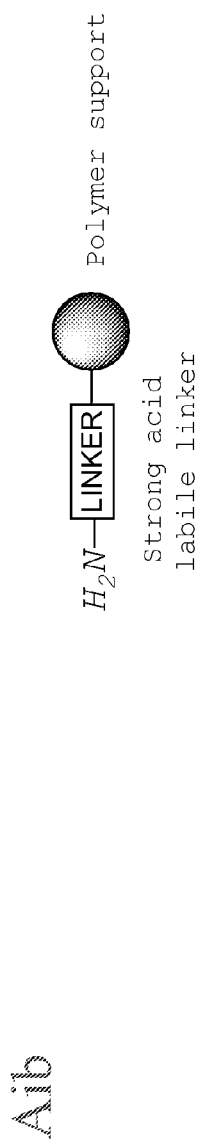
FIG. 3 illustrates an exemplary approach for synthesizing an analog that includes a Gly substitution at position 8, an Aib substitution at position 22 and the addition of a cysteine and an alanine at the C-terminus (i.e., SEQ ID NO:18).
Figure 3:
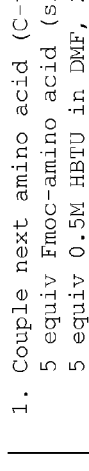
Figure 3:
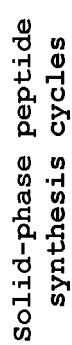
Figure 3:

A synthetic protocol for synthesizing a GLP-1 compound without a ring is presented in FIG. 3, which illustrates the approach for synthesizing an analog that includes a Gly substitution at position 8, an Aib substitution at position 22 and the addition of a cysteine and an alanine at the C-terminus (i.e., SEQ ID NO:18).

Figure 4:
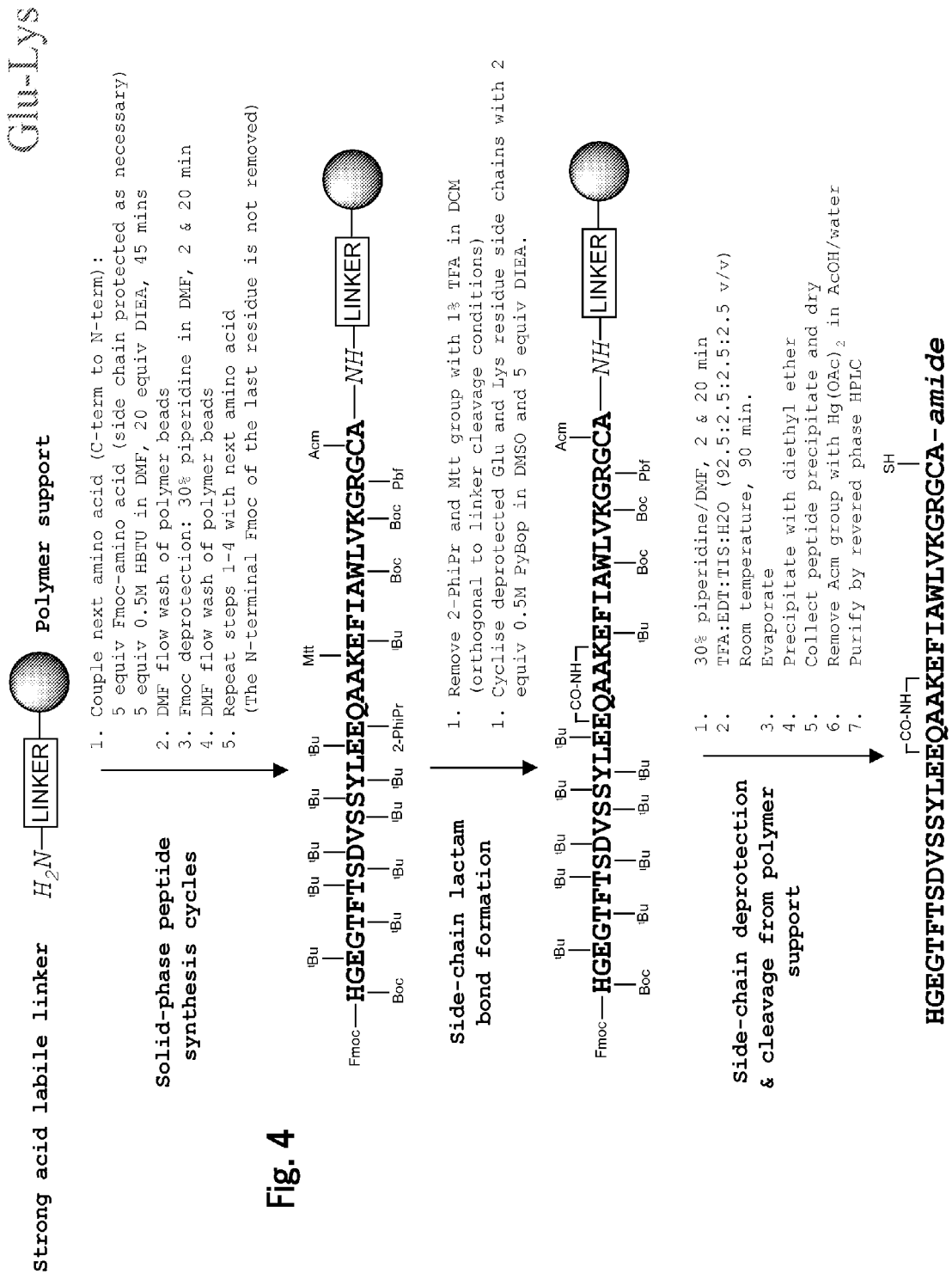
FIG. 4 provides an exemplarly synthetic scheme for preparing a cyclic GLP-1 compound in which the side chains of a glutamic acid and lysine residue are joined to form a cyclic lactam.
Figure 5:
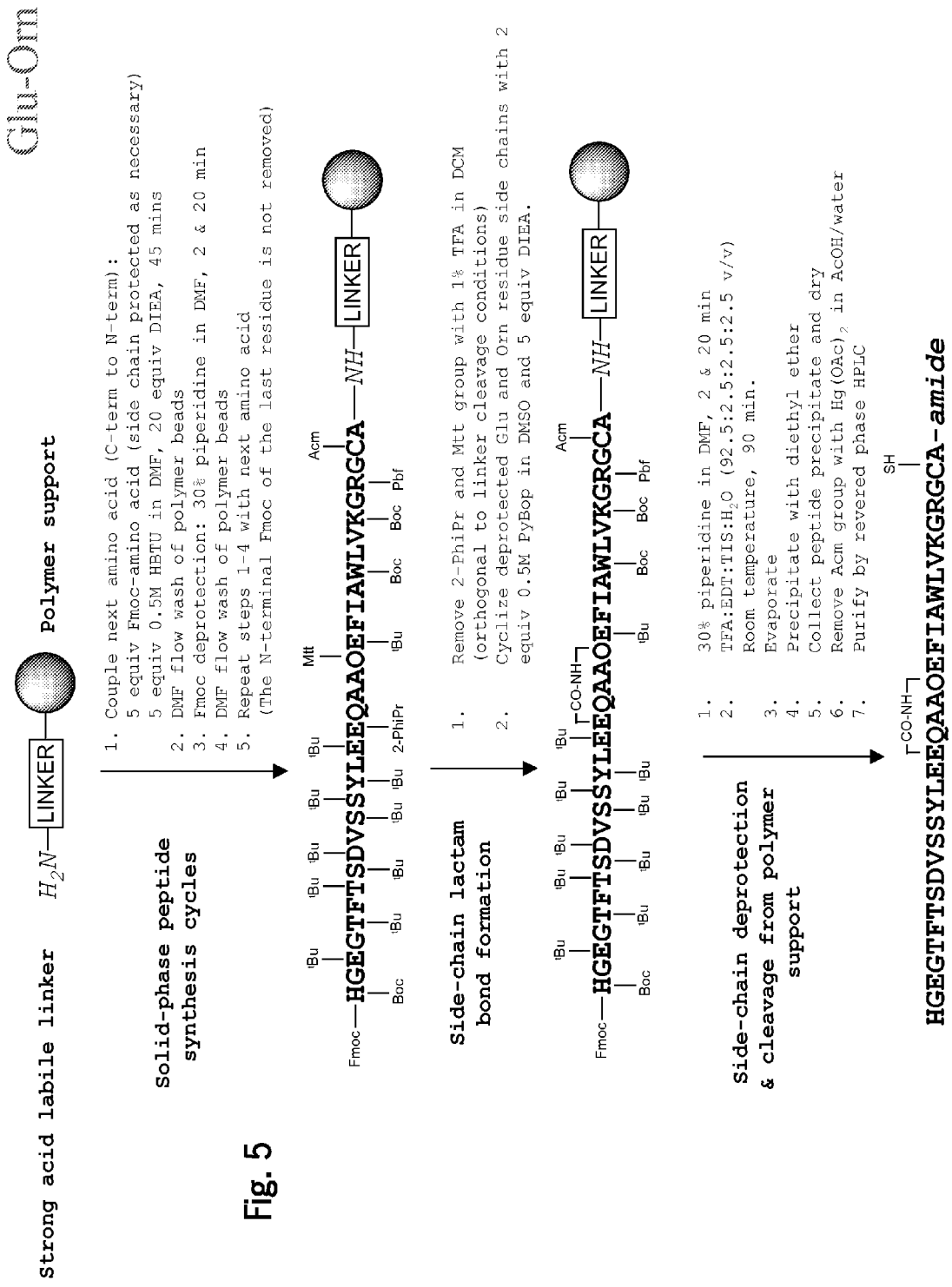
FIG. 5 provides an exemplarly synthetic scheme for preparing a cyclic GLP-1 compound in which the side chains of glutamic acid and ornithine are joined to form a cyclic lactam.
Figure 6:
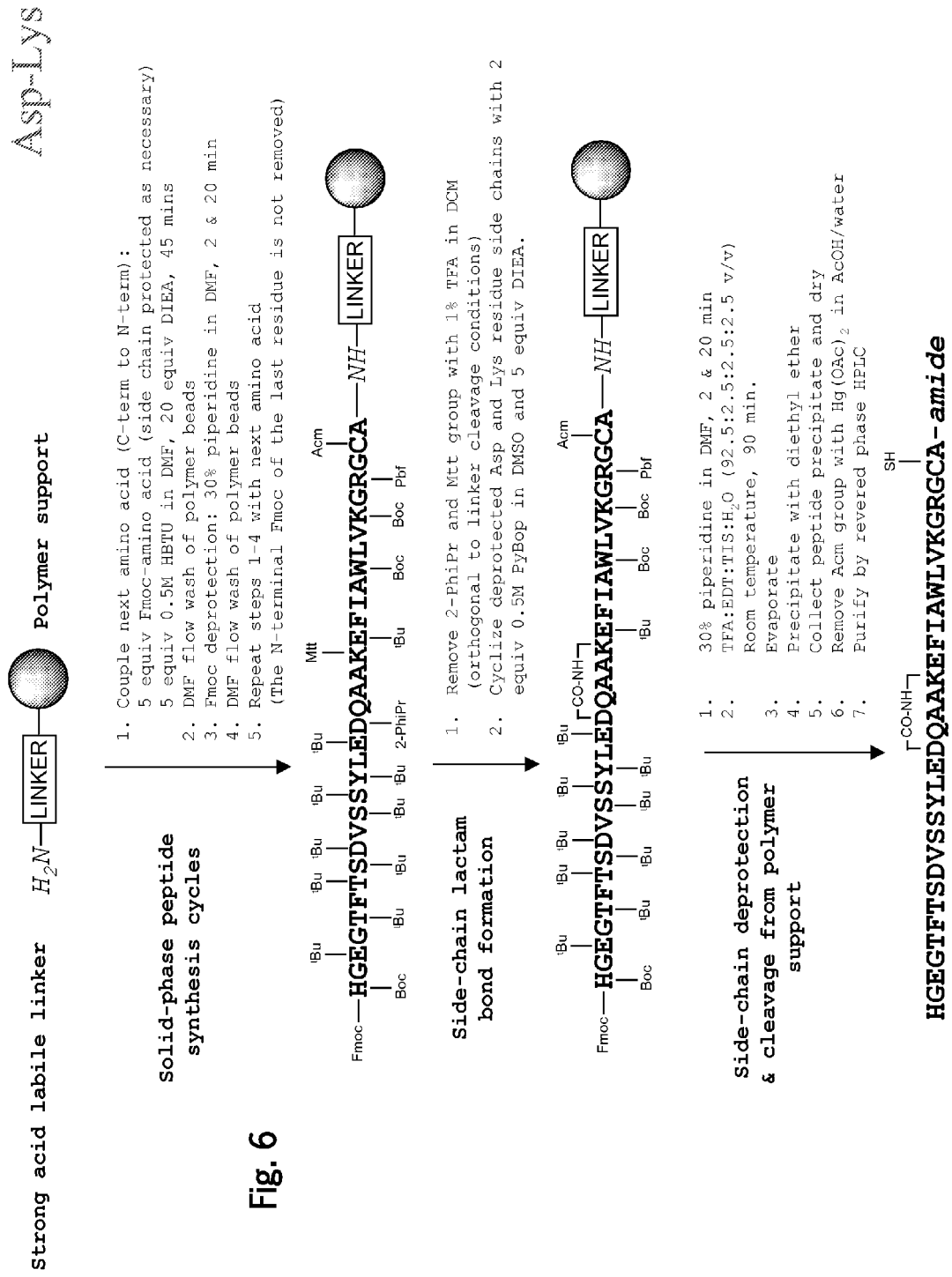
FIG. 6 provides an exemplarly synthetic scheme for preparing a cyclic GLP-1 compound in which the side chains of an aspartic acid and lysine residue are joined to form a cyclic lactam.
Figure 7:
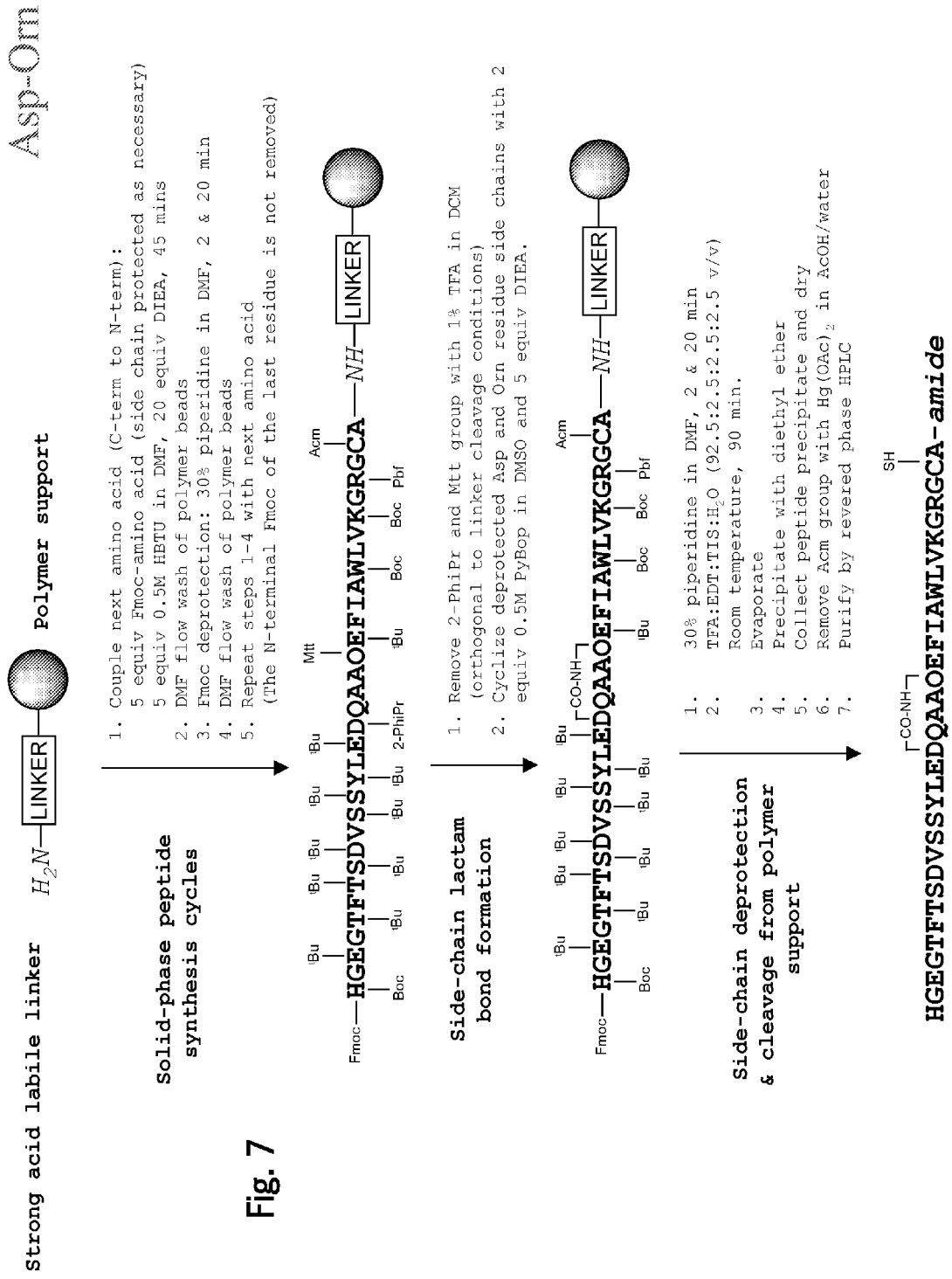
FIG. 7 provides an exemplarly synthetic scheme for preparing a cyclic GLP-1 compound in which the side chains of aspartic acid and ornithine are joined to form a cyclic lactam.
Figure 8:
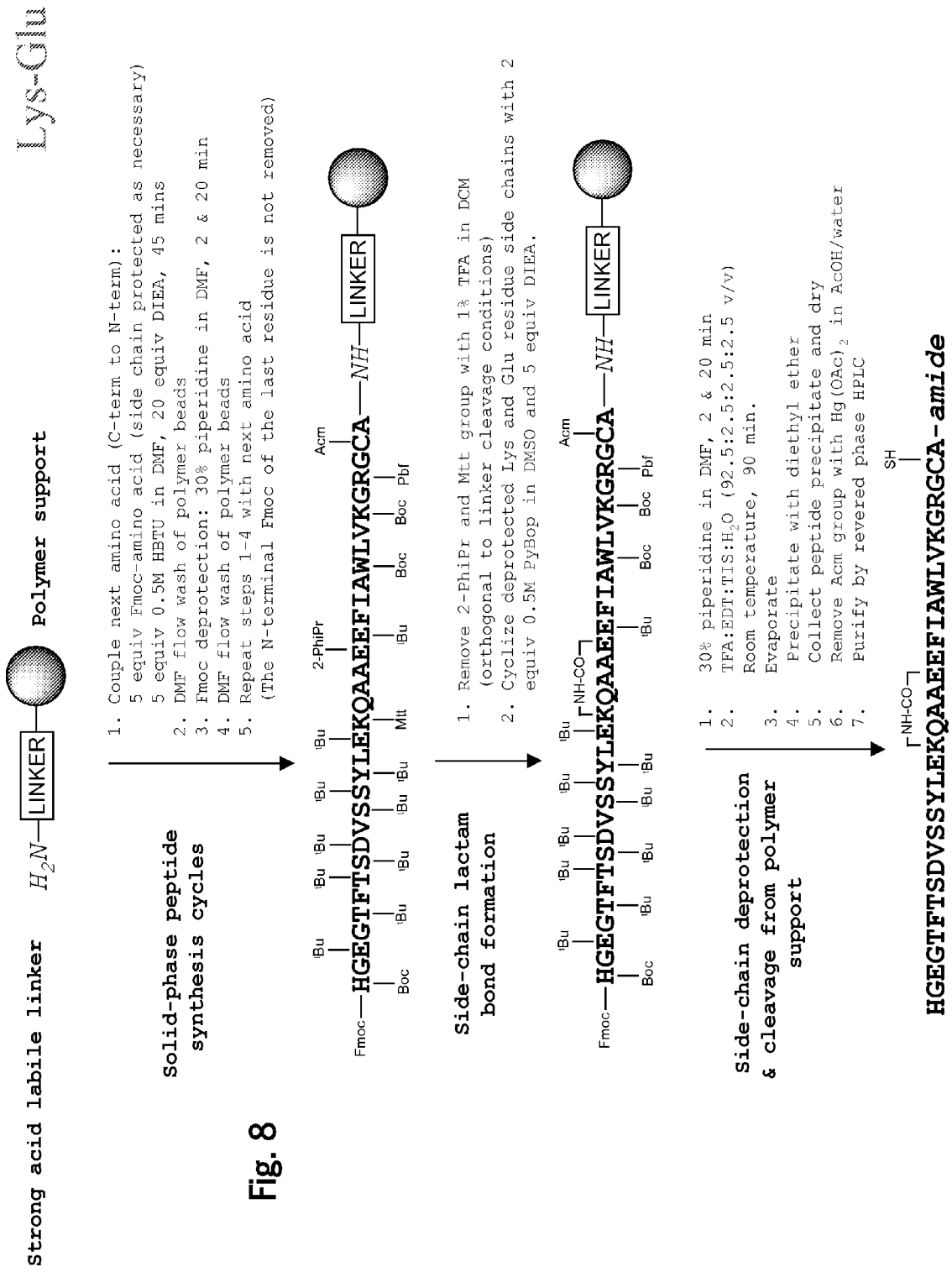
FIG. 8 provides an exemplarly synthetic scheme for preparing a cyclic GLP-1 compound in which the side chains of a lysine and glutamic acid residue are joined to form a cyclic lactam.
Figure 9:
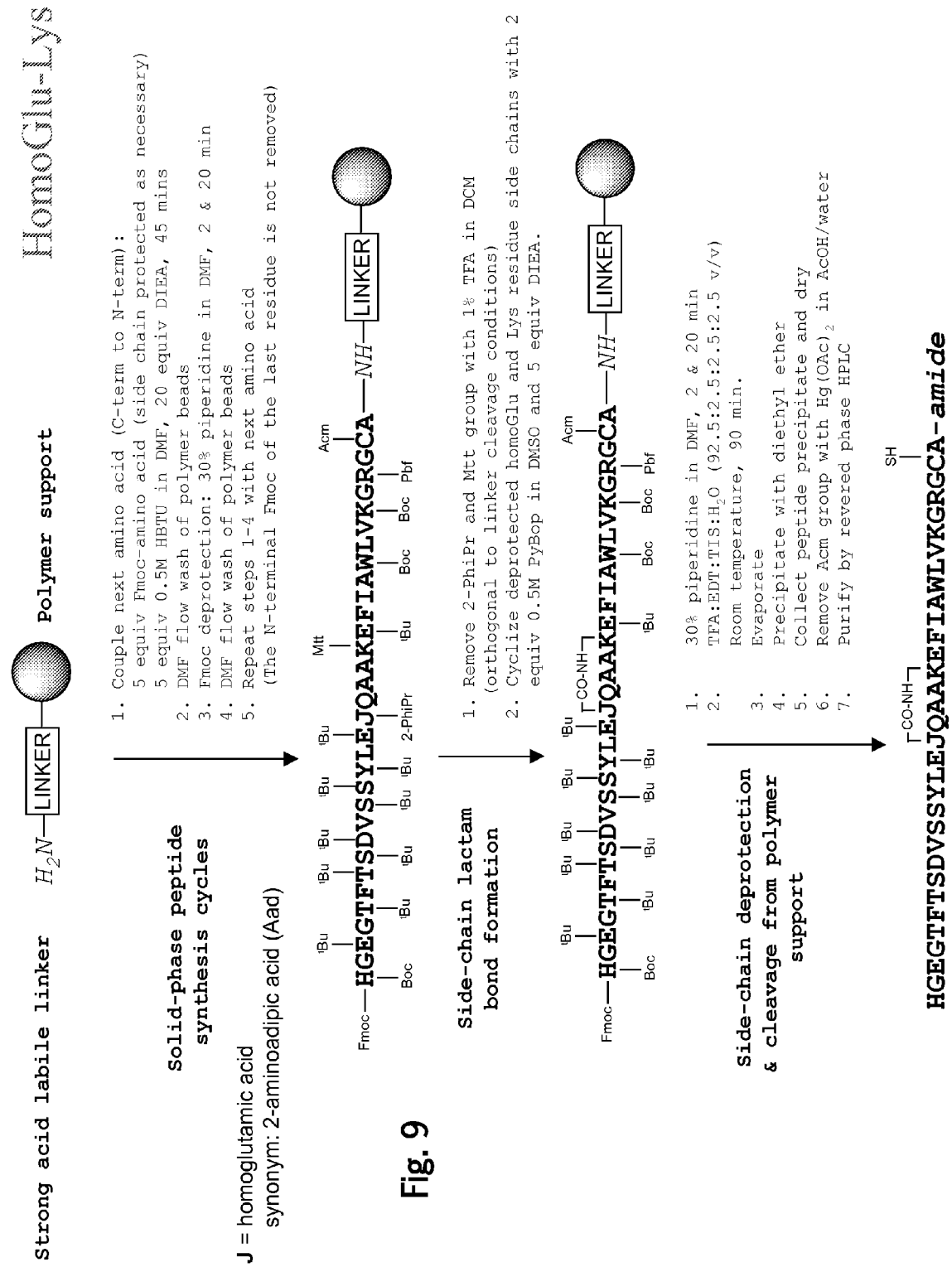
FIG. 9 provides an exemplarly synthetic scheme for preparing a cyclic GLP-1 compound in which the side chains of homoglutamic acid and lysine are joined to form a cyclic lactam.
Figure 10:
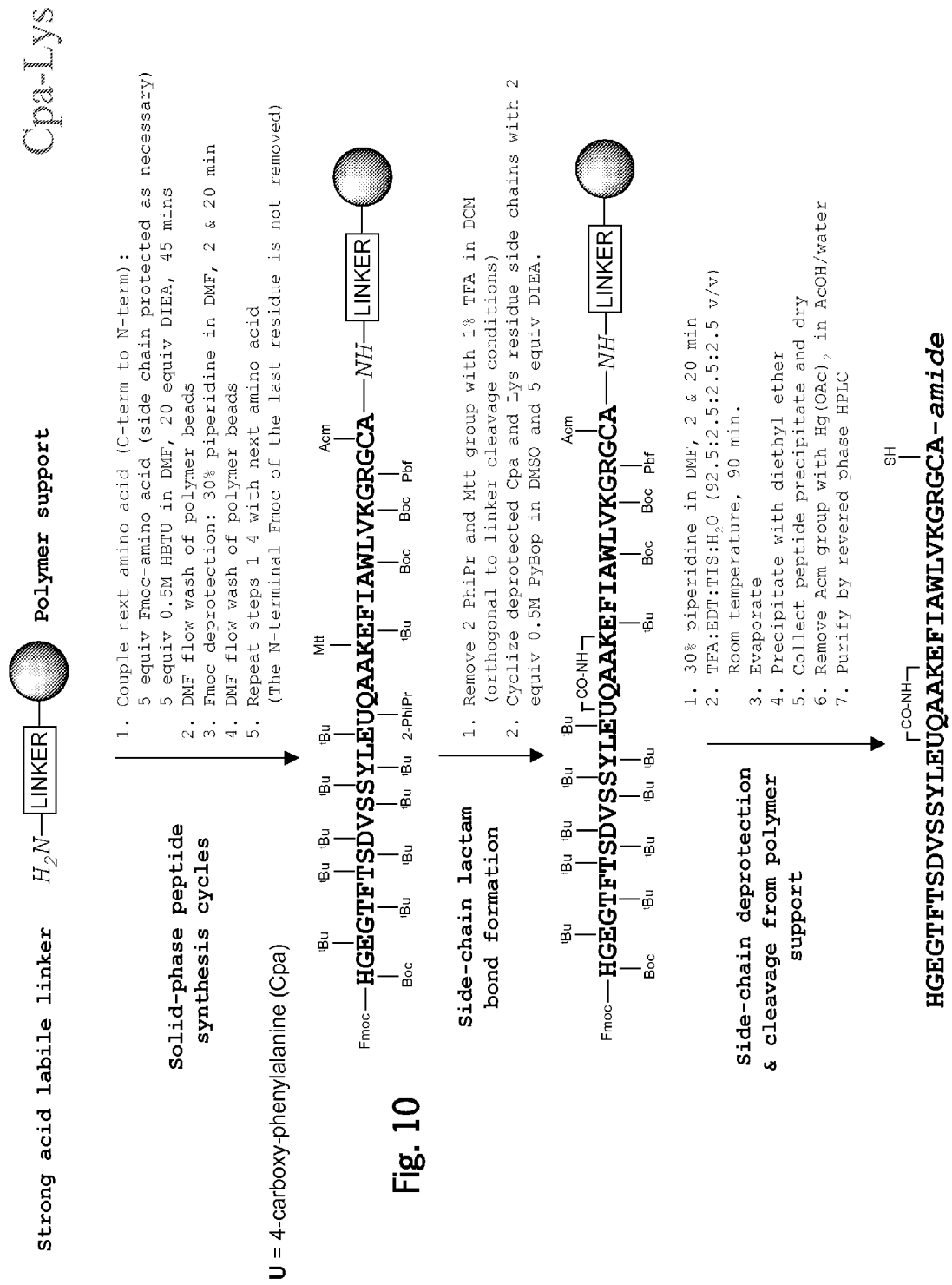
FIG. 10 provides an exemplarly synthetic scheme for preparing a cyclic GLP-1 compound in which the side chains of 4-carboxy-phenylalanine and lysine are joined to form a cyclic lactam.
Figure 11:
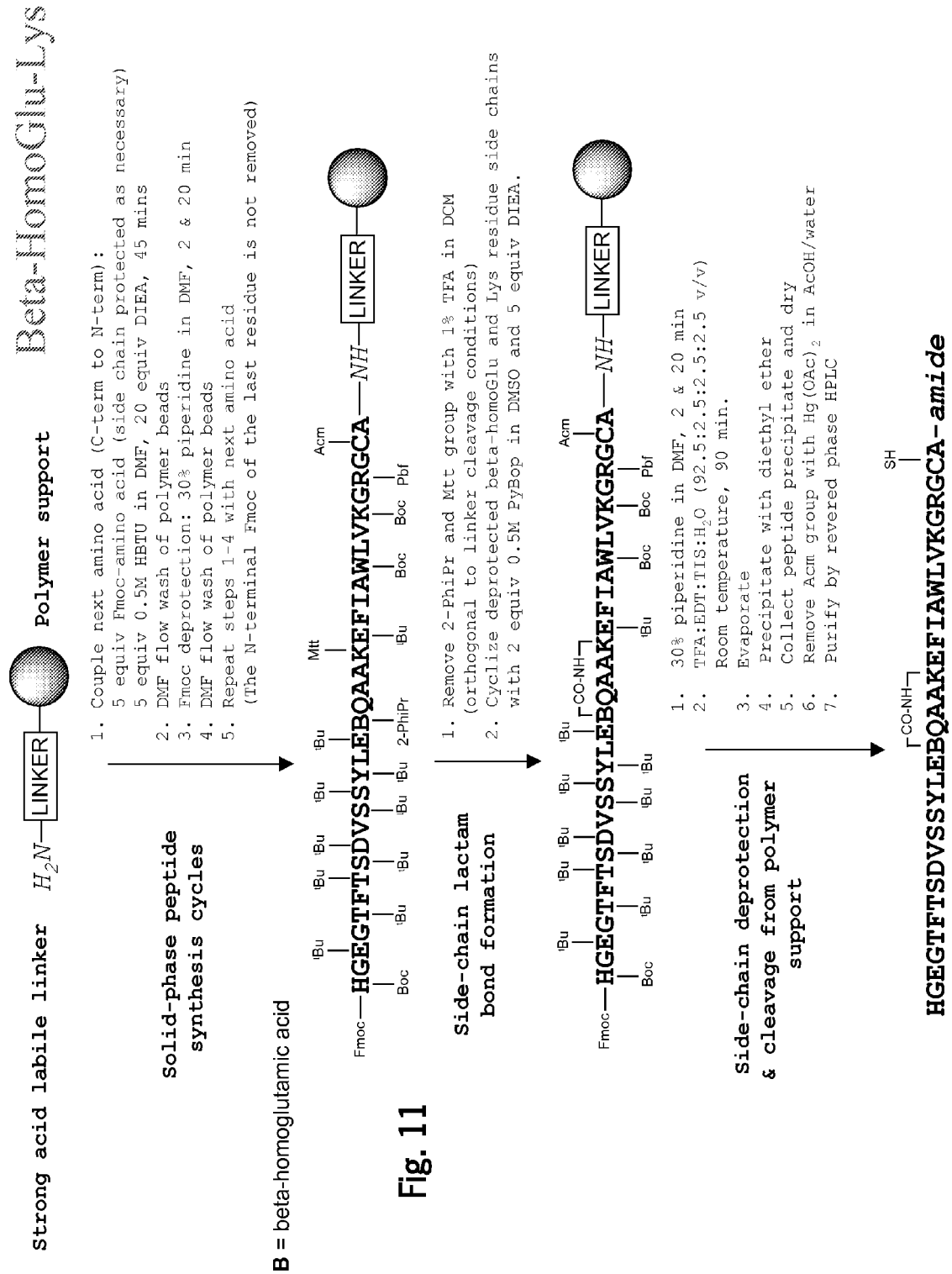
FIG. 11 provides an exemplarly synthetic scheme for preparing a cyclic GLP-1 compound in which the side chains of beta-Homoglutamic acid and lysine are joined to form a cyclic lactam.

FIGS. 4-11 illustrate the approach for synthesizing a variety of different cyclic GLP-1 compounds. FIG. 4, for instance, shows a scheme for forming a cyclic GLP-1 compound in which the side chains of a glutamic acid and lysine residue are joined to form a cyclic lactam. FIG. 5, provides an approach for synthesizing a cyclic GLP-1 compound in which the side chains of a glutamic acid and ornithine side chain are joined to form a cyclic lactam. FIG. 6, provides an approach for synthesizing a cyclic GLP-1 compound in which the side chains of an aspartic acid and lysine side chain are joined to form a cyclic lactam. FIG. 7, provides an approach for synthesizing a cyclic GLP-1 compound in which the side chains of an aspartic acid and ornithine side chain are joined to form a cyclic lactam. FIG. 8, provides an approach for synthesizing a cyclic GLP-1 compound in which the side chains of a lysine and glutamic acid chain are joined to form a cyclic lactam. FIG. 9, provides an approach for synthesizing a cyclic GLP-1 compound in which the side chains of a homoglutamic acid and lysine side chain are joined to form a cyclic lactam. FIG. 10, provides an approach for synthesizing a cyclic GLP-1 compound in which the side chains of a 4-carboxy-phenylalanine and lysine side chain are joined to form a cyclic lactam. FIG. 11, provides an approach for synthesizing a cyclic GLP-1 compound in which the side chains of a beta-Homoglutamic acid and lysine side chain are joined to form a cyclic lactam.

Reversed-Phase HPLC Purification

Reversed-phase high-performance liquid chromatography was performed on an analytical (C18, 5 µm, 0.46 cm×25 cm) or a preparative (C18, 10 µm, 2.2 cm×25 cm) column. Chromatographic separations were achieved using linear gradients of buffer B in A (A=0.1% aqueous TFA; B=90% aq. ACN containing 0.09% TFA) typically 5-95% over 35 min at a flow rate of 1 mL/min for analytical analysis and 5-65% over 90 min at 20 mL/min for preparative separations. Analytical and preparative HPLC fractions were characterized by ESMS and photodiode array (PDA) HPLC, and selected fractions combined and lyophilized.

Mass Spectrometry

Mass spectra were acquired on a single quadrupole mass spectrometer equipped with an Ionspray atmospheric pressure ionization source. Samples (25 µL) were injected into a moving solvent (10 µL/min; 30:50:20 ACN/MeOH containing 0.05% TFA) coupled directly to the ionization source via a fused silica capillary interface (50 µm i.d.). Sample droplets were ionized at a positive potential of 5 kV and entered the analyzer through an interface plate and subsequently through an orifice (100-120 µm diameter) at a potential of 60 V. Full scan mass spectra were acquired over the mass range 400-2200 Da with a scan step size of 0.1 Da. Molecular masses were derived from the observed m/z values.

Pegylation

The thioether-linked PEG-peptides were derived from GLP analogs with reactive cysteine thiols engineered at the desired conjugation site (See Table 2). The activated PEG derivatives were all mono-functional methoxyPEG-maleimides (mPEG-mal) with MWs of 5 kD to 40 kD. Conjugation was achieved by alkylation at pH 6. Briefly, the peptide was dissolved at 2 mg/ml in an amine-free buffer (50 mM sodium phosphate, 5 mM EDTA, pH 6), the mPEG-mal was added in a modest stoichiometric excess (1.2-1.5 fold) and allowed to react 0.5-2 hrs at room temperature. The reaction was monitored by reverse phase HPLC, quenched with 5 mM β-mercaptoethanol, allowed to incubate at room temperature another 30 min and then purified.

Purification was achieved by preparative cation-exchange chromatography using SP Sepharose HP (GE Healthcare) and eluting with a linear 0-500 mM sodium chloride gradient. The eluted PEG-peptide was evaluated by RP-HPLC and SDS-PAGE, pooled then concentrated and dialyzed into 10 mM sodium acetate, 5% sorbitol, and pH 4. Purities of >99% were determined for all the final pools by RP-HPLC. Peptide mapping and sequencing were used to confirm conjugation with PEG at each of the targeted attachment sites.

Example 2

In Vitro Assays

In Vitro Efficacy of GLP-1 Constructs

A. GLP-1R Reporter Assay:

To compare the potency of test compounds with GLP-1, reporter cell lines expressing human or mouse GLP-1 receptors were generated. Increased cAMP levels were measured through enhanced expression of a luciferase reporter gene. Briefly, CHOK1 cells expressing the mouse or human GLP-1 receptor, in addition to harboring a luciferase reporter gene construct regulated by cyclic AMP levels, were plated 2 days prior to the assay, then cultured at 37° C., 5% $CO_2$. The evening prior to assay, the cells were washed, the medium replaced with serum-free medium containing 0.5% protease-free bovine serum albumin (BSA), and then cultured overnight. Cells were exposed to a range of concentrations of test compound or GLP-1 for a period of 6 hours at 37° C. in medium containing 0.5% protease-free BSA and 100 µM IBMX. Cell lysates were assayed for luciferase activity using the Luciferase Assay System (Promega Corporation, Madison, Wis.). Luciferase activity was measured using a Luminoskan Ascent (Thermo Electron Corporation, Marietta, Ohio). Nonlinear regression analyses of resultant compound concentration curves were performed using GraphPad Prism (GraphPad Software, Inc., San Diego, Calif.). The "$EC_{50}$" represents the concentration of compound at which 50 percent of the maximal activity is achieved.

B. In Vitro GLP-1 Receptor Binding of Constructs

Membrane Preparation. CHOK1 cells expressing either human mouse GLP-1 receptor were harvested from 150 mm culture dishes using PBS. Cells were sedimented at 1500 rpm for 10 minutes. The resulting pellets were homogenized in 15 mls of ice cold sucrose buffer (25 mM Tris-HCl, 0.32 M Sucrose, 0.25 g/L, sodium azide, pH 7.4) with a motorized, glass fitted, Teflon homogenizer. The homogenate was centrifuged at 48,000×g at 4° C. for 10 minutes, resuspended in 25 ml assay buffer (50 mM Tris-HCl, 5 mM $MgCl_2$, 10 mg/ml protease-free BSA, 0.1 mg/ml STI, and 0.1 mg/ml Pefabloc, pH 7.4) with a Tissue-Tearor (Biospec Products), then centrifuged again at 48,000×g for 10 minutes. The pellets were homogenized for a third time in 15 ml assay buffer using the Tissue-Tearor and again centrifuged at 48,000×g for 10 minutes. The resulting pellet was resuspended in assay buffer at a wet weight concentration of 4 mg/ml.

Ligand Binding Assay. Binding assays were performed in 96-well U-bottom plates. Membranes (200 µg tissue) were incubated at room temperature for 2 hours in assay buffer containing 0.2 nM $^{125}$I-GLP-1 (PerkinElmer Life Sciences, Boston, Mass.) and with a range of concentrations of test compound or GLP-1 in a total volume of 100 µl. In addition, non-specific binding was assessed in the presence of 1 µM unlabeled GLP-1. The reaction was terminated by rapid filtration through Unfilter-96 GF/C glass fiber filter plates (FilterMate 196 Packard Harvester, PerkinElmer, Shelton, Conn.) pre-soaked in 0.5% polyethylenimine, followed by three washes with 300 µl of cold 50 mM Tris-HCl, pH 7.4. Bound radioactivity was determined using a TopCount microplate scintillation and luminescence counter (Packard Instrument Company, PerkinElmer, Shelton, Conn.). Nonlinear regression analyses of resulting concentration curves were performed using GraphPad Prism (GraphPad Software, Inc., San Diego, Calif.). The "$IC_{50}$" represents the concentration of compound that reduces the maximal specific $^{125}I$-GLP-1 binding by 50 percent.

Example 3

In vivo Assays

A. Db/db Mice:

The db/db diabetic mouse model was used in this screen to further examine GLP-1 compounds in regard to fed blood glucose, with this measurement monitored at 1, 2, 4, 6 and 24 h. The db/db mice are commercially available from The Jackson Laboratory JAX® GEMM® Strain—Spontaneous Mutation Congenic Mice, and are homozygous for the diabetes spontaneous mutation ($Lepr^{db}$). These mice become identifiably obese around 3 to 4 weeks of age. The criterion for selection for each mouse to enter the study was blood glucose of at least 300 mg/dL. Db/db mice at 8.5 weeks of age (for a chronic 1-2 wk study) to about 10-11 weeks of age (for an acute 1-3 day study) were injected once with each tested compound (acute experiment) or multiple times (chronic experiment).

On the day of the experiment, the mice were bled at 9 am (baseline value) and then immediately handed over to the injector, who then injected the appropriate GLP-1 compound or +/−control. The mice were then placed in a fresh cage without any chow, so as to limit any variability in blood glucose levels associated with eating behaviors. Time points of 1 hr, 4 hr, 6 hr, and 24 hr were normally taken. When at the 24 hour time point blood glucose values were below where they started, further time points at every 24 hrs were taken until blood glucose returned to the baseline levels. Normal chow was given back after the 6 hr time point.

Tachyphylaxis was determined by multiple injections. A second injection of the compound was administered after the blood glucose levels sufficiently returned to starting baseline levels. At this point, it was evident whether the compound had the same effect/efficacy, or if there was any noticeable tachyphylaxis.

B. C57b16 Mice:

C57B16 (normal lean) mice were used at 10 to 12 weeks of age. These mice are commercially available through any vendor, such as Jackson Laboratories or Charles River, and are considered to be normal. The term "lean" is used to contrast these mice to obese db/db mice. C57B16 mice were randomized on body weight. 9 am bleed was performed to determine baseline blood glucose and GLP-1 compounds or PBS was administered prior to place the mice in a cage without food. After 4-5 hrs, an intraperitoneal glucose tolerance test (glucose tolerance test measures the body's ability to metabolize glucose) was performed using 2 g/kg of glucose dose. Blood glucose levels were measured 30 min and 90 minutes after the glucose load was administered and 24 hours or until blood glucose levels were back to the original values. From these studies, the enhanced effect of GLP-1 action in utilizing glucose can be seen as opposed to (−) control PBS.

Example 4

Results with GLP-1 Compounds Related to Formula I

In vitro experiments were conducted to determine receptor binding and potency for a class of molecules having a glycine substitution at position 8, a cysteine substitution at position 22 and a variable C-terminus. Experiments were performed as described in Example 2, and the results are summarized in Table 3 below.

TABLE 3

| INTERNAL REF # | SEQUENCE | $IC_{50}$ human | $EC_{50}$ human | $EC_{50}$ mouse |
|---|---|---|---|---|
| | HGEGT FTSDV SSYLE GCAAK EFIAW LVKGR G (SEQ ID NO: 6) | 70 nM | 0.24 nM | 1.4 nM |
| cgGLP-1 | SEQ ID NO: 6 + 20K PEG | >1 uM | 12 nM | 245 nM |
| cgGLP-2 | SEQ ID NO: 6 + 40k branched PEG | >1 uM | 0.7 nM | 3.6 nM |
| cgGLP-3 | SEQ ID NO: 6 + 8k PEG dumbbell | 84 nM | 0.2 nM | 5.7 nM |
| cgGLP-7 | SEQ ID NO: 6 + 30k PEG | >1 uM | 0.2 nM | 2.9 nM |
| cgGLP-9 | SEQ ID NO: 6 + 20k PEG dimer | >1 uM | 1 nM | 9 nM |
| | HGEGT FTSDV SSYLE GCAAK EFIAW LVKGR GSSGA PPPS (SEQ ID NO: 7) | 100 nM | 0.1 nM | 0.8 nM |
| cgGLP-12 | SEQ ID NO: 7 + 20k PEG monomer | 1 uM | 1 nM | 8 nM |
| cgGLP-14 | SEQ ID NO: 7 + 20k PEG dimer | 300 nM | 0.6 nM | 4 nM |
| | HGEGT FTSDV SSYLE GCAAK EFIAW LKNGG PSSGA PPPS (SEQ ID NO: 8) | 100 nM | 0.07 nM | 0.3 nM |
| cgGLP-13 | SEQ ID NO: 8 + 20k PEG monomer | >1 uM | 1 nM | 3 nM |
| cgGLP-15 | SEQ ID NO: 8 + 20k PEG dimer | 300 nM | 0.8 nM | 2 nM |

As indicated in Table 3, some of these molecules were conjugated to different forms of PEG, with the conjugation occurring at the cysteine at position 23. For instance, a 20 k PEG dimer is a single 20 kD linear PEG polymer with two peptides, both attached at the same end like a fork. "Forked" PEG-(maleimide)$_2$ can be obtained from Nektar Therapeutics (Huntsville, Ala., cat. #2D2MOPOF) and has the following structure:

Catalog Number: 2D2D0P0F
Product Name: M-PEG-(MAL)$_2$, MW 20,000
Lot Number: PT-02D-17 mal-PEG-mal polymer is also available from Nektar Therapeutics (Huntsville, Ala.), cat#ZF-066-05 and has the following structure:

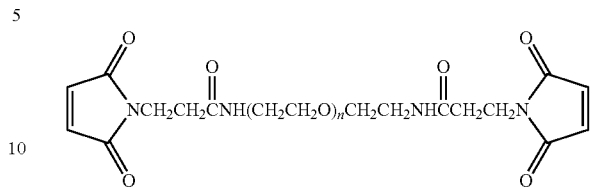

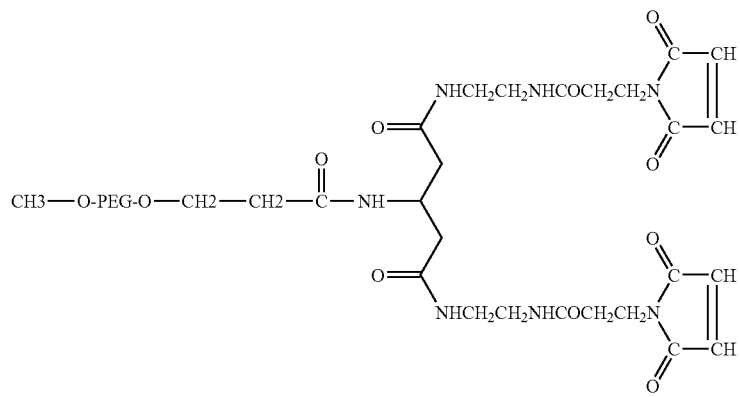

"Branched" PEG conjugates are 2 polymers attached at the same site on a single peptide. Branched PEG2-maleimide can also be obtained from Nektar Thearpeutics (Huntsville, Ala.), under cat#2D3X0P11 and has the following structure:
  Catalog Number: 2D3X0P11
  Product Name: mPEG2-MAL, MW 20,000
  Lot Number: PT-02B-15

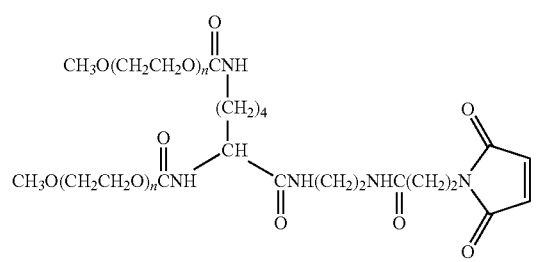

Other molecules (e.g., cgGLP-3) is a "dumbbell" PEG conjugate. In this configuration 2 peptides are conjugated to an 8 kD PEG, one at each end, like a "dumbbell". The 8 kD Example 5

Results with GLP-1 Compounds Related to Formula II

In vitro experiments were conducted to determine receptor binding and potency for GLP-1 compounds having a substitution at position 8 and either a CSG or CSGG C-terminal addition. The pegylated molecules were conjugated at the cysteine at position 38. Experiments were conducted as described in Example 2, and the results are summarized in Table 4 below.

TABLE 4

| INTERNAL REF # | SEQUENCE | IC$_{50}$ human | EC$_{50}$ human | EC$_{50}$ mouse |
|---|---|---|---|---|
| | HGEGT FTSDV SSYLE GQAAK EFIAW LVKGR GCSG (SEQ ID NO: 10) | 17 nM | 0.05 nM | 0.32 nM |
| cgGLP-4 & mgGLP-09A | SEQ ID NO: 10 + 20k PEG | 130 nM | 0.23 nM | 1.8 nM |
| cgGLP-5 | SEQ ID NO: 10 + 40k branched PEG | >1 uM | 0.3 nM | 1.5 nM |
| cgGLP-6 | SEQ ID NO: 10 + 8k PEG dumbbell | 11 nM | ~0.1 nM | 0.8 nM |
| cgGLP-8 | SEQ ID NO: 10 + 30k PEG | 170 nM | 0.4 nM | 3 nM |
| cgGLP-10 | SEQ ID NO: 10 + 20k PEG dimer | 100 nM | 0.6 nM | 4 nM |
| cgGLP-16 | SEQ ID NO: 10 + 30k PEG | 1 uM | 0.39 nM | 4 nM |
| | H[Aib]EGT FTSDV SSYLE GQAAK EFIAW LVKGR GCSGG (SEQ ID NO: 11) | 100 nM | 4 nM | >50 nM |
| cgGLP-17 | SEQ ID NO: 11 + 20k PEG | 1 uM | 20 nM | >100 nM |
| | H[bAla]EGT FTSDV SSYLE GQAAK EFIAW LVKGR GCSGG (SEQ ID NO: 12) | 400 nM | >100 nM | undet'd |
| cgGLP-18 | SEQ ID NO: 12 + 20k PEG | >1 uM | undet'd | undet'd |

Aib = alpha aminobutyric acid
bAla = beta aminopropionic acid

Example 6

Results with Compounds Related to Formula III

In vitro experiments were conducted to determine receptor binding and potency for GLP-1 compounds having either an Aib (2-aminoisobutyric acid) or Aad (2-aminoadipic acid) substitution at position 22 and optional substitution at position 8 and at the C-terminus. The pegylated molecules were conjugated at the cysteine at position 38. Experiments were performed as described in Example 2, and the results are summarized in Table 5 below.

TABLE 5

| INTERNAL REF # | SEQUENCE | IC$_{50}$ human | EC$_{50}$ human | EC$_{50}$ mouse |
|---|---|---|---|---|
| | HGEGT FTSDV SSYLE [Aib]QAAK EFIAW LVKGR-AMIDE (SEQ ID NO: 14) | 2.5 nM | 16 pM | 0.15 nM |
| | HGEGT FTSDV SSYLE [Aib]QAAK EFIAW LVKGR G-AMIDE (SEQ ID NO: 15) | 3.5 nM | 27 pM | 0.12 nM |
| cgGLP-23 | HGEGT FTSDV SSYLE [Aib]QAAK EFIAW LVKGR GC-AMIDE SEQ ID NO: 17 + 20k PEG | 300 nM | 0.2 nM | 3 nM |
| | HGEGT FTSDV SSYLE [Aib]QAAK EFIAW LVKGR GCA-AMIDE (SEQ ID NO: 18) | | 25 pM | 0.2 nM |
| mgGLP32 & mgGLP-20 | SEQ ID NO: 18 + 20k PEG | 56 nM | 0.13 nM | 0.84 nM |
| | HGEGT FTSDV SSYLE [Aib]QAAK EFIAW LVKGR GCG-AMIDE (SEQ ID NO: 20) | | | |
| mgGLP-16 | SEQ ID NO: 20 + 20k PEG | 50 nM | 0.2 nM | 1.6 nM |
| | HGEGT FTSDV SSYLE [Aib]QAAK EFIAW LVKGR GCSG (SEQ ID NO: 21) | 18 nM | 68 pM | 300 pM |
| mgGLP19 & cgGLP- | SEQ ID NO: 21 + 20k PEG | 230 nM | 0.32 pM | 4 nM |
| | HGEGT FTSDV SSYLE [Aib]QAAK EFIAW LVKGR GCSG-AMIDE (SEQ ID NO: 22) | 17 nM | 45 pM | 0.27 nM |
| cgGLP-24 cgGLP-27, mgGLP-22, mgGLP-33 & mgGLP-27 | SEQ ID NO: 22 + 20k PEG | 47 nM | 0.1 nM | 0.84 nM |

TABLE 5-continued

| INTERNAL REF # | SEQUENCE | IC$_{50}$ human | EC$_{50}$ human | EC$_{50}$ mouse |
|---|---|---|---|---|
| cpGLP-25 | SEQ ID NO: 22 + 5k PEG | 15 nM | 39 pM | 0.9 nM |
| cgGLP-26 | SEQ ID NO: 22 + 10k PEG | 23 nM | 59 pM | 0.9 nM |
| cgGLP-28 | SEQ ID NO: 22 + 30k PEG | 71 nM | 0.1 nM | 0.8 nM |
| cgGLP-29 | SEQ ID NO: 22 + 40k branched PEG | 800 nM | 0.15 nM | 1 nM |
|  | HGEGT FTSDV SSYLE [Aib]QAAK EFIAW LVKGR GCSGG-AMIDE (SEQ ID NO: 24) |  |  |  |
| mgGLP-15 | SEQ ID NO: 24 + 20k PEG | 100 nM | 0.2 nM | 1.8 nM |
|  | H[Aib]EGT FTSDV SSYLE [Aib]QAAK EFIAW LVKGR GCSG (SEQ ID NO: 25) |  |  |  |
| cgGLP-20 | SEQ ID NO: 25 + 20k mPEG | 30 nM | 99 pM | 1.5 nM |

Example 7

Results with Cyclic GLP-1 Compounds

In vitro experiments were conducted to determine receptor binding and potency for a variety of GLP-1 compounds in which the side chains of certain amino acids were joined to form a ring (a cyclic lactam). Experiments were performed as described in Example 2. The sequences of the cyclic compounds tested are shown in Table 6 together with the results. The side chains of the amino acids involved in forming the cyclic lactam are shown in bold type and underlined. Of the compounds listed in Table 6, only mgGLP-24 was pegylated.

TABLE 6

| INTERNAL REF # | SEQUENCE | IC$_{50}$ human | EC$_{50}$ human | EC$_{50}$ mouse |
|---|---|---|---|---|
| [Gly8]GLP1(7-37) cyclo[Glu14-Lys18] | HGEGT FTSDV SSYEE GQKAK EFIAW LVKGR G AMIDE (SEQ ID NO: 35) |  | 12 pM | 0.21 nM |
| [Gly8]GLP1(7-37) cyc[Glu15-Lys19] | HGEGT FTSDV SSYLE GQAKK EFIAW LVKGR G AMIDE (SEQ ID NO: 36) |  | 0.15 nM | 66 pM |
| GLP1(7-37) cyclo[Glu15-Lys19; 27-31] | HGEGT FTSDV SSYLE GQAKK EFIAW LEKGR K AMIDE (SEQ ID NO: 277) |  | undet'd | undet'd |
| [Gly8]cyclo[21-26] GLP1(7-37)-amide | HGEGT FTSDV SSYLE GQAAK EFIAW LVKGR G AMIDE (SEQ ID NO: 42) |  | 0.6 nM | undet'd |
| cycloE22-K26 | HGEGT FTSDV SSYLE EQAAK EFIAW LVKGR G-AMIDE (SEQ ID NO: 30) | 1.1 nM | 9 pM | 68 pM |
| mgGLP24 | SEQ ID NO: 30 + 20k mPEG | 48 nM | 0.25 nM | 0.9 nM |
| cycloE22-O26 | HGEGT FTSDV SSYLE EQAAO EFIAW LVKGR G-AMIDE (SEQ ID NO: 69) | 3.7 nM | 51 pM | 0.25 nM |
| GLP1(7-37) cyclo[Lys16-Glu20] | HGEGT FTSDV SSYLE KQAAE EFIAW LVKGR G AMIDE (SEQ ID NO: 159) |  | 16 pM | 0.1 nM |
| [Gly8]GLP1(7-37) cyclo[Glu17-Lys21] | HGEGT FTSDV SSYLE GEAAK KFIAW LVKGR G AMIDE (SEQ ID NO: 38) |  | 18 pM | 0.17 nM |
| [Gly8]GLP1(7-37) cyclo[Glu18-Lys22] | HGEGT FTSDV SSYLE GQEAK EKIAW LVKGR G AMIDE (SEQ ID NO: 39) |  | 0.8 nM | undet'd |

O = ornithine = aa w/ CH2CH2CH2NH3 side chain

Example 8

Results with GLP-1 Compounds Having N-Terminal Extension

Figure 13:
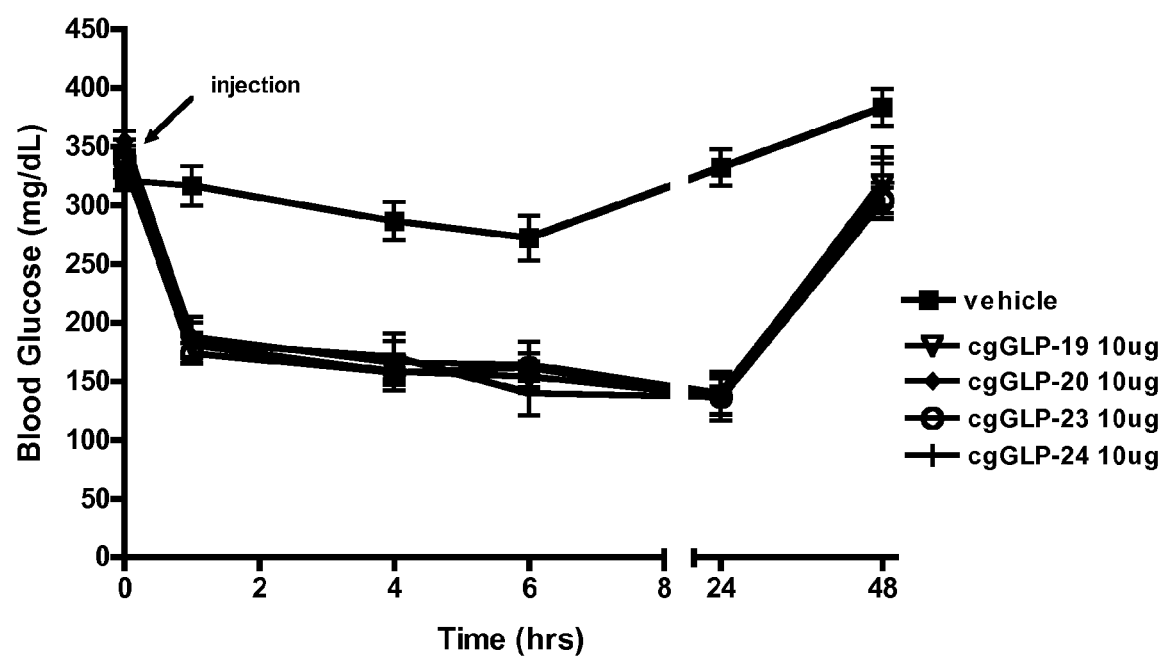
FIG. 13 shows a graph depicting blood glucose levels in mice treated with cgGLP-19, cgGLP-20, cgGLP-23, or cgGLP-24.

In vitro experiments were conducted to determine receptor binding and potency for GLP-1 compounds having an N-terminal extension. Experiments were performed as described in Example 2, and the results are summarized in Table 7 below. None of the compounds listed in Table 7 were pegylated.

lowering blood glucose for the longest period of time (72 hours was needed at a 10 ug/mouse dose for glucose levels in the mouse to return to normal levels). Another set of experiments were conducted with cgGLP-19, cgGLP-20, cgGLP-23, cgGLP-24 (see Table 5 for sequences and size and type of PEG). 10 ug of GLP-1 compound was injected into each mouse. As shown in FIG. 13, these four GLP-1 compounds showed similar ability to decrease blood glucose levels over time, each causing a significant decrease in blood glucose levels over a 48 hour time period.

TABLE 7

| INTERNAL REF # | SEQUENCE | $IC_{50}$ human | $EC_{50}$ human | $EC_{50}$ mouse |
|---|---|---|---|---|
| A-GLP-1 | A HAEGT FTSDV SSYLE GQAAK EFIAW LVKGR (SEQ ID NO: 247) | 38 nM | 0.2 nM | 0.8 nM |
| G-GLP-1 | G HAEGT FYSDV SSYLE GQAAK EFIAW LVKGR (SEQ ID NO: 248) | 80 nM | 1 nM | 3 nM |
| P-GLP-1 | P HAEGT FTSDV SSYLE GQAAK EFIAW LVKGR (SEQ ID NO: 249) | 38 nM | 0.2 nM | 1 nM |
| S-GLP-1 | S HAEGT FTSDV SSYLE GQAAK EFIAW LVKGR (SEQ ID NO: 250) | 53 nM | 0.4 nM | 2 nM |
| T-GLP-1 | T HAEGT FYSDV SSYLE GQAAK EFIAW LVKGR (SEQ ID NO: 251) | 53 nM | 0.3 nM | 2 nM |
| V-GLP-1 | V HAEGT FTSDV SSYLE GQAAK EFIAW LVKGR (SEQ ID NO: 252) | 32 nM | 0.2 nM | 1 nM |
| MQ-GLP1 | MQ HAEGT FTSDV SSYLE GQAAK EFIAW LVKGR (SEQ ID NO: 253) | 64 nM | 0.5 nM | 3.0 nM |
| MR-GLP1 | MR HAEGT FTSDV SSYLE GQAAK EFIAW LVKGR (SEQ ID NO: 254) | 590 nM | 8 nM | 41 nM |
| MK-GLP1 | MR HAEGT FTSDV SSYLE GQAAK EFIAW LVKGR (SEQ ID NO: 255) | 760 nM | 4 nM | 12 nM |
| M-GLP1 | M HAEGT FTSDV SSYLE GQAAK EFIAW LVKGR (SEQ ID NO: 256) | 18 nM | 86 pM | 0.5 nM |
| MH-GLP1 | MH HAEGT FTSDV SSYLE GQAAK EFIAW LVKGR (SEQ ID NO: 257) | 350 nM | 2 nM | 11 nM |
| MHH-GLP1 | MHH HAEGT FTSDV SSYLE GQAAK EFIAW LVKGR (SEQ ID NO: 258) | 350 nM | 1.0 nM | 5 nM |
| MY-GLP1 | MY HAEGT FTSDV SSYLE GQAAK EFIAW LVKGR (SEQ ID NO: 259) | 57 nM | 0.4 nM | 1 nM |
| MI-GLP1 | MI HAEGT FTSDV SSYLE GQAAK EFIAW LVKGR (SEQ ID NO: 260) | 75 nM | 0.6 nM | 6 nM |
| MD-GLP1 | MD HAEGT FTSDV SSYLE GQAAK EFIAW LVKGR (SEQ ID NO: 261) | 82 nM | 0.3 nM | 2 nM |
| ML-GLP1 | ML HAEGT FTSDV SSYLE GQAAK EFIAW LVKGR (SEQ ID NO: 262) | 160 nM | 0.7 nM | 6 nM |
| MN-GLP1 | MN HAEGT FTSDV SSYLE GQAAK EFIAW LVKGR (SEQ ID NO: 263) | 50 nM | 0.3 nM | 2 nM |
| ME-GLP1 | ME HAEGT FTSDV SSYLE GQAAK EFIAW LVKGR (SEQ ID NO: 264) | 95 nM | 1 nM | 4 nM |
| MW-GLP1 | MW HAEGT FTSDV SSYLE GQAAK EFIAW LVKGR (SEQ ID NO: 265) | 79 nM | 0.8 nM | 5 nM |
| MF-GLP1 | MF HAEGT FTSDV SSYLE GQAAK EFIAW LVKGR (SEQ ID NO: 266) | 180 nM | 1 nM | 6 nM |
| MM-GLP1 | MM HAEGT FYSDV SSYLE GQAAK EFIAW LVKGR (SEQ ID NO: 267) | 100 nM | 0.5 nM | 3 nM |

Example 9

In vivo Results—Effect on Blood Glucose Levels with Time

A variety of different GLP-1 compounds, including representatives from the different classes disclosed herein (e.g., compounds having the general structure of formulas I-IV described above), were tested for their ability to affect blood glucose levels. In these experiments, blood glucose was measured in db/db mice as described in Example 3.

Figure 12:
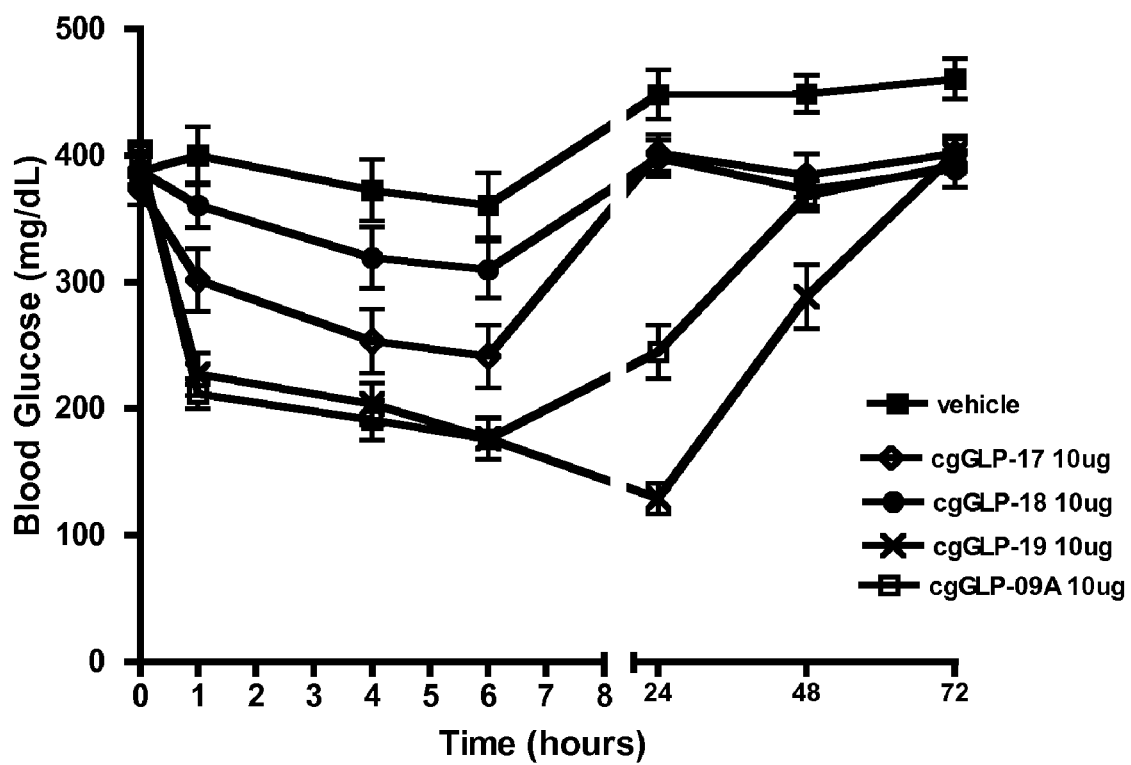
FIG. 12 shows a graph depicting blood glucose levels in mice treated with cgGLP-17, cgGLP-18, cgGLP-19, or cgGLP-09A.

FIG. 12 shows the ability of cgGLP-17, cgGLP-18, cgGLP-19, mgGLP-09A (see Tables 4 and 5 for sequences and size and type of PEG) and mg-GLP-09A to lower blood glucose over a 72 hour time span. Each of these compounds lowered blood glucose relative to control, with cg-GLP-19

Figure 14:
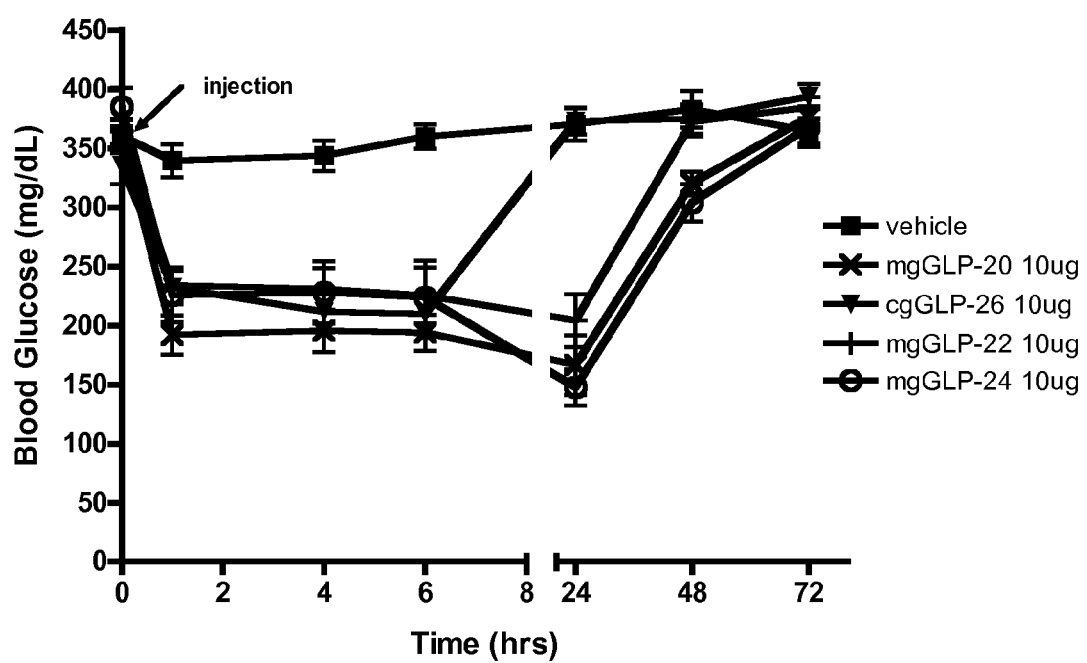
FIG. 14 shows a graph depicting blood glucose levels in mice treated with mgGLP-20, cgGLP-26, mgGLP-22, or mgGLP-24.

Another set of experiments were conducted using mgGLP-20, cgGLP-26, mgGLP-22, and mgGLP-24 (see Tables 5 and 6 for sequences and size and type of PEG). Dosage was 10 ug per mouse. As shown in FIG. 14, although each compound lowered blood glucose levels, they did so differently. In this example, mgGLP-20 and mgGLP-24 lowered glucose for the longest period of time. With these two compounds, 72 hours was needed for blood glucose levels to return to normal levels.

Example 10

Lowering of Blood Glucose in Dose Dependent Fashion

Figure 15:
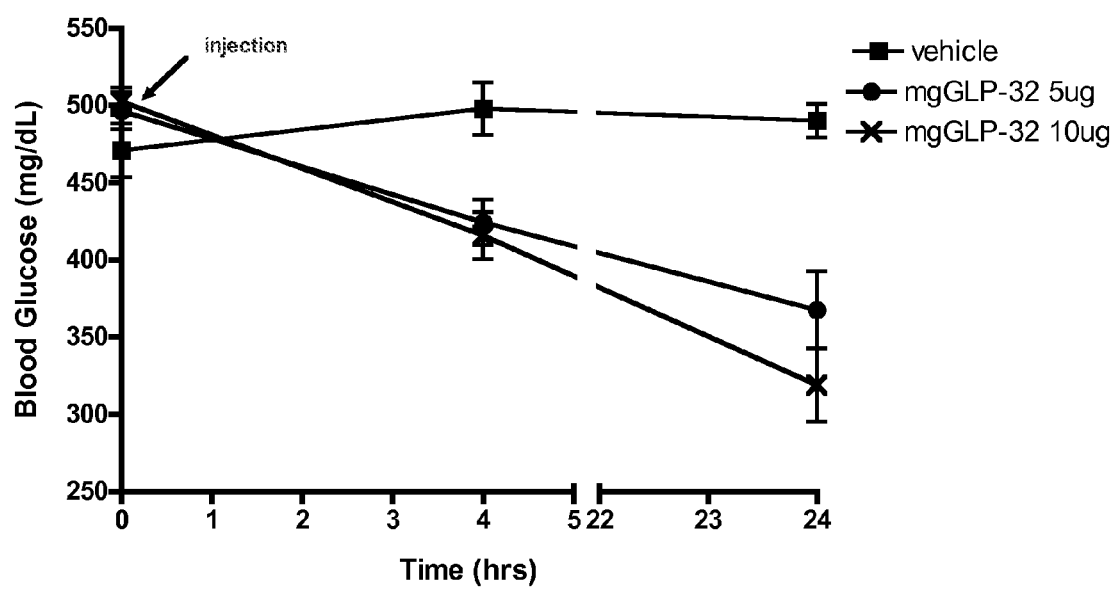
FIG. 15 shows a graph depicting blood glucose levels in mice treated with mgGLP32.

As described in Example 3, db/db mice were injected with mgGLP-32 (see Table 5 for sequence and PEG size) at different doses (5 and 10 μg/mouse). As shown in FIG. 15, mgGLP-32 lowered blood glucose levels for 24 hours in a dose dependent fashion.

Example 11

Lean GTT Experiments

Figure 16:
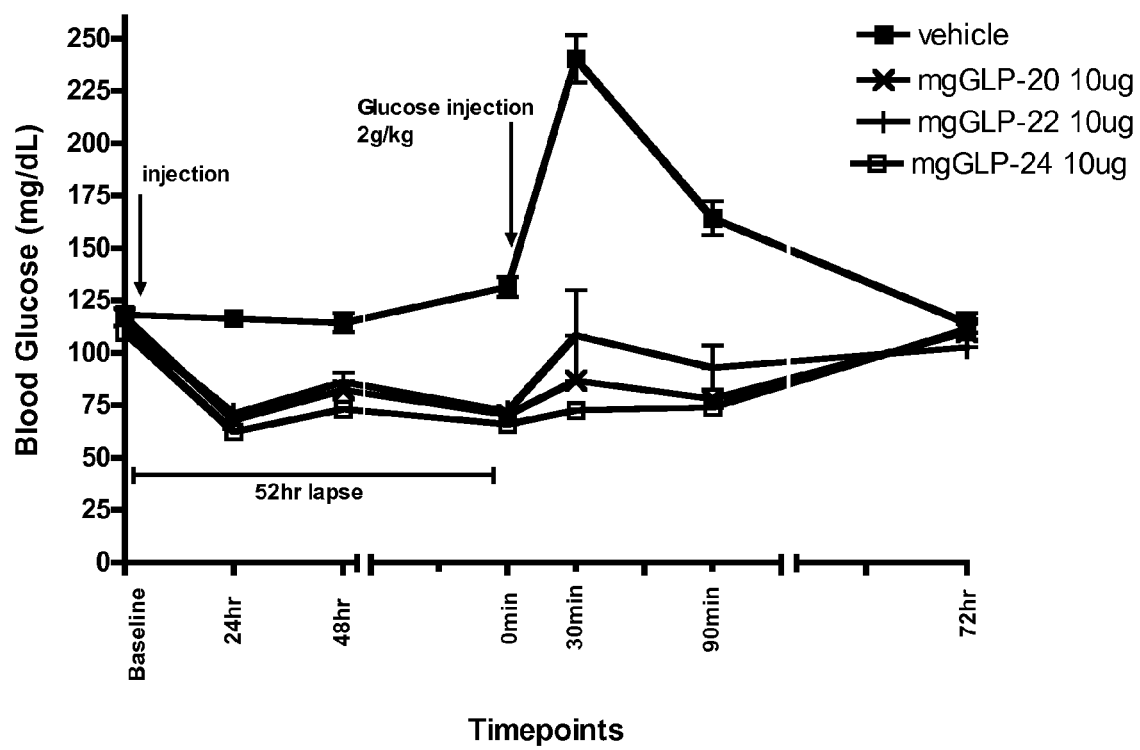
FIG. 16 shows a graph depicting blood glucose levels during a set of GTT (glucose tolerance test) experiments conducted with mice treated with mgGLP-20, mgGLP-22 or mgGLP-24.

GLP-1 action on insulin release is greater in presence of glucose than in the absence of glucose. C57B16 mice have normal blood glucose, it is then challenging to determine differences in efficacy between different GLP-1 analogs (window for efficacy is not very broad). In order to determine efficacy between tested GLP-1 analogs, GTT was performed in C57B16 mice 52 hours post the GLP-1 analogs or PBS injections as described in example 3. FIG. 16 shows mgGLP-20, mgGLP-22 and mgGLP-24 decreased blood glucose to the same extent during the first 52 hours after injection of the GLP-1 analogs or PBS (see Tables 5 and 6 for sequences and size and type of PEG molecule). At 30 min into the GTT, the separation between glucose levels of the vehicle treated mice and the GLP-1 analogs treated mice, demonstrating the expected effect of GLP-1 analogs on reducing blood glucose. Also, at 30 min mgGLP-24 showed a greater efficacy than mgGLP-22 and mgGLP-22 showed a greater efficacy than mgGLP-20 at lowering blood glucose during the GTT.

Example 12

Multi Dose Experiments

Figure 17:
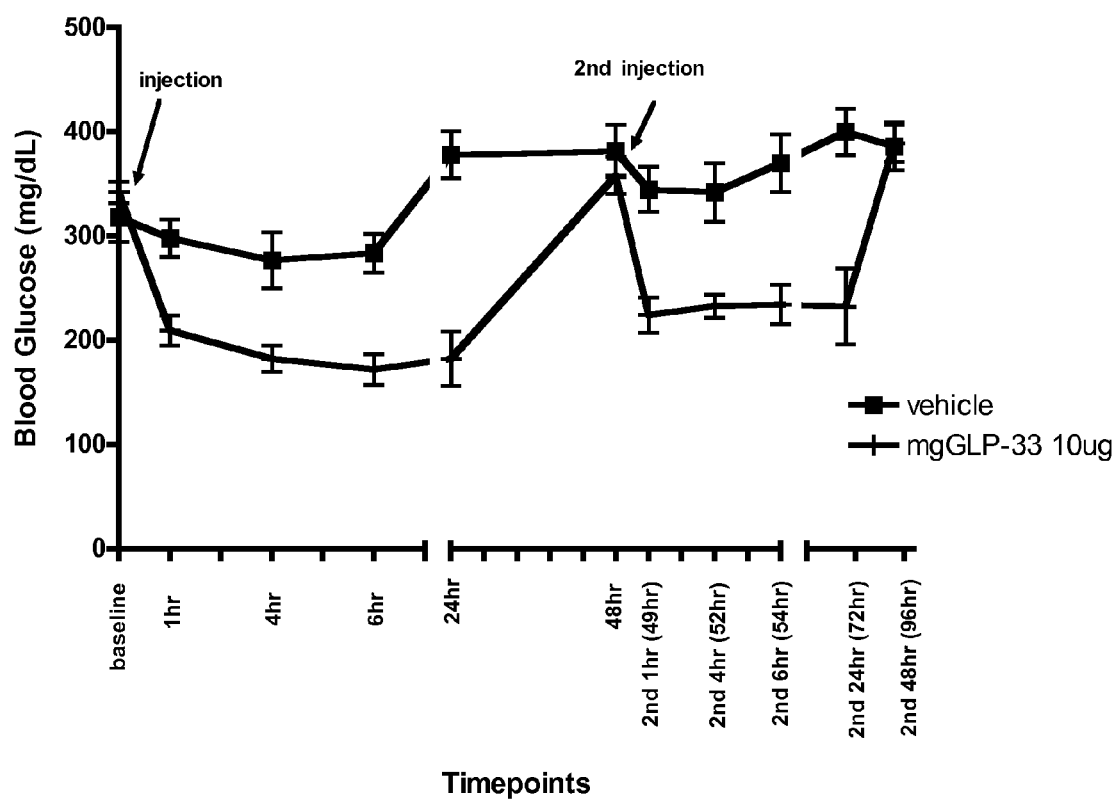
FIG. 17 shows a graph depicting blood glucose levels in mice treated with mgGLP-33.

To test whether tachyphylaxis was an issue with long acting forms of GLP-1 compounds, a multiple dose experiment was performed in db/db mice. The method described in Example 3 was used, except that a second bolus of the GLP-1 compound was injected the next day, right after the 24 hour blood glucose measurement. As shown in FIG. 17, blood glucose was decreased to the same extent on the second day with mgGLP-33 (see Table 5 for sequence and PEG size). No tachyphylaxyis was observed with the tested GLP-1 compound. The same result was observed with mgGLP-20 (see Table 5 for sequence and size and type of PEG).

Figure 18:
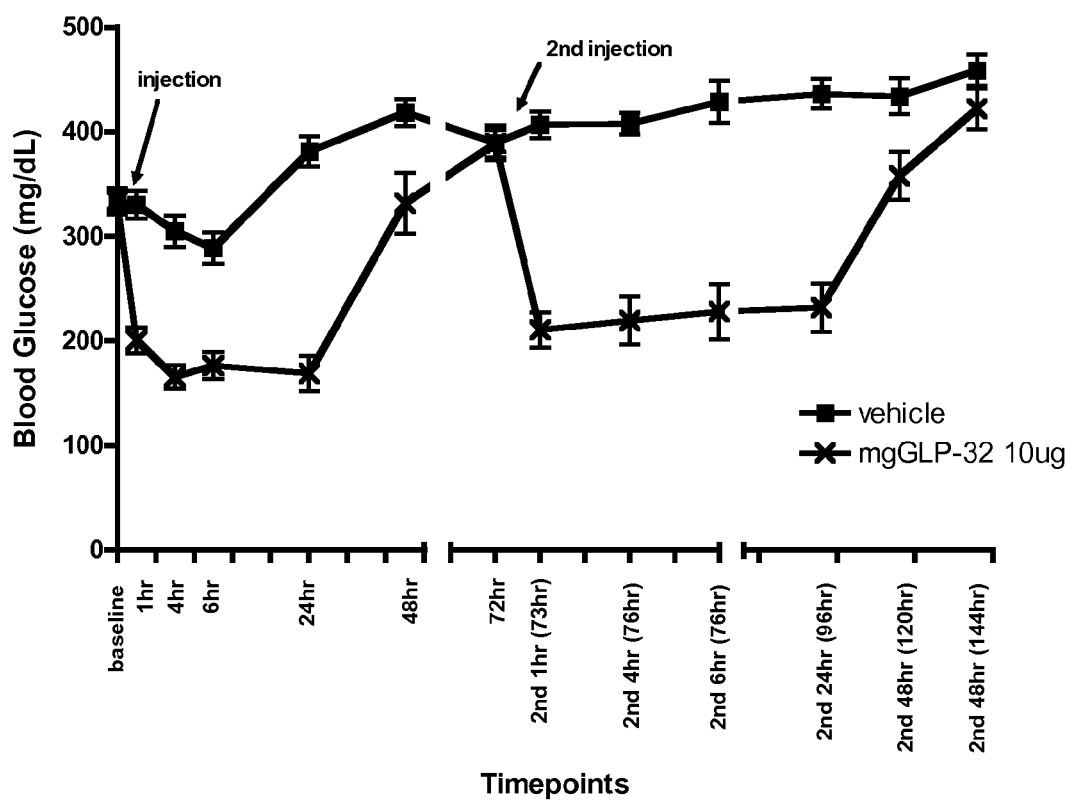
FIG. 18 shows a graph depicting blood glucose levels in mice treated with mgGLP-32.

In addition, a 4-day, multiple dose experiment with mgGLP-32 was performed (see Table 5 for sequence and size and type of PEG) in normal C57B16 mice. Also, to determine efficacy, a GTT was performed after the first injection, and a second GTT was performed after the $4^{th}$ injection. GTT were performed as described in Example 3. Results showing GLP-1 analogs efficiency on blood glucose are shown in FIG. 18.

Figure 19:
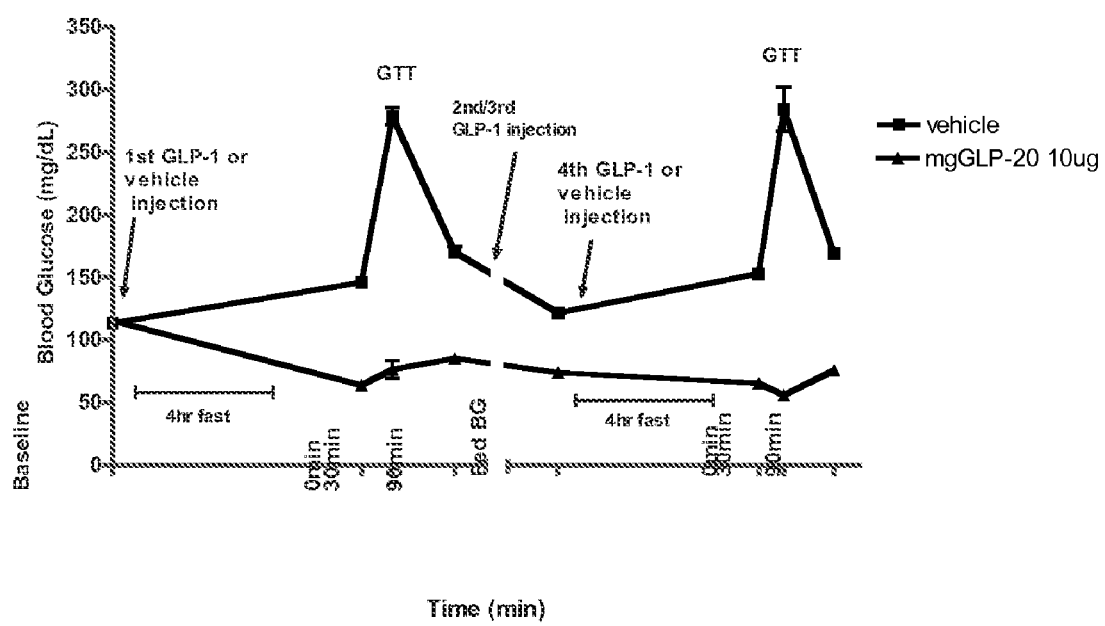
FIG. 19 shows a graph depicting blood glucose levels in mice treated with mgGLP-20.

As shown in FIG. 19, blood glucose was decreased during the 4 hour fast with mgGLP-20. Also, no blood glucose spike was seen during the first and second GTT in the mice treated with mgGLP-20. No tachyphylaxyis was observed after the $4^{th}$ dose of mgGLP-20.

Example 13

Pegylation Studies

All activated PEG polymers were obtained from Nektar Therapeutics (Huntsville, Ala.). A discussion of the different forms of PEG molecules used is provided in Example 4.

Numerous PEG-maleimide polymers are available ranging in size from 5-40 kD, and may also contain branched PEG polymers or have multivalent functional groups.

These polymers were used to determine an optimal balance of PEG size, polymer branching and peptide valence for improved pharmacokinetics with minimal impact on receptor binding. GLP-1 analogues were prepared from linear, monofunctional PEG-maleimides of: 5 kD, 10 kD, 20 kD and 30 kD. Also, a 40 kD branched PEG (2×20 kD polymers) maleimide was tested. The in vitro binding assay highlights an inverse relationship between PEG size and receptor affinity, with the branched 40 kD polymer having a very significant impact on receptor binding (Tables 3-5). Similarly, PEG size influences the duration of glucose decrease in vivo, with larger polymers typically achieving the greatest duration (data not shown). However, there is a limit to this effect and the largest PEG-GLP analogue (cgGLP-29) with a branched 40 kD polymer was not the most active in vivo.

Figure 20:
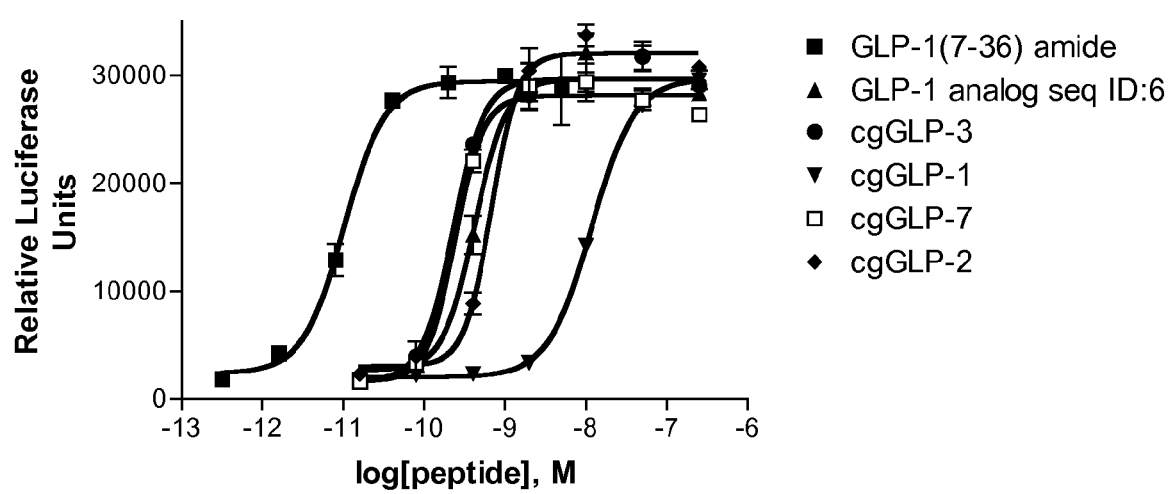
FIG. 20 shows a graph depicting the effect of PEG size and shape on certain cgGLP-3, cgGLP-1, cgGLP-7 and cgGLP-2.
Figure 21:
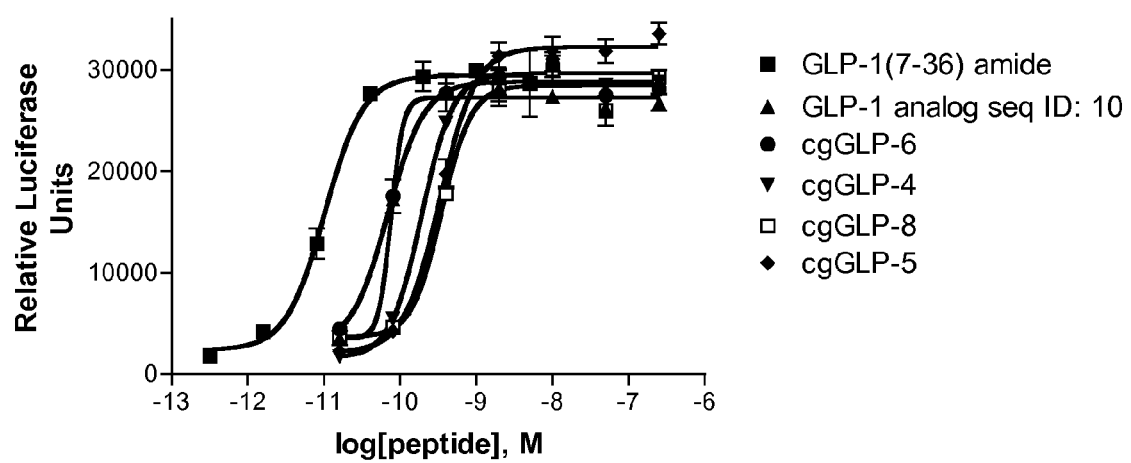
FIG. 21 shows a graph depicting the effect of PEG size and shape on cgGLP-6, cgGLP-4, cgGLP-8, cgGLP-5.
Figure 22:
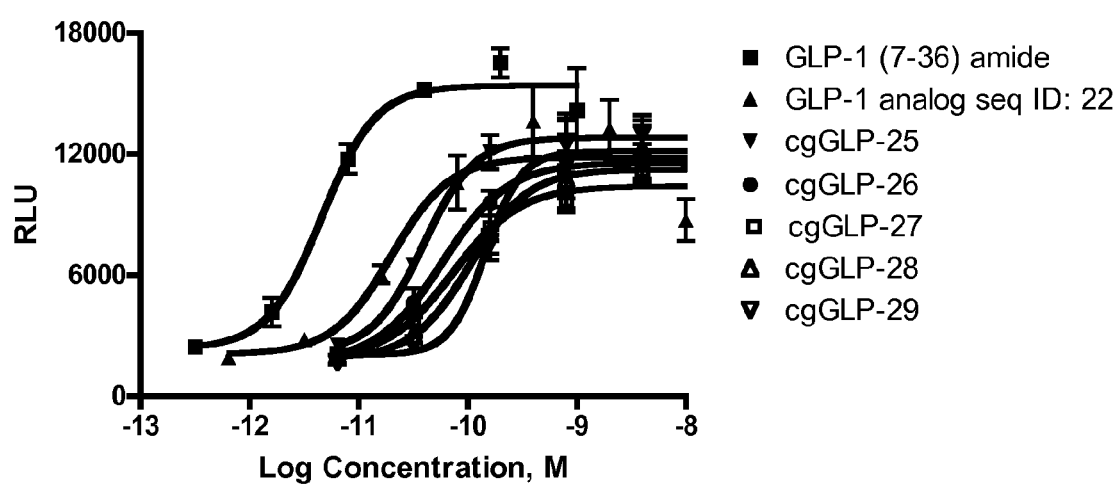
FIG. 22 shows a graph depicting the effect of PEG size and shape on cgGLP-25, cgGLP-26, cgGLP-24, cgGLP-28, cgGLP-29.
Figure 23:
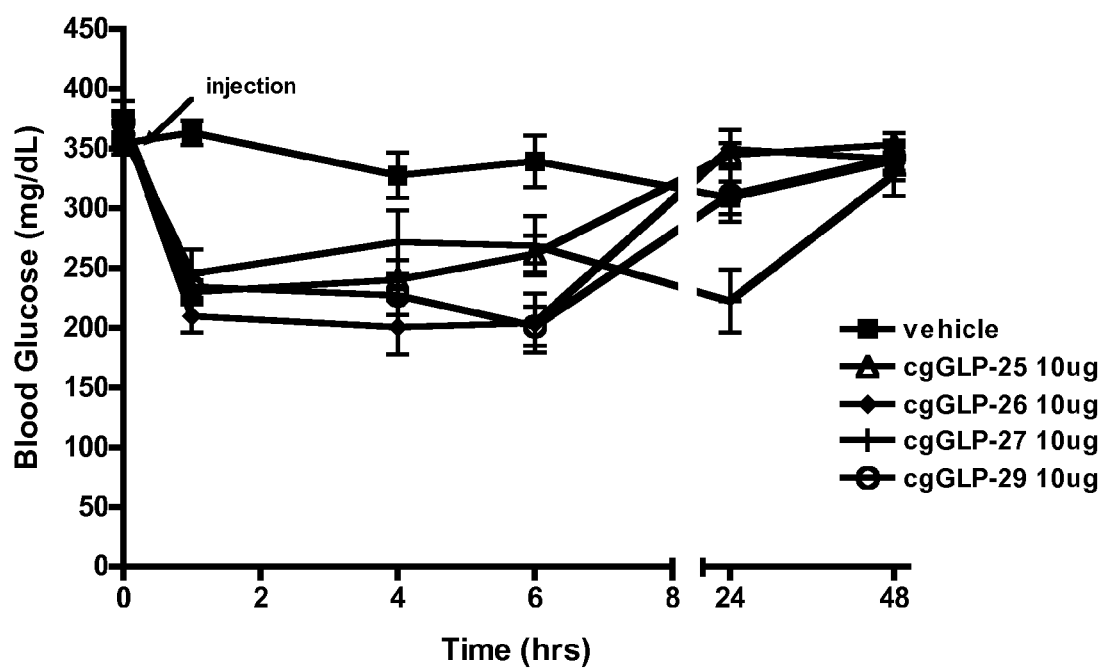
FIG. 23 shows a graph depicting the effect of PEG size and shape in vivo on db/db mice treated with a GLP-1 compound having the amino acid sequence set forth in SEQ ID NO:22 and either a cgGLP-25, cgGLP-26, cgGLP-27, cgGLP-29.

FIGS. 20 & 21 show results for a GLP-1 reporter assay for the activation of the human GLP-1 receptor by SEQ ID NOS: 6 and 10 respectively conjugated to: 1) two 8 kD PEG polymers, one at each end, like a "dumbbell"; 2) 20 kD PEG polymer; 3) 30 kD PEG polymer; or 4) 40 kD branched PEG polymer. Interestingly, while SEQ ID NO:10 shows similar functional activity for the 20, 30 and 40 kD PEG conjugates, SEQ ID NO:6 shows a marked reduction in activity with the 20 kD conjugate, while the 40 kD branched conjugate shows similar potency to the 30 kD and 8 kD dumbbell conjugates. This is in contrast to the observed inverse relationship between receptor binding affinity and PEG size. FIG. 22 shows similar results from the GLP-1 receptor functional assay using SEQ ID NO:22 conjugated to: 1) 5 kD PEG polymer; 2) 10 kD PEG polymer; 3) 20 kD PEG polymer; 4) 30 kD PEG polymer; or 5) 40 kD branched PEG polymer. The $EC_{50}$ values corresponding to these results are summarized in Tables 3-5. With these peptide conjugates, we see similar in vitro potency with all sizes of PEG conjugates with the exception of the 5 kD PEG conjugate having potency similar to the unconjugated peptide. An in vivo set of experiments were conducted using cgGLP-25 (5 kDa PEG), cgGLP-26 (10 kDa PEG), cgGLP-27 (20 kDa PEG) and cgGLP-28 (branched 40 kDa PEG) to determine the effect of different sizes and shapes of PEG have on the ability to lower glucose levels. Each of these compounds has the amino acid sequence of SEQ ID NO:22 but differ in the size or shape of the PEG that is attached as indicated. Blood glucose was measured in db/db mice as described in Example 3. The different compounds lowered blood glucose differently, with cgGLP-27 lowering blood glucose for the longest period of time (FIG. 23).

\* \* \*

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

What is claimed is:

1. A GLP-1 compound comprising a GLP-1 analog that comprises the amino acid sequence of SEQ ID NO:18.

2. The GLP-1 compound of claim 1, further comprising a water-soluble polymer.

3. The GLP-1 compound of claim 2, wherein the water-soluble polymer is selected from the group consisting of polyethylene glycol, monomethoxy-polyethylene glycol, dextran, cellulose, poly-(N-vinyl pyrrolidone) polyethylene glycol, propylene glycol homopolymers, polypropylene oxide/ethylene oxide co-polymers, polyoxyethylated polyols, and polyvinyl alcohol.

4. A method for treating a subject with a metabolic disorder, comprising administering to the subject an effective amount of a GLP-1 compound of claim 1, wherein the metabolic disorder is selected from the group of diabetes, impaired glucose tolerance, insulin resistance, irritable bowel syndrome, obesity and metabolic syndrome.

5. A method for treating a coronary disease or a lipid disorder in a subject, comprising administering to the subject a GLP-1 compound of claim 1, wherein the coronary disease or lipid disorder is selected from the group consisting of hypertension, coronary artery disease, hyperlipidemia, cardiovascular disease, atherosclerosis, hypercholesteremia and myocardial infarction.

6. A method for treating a subject, comprising administering to the subject a GLP-1 compound of claim 1, wherein the amount of the GLP administered is an amount sufficient to stimulate insulin release, reduce blood glucose levels, increase plasma insulin levels, increase beta-cell mass, induce satiety, reduce gastric secretion, delay gastric emptying or reduce gastric motility in the subject.

7. A pharmaceutical composition comprising the GLP-1 compound of claim 1.

* * * * *